United States Patent
Dutheil et al.

(10) Patent No.: US 12,414,948 B2
(45) Date of Patent: Sep. 16, 2025

(54) METHODS

(71) Applicant: INTRA-CELLULAR THERAPIES, INC., New York, NY (US)

(72) Inventors: Sophie Dutheil, Stamford, CT (US); Gretchen Snyder, New York, NY (US); Peng Li, New Milford, NJ (US); Robert E. Davis, San Diego, CA (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 0 days.

(21) Appl. No.: 18/518,436

(22) Filed: Nov. 22, 2023

(65) Prior Publication Data

US 2024/0122924 A1 Apr. 18, 2024

Related U.S. Application Data

(63) Continuation-in-part of application No. 18/320,173, filed on May 18, 2023.

(60) Provisional application No. 63/343,192, filed on May 18, 2022.

(51) Int. Cl.
*A61K 31/4985* (2006.01)
*A61P 25/18* (2006.01)
*A61P 25/22* (2006.01)
*A61P 25/24* (2006.01)
*A61P 29/00* (2006.01)

(52) U.S. Cl.
CPC .......... *A61K 31/4985* (2013.01); *A61P 25/18* (2018.01); *A61P 25/22* (2018.01); *A61P 25/24* (2018.01); *A61P 29/00* (2018.01)

(58) Field of Classification Search
CPC .................................. A61K 31/4985
USPC ....................................... 514/250
See application file for complete search history.

(56) References Cited

U.S. PATENT DOCUMENTS

| | | |
|---|---|---|
| 2,490,813 A | 12/1949 | Hughes et al. |
| 3,299,078 A | 1/1967 | Pachter |
| 3,813,392 A | 5/1974 | Sellstedt et al. |
| 3,914,421 A | 10/1975 | Rajagopalan |
| 4,001,263 A | 1/1977 | Plattner et al. |
| 4,115,577 A | 9/1978 | Rajagopalan |
| 4,136,145 A | 1/1979 | Fuchs et al. |
| 4,183,936 A | 1/1980 | Rajagopalan |
| 4,219,550 A | 8/1980 | Rajagopalan |
| 4,238,607 A | 12/1980 | Rajagopalan |
| 4,389,330 A | 6/1983 | Tice et al. |
| 4,522,944 A | 6/1985 | Doria et al. |
| 4,530,840 A | 7/1985 | Tice et al. |
| 4,767,628 A | 8/1988 | Hutchinson |
| 4,849,246 A | 7/1989 | Schmidt |
| 4,971,971 A | 11/1990 | Tokunaga et al. |
| 4,985,432 A | 1/1991 | Tokunaga et al. |
| 5,004,602 A | 4/1991 | Hutchinson |
| 5,114,976 A | 5/1992 | Norden |
| 5,151,419 A | 9/1992 | Perenyi et al. |
| 5,538,739 A | 7/1996 | Bodmer et al. |
| 5,629,003 A | 5/1997 | Horstmann et al. |
| 5,648,539 A | 7/1997 | Goodbrand et al. |
| 5,648,542 A | 7/1997 | Goodbrand et al. |
| 5,654,482 A | 8/1997 | Goodbrand et al. |
| 5,688,801 A | 11/1997 | Mesens et al. |
| 5,705,697 A | 1/1998 | Goodbrand et al. |
| 5,723,669 A | 3/1998 | Goodbrand et al. |
| 5,723,671 A | 3/1998 | Goodbrand et al. |
| 5,763,476 A | 6/1998 | Delbressine et al. |
| 5,779,231 A | 7/1998 | Okazaki et al. |
| 5,834,493 A | 11/1998 | Gil Quintero et al. |
| 5,847,166 A | 12/1998 | Buchwald et al. |
| 5,902,901 A | 5/1999 | Goodbrand et al. |
| 5,922,338 A | 7/1999 | Brich et al. |
| 5,922,682 A | 7/1999 | Brich et al. |
| 5,948,430 A | 9/1999 | Zerbe et al. |
| 5,965,168 A | 10/1999 | Mesens et al. |
| 6,043,370 A | 3/2000 | Kubo et al. |
| 6,110,921 A | 8/2000 | Mesens et al. |
| 6,221,335 B1 | 4/2001 | Foster |
| 6,307,087 B1 | 10/2001 | Buchwald et al. |
| 6,323,366 B1 | 11/2001 | Wolfe et al. |
| 6,368,632 B1 | 4/2002 | Mesens et al. |
| 6,407,092 B1 | 6/2002 | Hester et al. |
| 6,419,952 B2 | 7/2002 | Wong et al. |
| 6,440,710 B1 | 8/2002 | Keinan et al. |
| 6,541,639 B2 | 4/2003 | Zhou et al. |

(Continued)

FOREIGN PATENT DOCUMENTS

| | | |
|---|---|---|
| CN | 109867674 A | 6/2019 |
| EP | 0 058 481 A1 | 8/1982 |

(Continued)

OTHER PUBLICATIONS

Snyder et al., Psychopharmacology (Heidelberg, Germany) (2015), 232(3), 605-621.*

(Continued)

*Primary Examiner* — Niloofar Rahmani
(74) *Attorney, Agent, or Firm* — Hoxie & Associates LLC

(57) ABSTRACT

The disclosure provides methods the treatment of psychiatric disorders caused by viral, bacterial, or autoimmune encephalitis, and for treatment of psychiatric symptoms of viral, bacterial, and autoimmune encephalitis, and for protecting or reinforcing the blood-brain barrier, comprising administering to a patient in need thereof, a therapeutically effective amount of a 5-$HT_{2A}$.

27 Claims, No Drawings

(56) References Cited

U.S. PATENT DOCUMENTS

| | | |
|---|---|---|
| 6,544,599 B1 | 4/2003 | Mesens et al. |
| 6,548,493 B1 | 4/2003 | Robichaud et al. |
| 6,552,017 B1 | 4/2003 | Robichaud et al. |
| 6,552,024 B1 | 4/2003 | Chen et al. |
| 6,579,881 B2 | 6/2003 | Kitazawa et al. |
| 6,603,008 B1 | 8/2003 | Ando et al. |
| 6,699,852 B2 | 3/2004 | Robichaud et al. |
| 6,713,471 B1 | 3/2004 | Robichaud et al. |
| 6,762,329 B2 | 7/2004 | Marcoux et al. |
| 6,803,055 B2 | 10/2004 | Mesens et al. |
| 6,828,091 B2 | 12/2004 | Kasibhatla et al. |
| 6,849,619 B2 | 2/2005 | Robichaud et al. |
| 6,849,640 B2 | 2/2005 | Ennis et al. |
| 6,884,429 B2 | 4/2005 | Koziak et al. |
| 6,929,803 B2 | 8/2005 | Wong et al. |
| 7,071,186 B2 | 7/2006 | Robichaud et al. |
| 7,071,201 B2 | 7/2006 | Kitazawa et al. |
| 7,081,455 B2 | 7/2006 | Robichaud et al. |
| 7,109,339 B2 | 9/2006 | Lee et al. |
| 7,118,763 B2 | 10/2006 | Mesens et al. |
| 7,183,282 B2 | 2/2007 | Robichaud et al. |
| 7,223,870 B2 | 5/2007 | Ghosh et al. |
| RE39,679 E | 6/2007 | Robichaud et al. |
| RE39,680 E | 6/2007 | Robichaud et al. |
| 7,238,690 B2 | 7/2007 | Robichaud et al. |
| 7,244,734 B2 | 7/2007 | Iwema Bakker et al. |
| 7,375,226 B2 | 5/2008 | Jolidon et al. |
| 7,462,641 B2 | 12/2008 | Igo et al. |
| 7,517,990 B2 | 4/2009 | Ito et al. |
| 7,547,452 B2 | 6/2009 | Mesens et al. |
| 7,592,454 B2 | 9/2009 | Lee et al. |
| 7,598,273 B2 | 10/2009 | Gant et al. |
| 7,601,740 B2 | 10/2009 | Weiner et al. |
| 7,614,727 B2 | 11/2009 | Hori |
| 7,645,752 B2 | 1/2010 | McDevitt et al. |
| 7,659,285 B2 | 2/2010 | Weiner et al. |
| 7,713,995 B2 | 5/2010 | Weiner et al. |
| 7,732,462 B2 | 6/2010 | Weiner et al. |
| 7,750,168 B2 | 7/2010 | Potyen et al. |
| 7,968,538 B2 | 6/2011 | Becker et al. |
| 7,994,193 B2 | 8/2011 | Weiner et al. |
| 7,998,971 B2 | 8/2011 | Barlow et al. |
| 8,008,323 B2 | 8/2011 | Weiner et al. |
| 8,227,487 B2 | 7/2012 | Weiner et al. |
| 8,309,722 B2 | 11/2012 | Tomesch et al. |
| 8,309,772 B2 | 11/2012 | Weiner et al. |
| 8,377,959 B2 | 2/2013 | Weiner et al. |
| 8,414,922 B2 | 4/2013 | Bryson et al. |
| 8,461,148 B2 | 6/2013 | Hollander |
| 8,475,793 B2 | 7/2013 | De Waal Malefyt et al. |
| 8,598,119 B2 | 12/2013 | Mates et al. |
| 8,603,514 B2 | 12/2013 | Yang et al. |
| 8,604,021 B2 | 12/2013 | Becker et al. |
| 8,618,130 B2 | 12/2013 | Weiner et al. |
| 8,648,077 B2 | 2/2014 | Tomesch et al. |
| 8,652,378 B1 | 2/2014 | Yang et al. |
| 8,697,700 B2 | 4/2014 | Surman et al. |
| 8,778,893 B2 | 7/2014 | Gong et al. |
| 8,779,139 B2 | 7/2014 | Tomesch et al. |
| 8,791,138 B2 | 7/2014 | Seeman et al. |
| 8,835,459 B2 | 9/2014 | Kottayil et al. |
| 8,900,497 B2 | 12/2014 | Yang et al. |
| 8,900,498 B2 | 12/2014 | Yang et al. |
| 8,906,277 B2 | 12/2014 | Yang et al. |
| 8,921,393 B2 | 12/2014 | Weiner et al. |
| 8,993,572 B2 | 3/2015 | Mates et al. |
| 9,108,340 B2 | 8/2015 | Yang et al. |
| 9,168,258 B2 | 10/2015 | Mates et al. |
| 9,199,995 B2 | 12/2015 | Tomesch et al. |
| 9,211,289 B2 | 12/2015 | Weiner et al. |
| 9,216,175 B2 | 12/2015 | Amancha et al. |
| 9,315,504 B2 | 4/2016 | Tomesch et al. |
| 9,371,324 B2 | 6/2016 | Mates et al. |
| 9,393,192 B2 | 7/2016 | Yam et al. |
| 9,427,412 B2 | 8/2016 | Bryson et al. |
| 9,428,506 B2 | 8/2016 | Mates et al. |
| 9,566,271 B2 | 2/2017 | Weiner et al. |
| 9,567,327 B2 | 2/2017 | Xiong et al. |
| 9,586,960 B2 | 3/2017 | Tomesch et al. |
| 9,616,061 B2 | 4/2017 | Mates et al. |
| 9,708,322 B2 | 7/2017 | Li et al. |
| 9,745,300 B2 | 8/2017 | Mates et al. |
| 9,751,883 B2 | 9/2017 | Tomesch et al. |
| 9,956,227 B2 | 5/2018 | Vanover et al. |
| 10,028,944 B2 | 7/2018 | Weiner et al. |
| 10,072,010 B2 | 9/2018 | Li et al. |
| 10,077,267 B2 | 9/2018 | Mates et al. |
| 10,117,867 B2 | 11/2018 | Mates et al. |
| 10,118,926 B2 | 11/2018 | Koolman et al. |
| 10,179,776 B2 | 1/2019 | Davis et al. |
| 10,221,176 B2 | 3/2019 | Tomesch et al. |
| 10,245,260 B2 | 4/2019 | Yao et al. |
| 10,322,134 B2 | 6/2019 | Vanover et al. |
| 10,464,938 B2 | 11/2019 | Tomesch et al. |
| 10,472,359 B2 | 11/2019 | Li et al. |
| 10,525,046 B2 | 1/2020 | Weiner et al. |
| 10,597,394 B2 | 3/2020 | Mates et al. |
| 10,597,395 B2 | 3/2020 | Tomesch et al. |
| 10,654,854 B2 | 5/2020 | Li et al. |
| 10,682,354 B2 | 6/2020 | Wennogle |
| 10,688,097 B2 | 6/2020 | Yao et al. |
| 10,695,345 B2 | 6/2020 | Li et al. |
| 10,702,522 B2 | 7/2020 | Mates et al. |
| 10,716,786 B2 | 7/2020 | Li et al. |
| 10,799,500 B2 | 10/2020 | Yao et al. |
| 10,844,061 B2 | 11/2020 | Li et al. |
| 10,899,762 B2 | 1/2021 | Mates et al. |
| 10,906,906 B2 | 2/2021 | Li et al. |
| 10,960,009 B2 | 3/2021 | Vanover et al. |
| 10,960,010 B2 | 3/2021 | Vanover et al. |
| 10,961,245 B2 | 3/2021 | Li et al. |
| 11,014,925 B2 | 5/2021 | Li et al. |
| 11,026,951 B2 | 6/2021 | Vanover et al. |
| 11,052,083 B2 | 7/2021 | Li et al. |
| 11,053,245 B2 | 7/2021 | Mates et al. |
| 11,066,407 B2 | 7/2021 | Tomesch et al. |
| 11,096,944 B2 | 8/2021 | Yao et al. |
| 11,124,514 B2 | 9/2021 | Mates et al. |
| RE48,825 E | 11/2021 | Tomesch et al. |
| RE48,839 E | 12/2021 | Mates et al. |
| 11,311,536 B2 | 4/2022 | Li et al. |
| 11,331,316 B2 | 5/2022 | Li et al. |
| 11,376,249 B2 | 7/2022 | Li et al. |
| 11,407,751 B2 | 8/2022 | Tomesch et al. |
| 11,427,587 B2 | 8/2022 | Li et al. |
| 11,440,911 B2 | 9/2022 | Wennogle et al. |
| 11,453,670 B2 | 9/2022 | Li et al. |
| 11,560,382 B2 | 1/2023 | Mates et al. |
| 11,680,065 B2 | 6/2023 | Li et al. |
| 11,690,842 B2 | 7/2023 | Li et al. |
| 11,723,909 B2 | 8/2023 | Li et al. |
| 11,753,419 B2 | 9/2023 | Li et al. |
| 11,806,347 B2 | 11/2023 | Li et al. |
| 11,806,348 B2 | 11/2023 | Li et al. |
| 11,957,791 B2 | 4/2024 | Li et al. |
| 11,980,617 B2 | 5/2024 | Snyder et al. |
| 12,023,331 B2 | 7/2024 | Snyder et al. |
| 12,070,459 B2 | 8/2024 | Li et al. |
| 12,090,155 B2 | 9/2024 | Mates et al. |
| 12,122,792 B2 | 10/2024 | Li et al. |
| 12,128,043 B2 | 10/2024 | Li et al. |
| 12,144,808 B2 | 11/2024 | Li et al. |
| 12,194,044 B2 | 1/2025 | Yao et al. |
| 2003/0144319 A1 | 7/2003 | Bigge et al. |
| 2004/0009970 A1 | 1/2004 | Ramamoorthy |
| 2004/0034015 A1 | 2/2004 | Robichaud et al. |
| 2004/0092534 A1 | 5/2004 | Yam et al. |
| 2004/0127482 A1 | 7/2004 | Robichaud et al. |
| 2004/0142970 A1 | 7/2004 | Chung et al. |
| 2004/0186136 A1 | 9/2004 | Alken et al. |
| 2005/0166771 A1 | 8/2005 | Gygi et al. |
| 2005/0182749 A1 | 8/2005 | Matsui |
| 2005/0222209 A1 | 10/2005 | Zeldis et al. |
| 2005/0222238 A1 | 10/2005 | Alken |

(56) References Cited

U.S. PATENT DOCUMENTS

| | | |
|---|---|---|
| 2006/0178362 A1 | 8/2006 | Robichaud et al. |
| 2006/0205787 A1 | 9/2006 | Muller et al. |
| 2008/0069885 A1 | 3/2008 | Mesens et al. |
| 2008/0132552 A1 | 6/2008 | Kleinman et al. |
| 2008/0280941 A1 | 11/2008 | Lourtie |
| 2008/0287450 A1 | 11/2008 | Cid-Nunez et al. |
| 2009/0076159 A1 | 3/2009 | Czarnik |
| 2009/0209608 A1 | 8/2009 | Czarnik |
| 2010/0159033 A1 | 6/2010 | Gant et al. |
| 2010/0204470 A1 | 8/2010 | Wieser et al. |
| 2011/0071080 A1 | 3/2011 | Mates et al. |
| 2011/0269777 A1 | 11/2011 | Bachurin et al. |
| 2014/0080816 A1 | 3/2014 | Koolman et al. |
| 2014/0210117 A1 | 7/2014 | Friesen et al. |
| 2015/0004237 A1 | 1/2015 | Edgar et al. |
| 2015/0031804 A1 | 1/2015 | Shiramizu et al. |
| 2015/0072964 A1 | 3/2015 | Mates et al. |
| 2015/0079172 A1 | 3/2015 | Mates et al. |
| 2015/0080404 A1 | 3/2015 | Mates et al. |
| 2015/0374684 A1 | 12/2015 | Javitt et al. |
| 2016/0235720 A1 | 8/2016 | Foster et al. |
| 2016/0310502 A1 | 10/2016 | Vanover et al. |
| 2016/0354315 A1 | 12/2016 | Li |
| 2017/0114037 A1 | 4/2017 | Davis et al. |
| 2017/0183350 A1 | 6/2017 | Mates et al. |
| 2017/0319580 A1 | 11/2017 | Yao et al. |
| 2018/0044337 A1 | 2/2018 | Tomesch et al. |
| 2018/0200256 A1 | 7/2018 | Vanover et al. |
| 2019/0071445 A1 | 3/2019 | Li et al. |
| 2019/0183888 A1 | 6/2019 | Mates et al. |
| 2019/0192511 A1 | 6/2019 | Li et al. |
| 2019/0211015 A1 | 7/2019 | Mittleman et al. |
| 2019/0231780 A1 | 8/2019 | Yao et al. |
| 2019/0290655 A1 | 9/2019 | Vanover et al. |
| 2019/0298730 A1 | 10/2019 | Vanover et al. |
| 2019/0328692 A1 | 10/2019 | Doller et al. |
| 2019/0328745 A1 | 10/2019 | Vanover et al. |
| 2019/0388418 A1 | 12/2019 | Li et al. |
| 2020/0087305 A1 | 3/2020 | Tomesch et al. |
| 2020/0102304 A1 | 4/2020 | Li et al. |
| 2020/0148683 A1 | 5/2020 | Peddy et al. |
| 2020/0157100 A1 | 5/2020 | Li |
| 2020/0392135 A1 | 12/2020 | Wennogle et al. |
| 2020/0405713 A1 | 12/2020 | Mates et al. |
| 2020/0407362 A1 | 12/2020 | Mates et al. |
| 2021/0002280 A1 | 1/2021 | Mates |
| 2021/0008065 A1 | 1/2021 | Li et al. |
| 2021/0009592 A1 | 1/2021 | Li et al. |
| 2021/0032247 A1 | 2/2021 | Li et al. |
| 2021/0060009 A1 | 3/2021 | Synder et al. |
| 2021/0070755 A1 | 3/2021 | Zrt et al. |
| 2021/0093634 A1 | 4/2021 | Snyder et al. |
| 2021/0145829 A1 | 5/2021 | Li et al. |
| 2021/0163481 A1 | 6/2021 | Li et al. |
| 2021/0186962 A1 | 6/2021 | Davis et al. |
| 2021/0322433 A1 | 10/2021 | Vanover et al. |
| 2022/0024924 A1 | 1/2022 | Janton et al. |
| 2022/0041600 A1 | 2/2022 | Li et al. |
| 2022/0056031 A1 | 2/2022 | Li et al. |
| 2023/0312573 A1 | 10/2023 | Li et al. |
| 2023/0372336 A1 | 11/2023 | Dutheil et al. |

FOREIGN PATENT DOCUMENTS

| | | | |
|---|---|---|---|
| EP | 0 856 508 A1 | 8/1998 | |
| EP | 0 976 732 A1 | 2/2000 | |
| EP | 1 539 115 A1 | 6/2005 | |
| EP | 1 564 671 A1 | 8/2005 | |
| GB | 1476087 A | 6/1977 | |
| GB | 2145422 A | 3/1985 | |
| RU | 2 465 267 C2 | 10/2012 | |
| WO | WO-94/024125 A1 | 10/1994 | |
| WO | WO-95/013814 A1 | 5/1995 | |
| WO | WO-95/026325 A2 | 10/1995 | |
| WO | WO-1995/026325 A2 | 10/1995 | |
| WO | WO-98/043956 A1 | 10/1998 | |
| WO | WO-2000/035419 A2 | 6/2000 | |
| WO | WO-2000/048610 A1 | 8/2000 | |
| WO | WO-2000/064899 A1 | 11/2000 | |
| WO | WO-2000/077001 A1 | 12/2000 | |
| WO | WO-2000/077002 A1 | 12/2000 | |
| WO | WO-2000/077010 A2 | 12/2000 | |
| WO | WO-2002/059129 A2 | 8/2002 | |
| WO | WO-2003/014118 A1 | 2/2003 | |
| WO | WO-2004/010981 A1 | 2/2004 | |
| WO | WO-2004/039788 A1 | 5/2004 | |
| WO | WO-2004/045668 A1 | 6/2004 | |
| WO | WO-2004/056324 A2 | 7/2004 | |
| WO | WO-2004/064738 A2 | 8/2004 | |
| WO | WO-2005/030214 A1 | 4/2005 | |
| WO | WO-2006/034187 A2 | 3/2006 | |
| WO | WO-2006/081251 A2 | 8/2006 | |
| WO | WO-2006/081332 A1 | 8/2006 | |
| WO | WO-2007/084841 A2 | 7/2007 | |
| WO | WO-2008/112280 A1 | 9/2008 | |
| WO | WO-2009/017836 A1 | 2/2009 | |
| WO | WO-2009/100324 A1 | 8/2009 | |
| WO | WO-2017/117514 A1 | 7/2017 | |
| WO | WO-2017120012 A1 * | 7/2017 | ........... A61K 31/135 |
| WO | WO-2018/031535 A1 | 2/2018 | |
| WO | WO-2018/106916 A1 | 6/2018 | |
| WO | WO-2019/102240 A1 | 5/2019 | |
| WO | WO-2019/178484 A1 | 9/2019 | |
| WO | WO-2020/112941 A2 | 6/2020 | |
| WO | WO-2020/182978 A1 | 9/2020 | |
| WO | WO-2022/199708 A1 | 9/2022 | |
| WO | WO-2022/261633 A1 | 12/2022 | |

OTHER PUBLICATIONS

Davis et al., Psychopharmacology (Heidelberg, Germany) (2015), 232(15), 2863-2872.*
Mazza et al, CNS § Neurological Disorders-Drug Targets, (2020), 19, 243-247.*
Corponi et al., European Neuropsychopharmacology, (2019), 29, 971-985.*
Jairo et al., Neuroscience and Biobehavioral reviews 83 (2017), 97-108.*
Galea et al., Cellular & Molecular Immunology, 18, (2021), 2489-2501.*
Dutheil et al., The journal of Neurosicence, Feb. 1, 2023, 43(5), 863-877.*
U.S. Appl. No. 61/911,416, filed Dec. 3, 2013, Vanover et al.
U.S. Appl. No. 61/925,607, filed Jan. 9, 2014, Vanover et al.
U.S. Appl. No. 61/975,502, filed Apr. 4, 2014, Mates et al.
U.S. Appl. No. 61/975,610, filed Apr. 4, 2014, Mates et al.
U.S. Appl. No. 61/975,702, filed Apr. 4, 2014, Mates et al.
U.S. Appl. No. 62/009,849, filed Jun. 9, 2014, Davis et al.
U.S. Appl. No. 62/015,120, filed Jun. 20, 2014, Mates et al.
"Clinical Trial Evaluating ITI-007 (Lumateperone) as a Monotherapy for the Treatment of Bipolar Depression," ClinicalTrials.gov, 5 pages, Nov. 9, 2015.
"Clinical Trial Evaluating ITI-007 (Lumateperone) as a Monotherapy for the Treatment of Bipolar," ClinicalTrials.gov (Identifier: NCT02600494), 5 pages, (2015).
"Clinical Trial Evaluating ITI-007 as an Adjunctive Therapy to Lithium or Valproate for the Treatment of Bipolar Depression," ClinicalTrials.gov, 6 pages, Nov. 9, 2015.
"Study of a Novel Antipsychotic ITI-007 in Schizophrenia," Clinical Trials.gov, 6 pages, Dec. 26, 2011.
Aiken, C., "An Overview of Atypical Antipsychotics for Bipolar Depression," published on Jan. 3, 2020 at https://www.psychiatrictimes.com/view/overview-atypical-antipsychotics-bipolar-depression, 11 pages.
Angst et al. "Prevalence and Characteristics of Undiagnosed Bipolar Disorders in Patients With a Major Depressive Episode", Arch Gen Psychiatry, vol. 68, No. 8, pp. 701-709, (2011).
Balbach, et al. "Pharmaceutical evaluation of early development candidates 'the 100 mg-approach', " International Journal of Pharmaceutics, vol. 275, pp. 1-12 (2004).

(56) References Cited

OTHER PUBLICATIONS

Barman et al., "Newer Antipsychotics: Brexpiprazole, Cariprazine, and Lumateperone: A Pledge or Another Unkept Promise?," World J. Psychiatr., vol. 11, No. 12, pp. 1228-1238 (2021).
Barry et al. "Schizophrenia," Clinical Evidence, vol. 6, No. 1007, pp. 1-170, (2012).
Bastin et al., "Salt Selection and Optimized Procedures for Pharmaceutical New Chemical Entities," Organic Process and Research Development, vol. 4, No. 5, pp. 427-435 (2000).
Bavin, M, "Polymorphism in Process Development," Chemistry & Industry, pp. 527-529 (1989).
Bechtold, D.A., et al. "Circadian Dysfunction in Disease," Trends in Pharmacological Sciences, vol. 31, No. 5, pp. 191-198, (2010); DOI: 10.1016/j.tips.2010.01.002.
Bennett, J.C., et al., "Cecil Textbook of Medicine," 20th Edition, vol. 1, pp. 1004-1010, (1996).
Berge, S. et al., "Pharmaceutical Salts," J. Pharm. Sci., vol. 66, No. 1, pp. 1-19, (1977).
Bharate, S.S., "Recent Developments in Pharmaceutical Salts: FDA Approvals From 2015 to 2019," Drug Discovery Today, vol. 26, No. 2, pp. 384-398, (2021).
Bobo, W. V., et al. "Fluoxetine and olanzapine combination therapy in treatment-resistant major depression: review of efficacy and safety data," Expert Opinion on Pharmacotherapy, vol. 10, No. 13, pp. 2145-2159, (2009).
Bowers, K.M., et al. "Neuroinfections: Presentation, Diagnosis, and Treatment of Meningitis and Encephalitis," Neurology, pp. 93-102, (2020).
Bremner et al., "Neuroimaging of Posttraumatic Stress Disorder," Psychiatric Annals Journal, vol. 28, No. 8, pp. 445-450, (1998).
Brittain et al., "Chapter 5: Generation of Polymorphs, Hydrates, Solvates, and Amorphous Solids," Polymorphism in Pharmaceutical Solids, 25 pages, (1999).
Bryan-Lluka et al., "Potencies of Haloperidol Metabolites as Inhibitors of the Human Noradrenaline, Dopamine and Serotonin Transporters in Transfected COS-7 Cells," Naunyn-Shemiedeberg's Arch Pharmacol, vol. 360, pp. 109-115, (1999).
Byrn, "Pharmaceutical Solids: A Strategic Approach to Regulatory Considerations," vol. 12, No. 7, pp. 945-954 (1995).
Calabrese et al., "Efficacy and Safety of Lumateperone for Major Depressive Episodes Associated with Bipolar I or Bipolar II Disorder: A Phase 3 Randomized Placebo-Controlled Trial," American Journal of Psychiatry, vol. 178, No. 12, p. 1098-1106, (2021), published online Sep. 23, 2021, <<https://doi.org/10.1176/appi.aip.2021.20091339>>.
Chang, C-C., et al. "Melatonin inhibits matrix metalloproteinase-9 (MMP-9) activation in the lipopolysaccharide (LPS)-stimulated RAW 264.7 and BV2 cells and a mouse model of meningitis," J. Pineal Res., vol. 53, pp. 188-197, (2012).
Correll et al., "Efficacy and Safety of Lumateperone for Treatment of Schizophrenia A Randomized Clinical Trial," JAMA Psychiatry, vol. 77, No. 4, pp. 349-358 (2020).
Coyle et al., "Beyond the dopamine receptor: novel therapeutic targets for treating schizophrenia," Dialogues Clin Neurosci., vol. 12, No. 3, p. 359-382, (2010).
Darmani et al., "Do Functional Relationships Exist Between 5-HT1A and 5-HT2 Receptors?" Pharmacology and Biochemistry & Behavior, vol. 36, pp. 901-906, (1990).
Davis et al., "ITI-007 demonstrates brain occupancy at serotonin 5-HT2A and dopamine D2 receptors and serotonin transporters using positron emission tomography in healthy volunteers," Psychopharmacology, vol. 232, pp. 2863-2872, (2015); DOI: 10.1007/s00213-015-3922-1.
Davis et al., "ITI-007: A Novel Treatment for Behavioral Disturbances Associated with Dementia and Related Disorders," Clinical Trials in Alzheimer's Disease (CTAD) Congress 2014 (2014) (poster presentation).
Davis et al., "Rationale for the Development of Low Doses of ITI-007 for the Treatment of Behavioral Disturbances Associated with Dementia," The Journal of Prevention of Alzheimer's Disease, 2(4):302 (2015) (Clinical Trials in Alzheimer's Disease (CTAD) Congress, Symposium Summary OC51).
Davis, et al., "ITI-007 in the treatment of schizophrenia: from novel pharmacology to clinical outcomes," Expert Review of Neurotherapeutics, vol. 16, No. 6, pp. 601-614 (2016).
Davis, et al., "Lumateperone (ITI-007), A Novel Drug in Development for the Treatment of Agitation in Patients with Dementia, including Alzheimer's Disease: Rationale and Clinical Design," The Journal of Prevention of Alzheimer's Disease, 4(4):372 (2017) (Clinical Trials in Alzheimer's Disease (CTAD) Congress, Symposium Summary P93).
De Sousa, A.K., et al. "SARS-CoV-2-mediated encephalitis: Role of AT2R receptors in the blood-brain barrier," Medical Hypotheses, vol. 144, pp. 1-4, (2020).
Del-Monte et al., "Nonverbal expressive behaviour in schizophrenia and social phobia," Psychiatry Res., vol. 210, p. 29-35, (2013).
Docherty et al., "Effect of aripiprazole versus haloperidol on PANSS Prosocial items in early-episode patients with schizophrenia," Schizophrenia Res., vol. 120, pp. 199-203, (2010).
Dutheil, S., et al. "Lumateperone Normalizes Pathological Levels of Acute Inflammation through Important Pathways Known to Be Involved in Mood Regulation," The Journal of Neuroscience, vol. 43, No. 5, pp. 863-877, (2023).
Edinoff et al., "Lumateperone for the Treatment of Schizophrenia," Psychopharmacology Bulletin, vol. 50, No. 4, pp. 32-59 (2020).
Ellenbroeck et al. "Animal Models for the Negative Symptoms of Schizophrenia, " Behavioural Pharmacology, vol. 11, pp. 223-233, (2000).
Fletcher, P., et al. "Perceiving is Believing: Perceiving is Bayesian approach to explaining the positive symptoms of schizophrenia," Nature Reviews/Neuroscience, vol. 10, pp. 48-58, (2009).
Foster et al. "Emerging Approaches for Treatment of Schizophrenia: Modulation of Cholinergic Signaling," Discov Med., vol. 14, No. 79, pp. 413-420, (2012).
Gadade, et al., "Pharmaceutical Cocrystals: Regulatory and Strategic Aspects, Design and Development," Adv Pharm Bull, vol. 6, No. 4, pp. 479-494, (2016).
Gramigna, J, "Lumateperone Safe, Effective for Depressive Symptoms Among Patients with Bipolar Disorders," American Society of Clinical Psychopharmacology Annual Meeting, Jun. 2, 2020, 3 pages.
Grant, D., "Theory and Origin and Polymorphism," Polymorphism in Pharmaceutical Solids, Chapter 1, pp. 1-10, (1999).
Guillory, "Generation of Polymorphs, Hydrates, Solvates, and Amorphous Solids", Polymorphism in Pharmaceutical Solids, Chapter 5, pp. 183-226 (1999).
Hackam, D., et al. "Translation of Research Evidence from Animals to Humans," JAMA, vol. 296, No. 14, pp. 1731-1732, (2006).
Harbert et al., "Neuroleptic Activity in 5-Aryltetrahydro-y-carbolines," J. Med. Chem., vol. 23, pp. 635-643, (1980).
Harvey et al., "Lumateperone Improves Negative Symptoms Related to Emotional Experience (Avolition) in Patient with Schizophrenia," Abstract presented at the American Society of Clinical Psychopharmacology (ASCP) Annual Meeting: May 29-Jun. 1, 2018: Miami, FL.
Harvey, B.H., et al. "Serotonin and Stress: Protective or Malevolent Actions in the Biobehavioral Response to Repeated Trauma?," Annals of the New York Academy of Sciences, vol. 1032, pp. 267-272, (2004).
Harvey, P.D., "Ziprasidone and Cognition: The Evolving Story," J Clin Psychiatry, vol. 64, Suppl. 19, pp. 33-39, (2003).
Haynes et al., "Occurrence of Pharmaceutically Acceptable Anions and Cations in the Cambridge Database," Journal of Pharmaceutical Sciences, vol. 94, No. 10, pp. 2111-2120, (2005).
Helfer et al., "Efficacy and Safety of Antidepressants Added to Antipsychotics for Schizophrenia: A Systematic Review and Meta-Analysis," Am J Psychiatry, vol. 173, No. 9, pp. 876-886, (2016).
Hlavinka, E., "Schizophrenia Tx Eases Depression in Bipolar Disorder: Lumateperone Offers Greater Rate of Response, Remission versus Placebo," Medpage Today, 7 pages, (2020); https://www.medpagetoday.com/meetingcoverage/psychcongress/88584.

(56) References Cited

OTHER PUBLICATIONS

Howes et al., "Glutamate and dopamine in schizophrenia: An update for the 21st century," J Psychopharmacol., vol. 29, No. 2, p. 97-115, (2015).
International Search Report issued in International Application No. PCT/US2020/041063, mailed Oct. 8, 2020, 3 pages.
Intra-Cellular Therapies, Inc., "Corporate Presentation" (Jun. 30, 2019).
Intra-Cellular Therapies, Inc., "Corporate Presentation" (Sep. 24, 2019), downloaded from https://ir.intracellulartherapies.com/static-files/93b08960-f01c-4864-aa22-8cadb3539753 (last accessed Mar. 13, 2023).
Izrayelit, L. "Schizoaffective Disorder and PTSD Successfully Treated With Olanzapine and Supportive Psychotherapy," Psychiatric Annals journal, vol. 28, No. 8, pp. 424-426, (1998).
Jain, et al., "Polymorphism in Pharmacy", Indian Drugs, vol. 23, No. 6, pp. 315-316 (1986).
Johnson, O., et al. "Serotonin receptor activity is necessary for olfactory learning and memory in Drosophila melanogaster," Neuroscience, vol. 192, pp. 372-381, (2011).
Jozwiakowski, MJ, Liu, R (Ed.), "Alteration of the Solid State of the Drug Substance: Polymorphs, Solvates, and Amorphous Forms," Water-Insoluble Drug Formulation, Interpharm Press, pp. 525, 557-561 (2000).
Kahn, A.Y., et al. "Residual symptoms of schizophrenia: What are realistic treatment goals? Lingering symptoms require you to evaluate pharmacotherapy and offer psychosocial interventions," Current Psychiatry, vol. 16, No. 3, pp. 35-40 (2017).
Kantrowitz, J.T., "The Potential Role of Lumateperone-Something Borrowed? Something New?," JAMA Psychiatry, vol. 77, No. 4, p. 343-344, (2020); Abstract Only.
Kay et al., "The Positive an negative Syndrome Scale (PANSS) for Schizophrenia," Schizophrenia Bulletin, vol. 13, No. 2, pp. 261-276, (1987).
Kendrick, T. "The Newer, 'Atypical' Antipsychotic Drugs—Their Development and Current Therapeutic Use," British J. General Practice, vol. 49, p. 745-749 (1999).
Kessler et al., "Lifetime Prevalence and Age-of-Onset Distributions of DSM-IV Disorders in the National Comorbidity Survey Replication," Arch Gen Psychiatry, vol. 62, pp. 593-602, (2005).
Khorana, N., et al., "Gamma-Carbolines: Binding at 5-HT5A Serotonin Receptors", Bioorganic & Medicinal Chemistry, vol. 11, DD. 717-722, p. 718 Table 1, (2003).
Kumar et al., "Lumateperone: A New Treatment Approach for Neuropsychiatric Disorders," Drugs of Today, vol. 54, No. 12, pp. 713-719, (2018).
Lammers et al., "Risperidone Long-acting Injection in Schizophrenia Spectrum Illnesses Compared to First Generation Depot Antipsychotics in an Outpatient Setting in Canada," BMC Psychiatry, vol. 13, No. 155, 9 pages, (2013); http://www.biomedcentral.com/1471-244X/13/155.
Lee, et al., "Novel, Highly Potent, Selective 5-HT2A/D2 Receptor Antagonists as Potential Atypical Antipsychotics," Bioorg. Med. Chem. Lett., vol. 13, p. 767-770, (2003).
Li et al., "Discovery of a Tetracyclic Quinoxaline Derivative as a Potent and Orally Active Multifunctional Drug Candidate for the Treatment of Neuropsychiatric and Neurological Disorders", Journal of Medicinal Chemistry, vol. 57, p. 2670-2682 (2014).
Liebermann et al., "ITI-007 for the Treatment of Schizophrenia: A 4-Week Randomized, Double-Blind, Controlled Trial," Biological Psychiatry, vol. 79, pp. 952-961, (2016).
Lin et al., "Dosage and duration of antipsychotic treatment in demented outpatients with agitation or psychosis," Journal of the Formosan Medical Association, vol. 114, pp. 147-153, (2015).
Lindstrom et al., "Principal component analysis of the Swedish version of the Positive and Negative Syndrome Scale for schizophrenia," Nord J Psychiatry, vol. 47, No. 4, p. 257-263, (1993).
Lipschitz, D.S., et al. "Childhood Posttraumatic Stress Disorder: A Review of Neurobiologic Sequelae," Psychiatric Annals Journal, vol. 28, No. 8, pp. 452-457, (1998).
Lustig, S., et al. "Viral Neuroinvasion and Encephalitis Induced by Lipopolysaccharide and its Mediators," J. Exp. Med., vol. 176, pp. 707-712, (1992).
Makadia et al., "Poly Lactic-co-Glycolic Acid (PLGA) as Biodegradable Controlled Drug Delivery Carrier," Polymers (Basel), vol. 3, No. 3, pp. 1377-1397, (2011).
Marek, et al., "Synergistic Action of 5-HT2A Antagonists and Selective Serotonin Reuptake Inhibitors in Neuropsychiatric Disorders," Neuropsychopharmacology, vol. 28, pp. 402-412 (2003).
Mass et al., "Psychopathological Syndromes of Schizophrenia: Evaluation of the Dimensional Structure of the Positive and Negative Syndrome Scale," Schizophrenia Bull., vol. 26, No. 1, p. 167-177, (2000).
McIntyre et al., "Rapid-acting Antidepressants in Psychiatry: Psychedelics, Episodic Treatments, Innovation, and Clarion Call for Methodologic Rigor in Drug Development," Expert Opinion on Drug Safety, vol. 21, No. 6, pp. 715-716, (2022).
Medisorb Fact Sheet in Medisorb Microspheres Technology (Jan. 2009) at https://static.secure.website/wscfus/6472891/uploads/Medisorb.pdf (retrieved from the internet May 18, 2020) (Year: 2009).
Menard, et al., "Social stress induces neurovascular pathology promoting depression," Nature Neuroscience, vol. 20, pp. 1752-1760 (2017).
Möller et al., "Pharmacological treatment of negative symptoms in schizophrenia," Eur Arch Psychiatry Clin Neurosci., vol. 265, p. 567-578, (2015).
Moriguchi, T., et al. "A first case of meningitis/encephalitis associated with SARS-Coronavirus-2," International Journal of Infectious Diseases, vol. 94, pp. 55-58, (2020).
Mueller et al., "Detection of Depression in Acute Schizophrenia: Sensitivity and Specificity of 2 Standard Observer Rating Scales," Can J Psychiatry, vol. 51, No. 6, pp. 387-392, (2006).
National Library of Medicine U.S., "History of Changes for Study: NCT03249376, Lumateperone Monotherapy for the Treatment of Bipolar Depression Conducted Globally," National Institute of Health, (2019), https://clinicaltrials.gov/ct2/history/NCT03249376?V_5=View#StudyPageTop (retrieved from the internet Apr. 14, 2021); 4 pages.
Newman, et al., "Solid-State Analysis of the Active Pharmaceutical Ingredient in Drug Products," Drug Discovery Today, vol. 8, No. 9, pp. 898-903 (2003).
O'Gorman, et al., "Lumateperone (ITI-007): A Novel Investigational Agent with Broad Therapeutic Potential Across Multiple Neuropsychiatric Disorders," Poster P.1.g.038, European College of Neuropsychopharmacology (ECNP) Congress (2017).
O'Hara, R., et al. "Serotonin Transporter Polymorphism, Memory, and Hippocampal Volume in the Elderly: Association and Interaction with Cortisol," Mol Psychiatry, vol. 12, No. 6, pp. 544-555, (2007).
Olivier, J.D.A., et al. "Serotonin transporter deficiency in rats contributes to impaired object memory," Genes, Brain, and Behavior, vol. 8, pp. 829-834, (2009).
Olsen, A.L., et al. "Correlation between breakdown of the blood-brain barrier and disease outcome of viral encephalitis in mice," Antiviral Research. vol. 75, pp. 104-112, (2007).
Palanisamy, M. et al., "Cellulose-Based Matrix Microspheres of Prednisolone Inclusion Complex; Preparation and Characterization," American Association of Pharmaceutical Scientists PharmSciTech, vol. 12, No. 1, pp. 388-400, (2011).
Perlis, et al., "Clinical Features of Bipolar Depression Versus Major Depressive Disorder in Large Multicenter Trials," Am J Psychiatry, vol. 163, pp. 225-231, (2006).
Peterson et al., "Expanding the Scope of Crystal Form Evaluation in Pharmaceutical Science," J Pharm Pharmaceut Sci., vol. 9, No. 3, pp. 317-326, (2006).
Pine et al. "Dopamine, Time, and Impulsivity in Humans," The Journal of Neuroscience, vol. 30, No. 26, pp. 8888-8896, (2010).
Pond et al. "Stereospecific Reduction of Haloperidol in Human Tissues," Biochemical Pharmacology, vol. 44, No. 5, pp. 867-871, (1992).
Press Release, "Intra-Cellular Therapies Announces Additional Results From Phase I/II Clinical Trial for ITI-007 in Healthy Geriatric

(56) References Cited

OTHER PUBLICATIONS

Subjects and Patients With Dementia.", Intra-Cellular Therapies, Press Release Date: Nov. 21, 2014.
Press Release, "Intra-Cellular Therapies Announces Positive Top-Line Results from a Phase 3 Trial of Lumateperone in Patient with Bipolar Depression," Intra-Cellular Therapies, Press Release Date: Jul. 8, 2019.
Press Release, "Intra-Cellular Therapies Presents Data on Symptom Improvement by Lumateperone on Negative Symptoms, Depression, and Social Function in Patients with Schizophrenia at the American Society of Clinical Psychopharmacology (ASCP) Annual Meeting," Intra-Cellular Therapies, Press Release Date: May 31, 2018, (https://ir intracellulartherapies com/newsreleases/.
Pubchem, OPEN Chemistry Database, Compound Summary for CID-22036753, pp. 4, (2007), 12 pages.
Pubchem, OPEN Chemistry Database, PubChem CID 90655118, (2012), 2 pages.
Pubchem, OPEN Chemistry Database, PubChem SID 103920954, PubChem CID 90655118, (2011), 6 pages.
Puig et al., "Serotonin and Prefrontal Cortex Function: Neurons, Networks, and Circuits," Mol. Neurobiol., vol. 44, No. 3, pp. 449-464, (2011).
Rackova et al. "Free Radical Scavenging and Antioxidant Activities of Substituted Hexahydropyridoindoles. Quantitative Structure-Activity Relationships." Journal of Medicinal Chemistry, vol. 49, No. 8, pp. 2543-2548, (2006).
Rainer, M.K., "Risperidone Long-acting Injection: A Review of its Long Term Safety and Efficacy," Neuropsychiatric Disease and Treatment, vol. 4, No. 5, pp. 919-927, (2008).
Romero, J.R., et al. "Viral Meningitis and Encephalitis: Traditional and Emerging Viral Agents," Seminars in Pediatric Infectious Diseases, vol. 14, No. 2, pp. 72-82, (2003).
Rotbart, H.A. "Meningitis and Encephalitis," Human Enterovirus Infections, pp. 271-289, (1995).
Rummel et al., "Antidepressants as add-on treatment to antipsychotics for people with schizophrenia and pronounced negative symptoms: A systematic review of randomized trials," Schizophrenia Res., vol. 80, p. 85-97, (2005).
Saal et al., "Pharmaceutical Salts: A Summary on Doses of Salt Formers from the Orange Book," European Journal of Pharmaceutical Sciences, vol. 49, pp. 614-623, (2013).
Satlin, et al., "ITI-007 (Lumateperone) for the Treatment of Agitation in Patients with Dementia, including Alzheimer's Disease," Alzheimer's & Dementia 14(7) (Suppl.): P678-79 (2018) (Alzheimer's Assoc. International Conference 2018, summary of Poster P2-032).
Satlin, et al., "ITI-007 (Lumateperone) for the Treatment of Agitation in Patients with Dementia, including Alzheimer's Disease," Poster P2-032, Alzheimer's Assoc. International Conference 2018 (2018).
Savjani et al., "Drug Solubility: Importance and Enhancement Techniques," International Scholarly Research Network Pharmaceutics (2012), vol. 2012, pp. 1-10.
Schennach, R., et al. "What are residual symptoms in schizophrenia spectrum disorder? Clinical description and 1-year persistence within a naturalistic trial," Eur Arch Psychiatry Clin Neurosci, vol. 265, pp. 107-116, (2015).
Seishinkei Shi, vol. 110, No. 7, pp. 557-584, (2008). Partial English translation only.
Sepehry et al., "Selective Serotonin Reuptake Inhibitor (SSRI) Add-On Therapy for the Negative Symptoms of Schizophrenia: A Meta-Analysis," J Clin Psychiatry, vol. 68, No. 4, pp. 604-610, (2007).
Serajuddin, Atm, "Salt formation to improve drug solubility," Advanced Drug Delivery Reviews, vol. 59, pp. 603-616 (2007).
Sigel et al. "Tenary Complexes in Solution", Inorganic Chemistry, vol. 13, No. 2, pp. 462-465, (1974).
Silver et al., "Multifunctional Pharmacotherapy: What Can We Learn from Study of Selective Serotonin Reuptake Inhibitor Augmentation of Antipsychotics in Negative-Symptom Schizophrenia?," Neurotherapeutics, vol. 6, pp. 86-93, (2009).
Singh et al., "Efficacy of antidepressants in treating the negative symptoms of chronic schizophrenia: meta-analysis, " The British Journal of Psychiatry, vol. 197, p. 174-179, (2010).
Singhal, et al., "Drug polymorphism and dosage form design: a practical perspective", Advanced Drug Delivery Reviews, vol. 56, pp. 335-347 (2004).
Smith, T.E., et al. "Schizophrenia (maintenance treatment)," Clinical Evidence, vol. 4, No. 1007, (2009).
Snyder et al., "Functional profile of a novel modulator of serotonin, dopamine, and glutamate neurotransmission," Psychopharmacology, vol. 232, pp. 605-621, (2015) Published online Aug. 2014, DOI 10.1007/s00213-014-3704-1.
Stahl & Wermouth (Eds.), "Handbook of Pharmaceutical Salts Properties, Selection, and Use," Wiley-VCH, pp. 167-168, 170-173, 216-217 (2002).
Stahl & Wermouth (Eds.), "Handbook of Pharmaceutical Salts Properties, Selection, and Use," Wiley-VCH, pp. 258-261 (2002).
Steffen Paulekuhn et al., "Trends in Active Pharmaceutical Ingredient Salt Selection based on Analysis of the Orange Book Database," J Med Chem., vol. 50, p. 6665-6672, (2007).
Taragano et al. "A Double-Blind, Randomized, Fixed-Dose Trial of Fluoxetine vs. Amitriptyline in the Treatment of Major Depression Complicating Alzheimer's Disease," Psychosomatics, vol. 38, No. 3, p. 246-252, (1997).
Tohen, M., et al., "Efficacy of Olanzapine and Olanzapine-Fluoxetine Combination in the Treatment of Bipolar I Depression," Arch Gen Psychiatry, vol. 60, pp. 1079-1088, (2003).
Tyler, K.L. "Herpes Simplex Virus Infections of the Central Nervous System: Encephalitis and Meningitis, Including Mollaret's," HERPES, vol. 11, Supplement 2, pp. 57-64, (2004).
Vanover et al., Abstracts of the 13th International Congress on Schizophrenia (ICOSR) (Apr. 2-6, 2011), Schizophrenia Bull. vol. 37, Suppl. 1., p. 325 (Mar. 2011).
Vanover, et al., "Dopamine D2 receptor occupancy of lumateperone (ITI-007): a Positron Emission Tomography Study in patients with schizophrenia," Neuropsychopharmacology, 44:598-605, (2019).
Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018: Miami FL.
Vanover, et al., "Lumateperone (ITI-007): A Novel Investigational Agent with Broad Therapeutic Potential Across Multiple Neuropsychiatric Disorders," European Neuropsychopharmacology, vol. 27, pp. S660-S661 (2017) (Summary of ECNP Poster P.1.g.038).
Vanover, K., et al., "ITI-007: A Novel Therapy for the Treatment of Schizophrenia and Related Psychoses," International Clinical Psychopharamcology, vol. 26, e56, 1 page, (2011).
Vippagunta, et al., "Crystalline Solids," Advanced Drug Delivery Reviews, vol. 48, 24 pages, (2001).
Vloeberghs, E., et al., "Altered Circadian Locomotor Activity in APP23 Mice: A Model for BPSD Disturbances," European Journal of Neuroscience, vol. 20, pp. 2757-2766, (2004); DOI: 10.1111/j. 1460-9568.2004.03755.x.
Vyas, P., et al., "An Evaluation of Lumateperone Tosylate for the Treatment of Schizophrenia," Expert Opinion on Pharmacotherapy, vol. 21, No. 2, pp. 139-145, (2020); https://doi.org/10.1080/14656566. 2019.1695778.
Wang et al., "Rapid-acting Antidepressants Targeting Modulation of the Glutamatergic System: Clinical and Preclinical Evidence and Mechanisms," General Psychiatry, vol. 35, No. e100922, 6 pages (2022).
Warner-Schmidt et al., "Antidepressant Effects of Selective Serotonin Reuptake Inhibitors (SSRIs) are Attenuated by Antiinflammatory Drugs in Mice and Humans," PNAS, vol. 108, No. 22, pp. 9262-9267 (2011).
Wennogle, et al., "Activation of NMDA and AMPA Receptors by Lumateperone (ITI-007): Implications for Antidepressant Activity," Abstract presented at the 2017 Collegium Internationale Neuro-

(56) References Cited

OTHER PUBLICATIONS

Psychopharmacologicum (CINP) Thematic Meeting: Treatment Resistant Depression; Jul. 20-22, 2017; Prague.
Weschules et al. "Acetylcholinesterase Inhibitor and N-Methyl-D-Aspartic Acid Receptor Antagonist Use among Hospice Enrollees with a Primary Diagnosis of Dementia," Journal of Palliative Medicine, vol. 11, No. 5, pp. 738-745, (2008).
Witkin et al., "Chapter 3: Rapid-acting Antidepressants," Advances in Pharmacology, vol. 86, 50 pages, (2019).
Yakuzai-Gaku , vol. 68, No. 2, pp. 136-142, (2008) (Japanese Only).
Yatham, L.N., "A clinical review of aripiprazole in bipolar depression and maintenance therapy of bipolar disorder," J. Affect. Disord., vol. 128, Suppl 1: s21-8, (2011).
Yudofsky et al., "Propranolol in the Treatment of Rage and Violent Behavior in Patients with Chronic Brain Syndromes," Am. J. Psychiatry, vol. 138, pp. 218-220, (1981).
Zhang et al., "The Role of Serotonin 5-HT2A Receptors in Memory and Cognition," Front Pharmacol., vol. 6, No. 225, pp. 1-17, (2015); DOI: 10.3389/fphar.2015.00225.
Zhang, W., et al. "The in vivo effects of olanzapine and other antipsychotic agents on receptor occupancy and antagonism of dopamine D1, D2, D3, 5HT2A and muscarinic receptors," Psychopharmacology, vol. 141, pp. 267-278, (1999).
"Highlights of Prescribing Information CAPLYTA (lumateperone) capsules, for oral use," Label—Prescribing Information, 16 pages, (2019); https://www.accessdata.fda.gov/drugsatfda_docs/label/2019/209500s000lbl.pdf.
Bundel, et al., "Dopamine D2 receptors gate generalization of conditioned threat responses through Mtorc1 signaling in the extended amygdala," Mol. Psychiatry, vol. 21, No. 11, pp. 1545-1553, (2016).
Cole et al., "ITI-007. 5HT2A Receptor Antagonist, Dopamine D2 Receptor Modulator, Treatment of Schizophrenia, Treatment of Insomnia," Drugs of the Future, vol. 40, No. 1, p. 643-650, (2015).
Kudla, L. et al., "Influence of G protein-biased agonists of μ-opioid receptor on addiction-related behaviors," Pharmacol Rep., vol. 73, No. 4, pp. 1033-1051, (2021).
Newton, W., "Intra-Cellular Reports Positive Phase III Trial of Caplyta in MDD and Bipolar Depression," ClinicalTrials Arena, Mar. 29, 2023, retrieved from https://www.clinicaltrialsarena.com/news/news-intra-cellular-positive-phase-ill-trial/ (last accessed, Mar. 7, 2024).
Snyder, G. et al., "Chapter 11: A review of the pharmacology and clinical profile of lumateperone for the treatment of schiophrenia," Advances in Pharmacology, vol. 90, pp. 253-276, 31 pages, (2021).
Suppes, T. et al., "Adjunctive lumateperone (ITI-007) in the treatment of bipolar depression: Results from a randomized placebo-controlled clinical trial," Bipolar Disorders, vol. 25, pp. 478-488, 11 pages, (2023).
Vanover, K. et al., "50. ITI-007, an Investigational New Antipsychotic Drug with a Novel Pharmacological Profile, is Safe and Well-Tolerated with Early Clinical Signs for Efficacy in Patients with Stabilized Schizophrenia," Abstract presented at the ANCP 49th Annual Conference in Poster Session III; Dec. 8, 2010; pages S321-S322; Neuropsychopharmacology, vol. 35, (2010).
Vanover, K. et al., "Safety, Pharmacokinetics and Early Signals for Efficacy with ITI-007, A Novel Investigational New Drug for the Treatment of Schizophrenia and Related Disorders," Schizophrenia Bulletin, vol. 37, Suppl. 1, p. 325, (2011), Abstract only.
Vanover, K. et al., "T184. Long-Term Safety for Lumateperone (ITI-007) in the Treatment of Schizophrenia," ANCP 57th Annual Meeting: Poster Session II, 4 pages, (2018).
Vanover, K. et al., "W201. Efficacy and Safety of Lumateperone 42 mg in the Treatment of Schizophrenia: A Pooled Analysis of Randomized Clinical Trials," ACNP 58th Annual Meeting: Poster Session III, vol. 44, Suppl. 1, pp. 492-494, Dec. 5, 2019.

\* cited by examiner

METHODS

CROSS-REFERENCE TO RELATED APPLICATIONS

This application is a continuation-in-part of U.S. Non-Provisional application Ser. No. 18/320,173, filed on May 18, 2023, which claims priority to, and the benefit of, U.S. Provisional Application Ser. No. 63/343,192, filed on May 18, 2022, the contents of each of which are hereby incorporated by reference in their entireties.

TECHNICAL FIELD

The present disclosure relates to use of a $5\text{-HT}_{2A}$ or $5\text{-HT}_{2A}$/D2 receptor ligand, for example a substituted heterocycle fused gamma-carbolines as described herein, in free, pharmaceutically acceptable salt or prodrug form, for the treatment of psychiatric disorders and peripheral serotonin deficiency, such as caused by viral, bacterial, or autoimmune encephalitis, and for treatment of psychiatric symptoms of viral, bacterial, and autoimmune encephalitis, and for protecting or reinforcing the blood-brain barrier.

BACKGROUND OF THE INVENTION

Substituted heterocycle fused gamma-carbolines such as lumateperone are known to be $5\text{-HT}_{2A}$ or $5\text{-HT}_{2A}$/D2 receptor ligands, which are useful in treating central nervous system disorders. These compounds antagonize the serotonin-2A ($5\text{-HT}_{2A}$) receptor, and/or modulate dopamine receptor signaling at the level of key intra-cellular phosphoproteins. Such compounds are principally known to be useful for the treatment of positive and negative symptoms of schizophrenia. At dopamine D2 receptors, these compounds have dual properties and act as both post-synaptic antagonists and pre-synaptic partial agonists. They also stimulate phosphorylation of glutamatergic NMDA NR2B, or GluN2B, receptors in a mesolimbic specific manner. It is believed that this regional selectivity in the brain areas thought to mediate the efficacy of antipsychotic drugs, together with the serotonergic, glutamatergic, and dopaminergic interactions, may result in antipsychotic efficacy for positive, negative, affective and cognitive symptoms associated with schizophrenia. The compounds also exhibit serotonin reuptake inhibition, providing antidepressant activity for the treatment of schizoaffective disorder, co-morbid depression, and/or as a stand-alone treatment for major depressive disorder. The $5\text{-HT}_{2A}$ or $5\text{-HT}_{2A}$/D2 receptor ligands as described are also useful for the treatment of bipolar disorder and other psychiatric and neurodegenerative disorders, particularly behavioral disturbances associated with dementia, autism and other CNS diseases. These features may be able to improve the quality of life of patients with schizophrenia and enhance social function to allow them to more fully integrate into their families and their workplace. These compounds display differential dose-dependent effects, selectively targeting the $5\text{-HT}_{2A}$ receptor at low doses, while progressively interacting with the D2 receptor at higher doses. As a result, at lower doses, they are useful in treating sleep, aggression and agitation. At a high-dose, they can treat acute exacerbated and residual schizophrenia, bipolar disorders, and mood disorders.

Lumateperone, having the formula:

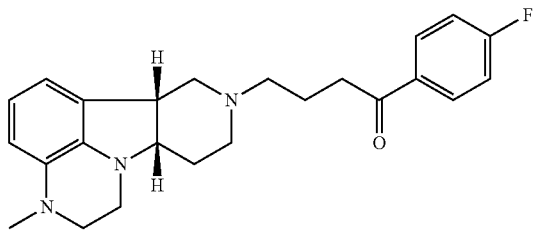 [SMILES: CN1CCN2c3c(cccc31)[C@@H]1CN(CCCC(=O)c3ccc(F)cc3)CC[C@@H]12]

is a novel therapeutic agent with potent (Ki=0.5 nM) $5\text{-HT}_{2A}$ receptor antagonism, activity as a mesolimbic/mesocortical-selective dopamine receptor protein phosphorylation modulator consistent with presynaptic D2 receptor partial agonism and postsynaptic D2 receptor antagonism (Ki=32 nM) in vivo, high D1 receptor affinity (Ki=52 nM), and inhibition of the serotonin transporter (SERT) (Ki=26-62 nM, using different assays for SERT activity). Lumateperone has been approved in the United States for the treatment for schizophrenia and bipolar depression in adults (depressive episodes associated with bipolar I disorder or bipolar II disorder), and it is in clinical development for the treatment of other neuropsychiatric disorders, such as major depressive disorder (MDD), and agitation in dementia, including Alzheimer's Disease.

Lumateperone and related compounds have been disclosed in U.S. Pat. Nos. 6,548,493; 7,238,690; 6,552,017; 6,713,471; U.S. RE39,680, and U.S. RE39,679, as novel compounds useful for the treatment of disorders associated with $5\text{-HT}_{2A}$ receptor modulation such as anxiety, depression, psychosis, schizophrenia, sleep disorders, sexual disorders, migraine, conditions associated with cephalic pain, and social phobias. WO 2000/077002 and U.S. Pat. No. 7,071,186, also disclose methods of making substituted heterocycle fused gamma-carbolines and uses of these gamma-carbolines as serotonin agonists and antagonists useful for the control and prevention of central nervous system disorders such as addictive behavior and sleep disorders. WO 2009/145900 and U.S. Pat. No. 8,598,119, and WO 2013/155504 and U.S. Pat. No. 11,053,245, and WO 2013/155506 and U.S. Pat. No. 11,124,514, each incorporated herein by reference, disclose the use of specific substituted heterocycle fused gamma-carbolines for the treatment of a combination of psychosis and depressive disorders as well as sleep, depressive and/or mood disorders in patients with psychosis or Parkinson's disease, for the treatment of post-traumatic stress disorder, impulse control disorders and related disorders, and for the treatment or prophylaxis of disorders associated with dementia, particularly behavioral or mood disturbances such as agitation, irritation, aggressive/assaultive behavior, anger, physical or emotional outbursts and psychosis and sleep disorders associated with dementia. WO 2009/114181 and U.S. Pat. No. 8,648,077, each incorporated herein by reference, disclose methods of preparing toluenesulfonic acid addition salt crystals of particular substituted heterocycle fused gamma-carbolines, e.g., toluenesulfonic acid addition salt of 4-((6bR,10aS)-3-methyl-2,3,6b,9,10,10a-hexahydro-1H-pyrido[3',4': 4,5]pyrrolo[1,2,3-de]quinoxaline-8(7H)-yl)-1-(4-fluorophenyl)-1-butanone.

WO 2011/133224 and U.S. Pat. No. 8,993,572, each incorporated herein by reference, disclose prodrugs/metabolites of substituted heterocycle fused gamma-carboline for improved formulation, e.g., extended/controlled release formulation. This application discloses that heterocycle fused gamma-carboline N-substituted with a 4-fluorophenyl(4-hydroxy)butyl moiety are shown to have high selectivity for the serotonin transporter (SERT) relative to the heterocycle fused gamma-carboline containing 4-fluorophenylbutanone.

WO 2009/145900 and U.S. Pat. No. 8,598,119 also disclose that selected substituted heterocycle fused gamma-carboline compounds have nanomolar affinity for the serotonin reuptake transporter (SERT) and so are selective serotonin reuptake inhibitors.

As disclosed in WO2015/154025, US 2017/0183350, U.S. Pat. No. 10,077,267, WO 2017/165843, US 2019/0231780, U.S. Pat. No. 10,688,097, WO 2019/183546, and US 2021/0008065, each incorporated herein by reference, deuterated forms of lumateperone and related compounds have been shown to have improved metabolic stability.

WO2019/178484 and US 2021/0060009, the contents of each of which are incorporated by reference in their entireties, disclose the use of lumateperone and related analogs for the treatment of acute depression and acute anxiety. Unlike traditional antidepressants, including selective serotonin reuptake inhibitors (SSRIs), such as sertraline (Zoloft, Lustral), escitalopram (Lexapro, Cipralex), fluoxetine (Prozac), paroxetine (Seroxat), and citalopram (Celexa), which generally take weeks or months to achieve their full effects (SSRIs typically have an onset of action 3-4 weeks after initiation of daily dosing), lumateperone is believed to achieve rapid efficacy, in as little as a week or less, and even an immediate onset of action (e.g., hours to days after initial dosing). In this regard, lumateperone and its analogs share the functional benefits of ketamine. Ketamine has recently been tested as a rapid-acting antidepressant for treatment-resistant depression, in bipolar disorder and major depressive disorder, but it has significant side effects and risk of overdose, and it is not orally active. Lumateperone has shown promise as an orally-available, rapid-acting treatment for depression and anxiety, alone or in conjunction with other anti-anxiety or anti-depressant drugs, such as in treating acute depression and acute anxiety with the rapid onset characteristic of ketamine, but without ketamine's side effects or lack of oral activity. It is believed that these effects are mediated through indirect dopamine D1 receptor-dependent enhancement of NMDA and AMPA currents coupled with activation of the mTOR (e.g., mTORC1) signaling pathway and paralleled by anti-inflammatory properties.

In addition, unlike benzodiazepine class agents, lumateperone and related compounds appear to be non-addictive, and therefore, particularly suitable for the treatment of acute depressive episodes, including suicidal ideation and severe acute depression and/or severe acute anxiety. Lumateperone has already been approved by the U.S. FDA for the treatment of schizophrenia and bipolar disorder, under the brand name Caplyta®, and it undergoing clinical study for the treatment of major depressive disorder and other disorders.

Immunological disturbances have been reported in subsets of patients suffering from generalized anxiety, major depressive disorder (MDD) and/or schizophrenia. See, e.g., Mechawar & Savitz, "Neuropathology of mood disorders: do we see the stigmata of inflammation?" *Translational Psychiatry* 6:e946-e946 (2016); Zhang et al., "Brain-derived Neurotrophic Factor (BDNF)-TrkB Signaling in Inflammation-related Depression and Potential Therapeutic Targets," *Curr. Neuropharmacol.* 14:721-731 (2016); Herman & Pasinetti, "Principles of inflammasome priming and inhibition: Implications for psychiatric disorders," *Brain Behav. Immun.* 73:66-84 (2018); Beurel et al., "The Bidirectional Relationship of Depression and Inflammation: Double Trouble," *Neuron* 107:234-256 (2020). In addition, exposure to infectious agents and subsequent heightened immune activity can also lead to transient depressive symptoms (e.g., anhedonia, fatigue, lethargy, and depressed mood). See, e.g., Nazimek et al., "The role of macrophages in anti-inflammatory activity of antidepressant drugs," *Immunobiology* 222:823-830 (2017); Beurel et al., (2020). This concept is supported by studies in which direct administration of pro-inflammatory factors induced stress-like and/or depressive-like effects in patients or animals (Mechawar & Savitz, 2016) and studies showing that adverse symptoms are reversed by direct blockade of certain immune pathways such as interleukin (1L)-1b (Koo & Duman, "IL-1beta is an essential mediator of the antineurogenic and anhedonic effects of stress," *Proc. Nat. Acad. Sci. USA* 105:751-756 (2008); Koo & Duman, "Evidence for IL-1 receptor blockade as a therapeutic strategy for the treatment of depression," *Curr. Opin, Invest. Drugs* 10:664-671 (2009)).

Viral infections and psychiatric illness have long been suspected of being linked. As early as the late 1800's, influenza epidemics were noted to be temporally associated with increases in psychiatric illness. More recently, evidence suggests that chronic inflammation of the central nervous system (CNS) is often reported to be associated with psychiatric states. To date, there have been several studies suggesting a cause-and-effect relationship between viral infections of the CNS, including herpes simplex 1 and 2 and measles, and psychiatric symptoms, including depression and schizophrenia. It has even been suggested that some psychiatric illnesses that were previously never suspected of having an infectious component, may in-fact be examples of very mild encephalitis.

One of the most common causes of viral encephalitis is the herpes simplex virus (HSV). Significant work has been done to examine psychological outcomes of HSV encephalitis, and the results show that a significant number of HSV patients develop neuropsychological deficits, such as impairments in attention, executive function, retrograde memory, working memory, and visuo-spatial processing, as well as mood disorders, including depression and anxiety. Some of these effects have been found to last long beyond the acute phase of infection. It has also been shown that some of these deficits correlated to cerebral damage visible by MRI (magnetic resonance imaging), such as medial temporal lobe damage.

West Nile Virus (WNV) infection can also involve neuroinvasive disease, resulting in encephalitis or meningitis. Depression has reported as a prominent outcome in such patients. An 8-year study following WNV survivors showed higher than expected rates of mild to severe depression in patients with no prior history of depression.

The Diagnostic and Statistical Manual of Mental Disorders, Fourth Edition (DSM-IV) introduced a new category of "psychopathological states due to a general medical condition," which included delirium, dementia, amnesia, psychosis, mood disorder (e.g., depression), anxiety disorder, sexual dysfunction, and sleep disorder. These have been associated with severe infections, such as bacterial or viral encephalitis and meningitis.

Pro-inflammatory cytokines, such as TNF-alpha and IL-6, are primarily secreted by peripheral monocytes and macrophages, and are thought to be secreted by CNS microglial cells as well. These cytokines activate other cellular components of the inflammatory response to infection. In addition, the anti-inflammatory cytokines IL-4 and IL-10 are also secreted by monocytes and macrophages, and perhaps microglial cells as well. C-reactive protein (CRP) is a common marker of an ongoing inflammatory response.

Recent evidence has shown that major depressive disorder (MDD) is also associated with higher levels of TNF-alpha, IL-6, IL-1-beta, IL-2, and interferon-gamma. In addition, interferon-alpha has been shown to induce severe depressive symptoms in about one-third of patients, including suicidality. However, it has not been clear whether this inflammatory state is a cause of MDD or an effect of MDD.

In the last twenty years, it has been discovered that a significant cause of encephalitis is an autoimmune reaction against neural proteins, especially against the NMDA receptor and the leucine-rich glioma 1 (LGL-1) receptor protein. This autoimmune encephalitis (AIE) presents a variety of neurological and psychiatric symptoms, including amnesia, confusion, seizures, cognitive deficits, and mood disorders. At least ten different synaptic antineuronal and antiglial antibodies have been identified, and many more are suspected to exist. The mainstay of AIE treatment remains intravenous immune globulin treatment to clear autoimmune antibodies, such as rituximab.

Although 5-$HT_{2A}$ or 5-$HT_{2A}$/D2 receptor ligands are known to be useful for treating schizophrenia, and mood disorders such as depression and anxiety, generally, including the acute treatment of depression or anxiety, such compounds have not been previously suggested or disclosed for the treatment of psychiatric disorders caused by encephalitis or for the treatment of affective symptoms of encephalitis.

New and improved methods for treating psychiatric disorders caused by viral, bacterial, or autoimmune encephalitis, and for treatment of psychiatric symptoms of viral, bacterial, and autoimmune encephalitis are urgently needed. New and improved methods for protecting and reinforcing the blood-brain barrier are also urgently needed.

In addition, some infectious agents, among them viruses including SARS-CoV-2, have been associated with persistent post-acute viral syndromes of unclear cause. These syndromes can last for weeks, months, or even years, after the acute infection is over, and they are not responsive to antiviral agents. Symptoms can include fatigue, malaise, memory loss, depression, and other neurocognitive impairments, and the syndromes may also be associated with platelet dysfunction and hypercoagulability. The so-called "Long COVID" syndrome is one of these post-viral syndromes, and it is thought to affect a significant number of patients infected with the SARS-CoV-2 virus. Although there have been many hypotheses about the cause of these syndromes, recent evidence suggests that post-viral syndrome may be due to peripheral serotonin deficiency secondary to virus-induced inflammatory responses or autoimmune responses. The resulting peripheral serotonin deficiency may cause reduced vagal nerve activity, leading to hippocampal dysfunction, and neurocognitive impacts. Indeed, evidence suggests that plasma levels of serotonin may be predictive of whether COVID patients develop Long COVID syndrome. There is evidence that other viral infections also cause long-term peripheral serotonin depletion, including vesicular stomatitis virus and lymphocytic choriomeningitis virus.

A recent study using mice examined the mechanism by which viral infection may lead to peripheral serotonin depletion and adverse cognitive effects. The data suggested that viral infection may cause a long-term rise in peripheral interferon production, particularly type I interferons, and that these interferons inhibit the expression of genes involved in gastrointestinal tryptophan absorption (via STAT1 transcription factor signaling). These genes included those encoding the neutral amino acid transporter $B^0AT1$, and the associated chaperone protein ACE2 (Slc6a19 and Ace2, respectively). The gastrointestinal epithelium may act as a long-term reservoir of low-level viral replication, thus impairing tryptophan absorption. Peripheral serotonin is synthesized largely from tryptophan in enterochromaffin cells in the gut, and thus, the loss in tryptophan absorption leads to reduced serotonin production. The data also showed that interferon independently causes increased platelet destruction and increased platelet aggregation (hypercoagulability), as well as increased intestinal monoamine oxidase (MAO) production. Because the majority of circulating serotonin is stored in platelets, platelet loss results in overall substantially reduced plasma serotonin, compounded with the increased metabolism of free serotonin by MAO.

Nevertheless, the above impacts to not directly affect CNS levels of serotonin because serotonin does not cross the blood-brain barrier. However, it was unexpectedly found in this study that cognitive and memory impairments common in post-viral syndromes are likely caused by a loss of peripheral serotonin-induced signaling at 5-$HT_3$ receptors in afferent sensory vagal neurons, which stimulate the hippocampus.

There remains an urgent need for the treatment of mood and cognitive impairments caused by viral infections, including long-term, post-viral syndromes.

BRIEF SUMMARY OF THE INVENTION

We have surprisingly found that substituted heterocycle fused gamma-carbolines as described herein, particularly lumateperone, are effective in reducing aberrantly elevated levels of proinflammatory cytokines in both brain and serum, alters key pathways involved in tissue integrity and the maintenance of the blood-brain barrier (BBB), conferred anxiolytic and antianhedonic properties in rats, and reinforced BBB protection during inflammatory and stress challenges. This suggests that such compounds will be effective in the treatment of psychiatric disorders caused by viral, bacterial, or autoimmune encephalitis, and for treatment of psychiatric symptoms of viral, bacterial, and autoimmune encephalitis.

The present disclosure thus provides a method for the treatment of psychiatric disorders caused by viral, bacterial, or autoimmune encephalitis, and for the treatment of psychiatric symptoms of viral, bacterial, and autoimmune encephalitis, the method comprising administering an therapeutically effective amount of (i) a 5-$HT_{2A}$ or 5-$HT_{2A}$/D2 receptor ligand, for example, a substituted heterocycle fused gamma-carboline, as described herein, in free base, pharmaceutically acceptable salt, or prodrug form, to a patient in need thereof.

In another aspect, the present disclosure provides a method for protecting or reinforcing the blood-brain barrier, comprising administering to a patient in need thereof, a therapeutically effective amount of (i) a 5-$HT_{2A}$ or 5-$HT_{2A}$/D2 receptor ligand, for example, a substituted heterocycle fused gamma-carboline, as described herein, in free base, pharmaceutically acceptable salt, or prodrug form, to a patient in need thereof.

In another aspect, the present disclosure provides a method for treating or normalizing pathologic inflammation, comprising administering to a patient in need thereof, a therapeutically effective amount of (i) a 5-$HT_{2A}$ or 5-$HT_{2A}$/D2 receptor ligand, for example, a substituted heterocycle fused gamma-carboline, as described herein, in free base, pharmaceutically acceptable salt, or prodrug form, to a patient in need thereof.

In another aspect, the present disclosure provides a method for treating or preventing post-viral syndrome, comprising administering to a patient in need thereof, a therapeutically effective amount of (i) a 5-HT$_{2A}$ or 5-HT$_{2A}$/D2 receptor ligand, for example, a substituted heterocycle fused gamma-carboline, as described herein, in free base, pharmaceutically acceptable salt, or prodrug form, to a patient in need thereof.

In another aspect, the present disclosure provides a method for treating or preventing peripheral serotonin deficiency, comprising administering to a patient in need thereof, a therapeutically effective amount of (i) a 5-HT$_{2A}$ or 5-HT$_{2A}$/D2 receptor ligand, for example, a substituted heterocycle fused gamma-carboline, as described herein, in free base, pharmaceutically acceptable salt, or prodrug form, to a patient in need thereof In some embodiments, the present disclosure provides the above methods, wherein such methods further comprise the concurrent administration of a PDE1 inhibitor, for example, the compounds of Formula II, as disclosed herein. Such compounds are disclosed in, for example, U.S. Pat. No. 9,545,406, the contents of which is hereby incorporated by reference in its entirety, as having utility in the treatment of central nervous system diseases, disorders and injuries, and as neuroprotective and/or neural regenerative agents. Such compounds are further disclosed in, for example, WO 2018/049417, the contents of which is hereby incorporated by reference in its entirety, as having utility in the treatment of diseases and disorders characterized by neuroinflammation.

In particular embodiments of the aforementioned methods, the present disclosure further provides that the patient is suffering from, or at risk of suffering from, peripheral serotonin deficiency and/or that the psychiatric or other CNS disorder or infectious disorder is caused by peripheral serotonin deficiency.

DETAILED DESCRIPTION

Lumateperone is a therapeutic agent with potent binding to the 5-HT$_{2A}$ receptor (Ki=0.5 nM) and moderate binding to the D1 and D2 receptors and the serotonin transporter (SERT). Functionally, receptor binding can generally result in either agonist activity, partial agonist activity, or antagonist activity. Lumateperone has been found to exhibit potent antagonist activity at the 5-HT$_{2A}$ receptor and SERT, and mixed agonist/antagonist activity at the D$_1$ and D$_2$ receptors (depending on cell type). In particular, lumateperone shows activity as a mesolimbic/mesocortical-selective dopamine receptor protein phosphorylation modulator consistent with presynaptic D2 receptor partial agonism and postsynaptic D2 receptor antagonism (Ki=32 nM) in vivo, with high D1 receptor affinity (Ki=52 nM), and inhibition of serotonin transporter activity (SERT) (Ki=26-62 nM, using different assays for SERT activity). Lumateperone also indirectly enhances NMDA- and AMPA-mediated neurotransmission (Titulaer et al., "Lumateperone increases glutamate release in the rat medial prefrontal cortex," *Eur. Neuropsychopharmacol.* 53:5556-5557 (2022)). Lumateperone is approved in the United States as a treatment for schizophrenia and for bipolar depression, and it is being studied for the treatment of major depressive disorder, agitation in dementia, including Alzheimer's Disease, and other psychiatric disorders.

It has been unexpectedly found that lumateperone has the potential to ameliorate pathological levels of inflammation in brain, microglia, and serum, and to preserve the integrity of the BBB following immunological insult and stress in rodents. When administered over a range of doses at different time points, lumateperone reduces key pro-inflammatory markers elevated by an inflammogen (e.g., lipopolysaccharide, LPS) or by acute restraint stress. Surprisingly, the cytokines IL-1β, IL-6, and TNF-α that are normalized by lumateperone treatment are known to be elevated in patients with psychiatric disorders, and in human post-mortem tissues including prefrontal cortex from suicide victims.

Lumateperone treatment reduces expression of the Nlrp3 inflammasome, which is a large multiprotein complex containing NLRP3, a cytosolic sensor involved in innate immunity. Although the inflammasome has no baseline activity, once activated by stress, infections, or other stimuli, the complex is believed to generate active forms of the inflammatory cytokines IL-1β and IL-18. In preclinical studies, Nlrp3-null mutant mice were reported to be resilient to the effects of stress on depression-like behavior, and Nlrp3 expression was increased in peripheral blood mononuclear cells (PBMCs) from untreated patients with MDD.

The present disclosure shows that lumateperone treatment decreases Nlrp3 transcript levels under conditions evoking pathological inflammation, which may contribute, in part, to the antidepressant-like action of lumateperone. In addition, it is shown that lumateperone has anxiolytic-like effects and reverses anhedonia in rats.

Stress and inflammation are thought to compromise BBB integrity and functionality in many pathological states. The BBB regulates ion and nutrient exchange between the brain and blood while protecting brain tissue from harmful agents. Malfunctioning BBB can result in chemical exposure and infections, and there have been reports suggesting that the BBB may be compromised in persons with psychiatric disorders, such as schizophrenia or depression, or in neurodegenerative diseases, such as Alzheimer's disease (substantial evidence has documented BBB disruption in these diseases).

The present disclosure provides evidence of an increased RNA copy number of hippocampal Cldn5 in naïve mice after receiving lumateperone two hours prior to measurement, and confirms these results in the brain of acutely stressed or LPS-treated mice. Claudins such as Cldn5 are small proteins (20-27 kDa) expressed in the tight junctions between brain endothelial cells, and they help to maintain BBB integrity. In mice, Cldn5 ablation enhances BBB permeability and allows infiltration of large proteins up to ~69 kD (e.g., IL-6) into brain parenchyma; this result has been associated with depressive-like behavior and behavioral impairments characteristic of schizophrenia and depression. Lumateperone-mediated upregulation of Cldn5 gene expression is thus consistent with enhanced protein expression observed in mice treated with other chronic antipsychotic or antidepressant medications. Whereas chronic but not acute imipramine treatment rescued social avoidance and restored Cldn5 levels that were altered by social defeat stress, acute lumateperone treatment is unexpectedly efficacious in improving similar behavioral states.

This finding highlights another potential difference between classic antidepressant treatment and lumateperone treatment. Since it is observed that reduced sodium fluorescein (NaFl) brain uptake and differences in anti-inflammatory cytokine expression between the central nervous system and the periphery, without being bound by theory, it is believed that Cldn5 may change early after lumateperone administration resulting, in the preservation of BBB integrity and limiting the infiltration of large proteins (e.g., IL-6), infectious agents, and other potential pro-inflammatory stimuli into the CNS. Moreover, TNF-α/NFκ-B signaling increases BBB permeability by decreasing tight junction protein expression of Cldn5.

Classical antidepressants are also reported to modulate levels of ICAM-1, which is involved in leukocyte brain infiltration and BBB hyperpermeability. Levels of ICAM-1, a cell adhesion molecule and a member of the immunoglobulin gene superfamily, have been shown to be increased in the orbitofrontal cortex of patients with depression. The present disclosure shows that lumateperone acutely decreases Icam1 expression in preclinical models. These findings are also consistent with literature showing that ICAM1 upregulation favors leukocyte migration through the endothelium and blood vessel wall regulating the BBB. Collectively, the results described herein suggest that lumateperone regulates a repertoire encompassing signaling networks involved in a variety of biological processes relevant to maintenance of BBB integrity and control deleterious inflammatory states.

Increased BBB integrity is also known to activate microglia and lead to changes in microglia phenotype. In the CNS, microglia are an important component of the local brain immune response. It is disclosed herein that in acute inflammatory conditions, lumateperone significantly increases expression of genes related to microglia physiological functions and anti-inflammatory phenotype, and decreases expression of microglia markers related to immune modulation. It is unexpectedly shown that enriched hippocampal microglia recapitulated the anti-inflammatory responses seen in whole brain homogenates. One of the genes overexpressed in hippocampi from LPS-treated mice was Csf1. This gene encodes the ligand for the microglia receptor CSF1R which is involved in maintaining microglia viability and immunologic surveillance. LPS-induced increases in Csf1 expression are found to be significantly reduced with lumateperone coadministration. Furthermore, the results described herein show that lumateperone upregulates the anti-inflammatory cytokine IL-10, which could add to the repertoire of inflammation-resolving mechanisms following abnormal levels of stress and inflammation, possibly by influencing microglia function. Overall, the data described herein shows that the ability of lumateperone to alter microglial gene expression and to reduce Csf1 gene expression following an inflammatory challenge may prevent activation of microglial function after exposure to proinflammatory stimuli.

Stress and agents that elicit neuroinflammation are strongly implicated in the etiology of diverse brain diseases including neurodegenerative disorders, psychiatric disorders (e.g., schizophrenia), and mood disorders (e.g., bipolar disorder, depression, and anxiety). Many infectious agents, including herpes simplex virus 1 and 2, Epstein-Barr virus, and cytomegalovirus (CMV), can be elevated in individuals with psychiatric conditions including bipolar disorder and schizophrenia. Further, viruses such as CMV can trigger psychiatric pathology in part by directly elevating pro-inflammatory cytokines including TNF-α and IL-6. Coronaviruses, such as severe acute respiratory syndrome coronavirus 2 (SARS-Cov-2) which leads to coronavirus disease 2019 (COVID-19) infection, elicit hyperimmune responses (cytokine storm) that may precipitate psychiatric episodes in infected patients, although the precise precipitating event (e.g., stress or the virus itself) remains to be elucidated. It is notable, however, that the SARS-CoV-2 virus crosses the BBB of mice and passes the olfactory mucosa in humans, which supports potential routes/mechanisms for virus entry into brain tissue. Consequently, without being bound by theory, it is believed that therapeutics with anti-inflammatory benefit, such as lumateperone and its analogs, may provide further benefit in normalizing aberrant neuroinflammatory events and mitigating their impact on brain dysfunction, particularly with reference to maintenance of BBB integrity.

Without being bound by theory, it is believed that perturbation of the BB B may underlie the development of a variety of psychiatric disorders, including schizophrenia, autism spectrum disorder (ASD), and affective disorders. Increased permeability of the BBB appears to be a common factor in these disorders, leading to increased infiltration of peripheral material into the brain culminating in neuroinflammation and oxidative stress. Loss of BBB integrity is an early and prominent pathological feature of neuroinflammatory disorders. 1BB permeability is increased in response to many proinflammatory stimuli, such as lipopolysaccharide, tumor necrosis factor α (TNFα), IL-6, MCP-1 and IL-1β, with concomitant downregulation of tight junction proteins, such as claudin-5 (Cldn5). In response to danger signals, brain endothelial cells become activated and are characterized by upregulated expression of cell adhesion molecules such as ICAM-1 and VCAM-1, and down regulation of claudin-5, to facilitate leukocyte entry to the CNS and facilitate an immune response. Therefore, measurement of the presence, absence or concentrations of these various biomarker signals can indicate the presence of neuroinflammation and breakdown of BBB integrity.

In a particular embodiment, the present disclosure provides a method (Method 1) for the treatment of psychiatric disorders caused by viral, bacterial, or autoimmune encephalitis, and for treatment of psychiatric symptoms of viral, bacterial, and autoimmune encephalitis, comprising administering to a patient in need thereof, a therapeutically effective amount of a 5-HT$_{2A}$ or 5-HT$_{2A}$/D2 receptor ligand, for example, a compound of Formula I:

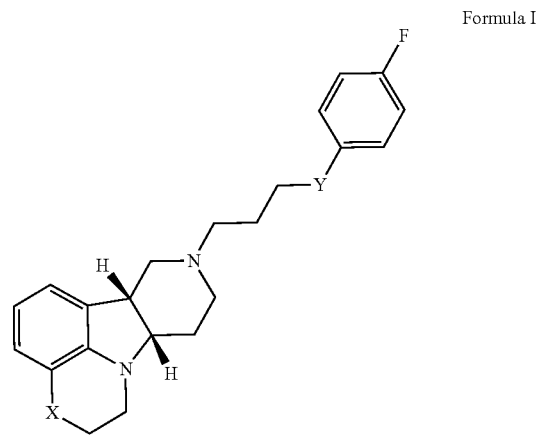

Formula I wherein:
X is —N(H)—, —N(CH$_3$)— or —O—;
Y is —C(=O)—, —C(H)(OH)— or —C(H)(OR$_1$)—;
R$_1$ is —C(O)—C$_{1-21}$alkyl (e.g., —C(O)—C$_{1-5}$alkyl, —C(O)—C$_{6-15}$alkyl or —C(O)—C$_{16-21}$alkyl), preferably said alkyl is a straight chain, optionally saturated or unsaturated and optionally substituted with one or more hydroxy or C$_{1-22}$alkoxy (e.g., ethoxy) groups, for example R$_1$ is —C(O)—C$_6$alkyl, —C(O)—C$_7$alkyl, —C(O)—C$_9$alkyl, —C(O)—C$_{11}$alkyl, —C(O)—C$_{13}$alkyl or —C(O)—C$_{15}$alkyl, wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand, optionally in deuterated form, in free base, pharmaceutically acceptable salt, or prodrug form. For example, Method 1 may be as follows:

1.1. Method 1, wherein X in the compound of Formula I is —N(H)—, —N(CH$_3$)— or —O—;

1.2. Method 1 or 1.1, wherein X in the compound of Formula I is —N(H);

1.3. Method 1 or 1.1, wherein X in the compound of Formula I is —N(CH$_3$)—;

1.4. Method 1 or 1.1, wherein X in the compound of Formula I is —O—;

1.5. Method 1 or any of formulae 1.1-1.4, wherein Y in the compound of Formula I is —C(=O)—, —C(H)(OH)— or —C(H)(OR$_1$)—;

1.6. Method 1 or any of formulae 1.1-1.4, wherein Y in the compound of Formula I is —C(=O)—;

1.7. Method 1 or any of formulae 1.1-1.4, wherein Y in the compound of Formula I is —C(H)(OH)—;

1.8. Method 1 or any of formulae 1.1-1.4, wherein Y in the compound of Formula I is —C(H)(OR$_1$)—;

1.9. Method 1, or any of 1.1-1.5 or 1.8, wherein R$_1$ in the compound of Formula I is —C(O)—C$_{1-21}$alkyl (e.g., —C(O)—C$_{1-5}$alkyl, —C(O)—C$_{6-15}$alkyl or —C(O)—C$_{16-21}$alkyl), preferably said alkyl is a straight chain, optionally saturated or unsaturated and optionally substituted with one or more hydroxy or C$_{1-22}$alkoxy (e.g., ethoxy) groups, for example R$_1$ is —C(O)—C$_6$alkyl, —C(O)—C$_7$alkyl, —C(O)—C$_9$alkyl, —C(O)—C$_{11}$alkyl, —C(O)—C$_{13}$alkyl or —C(O)—C$_{15}$alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand; e.g., wherein R$_1$ in the compound of Formula I is —C(O)—C$_{6-15}$alkyl, e.g., —C(O)—C$_9$alkyl; or wherein R$_1$ in the compound of Formula I is —C(O)—C$_{1-5}$alkyl, e.g., —C(O)—C$_3$alkyl;

1.10. Method 1 or any of 1.1-1.5 or 1.7, wherein the Compound of Formula I is:

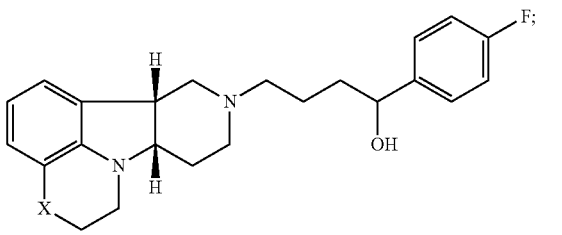

1.11. Method 1 or any of 1.1-1.5 or 1.7, wherein the Compound of Formula I is:

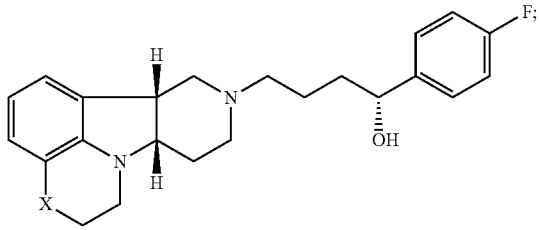

1.12. Method 1, or any of 1.1, 1.3, 1.5, or 1.6, wherein the Compound of Formula I is lumateperone:

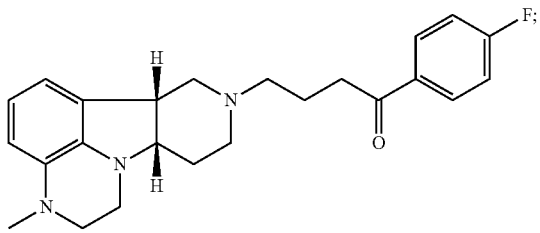 [SMILES: CN1CCN2c3c(cccc31)[C@@H]1CN(CCCC(=O)c3ccc(F)cc3)CC[C@@H]12]

1.13. Method 1, or any of 1.1-1.12, e.g., Method 1.12, wherein the Compound of Formula I is in the form of a pharmaceutically acceptable salt, e.g., a tosylate salt;

1.14. Method 1, or any of 1.1-1.12, e.g., Method 1.12, wherein the Compound of Formula I is in the form of the free base;

1.15. Method 1 or any of 1.1-1.14 wherein the Compound of Formula I is in deuterated form, e.g., wherein the deuterium:protium ratio for a specified carbon-bound hydrogen atom is significantly higher, e.g., at least 2×, for example at least 10× higher, than the natural isotope ratios;

1.16. Method 1.15, wherein the Compound of Formula I is a deuterated form of lumateperone, for example, selected from:

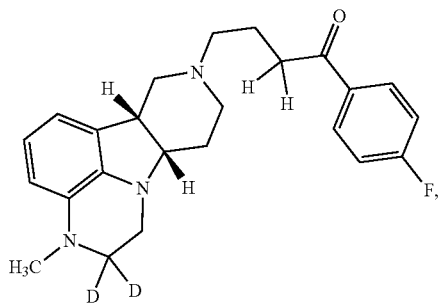

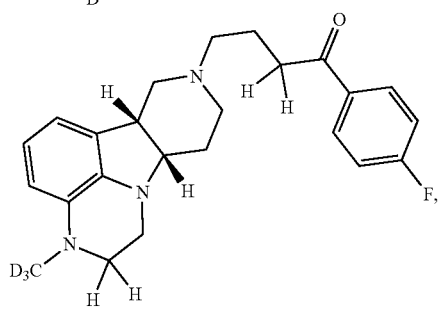

-continued

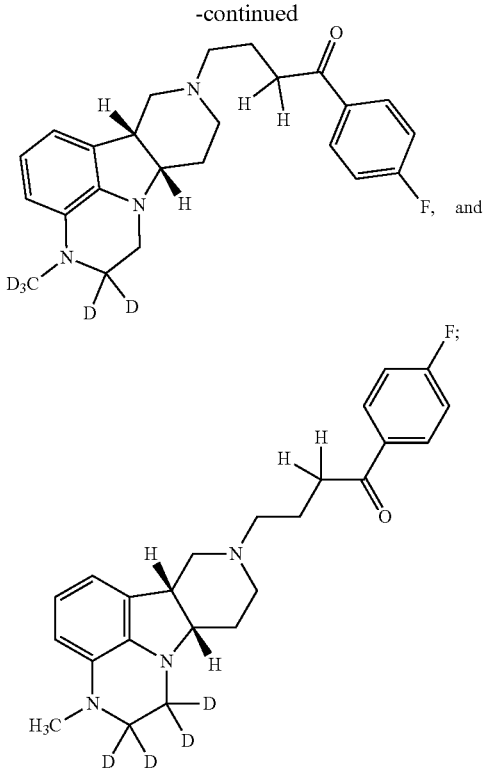

wherein D represents a hydrogen position with substantially greater than natural deuterium incorporation (i.e., substantially greater than 0.0156%), e.g., greater than 60%, or greater than 70%, or greater than 80%, or greater than 90% or greater than 95%, or greater than 96%, or greater than 97%, or greater than 98%, or greater than 99%, in free base or pharmaceutically acceptable salt form, e.g., tosylate salt form;

1.17. Any foregoing method, wherein the 5-HT$_{2A}$ or 5-HT$_{2A}$/D2 receptor ligand is a compound of Formula I in free base or pharmaceutically acceptable salt form, e.g., tosylate salt form, administered in a daily dose equivalent to 1 to 100 mg of free base, e.g., in an amount equivalent to 1 to 75 mg, or 1 to 60 mg, or 1 to 40 mg, or 1 to 20 mg, or 1 to 10 mg, of free base;

1.18. Method 1.17, wherein the method comprises once daily administration of a unit dosage for oral administration, for example a tablet or capsule, comprising the compound of Formula I in free base or pharmaceutically acceptable salt form, e.g., in tosylate salt form, in an amount equivalent 1 to 100 mg of free base, e.g., in an amount equivalent to 1 to 75 mg, or 1 to 60 mg, or 1 to 40 mg, or 1 to 30 mg, or 1 to 20 mg, or 1 to 10 mg, or 1 to 5 mg, or 40 to 60 mg, or 20 to 40 mg, or 10 to 20 mg, or about 60 mg, or about 40 mg, or about 30 mg, or about 20 mg, or about 10 mg, or about 5 mg, of free base, and a pharmaceutically acceptable diluent or carrier;

1.19. Method 1.17, wherein the method comprises once daily administration of a unit dosage for oral transmucosal administration, e.g., a sublingual or buccal orally disintegrating tablet, wafer, or film, comprising the compound of Formula I in free base or pharmaceutically acceptable salt form, e.g., in tosylate salt form, in an amount equivalent to 0.5 to 30 mg of free base, e.g., in an amount equivalent to 1 to 30 mg, or 1 to 20 mg, or 1 to 15 mg, or 1 to 10 mg, or 20 to 30 mg, or 10 to 20 mg, or about 5 mg, or about 10 mg, or about 15 mg, or about 20 mg, of free base, and a pharmaceutically acceptable diluent or carrier;

1.20. Any foregoing method wherein the condition to be treated is alleviated within one week, e.g., within three days, e.g., within one day;

1.21. Any foregoing method, wherein the method is a method of treatment of psychiatric disorders caused by viral, bacterial, or autoimmune encephalitis;

1.22. Any foregoing method, wherein the method is a method for treatment of psychiatric symptoms of viral, bacterial, and autoimmune encephalitis;

1.23. Method 1.21 or 1.22, wherein the encephalitis is viral encephalitis;

1.24. Method 1.23, wherein the encephalitis is caused by, or suspected to be caused by, Herpes simplex Virus 1, Herpes Simplex Virus 2, West Nile Virus, Nipah Virus, human immunodeficiency virus, rabies virus, Epstein-Barr Virus, cytomegalovirus, coronavirus (e.g., MERS-CoV, SARS-CoV, SARS-Cov2), or influenza virus (e.g., influenza A, such as H1N1, H2N2, H3N2, H5N1, H7N7);

1.25. Method 1.23 or 1.24, wherein the patient has acute viral encephalitis;

1.26. Method 1.21 or 1.22, wherein the encephalitis is bacterial encephalitis;

1.27. Method 1.26, wherein the encephalitis is caused by, or believed to be caused by, toxoplasmosis, *rickettsia, mycoplasma, Borrelia* (e.g., Lyme disease), or malaria;

1.28. Method 1.21 or 1.22, wherein the encephalitis is autoimmune encephalitis;

1.29. Method 1.28, wherein the encephalitis is caused by, or believed to be caused by, autoantibodies against the NMDA receptor, the AMPA receptor, the voltage-gated potassium, channel (VGKC), the LGL1 protein, the GABA receptor, the glycine receptor, the glutamate receptor, or the CASPR2 receptor;

1.30. Any foregoing method, wherein the psychiatric disorder and/or the psychiatric symptom is depression (e.g., acute depression, depression of MDD, depression of bipolar disorder), anxiety, (e.g., acute anxiety), psychosis (e.g., schizophrenia), post-traumatic stress-disorder, anhedonia, memory loss, impairment of executive functioning, difficulty concentrating, seizures, difficulty sleeping, hallucination, change in personality, or any combination thereof;

1.31. Any foregoing method wherein the psychiatric disorder and/or the psychiatric symptom is depression (e.g., acute depression, depression of MDD, depression of bipolar disorder);

1.32. Any foregoing method wherein the psychiatric disorder and/or the psychiatric symptom is anxiety (e.g., acute anxiety);

1.33. Any foregoing method wherein the psychiatric disorder and/or the psychiatric symptom is anhedonia;

1.34. Any foregoing method wherein the patient is diagnosed as having suicidal ideation and/or suicidal tendencies;

1.35. Any foregoing method, wherein the patient has no prior history of psychiatric disorders or psychiatric symptoms;

1.36. Any foregoing method wherein the 5-HT$_{2A}$ or 5-HT$_{2A}$/D2 receptor ligand is administered in combination (e.g., a fixed combination in a unit dosage form, or a free combination administered sequentially or simultaneously or within a 24-hour period) with a therapeutically effective amount of an anxiolytic or antidepressant agent;

1.37. Method 1.36, wherein the anxiolytic or antidepressant agent is selected from one or more compounds in free base or pharmaceutically acceptable salt form, selected from selective serotonin reuptake inhibitors (SSRIs), serotonin-norepinephrine reuptake inhibitors (SNRIs), tricyclic antidepressants (TCAs), and atypical antipsychotics, e.g., one or more compounds in free base or pharmaceutically acceptable salt form, selected from:
  (a) Selective serotonin reuptake inhibitors (SSRIs), e.g., Citalopram (Celexa), Escitalopram (Lexapro, Cipralex), Paroxetine (Paxil, Seroxat), Fluoxetine (Prozac), Fluvoxamine (Luvox) Sertraline (Zoloft, Lustral);
  (b) Serotonin-norepinephrine reuptake inhibitors (SNRIs), e.g., Desvenlafaxine (Pristiq), Duloxetine (Cymbalta), Levomilnacipran (Fetzima), Milnacipran (Ixel, Savella), Tofenacin (Elamol, Tofacine), Venlafaxine (Effexor);
  (c) Tricyclic antidepressants (TCAs), e.g., Amitriptyline (Elavil, Endep), Amitriptylinoxide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Nitroxazepine (Sintamil), Nortriptyline (Pamelor, Aventyl), Noxiptiline (Agedal, Elronon, Nogedal), Pipofezine (Azafen/Azaphen), Protriptyline (Vivactil), Trimipramine (Surmontil);
  (d) Benzodiazepines, e.g., selected from 2-keto compounds (e.g., clorazepate, diazepam, flurazepam, halazepam, prazepam); 3-hydroxy compounds (lorazepam, lormetazepam, oxazepam, temazepam); 7-nitro compounds (e.g., clonazepam, flunitrazepam, nimetazepam, nitrazepam); triazolo compounds (e.g., adinazolam, alprazolam, estazolam, triazolam); and imidazo compounds (climazolam, loprazolam, midazolam);

1.38. Any foregoing method, wherein the 5-HT$_{2A}$ or 5-HT$_{2A}$/D2 receptor ligand, e.g., the compound of Formula I is administered intra-nasally, subcutaneously, intramuscularly, intravenously, orally, sub-lingually, intra-peritoneally, or buccally, such as an oral rapidly dissolving tablet, wafer, or film, which dissolves in the oral cavity for transmucosal absorption;

1.39. Any foregoing method, wherein the method further comprises the concurrent administration of an antidepressant agent (e.g., selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), a serotonin receptor antagonist, or any combination thereof), e.g., administered simultaneously, separately or sequentially;

1.40. Any foregoing method, wherein the method further comprises the concurrent administration of an NMDA receptor antagonist, for example, selected from ketamine (e.g., S-ketamine and/or R-ketamine), hydroxynorketamine, memantine, dextromethorphan, dextroallorphan, dextrorphan, amantadine, and agmatine, or any combination thereof, e.g., administered simultaneously, separately or sequentially;

1.41. Any foregoing method, wherein the method further comprises the concurrent administration of a NMDA receptor allosteric modulator, e.g., a NMDA receptor glycine-site modulator, such as rapastinel, nebostinel, apimostinel, D-cycloserine, or any combination thereof, e.g., administered simultaneously, separately or sequentially;

1.42. Any foregoing method, wherein the method provides the patient with an acute response to treatment with the therapeutic agent or agents (e.g., the 5-HT$_{2A}$ or 5-HT$_{2A}$/D2 receptor ligand, the Compound of Formula I, or the combination of the Compound or Formula I and the Compound of Formula II, and/or any additional antidepressant agents);

1.43. Method 1.42, wherein the patient shows an acute response to treatment within less than 3 weeks, for example, less than 2 weeks, or less than 1 week, or from 1 to 7 days, or 1 to 5 days, or 1 to 3 days, or 1 to 2 days, or about 1 day, or less than 2 days, or less than 1 day (e.g., 12-24 hours, 6-12 hours, or 3-6 hours);

1.44. Any foregoing method, wherein the patient has not responded to, or has not responded adequately to, or who suffers undesirable side effects from, treatment with another antidepressant agent, for example, any one or more of a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor, or a serotonin receptor antagonist;

1.45. Any foregoing method, wherein the psychiatric disorder or symptoms is not associated with schizophrenia or dementia;

1.46. Any foregoing method, wherein the patient does not suffer from (or has not previously been diagnosed with) schizophrenia or dementia;

1.47. Any foregoing method, wherein the method protects or reinforces the blood-brain barrier;

1.48. Any foregoing method, wherein the patient has elevated levels of pro-inflammatory cytokines in the CNS (e.g., in the cerebrospinal fluid), such as TNF-α, IFN-γ, IL-1 (IL-1α and/or IL-1β), IL-6, IL-8, IL-12, IL-15, IL-17, IL-18, or elevated levels of C-reactive protein (CRP) of Csf1, and/or depressed levels of anti-inflammatory cytokines in the CNS (e.g., in the cerebrospinal fluid), such as TNF-β, IFN-α, IL-4, and IL-10;

1.49. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the 5-HT$_{2A}$ receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

1.50. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the D2 receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

1.51. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the D1 receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

1.52. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the serotonin transporter (SERT), e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said transporter (agonism or antagonism);

1.53. Any foregoing method, wherein the 5-HT$_{2A}$ or 5-HT$_{2A}$/D2 receptor ligand is lumateperone, in free base or pharmaceutically acceptable salt form, optionally in a deuterated form;

1.54. Any foregoing method, wherein the 5-HT$_{2A}$ or 5-HT$_{2A}$/D2 receptor ligand is lumateperone, in a tosylate salt form (e.g., monotosylate salt), optionally in a deuterated form, and optionally in crystalline or amorphous tosylate salt form;

1.55. Any foregoing method, wherein the 5-HT$_{2A}$ or 5-HT$_{2A}$/D2 receptor ligand is lumateperone, in free base form, optionally in a deuterated form;

1.56. Any foregoing method, wherein the 5-HT$_{2A}$ or 5-HT$_{2A}$/D2 receptor ligand is administered in the form of a long-acting injectable (LAI) composition, e.g., for intramuscular or subcutaneous injection;

1.57. Method 1.56, wherein the dose of the LAI composition is sufficient to provide the equivalent of a daily dose of 1 to 100 mg of free base, e.g., 1 to 75 mg, or 1 to 60 mg, or 1 to 40 mg, or 1 to 20 mg, or 1 to 10 mg, of free base, released over a period of time ranging from about 1 week to about 3 months, e.g., about 1 week to about 8 weeks, or about 1 week to about 6 weeks, or about 1 week to about 4 weeks, or about 1 week to about 3 weeks, or about 1 week to about 2 weeks;

1.58. Method 1.56 or 1.57, wherein the LAI composition comprises the compound of Formula I dissolved, dispersed, suspended, or encapsulated in a polymeric matrix;

1.59. Method 1.58, wherein the polymeric matrix comprises one or more biocompatible and biodegradable polymers as defined herein, e.g., poly(hydroxycarboxylic acids), poly(amino acids), cellulose polymers, modified cellulose polymers, polyamides, and polyesters;

1.60. Method 1.59, wherein the one or more polymers comprises polylactic acid, polyglycolic acid, polycitric acid, polymalic acid, poly-beta-hydroxybutyric acid, poly(lactic acid-glycolic acid) copolymer, 2-hydroxybutyric acid-glycolic acid copolymer, polylactic acid-polyethylene glycol copolymer, polyglycolic acid-polyethylene glycol copolymer, PEG-PLGA copolymer or block copolymer, PEG-PLGA copolymer or block copolymer, poly(alkyl alpha-cyanoacrylate) such as poly(butyl cyanoacrylate) or poly(2-octyl cyanoacrylate), poly(ortho ester), polycarbonate, poly-ortho-carbonate, a polyamino acid, (for example poly-gamma.-L-alanine, poly-.gamma.-benzyl-L-glutamic acid or poly-y-methyl-L-glutamic acid), and/or hyaluronic acid ester;

1.61. Method 1.60, wherein the one or more polymers comprises polyortho esters (POE), polylactic acid, polyglycolic acid, polycitric acid, polymalic acid, or a poly(lactic acid-glycolic acid) copolymer;

1.62. Method 1.60, wherein the one or more polymers comprises a poly(lactic acid-glycolic acid) copolymer, e.g., poly-d,l-lactide-co-glycolide (PLGA), for example, a PLGA copolymer with a lactide-to-glycolide molar ratio of about 50:50 to 90:10, or 50:50 to 85:15, or 50:50 to 75:25, and/or a molecular weight of 5,000 to 500,000 Daltons, or 5,000 to 150,000 Daltons, or 20,000 to 200,000 Daltons, or 24,000 to 38,000 Daltons;

1.63. Any foregoing method, wherein the 5-HT$_{2A}$ or 5-HT$_{2A}$/D2 receptor ligand is administered as monotherapy, e.g., it is not administered concurrently or in conjunction with an anti-depressant, anti-psychotic, or anti-anxiety agent;

1.64. Any foregoing method, wherein the 5-HT$_{2A}$ or 5-HT$_{2A}$/D2 receptor ligand is administered without the direct supervision of a health care professional (e.g., the compound is self-administered by the patient);

1.65. Any foregoing method, wherein the method does not comprise supervision or observation of the patient by a health care professional during or after (e.g., within 2 hours after) administration of a dose of the 5-HT$_{2A}$ or 5-HT$_{2A}$/D2 receptor ligand;

1.66. Any foregoing method, wherein the method does not put the patient at risk for sedation, dissociation, abuse, misuse, or suicidal ideation;

1.67. Any foregoing method, wherein the method does not result in hypertension (e.g., systolic and/or diastolic hypertension) within four hours after administration of a dose of the 5-HT$_{2A}$ or 5-HT$_{2A}$/D2 receptor ligand, e.g., an increase of more than 10 mm Hg, or more than 20 mm Hg, or more than 30 mm Hg, or more than 40 mm Hg, in systolic and/or diastolic blood pressure within 30 minutes to 4 hours after said dose;

1.68. Any foregoing method, wherein the method does not result in cognitive decline;

1.69. Any foregoing method, wherein the patient has (e.g., has been diagnosed with), or is at risk of, aneurysmal vascular disease (e.g., thoracic aorta, abdominal aorta, intracranial, or peripheral arterial aneurysms), arteriovenous malformation or intracerebral hemorrhage;

1.70. Any foregoing method, wherein the patient is under concurrent treatment with an oral antidepressant selected from duloxetine, escitalopram, sertraline, or venlafaxine;

1.71. Any foregoing method, wherein the patient is not under concurrent treatment with an oral antidepressant selected from duloxetine, escitalopram, sertraline, or venlafaxine;

1.72. Any foregoing method, wherein the patient is unresponsive to, or cannot be treated with ketamine (e.g., S-ketamine), e.g., because it is contraindicated in said patient;

1.73. Any foregoing method, wherein the 5-HT$_{2A}$ or 5-HT$_{2A}$/D2 receptor ligand is administered to the patient concurrently with a PDE1 (cyclic nucleoside phosphodiesterase 1) inhibitor (e.g., administered simultaneously, separately, or sequentially), in free base or pharmaceutically acceptable salt form;

1.74. Method 1.73, wherein the PDE1 inhibitor is a compound according to Formula II:

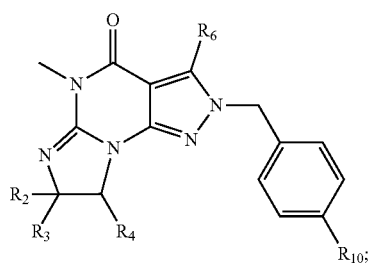

wherein $R_2$ is H and $R_3$ and $R_4$ together form a tri- or tetra-methylene bridge [pref. with the carbons carrying $R_3$ and $R_4$ having the R and S configuration respectively]; or $R_2$ and $R_3$ are each methyl and $R_4$ is H; or $R_2$ and $R_4$ are H and $R_3$ is isopropyl [pref. the carbon carrying $R_3$ having the R configuration];

$R_6$ is (optionally halo-substituted) phenylamino or (optionally halo-substituted) benzylamino;

$R_{10}$ is (optionally halo-substituted) phenyl, (optionally halo-substituted) pyridyl (for example 3-fluoropyrid-2-yl), thiadiazolyl (e.g., 1,2,3-thiadiazol-4-yl), or $C_{1-6}$alkylcarbonyl (e.g., methylcarbonyl);

in free base or pharmaceutically acceptable salt form;

1.75. Method 1.74, wherein, in the Compound of Formula II, $R_6$ is phenylamino or 4-fluorophenylamino;

1.76. Method 1.74, wherein, in the Compound of Formula II, $R_{10}$ is 3-fluoropyrid-2-yl or methylcarbonyl;

1.77. Method 1.74, wherein, in the Compound of Formula II, $R_6$ is phenylamino or 4-fluorophenylamino and $R_{10}$ is 3-fluoropyrid-2-yl or methylcarbonyl;

1.78. Any Methods 1.74-1.77, wherein the Compound of Formula II is

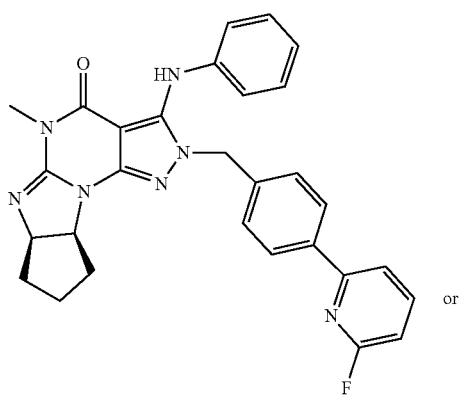

or

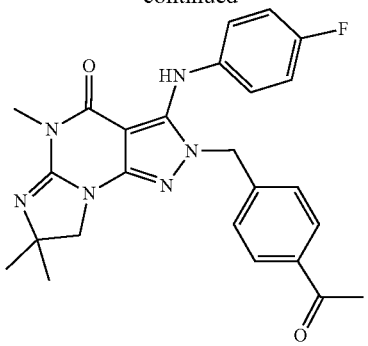

in free base or pharmaceutically acceptable salt form;

1.79. Method 1.77, wherein the Compound of Formula II is in the form of the monophosphate salt;

1.80. Any of Methods 1.74-1.79, wherein the Compound of Formula I is:

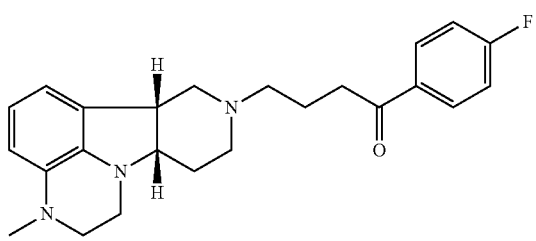 [SMILES: CN1CCN2c3c(cccc31)[C@@H]1CN(CCCC(=O)c3ccc(F)cc3)CC[C@@H]12]

in free base or pharmaceutically acceptable salt form, e.g., tosylate salt form, optionally in a deuterated form; and the Compound of Formula II is:

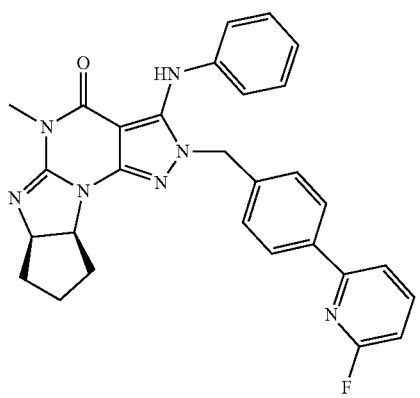 [SMILES: CN1C(=O)c2c(nn(Cc3ccc(-c4cccc(F)n4)cc3)c2Nc2ccccc2)N2C1=N[C@@H]1CCC[C@@H]12]

in free base or pharmaceutically acceptable salt form, e.g., monophosphate salt form;

1.81. Any of Methods 1.74-1.80, comprising administration of a pharmaceutical composition comprising therapeutically effective amounts of both a Compound of Formula I and a Compound of Formula II;

1.82. Any preceding method, wherein the 5-$HT_{2A}$ or 5-$HT_{2A}$/D2 receptor ligand is a compound of Formula I, in free base or pharmaceutically acceptable salt from, optionally in deuterated form, and wherein the compound is administered in the form of a long-acting injectable (LAI) composition comprising the compound of Formula I dissolved or dispersed or in a pharmaceutically acceptable carrier and a polymeric matrix comprising polymers selected from polyortho esters (POE), polylactic acid, polyglycolic acid, polycitric acid, polymalic acid, or a poly(lactic acid-glycolic acid) copolymer;

1.83. Method 1.82, wherein the pharmaceutically acceptable carrier comprises water (e.g., an aqueous buffer) and/or an organic solvent (e.g., a water-miscible organic solvent);

1.84. Method 1.82 or 1.83, wherein the polymers comprise a polylactic acid and/or a polyglycolic acid polymer;

1.85. Method 1.82 or 1.83, wherein the polymers comprise a poly(lactic acid-glycolic acid) copolymer, e.g., poly-d,l-lactide-co-glycolide (PLGA), for example, a PLGA copolymer with a lactide-to-glycolide molar ratio of about 50:50 to 90:10, or 50:50 to 85:15, or 50:50 to 75:25, and/or a molecular weight of 5,000 to 500,000 Daltons, or 5,000 to 150,000 Daltons, or 20,000 to 200,000 Daltons, or 24,000 to 38,000 Daltons;

1.86. Any of Methods 1.82-1.85, wherein the LAI composition is administered by, or formulated for administration by, intramuscular or subcutaneous injection;

1.87. Method 1, or any of 1.1-1.86, wherein the patient has no prior history of depression;

1.88. Method 1, or any of 1.1-1.87, wherein the patient shows evidence of cerebral damage or cerebral disease on magnetic resonance imaging (MRI) prior to administration of the 5-HT$_{2A}$ or 5-HT$_{2A}$/D2 receptor ligand;

1.89. Method 1, or any of 1.1-1.88, wherein the patient has a positive serum antibody or antigen test for one or more of Herpes simplex Virus 1, Herpes Simplex Virus 2, West Nile Virus, Nipah Virus, human immunodeficiency virus, rabies virus, Epstein-Barr Virus, cytomegalovirus, coronavirus (e.g., MERS-CoV, SARS-CoV, SARS-Cov2, or influenza virus (e.g., influenza A, such as H1N1, H2N2, H3N2, H5N1, H7N7), prior to administration of the 5-HT$_{2A}$ or 5-HT$_{2A}$/D2 receptor ligand;

1.90. Method 1, or any of 1.1-1.89, wherein the patient has a positive serum antibody test for autoantibodies against the NMDA receptor, the AMPA receptor, the voltage-gated potassium, channel (VGKC), the LGL1 protein, the GABA receptor, the glycine receptor, the glutamate receptor, or the CASPR2 receptor;

1.91. Any foregoing method, wherein the patient has elevated levels of one or more biomarkers indicative of CNS inflammation, e.g., selected from TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1, in the blood, plasma, serum, peripheral blood mononuclear cells (PBMC) (e.g., isolated from blood), urine, CSF, and/or CNS microglial cells (e.g., isolated from CSF);

1.92. Any foregoing method, wherein the patient has changes in levels of one or more biomarkers indicative of CNS inflammation and/or loss of BBB integrity, e.g., increased levels of ICAM-1, VCAM-1, E-selectin, P-selectin, or soluble isoforms thereof (e.g., sICAM-1, sVCAM1, sP-selectin, sE-selectin), or reduced levels of Cldn5, Occludin, and/or ZO-1, in the serum or CSF;

1.93. Any foregoing method, wherein the patient has depressed levels of one or more anti-inflammatory biomarkers indicative of CNS inflammatory dysfunction, e.g., TNF-β, IFN-α, IL-4, and IL-10, in the blood, plasma, serum, peripheral blood mononuclear cells (PBMC) (e.g., isolated from blood), urine, CSF, and/or CNS microglial cells (e.g., isolated from CSF);

1.94. Any foregoing method, wherein after treatment with the 5-HT$_{2A}$ or 5-HT$_{2A}$/D2 receptor ligand (e.g., Compound of Formula I, optionally in deuterated form), the patient has a reduced level of one or more biomarkers indicative of CNS inflammation, e.g., TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1, in the blood, plasma, serum, peripheral blood mononuclear cells (PBMC) (e.g., isolated from blood), urine, CSF, and/or CNS microglial cells (e.g., isolated from CSF), compared to a pre-treatment baseline, e.g., within 28 days of the initiation of treatment;

1.95. Method 1.94, wherein the patient has at least a 5%, 10%, 15%, 20%, or 25%, 30%, 35%, 40%, 45%, or 50%, reduction in the level of the one or more biomarkers indicative of CNS inflammation, e.g., within 28 days of the initiation of treatment;

1.96. Any foregoing method, wherein after treatment with the 5-HT$_{2A}$ or 5-HT$_{2A}$/D2 receptor ligand (e.g., Compound of Formula I, optionally in deuterated form), the patient has favorable changes in levels of one or more biomarkers indicative of CNS inflammation and/or loss of BBB integrity, e.g., decreased levels of ICAM-1, VCAM-1, E-selectin, P-selectin, or soluble isoforms thereof (e.g., sICAM-1, sVCAM1, sP-selectin, sE-selectin), or increased levels of Cldn5, Occludin, and/or ZO-1, in the serum or CSF, compared to a pre-treatment baseline, e.g., within 28 days of the initiation of treatment;

1.97. Method 1.96, wherein the patient has at least a 5%, 10%, 15%, 20%, 25%, 30%, 35%, 40%, 45%, or 50%, reduction or increase in the level of the one or more biomarkers indicative of CNS inflammation, e.g., within 28 days of the initiation of treatment;

1.98. Any foregoing method, wherein after treatment with the 5-HT$_{2A}$ or 5-HT$_{2A}$/D2 receptor ligand (e.g., Compound of Formula I, optionally in deuterated form), the patient has an increased level of one or more anti-inflammatory biomarkers indicative of CNS inflammatory dysfunction, e.g., TNF-β, IFN-α, IL-4, and IL-10, in the blood, plasma, serum, peripheral blood mononuclear cells (PBMC) (e.g., isolated from blood), urine, CSF, and/or CNS microglial cells (e.g., isolated from CSF), compared to a pre-treatment baseline, e.g., within 28 days of the initiation of treatment;

1.99. Method 1.98, wherein the patient has an increase of at least 5%, 10%, 15%, 20%, 25%, 30%, 35%, 40%, 45%, or 50%, in the levels of the one or more anti-inflammatory biomarkers indicative CNS inflammatory dysfunction, e.g., within 28 days of the initiation of treatment, e.g., within 28 days of the initiation of treatment;

1.100. Any foregoing method, wherein the method further comprises the step of testing one or more body fluids or tissues from the patient for the presence and/or concentration of one or more biomarkers indicative of CNS inflammation or CNS inflammatory dysfunction or loss of BBB integrity prior to the initiation of treatment with the 5-HT$_{2A}$ or 5-HT$_{2A}$/D2 receptor ligand (e.g., Compound of Formula, optionally in deuterated form), and/or subsequent to the initiation of said treatment, and optionally comparing the pre-treatment and one or more post-treatment results thereof to quantify the effectiveness of the treatment in the patient and/or to adjust the treatment regimen;

1.101. Method 1.100, wherein the biomarkers are selected from one or more of TNF-α, IFN-γ, IL-1 (IL-1α and/or IL-1β), IL-6, IL-8, IL-12, IL-15, IL-17, IL-18, CRP, SAA, Csf1, YKL-40, Nlrp3, Flt-1, ICAM-1, VCAM-1, E-selectin, P-selectin, Cldn5, Occludin, and ZO-1, soluble isoforms thereof (e.g., sICAM-1, sVCAM1, sP-selectin, sE-selectin), TNF-β, IFN-α, IL-4, and IL-10;

1.102. Method 1.100 or 1.101, wherein the one or more body fluids or tissues are selected from blood, plasma, serum, peripheral blood mononuclear cells (PBMC) (e.g., isolated from blood), urine, CSF, and/or CNS microglial cells (e.g., isolated from CSF), or brain biopsy tissue samples;

1.103. Any foregoing method, wherein the method further comprises the step of non-invasively testing the central nervous system of the patient for the presence and/or concentration of one or more biomarkers indicative of CNS inflammation or CNS inflammatory dysfunction prior to the initiation of treatment with the 5-HT$_{2A}$ or 5-HT$_{2A}$/D2 receptor ligand (e.g., Compound of Formula I, optionally in deuterated form), and/or subsequent to the initiation of said treatment, and optionally comparing the pre-treatment and one or more post-treatment results thereof to quantify the effectiveness of the treatment in the patient and/or to adjust the treatment regimen;

1.104. Method 1.103, wherein the biomarkers are selected from one or more of TNF-α, IFN-γ, IL-1 (IL-1α and/or IL-1β), IL-6, IL-12, IL-15, IL-17, IL-18, CRP, SAA, Csf1, YKL-40, Nlrp3, Flt-1, ICAM-1, VCAM-1, E-selectin, P-selectin, Cldn5, Occludin, and ZO-1, soluble isoforms thereof (e.g., sICAM-1, sVCAM1, sP-selectin, sE-selectin), TNF-β, IFN-α, IL-4, and IL-10;

1.105. Method 1.103 or 1.104, wherein the step comprises an imaging method, such as magnetic resonance imaging (MRI), positron emission tomography (PET), functional MRI (fMRI), to evaluate the presence and/or concentration of said biomarkers;

1.106. Any of Methods 1.100-1.105, wherein the method comprises the step of initiating, altering, or terminating, the treatment regimen (e.g., the selected 5-HT$_{2A}$ or 5-HT$_{2A}$/D2 receptor ligand, the dose thereof, the route of administration thereof, the frequency of administration thereof, the form of administration thereof, and/or the combination of the selected 5-HT$_{2A}$ or 5-HT$_{2A}$/D2 receptor ligand with any another therapeutic agent), based on the observed changes in the levels of one or more of said biomarkers;

1.107. Any foregoing method, wherein the patient has elevated levels of one or more biomarkers indicative of peripheral inflammation, e.g., selected from type-I interferons, including IFN-α, IFN-β, and/or IFN-δ, in the blood, plasma, serum, peripheral blood mononuclear cells (PBMC) (e.g., isolated from blood), or urine;

1.108. Method 1.107, wherein after treatment with the 5-HT$_{2A}$ or 5-HT$_{2A}$/D2 receptor ligand (e.g., Compound of Formula I, optionally in deuterated form), the patient has a reduced level of the one or more biomarkers indicative of peripheral inflammation, e.g., selected type-I interferons, including IFN-α, IFN-β, and/or IFN-δ, in the blood, plasma, serum, peripheral blood mononuclear cells (PBMC) (e.g., isolated from blood), or urine, compared to a pre-treatment baseline, e.g., within 28 days of the initiation of treatment;

1.109. Method 1.108, wherein the patient has at least a 5%, 10%, 15%, 20%, or 25%, 30%, 35%, 40%, 45%, or 50%, reduction in the level of the one or more biomarkers indicative of peripheral inflammation, e.g., within 28 days of the initiation of treatment;

1.110. Any foregoing method, wherein the patient has peripheral serotonin deficiency, e.g., reduced concentration in the plasma and/or platelets, for example, a plasma serotonin concentration less than 3000 nM, less than 2500 nM, less than 2000 nM, less than 1800 nM, less than 1600 nM, less than 1400 nM, less than 1200 nM, less than 1000 nM, less than 800 nM, less than 600 nM, less than 500 nM, less than 400 nM, less than 300 nM, or less than 250 nM;

1.111. Method 1.110, wherein after treatment with the 5-HT$_{2A}$ or 5-HT$_{2A}$/D2 receptor ligand (e.g., Compound of Formula I, optionally in deuterated form), the patient has recovered from peripheral serotonin deficiency, e.g., a normal concentration in the plasma and/or platelets, for example, a plasma serotonin concentration of greater than 500 nM, or 500 to 3000 nM, or 1000 to 3000 nM, or 1500 to 3000 nM, or 2000 to 3000 nM, or greater than 3000 nM nM, less than 800 nM, less than 600 nM, less than 500 nM, less than 400 nM, less than 300 nM, or less than 250 nM;

1.112. Method 1.110 or 1.111, wherein the psychiatric disorder or psychiatric symptoms are caused by, or thought to be caused by, peripheral serotonin deficiency, e.g., due to reduced plasma serotonin concentration and/or reduced vagal nerve afferent sensory activity (e.g., due to reduced serotonin-mediated 5-HT$_3$ signaling)

1.113. Any foregoing method, wherein the patient is suffering from a post-viral syndrome, e.g., Long COVID;

1.114. Any foregoing method, wherein the patient has thrombocytopenia or platelet hypercoagulability (e.g., as shown by reduced prothrombin time and/or partial thromboplastin time), 1.115. Any foregoing method, wherein the method further comprises the step of obtaining a tissue sample from the patient and testing the tissue sample for the level of any one or more of: (a) serum antibody or antigen for one or more of Herpes simplex Virus 1, Herpes Simplex Virus 2, West Nile Virus, Nipah Virus, human immunodeficiency virus, rabies virus, Epstein-Barr Virus, cytomegalovirus, coronavirus (e.g., MERS-CoV, SARS-CoV, SARS-Cov2, or influenza virus (e.g., influenza A, such as H1N1, H2N2, H3N2, H5N1, H7N7); (b) serum autoantibodies against the NMDA receptor, the AMPA receptor, the voltage-gated potassium, channel (VGKC), the LGL1 protein, the GABA receptor, the glycine receptor, the glutamate receptor, or the CASPR2 receptor; (c) biomarkers selected from TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1; (d) biomarkers selected from ICAM-1, VCAM-1, E-selectin, P-selectin, or soluble isoforms thereof (e.g., sICAM-1, sVCAM1, sP-selectin, sE-selectin), Cldn5, Occludin, and/or ZO-1; (e) biomarkers selected from TNF-β, IFN-α, IL-4, and IL-10; (f) type-I interferons, including IFN-α, IFN-β, and/or IFN-δ; (f) serotonin; and (g) platelet count, prothrombin time, and/or partial thromboplastin time;

1.116. Method 1.115, wherein the tissue sample is selected from blood, plasma, serum, peripheral blood mononuclear cells (PBMC) (e.g., isolated from blood), urine, CSF, and/or CNS microglial cells (e.g., isolated from CSF);

1.117. Method 1.115 or 1.116, wherein the method further comprises adjusting the course of treatment based on the results of one more of said tissue sample measurements, optionally wherein said tissue sample measurements are taken at one or more times during the course of therapy, e.g., for comparison to earlier measurements or measurements taken before initiating therapy.

In another aspect, the disclosure provides a 5-HT$_{2A}$ or 5-HT$_{2A}$/D2 receptor ligand, e.g., a compound of Formula I, as hereinbefore described, for example lumateperone, in free base or salt form, optionally in deuterated form, for use in the treatment of psychiatric disorders caused by viral, bacterial, or autoimmune encephalitis, and for treatment of psychiatric symptoms of viral, bacterial, and autoimmune encephalitis, e.g., for use in any of Methods 1, et seq.

In another aspect, the disclosure provides the use of a 5-HT$_{2A}$ or 5-HT$_{2A}$/D2 receptor ligand, e.g., a compound of Formula I, as hereinbefore described, for example lumateperone, in free base or salt form, optionally in deuterated form, in in the manufacture of a medicament for treatment of psychiatric disorders caused by viral, bacterial, or autoimmune encephalitis, and for treatment of psychiatric symptoms of viral, bacterial, and autoimmune encephalitis, e.g., for any of Methods 1, et seq.

In a particular embodiment, the present disclosure provides a method (Method 2) for protecting or reinforcing the blood-brain barrier, comprising administering to a patient in need thereof, a therapeutically effective amount of a 5-HT$_{2A}$ or 5-HT$_{2A}$/D2 receptor ligand, for example, a compound of Formula I:

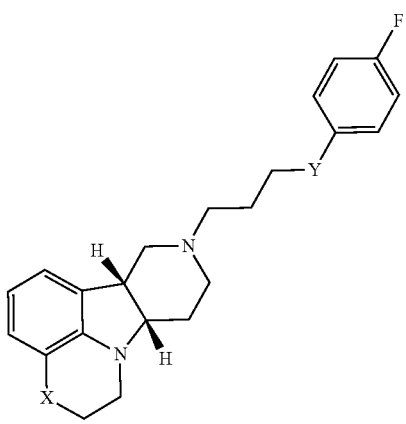

wherein:
X is —N(H)—, —N(CH$_3$)— or —O—;
Y is —C(=O)—, —C(H)(OH)— or —C(H)(OR$_1$)—;
R$_1$ is —C(O)—C$_{1-21}$alkyl (e.g., —C(O)—C$_{1-5}$alkyl, —C(O)—C$_{6-15}$alkyl or —C(O)—C$_{16-21}$alkyl), preferably said alkyl is a straight chain, optionally saturated or unsaturated and optionally substituted with one or more hydroxy or C$_{1-22}$alkoxy (e.g., ethoxy) groups, for example R$_1$ is —C(O)—C$_6$alkyl, —C(O)—C$_7$alkyl, —C(O)—C$_9$alkyl, —C(O)—C$_{11}$alkyl, —C(O)—C$_{13}$alkyl or —C(O)—C$_{15}$alkyl, wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand, optionally in deuterated form, in free base, pharmaceutically acceptable salt or prodrug form. For example, Method 2 may be as follows:

2.1. Method 2, wherein X in the compound of Formula I is —N(H)—, —N(CH$_3$)— or —O—;

2.2. Method 2 or 2.1, wherein X in the compound of Formula I is —N(H);

2.3. Method 2 or 2.1, wherein X in the compound of Formula I is —N(CH$_3$)—;

2.4. Method 2 or 2.1, wherein X in the compound of Formula I is —O—;

2.5. Method 2 or any of formulae 2.1-2.4, wherein Y in the compound of Formula I is —C(=O)—, —C(H)(OH)— or —C(H)(OR$_1$)—;

2.6. Method 2 or any of formulae 1.1-1.4, wherein Y in the compound of Formula I is —C(=O)—;

2.7. Method 2 or any of formulae 2.1-2.4, wherein Y in the compound of Formula I is —C(H)(OH)—;

2.8. Method 2 or any of formulae 2.1-2.4, wherein Y in the compound of Formula I is —C(H)(OR$_1$)—;

2.9. Method 2, or any of 2.2-2.5, or 2.8, wherein R$_1$ in the compound of Formula I is —C(O)—C$_{1-21}$alkyl (e.g., —C(O)—C$_{1-5}$alkyl, —C(O)—C$_{6-15}$alkyl or —C(O)—C$_{16-21}$alkyl), preferably said alkyl is a straight chain, optionally saturated or unsaturated and optionally substituted with one or more hydroxy or C$_{1-22}$alkoxy (e.g., ethoxy) groups, for example R$_1$ is —C(O)—C$_6$alkyl, —C(O)—C$_7$alkyl, —C(O)—C$_9$alkyl, —C(O)—C1lalkyl, —C(O)—C$_{13}$alkyl or —C(O)—C$_{15}$alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand); e.g., wherein R$_1$ in the compound of Formula I is —C(O)—C$_{6-15}$alkyl, e.g., —C(O)—C$_9$alkyl; or wherein R$_1$ in the compound of Formula I is —C(O)—C$_{1-5}$alkyl, e.g., —C(O)—C$_3$alkyl;

2.10. Method 2 or any of 2.1-2.5 or 2.7, wherein the Compound of Formula I is:

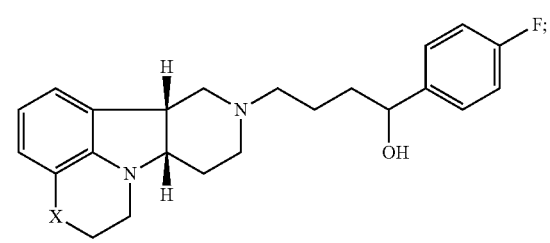

2.11. Method 2 or any of 2.1-2.5 or 2.7, wherein the Compound of Formula I is:

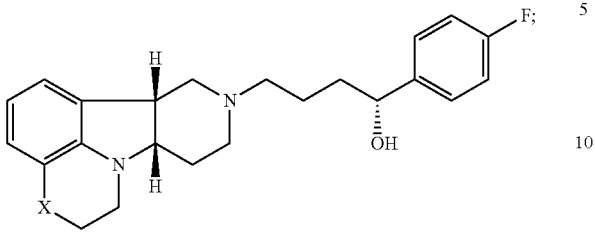

2.12. Method 2, or any of 2.1, 2.3, 2.5, or 2.6, wherein the Compound of Formula I is lumateperone:

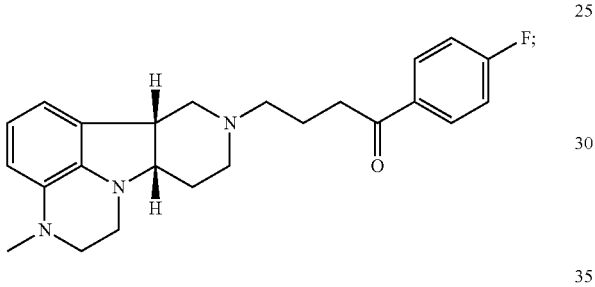

2.13. Method 2, or any of 2.1-2.12, e.g., Method 2.12, wherein the Compound of Formula I is in the form of a pharmaceutically acceptable salt, e.g., a tosylate salt;
2.14. Method 2, or any of 2.1-2.12, e.g., Method 2.12, wherein the Compound of Formula I is in the form of the free base;
2.15. Method 2 or any of 2.1-2.14, wherein the Compound of Formula I is in deuterated form, e.g., wherein the deuterium:protium ratio for a specified carbon-bound hydrogen atom is significantly higher, e.g., at least 2×, for example at least 10× higher, than the natural isotope ratios;
2.16. Method 2.15, wherein the Compound of Formula I is a deuterated form of lumateperone, for example, selected from:

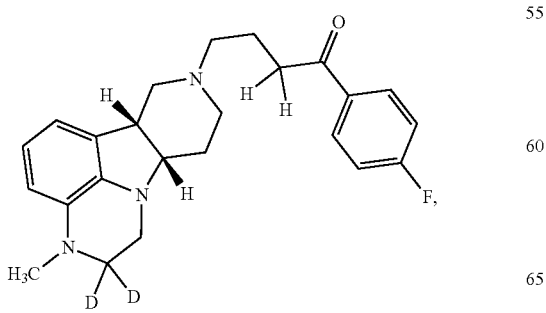

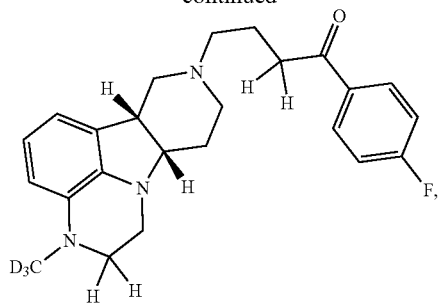

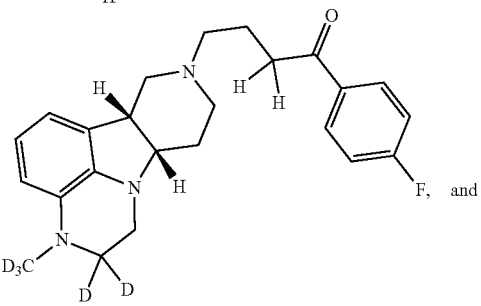

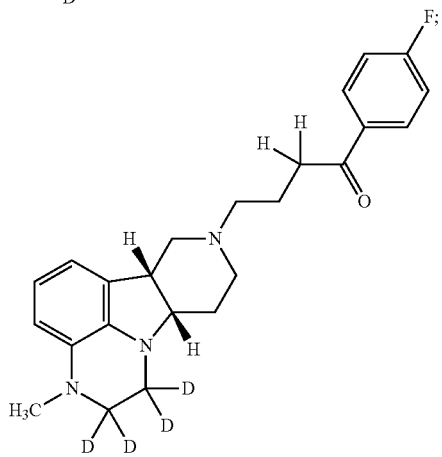

wherein D represents a hydrogen position with substantially greater than natural deuterium incorporation (i.e., substantially greater than 0.0156%), e.g., greater than 60%, or greater than 70%, or greater than 80%, or greater than 90% or greater than 95%, or greater than 96%, or greater than 97%, or greater than 98%, or greater than 99%, in free base or pharmaceutically acceptable salt form, e.g., tosylate salt form;
2.17. Any foregoing method, wherein the 5-HT$_{2A}$ or 5-HT$_{2A}$/D2 receptor ligand is a compound of Formula I in free base or pharmaceutically acceptable salt form, e.g., in tosylate salt form, administered in a daily dose equivalent to 1 to 100 mg of free base, e.g., in an amount equivalent to 1 to 75 mg, or 1 to 60 mg, or 1 to 40 mg, or 1 to 20 mg, or 1 to 10 mg, of free base;
2.18. Method 2.17, wherein the method comprises once daily administration of a unit dosage for oral administration, for example a tablet or capsule, comprising the compound of Formula I in free base or pharmaceutically acceptable salt form, e.g. in tosylate salt form in an amount equivalent to 1 to 100 mg of free base, e.g., in an amount equivalent to 1 to 75 mg, or 1 to 60 mg, or 1 to 40 mg, or 1 to 30 mg, or 1 to 20 mg, or 1 to 10 mg, or 1 to 5 mg, or 40 to 60 mg, or 20 to 40 mg, or 10 to 20 mg, or about 60 mg, or about 40 mg, or about 30 mg, or about 20 mg, or about 10 mg, or about 5 mg, of free base, and a pharmaceutically acceptable diluent or carrier;

2.19. Method 2.17, wherein the method comprises once daily administration of a unit dosage for oral transmucosal administration, e.g., a sublingual or buccal orally disintegrating tablet, wafer, or film, comprising the compound of Formula I in free base or pharmaceutically acceptable salt form, e.g., in tosylate salt form, in an amount equivalent to 0.5 to 30 mg of free base, e.g., in an amount equivalent to 1 to 30 mg, or 1 to 20 mg, or 1 to 15 mg, or 1 to 10 mg, or 20 to 30 mg, or 10 to 20 mg, or about 5 mg, or about 10 mg, or about 15 mg, or about 20 mg, of free base, and a pharmaceutically acceptable diluent or carrier;

2.20. Any foregoing method, wherein the patient has a viral, bacterial, or autoimmune encephalitis, e.g., caused by, or suspected to be caused by, Herpes simplex Virus 1, Herpes Simplex Virus 2, West Nile Virus, Nipah Virus, human immunodeficiency virus, rabies virus, Epstein-Barr Virus, cytomegalovirus, coronavirus (e.g., MERS-CoV, SARS-CoV, SARS-Cov2), influenza virus (e.g., influenza A, such as H1N1, H2N2, H3N2, H5N1, H7N7), toxoplasmosis, *rickettsia, mycoplasma, Borrelia* (e.g., Lyme disease), malaria, or autoantibodies against the NMDA receptor, the AMPA receptor, the voltage-gated potassium, channel (VGKC), the LGL1 protein, the GABA receptor, the glycine receptor, the glutamate receptor, or the CASPR2 receptor;

2.21. Any foregoing method wherein the patient is diagnosed as having suicidal ideation and/or suicidal tendencies;

2.22. Any foregoing method wherein the patient is diagnosed with a psychiatric disorder or psychiatric symptoms, e.g., depression (e.g., acute depression, depression of MDD, depression of bipolar disorder), anxiety, (e.g., acute anxiety), psychosis (e.g., schizophrenia), post-traumatic stress-disorder, anhedonia, memory loss, impairment of executive functioning, difficulty concentrating, seizures, difficulty sleeping, hallucination, change in personality, or any combination thereof;

2.23. Any foregoing method, wherein the patient is showing acute signs of psychiatric illness in the absence of a prior history of psychiatric disorders or psychiatric symptoms;

2.24. Any foregoing method, wherein the patient is at risk of damage or compromise of the blood-brain barrier, e.g., due to CNS inflammation, CNS infection (e.g., encephalitis), neurodegenerative disease, such as Alzheimer's disease, Huntington's disease, Parkinson's disease, amyotrophic lateral sclerosis, or due to cerebral trauma (e.g., traumatic brain injury, such as concussive injury);

2.25. Any foregoing method, wherein the patient has elevated levels of pro-inflammatory cytokines in the CNS (e.g., in the cerebrospinal fluid), such as TNF-α, IFN-γ, IL-1 (IL-1α and/or IL-1β), IL-6, IL-8, IL-12, IL-15, IL-17, IL-18, or elevated levels of C-reactive protein (CRP) of Csf1, and/or depressed levels of anti-inflammatory cytokines in the CNS (e.g., in the cerebrospinal fluid), such as TNF-β, IFN-α, IL-4, and IL-10;

2.26. Any foregoing method wherein the 5-HT$_{2A}$ or 5-HT$_{2A}$/D2 receptor ligand is administered in combination (e.g., a fixed combination in a unit dosage form, or a free combination administered sequentially or simultaneously or within a 24-hour period) with a therapeutically effective amount of an anxiolytic or antidepressant agent;

2.27. Method 2.26, wherein the anxiolytic or antidepressant agent is selected from one or more compounds in free base or pharmaceutically acceptable salt form, selected from selective serotonin reuptake inhibitors (SSRIs), serotonin-norepinephrine reuptake inhibitors (SNRIs), tricyclic antidepressants (TCAs), and atypical antipsychotics, e.g., one or more compounds in free base or pharmaceutically acceptable salt form, selected from:
  (a) Selective serotonin reuptake inhibitors (SSRIs), e.g., Citalopram (Celexa), Escitalopram (Lexapro, Cipralex), Paroxetine (Paxil, Seroxat), Fluoxetine (Prozac), Fluvoxamine (Luvox) Sertraline (Zoloft, Lustral);
  (b) Serotonin-norepinephrine reuptake inhibitors (SNRIs), e.g., Desvenlafaxine (Pristiq), Duloxetine (Cymbalta), Levomilnacipran (Fetzima), Milnacipran (Ixel, Savella), Tofenacin (Elamol, Tofacine), Venlafaxine (Effexor);
  (c) Tricyclic antidepressants (TCAs), e.g., Amitriptyline (Elavil, Endep), Amitriptylinoxide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Nitroxazepine (Sintamil), Nortriptyline (Pamelor, Aventyl), Noxiptiline (Agedal, Elronon, Nogedal), Pipofezine (Azafen/Azaphen), Protriptyline (Vivactil), Trimipramine (Surmontil);
  (d) Benzodiazepines, e.g., selected from 2-keto compounds (e.g., clorazepate, diazepam, flurazepam, halazepam, prazepam); 3-hydroxy compounds (lorazepam, lormetazepam, oxazepam, temazepam); 7-nitro compounds (e.g., clonazepam, flunitrazepam, nimetazepam, nitrazepam); triazolo compounds (e.g., adinazolam, alprazolam, estazolam, triazolam); and imidazo compounds (climazolam, loprazolam, midazolam);

2.28. Any foregoing method, wherein the 5-HT$_{2A}$ or 5-HT$_{2A}$/D2 receptor ligand, e.g., the compound of Formula I, is administered intra-nasally, subcutaneously, intramuscularly, intravenously, orally, sub-lingually, intra-peritoneally or buccally, such as an oral rapidly dissolving tablet, wafer, or film, which dissolves in the oral cavity for transmucosal absorption;

2.29. Any foregoing method, wherein the method further comprises the concurrent administration of an antidepressant agent (e.g., selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), a serotonin receptor antagonist, or any combination thereof), e.g., administered simultaneously, separately or sequentially;

2.30. Any foregoing method, wherein the method further comprises the concurrent administration of an NMDA receptor antagonist, for example, selected from ketamine (e.g., S-ketamine and/or R-ketamine), hydroxynorketamine, memantine, dextromethorphan, dextroallorphan, dextrorphan, amantadine, and agmatine, or any combination thereof, e.g., administered simultaneously, separately or sequentially;

2.31. Any foregoing method, wherein the method further comprises the concurrent administration of a NMDA receptor allosteric modulator, e.g., a NMDA receptor glycine-site modulator, such as rapastinel, nebostinel, apimostinel, D-cycloserine, or any combination thereof, e.g., administered simultaneously, separately or sequentially;

2.32. Any foregoing method, wherein the method provides the patient with an acute response to treatment with the therapeutic agent or agents (e.g., the 5-HT$_{2A}$ or 5-HT$_{2A}$/D2 receptor ligand, the Compound of Formula I, or the combination of the Compound or Formula I and the Compound of Formula II, and/or any additional antidepressant agents);

2.33. Method 2.32, wherein the patient shows an acute response to treatment within less than 3 weeks, for example, less than 2 weeks, or less than 1 week, or from 1 to 7 days, or 1 to 5 days, or 1 to 3 days, or 1 to 2 days, or about 1 day, or less than 2 days, or less than 1 day (e.g., 12-24 hours, 6-12 hours, or 3-6 hours);

2.34. Any foregoing method, wherein the patient has not responded to, or has not responded adequately to, or who suffers undesirable side effects from, treatment with another antidepressant agent, for example, any one or more of a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor, or a serotonin receptor antagonist;

2.35. Any foregoing method, wherein the patient does not suffer from (or has not previously been diagnosed with) schizophrenia or dementia;

2.36. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the 5-HT$_{2A}$ receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

2.37. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the D2 receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

2.38. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the D1 receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

2.39. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the serotonin transporter (SERT), e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said transporter (agonism or antagonism);

2.40. Any foregoing method, wherein the 5-HT$_{2A}$ or 5-HT$_{2A}$/D2 receptor ligand is lumateperone, in free base or pharmaceutically acceptable salt form, optionally in a deuterated form;

2.41. Any foregoing method, wherein the 5-HT$_{2A}$ or 5-HT$_{2A}$/D2 receptor ligand is lumateperone, in a tosylate salt form (e.g., monotosylate salt), optionally in a deuterated form, and optionally in crystalline or amorphous tosylate salt form;

2.42. Any foregoing method, wherein the 5-HT$_{2A}$ or 5-HT$_{2A}$/D2 receptor ligand is lumateperone, in free base form, optionally in a deuterated form;

2.43. Any foregoing method, wherein the 5-HT$_{2A}$ or 5-HT$_{2A}$/D2 receptor ligand is administered in the form of a long-acting injectable (LAI) composition, e.g., for intramuscular or subcutaneous injection;

2.44. Method 2.43, wherein the dose of the LAI composition is sufficient to provide the equivalent of a daily dose of 1 to 100 mg of free base, e.g., 1 to 75 mg, or 1 to 60 mg, or 1 to 40 mg, or 1 to 20 mg, or 1 to 10 mg, of free base, released over a period of time ranging from about 1 week to about 3 months, e.g., about 1 week to about 8 weeks, or about 1 week to about 6 weeks, or about 1 week to about 4 weeks, or about 1 week to about 3 weeks, or about 1 week to about 2 weeks;

2.45. Method 2.43 or 2.44, wherein the LAI composition comprises the compound of Formula I dissolved, dispersed, suspended, or encapsulated in a polymeric matrix;

2.46. Method 2.45, wherein the polymeric matrix comprises one or more biocompatible and biodegradable polymers as defined herein, e.g., poly(hydroxycarboxylic acids), poly(amino acids), cellulose polymers, modified cellulose polymers, polyamides, and polyesters;

2.47. Method 2.46, wherein the one or more polymers comprises polylactic acid, polyglycolic acid, polycitric acid, polymalic acid, poly-beta-hydroxybutyric acid, poly(lactic acid-glycolic acid) copolymer, 2-hydroxybutyric acid-glycolic acid copolymer, polylactic acid-polyethylene glycol copolymer, polyglycolic acid-polyethylene glycol copolymer, PEG-PLGA copolymer or block copolymer, poly(alkyl alpha-cyanoacrylate) such as poly(butyl cyanoacrylate) or poly (2-octyl cyanoacrylate), poly(ortho ester), polycarbonate, polyortho-carbonate, a polyamino acid, (for example poly-gamma.-L-alanine, poly-.gamma.-benzyl-L-glutamic acid or poly-y-methyl-L-glutamic acid), and/or hyaluronic acid ester;

2.48. Method 2.46, wherein the one or more polymers comprises polyortho esters (POE), polylactic acid, polyglycolic acid, polycitric acid, polymalic acid, or a poly(lactic acid-glycolic acid) copolymer;

2.49. Method 2.46, wherein the one or more polymers comprises a poly(lactic acid-glycolic acid) copolymer, e.g., poly-d,l-lactide-co-glycolide (PLGA), for example, a PLGA copolymer with a lactide-to-glycolide molar ratio of about 50:50 to 90:10, or 50:50 to 85:15, or 50:50 to 75:25, and/or a molecular weight of 5,000 to 500,000 Daltons, or 5,000 to 150,000 Daltons, or 20,000 to 200,000 Daltons, or 24,000 to 38,000 Daltons;

2.50. Any foregoing method, wherein the 5-HT$_{2A}$ or 5-HT$_{2A}$/D2 receptor ligand is administered as monotherapy, e.g., it is not administered concurrently or in conjunction with an anti-depressant, anti-psychotic, or anti-anxiety agent;

2.51. Any foregoing method, wherein the 5-HT$_{2A}$ or 5-HT$_{2A}$/D2 receptor ligand is administered without the direct supervision of a health care professional (e.g., the compound is self-administered by the patient);

2.52. Any foregoing method, wherein the method does not comprise supervision or observation of the patient by a health care professional during or after (e.g., within 2 hours after) administration of a dose of the 5-HT$_{2A}$ or 5-HT$_{2A}$/D2 receptor ligand;

2.53. Any foregoing method, wherein the method does not put the patient at risk for sedation, dissociation, abuse, misuse, or suicidal ideation;

2.54. Any foregoing method, wherein the method does not result in hypertension (e.g., systolic and/or diastolic hypertension) within four hours after administration of a dose of the 5-HT$_{2A}$ or 5-HT$_{2A}$/D2 receptor ligand, e.g., an increase of more than 10 mm Hg, or more than 20 mm Hg, or more than 30 mm Hg, or more than 40 mm Hg, in systolic and/or diastolic blood pressure within 30 minutes to 4 hours after said dose;

2.55. Any foregoing method, wherein the method does not result in cognitive decline;

2.56. Any foregoing method, wherein the patient has (e.g., has been diagnosed with), or is at risk of, aneurysmal vascular disease (e.g., thoracic aorta, abdominal aorta, intracranial, or peripheral arterial aneurysms), arterio-venous malformation or intracerebral hemorrhage;

2.57. Any foregoing method, wherein the patient is under concurrent treatment with an oral antidepressant selected from duloxetine, escitalopram, sertraline, or venlafaxine;

2.58. Any foregoing method, wherein the patient is not under concurrent treatment with an oral antidepressant selected from duloxetine, escitalopram, sertraline, or venlafaxine;

2.59. Any foregoing method, wherein the patient is unresponsive to, or cannot be treated with ketamine (e.g., S-ketamine), e.g., because it is contraindicated in said patient;

2.60. Any foregoing method, wherein the 5-HT$_{2A}$ or 5-HT$_{2A}$/D2 receptor ligand is administered to the patient concurrently with a PDE1 (cyclic nucleoside phosphodiesterase 1) inhibitor (e.g., administered simultaneously, separately or sequentially), in free base or pharmaceutically acceptable salt form;

2.61. Method 2.60, wherein the PDE1 inhibitor is a compound according to Formula II:

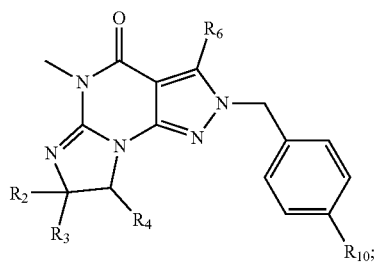

wherein R$_2$ is H and R$_3$ and R$_4$ together form a tri- or tetra-methylene bridge [pref. with the carbons carrying R$_3$ and R$_4$ having the R and S configuration respectively]; or R$_2$ and R$_3$ are each methyl and R$_4$ is H; or R$_2$ and R$_4$ are H and R$_3$ is isopropyl [pref. the carbon carrying R$_3$ having the R configuration];

R$_6$ is (optionally halo-substituted) phenylamino or (optionally halo-substituted) benzylamino;

R$_{10}$ is (optionally halo-substituted) phenyl, (optionally halo-substituted) pyridyl (for example 3-fluoro-pyrid-2-yl), thiadiazolyl (e.g., 1,2,3-thiadiazol-4-yl), or C$_{1-6}$alkylcarbonyl (e.g., methylcarbonyl);

in free base or pharmaceutically acceptable salt form 2.62. Method 2.61, wherein, in the Compound of Formula II, R$_6$ is phenylamino or 4-fluorophenylamino;

2.63. Method 2.61, wherein, in the Compound of Formula II, R$_{10}$ is 3-fluoropyrid-2-yl or methylcarbonyl;

2.64. Method 2.61, wherein, in the Compound of Formula II, R$_6$ is phenylamino or 4-fluorophenylamino and R$_{10}$ is 3-fluoropyrid-2-yl or methylcarbonyl;

2.65. Any Methods 2.61-2.64, wherein the Compound of Formula II is

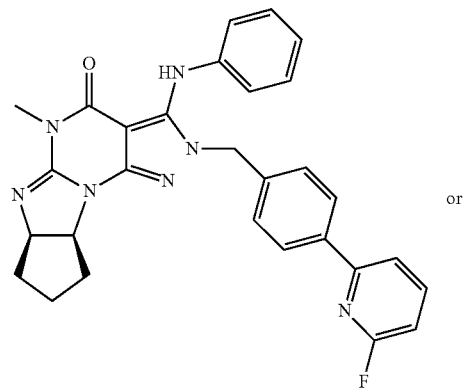

or

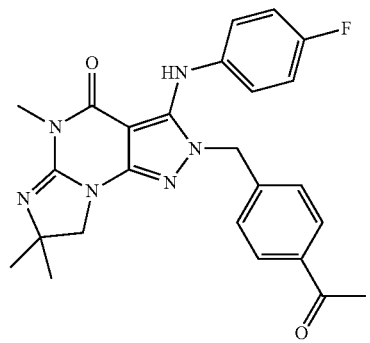

in free base or pharmaceutically acceptable salt form.

2.66 Method 2.65, wherein the Compound of Formula II is in the form of the monophosphate salt;

2.67 Any of Methods 2.61-2.66, wherein the Compound of Formula I is:

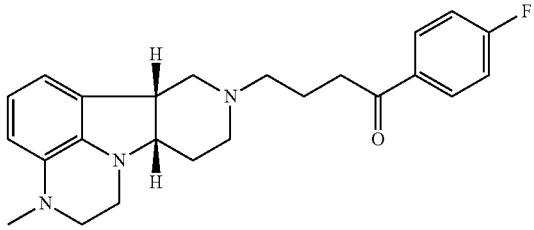 [SMILES: CN1CCN2c3c(cccc31)[C@@H]1CN(CCCC(=O)c3ccc(F)cc3)CC[C@@H]12]

in free base or pharmaceutically acceptable salt form, e.g., tosylate salt form, optionally in a deuterated form; and the Compound of Formula II is:

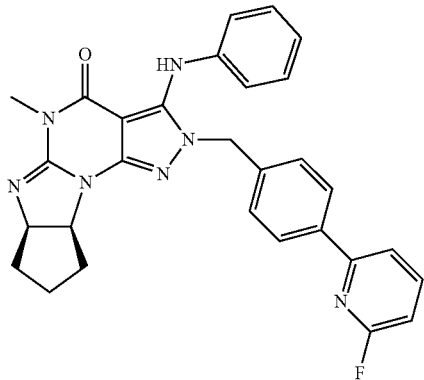 [SMILES: CN1C(=O)c2c(nn(Cc3ccc(-c4cccc(F)n4)cc3)c2Nc2ccccc2)N2C1=N[C@@H]1CCC[C@@H]12]

in free base or pharmaceutically acceptable salt form, e.g., monophosphate salt form;

2.68 Any of Methods 2.61-2.67, comprising administration of a pharmaceutical composition comprising therapeutically effective amounts of both a Compound of Formula I and a Compound of Formula II;

2.69 Any preceding method, wherein the $5\text{-HT}_{2A}$ or $5\text{-HT}_{2A}/D2$ receptor ligand is a compound of Formula I, in free base or pharmaceutically acceptable salt from, optionally in deuterated form, and wherein the compound is administered in the form of a long-acting injectable (LAI) composition comprising the compound of Formula I dissolved or dispersed or in a pharmaceutically acceptable carrier and a polymeric matrix comprising polymers selected from polyortho esters (POE), polylactic acid, polyglycolic acid, polycitric acid, polymalic acid, or a poly(lactic acid-glycolic acid) copolymer;

2.70 Method 2.69, wherein the pharmaceutically acceptable carrier comprises water (e.g., an aqueous buffer) and/or an organic solvent (e.g., a water-miscible organic solvent);

2.71 Method 2.69 or 2.70, wherein the polymers comprise a polylactic acid and/or a polyglycolic acid polymer;

2.72 Method 2.69 or 2.70, wherein the polymers comprise a poly(lactic acid-glycolic acid) copolymer, e.g., poly-d,l-lactide-co-glycolide (PLGA), for example, a PLGA copolymer with a lactide-to-glycolide molar ratio of about 50:50 to 90:10, or 50:50 to 85:15, or 50:50 to 75:25, and/or a molecular weight of 5,000 to 500,000 Daltons, or 5,000 to 150,000 Daltons, or 20,000 to 200,000 Daltons, or 24,000 to 38,000 Daltons;

2.73 Any of Methods 2.69-2.72, wherein the LAI composition is administered by, or formulated for administration by, intramuscular or subcutaneous injection;

2.74 Method 2, or any of 2.1-2.74, wherein the patient has no prior history of depression;

2.75 Method 2, or any of 2.1-2.75, wherein the patient shows evidence of cerebral damage or cerebral disease on magnetic resonance imaging (MRI) prior to administration of the $5\text{-HT}_{2A}$ or $5\text{-HT}_{2A}/D2$ receptor ligand;

2.76 Method 2, or any of 2.1-2.75, wherein the patient has a positive serum antibody or antigen test for one or more of Herpes simplex Virus 1, Herpes Simplex Virus 2, West Nile Virus, Nipah Virus, human immunodeficiency virus, rabies virus, Epstein-Barr Virus, cytomegalovirus, coronavirus (e.g., MERS-CoV, SARS-CoV, SARS-Cov2, or influenza virus (e.g., influenza A, such as H1N1, H2N2, H3N2, H5N1, H7N7), prior to administration of the $5\text{-HT}_{2A}$ or $5\text{-HT}_{2A}/D2$ receptor ligand;

2.77 Method 2, or any of 2.1-2.76, wherein the patient has a positive serum antibody test for autoantibodies against the NMDA receptor, the AMPA receptor, the voltage-gated potassium, channel (VGKC), the LGL1 protein, the GABA receptor, the glycine receptor, the glutamate receptor, or the CASPR2 receptor;

2.78 Any foregoing method, wherein the patient has elevated levels of one or more biomarkers indicative of CNS inflammation, e.g., selected from TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1, in the blood, plasma, serum, peripheral blood mononuclear cells (PBMC) (e.g., isolated from blood), urine, CSF, and/or CNS microglial cells (e.g., isolated from CSF);

2.79 Any foregoing method, wherein the patient has changes in levels of one or more biomarkers indicative of CNS inflammation and/or loss of BBB integrity, e.g., increased levels of ICAM-1, VCAM-1, E-selectin, P-selectin, or soluble isoforms thereof (e.g., sICAM-1, sVCAM1, sP-selectin, sE-selectin), or reduced levels of Cldn5, Occludin, and/or ZO-1, in the serum or CSF;

2.80 Any foregoing method, wherein the patient has depressed levels of one or more anti-inflammatory biomarkers indicative of CNS inflammatory dysfunction, e.g., TNF-β, IFN-α, IL-4, and IL-10, in the blood, plasma, serum, peripheral blood mononuclear cells (PBMC) (e.g., isolated from blood), urine, CSF, and/or CNS microglial cells (e.g., isolated from CSF);

2.81 Any foregoing method, wherein after treatment with the $5\text{-HT}_{2A}$ or $5\text{-HT}_{2A}/D2$ receptor ligand (e.g., Compound of Formula I, optionally in deuterated form), the patient has a reduced level of one or more biomarkers indicative of CNS inflammation, e.g., TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1, in the blood, plasma, serum, peripheral blood mononuclear cells (PBMC) (e.g., isolated from blood), urine, CSF, and/or CNS microglial cells (e.g., isolated from CSF), compared to a pre-treatment baseline, e.g., within 28 days of the initiation of treatment;

2.82 Method 1.94, wherein the patient has at least a 5%, 10%, 15%, 20%, or 25%, 30%, 35%, 40%, 45%, or 50%, reduction in the level of the one or more biomarkers indicative of CNS inflammation, e.g., within 28 days of the initiation of treatment;

2.83 Any foregoing method, wherein after treatment with the 5-HT$_{2A}$ or 5-HT$_{2A}$/D2 receptor ligand (e.g., Compound of Formula I, optionally in deuterated form), the patient has a favorable changes in levels of one or more biomarkers indicative of CNS inflammation and/or loss of BBB integrity, e.g., increased levels of ICAM-1, VCAM-1, E-selectin, P-selectin, or soluble isoforms thereof (e.g., sICAM-1, sVCAM1, sP-selectin, sE-selectin), or reduced levels of Cldn5, Occludin, and/or ZO-1, in the serum or CSF, compared to a pre-treatment baseline, e.g., within 28 days of the initiation of treatment;

2.84 Method 2.83, wherein the patient has at least a 5%, 10%, 15%, 20%, 25%, 30%, 35%, 40%, 45%, or 50%, reduction or increase in the level of the one or more biomarkers indicative of CNS inflammation and/or loss of BBB integrity, e.g., within 28 days of the initiation of treatment;

2.85 Any foregoing method, wherein after treatment with the 5-HT$_{2A}$ or 5-HT$_{2A}$/D2 receptor ligand (e.g., Compound of Formula I, optionally in deuterated form), the patient has an increased level of one or more anti-inflammatory biomarkers indicative of CNS inflammatory dysfunction, e.g., TNF-β, IFN-α, IL-4, and IL-10, in the blood, plasma, serum, peripheral blood mononuclear cells (PBMC) (e.g., isolated from blood), urine, CSF, and/or CNS microglial cells (e.g., isolated from CSF), compared to a pre-treatment baseline, e.g., within 28 days of the initiation of treatment;

2.86 Method 2.85, wherein the patient has an increase of at least a 5%, 10%, 15%, 20%, 25%, 30%, 35%, 40%, 45%, or 50%, in the levels of the one or more anti-inflammatory biomarkers indicative CNS inflammatory dysfunction, e.g., within 28 days of the initiation of treatment, e.g., within 28 days of the initiation of treatment;

2.87 Any foregoing method, wherein the method further comprises the step of testing one or more body fluids or tissues from the patient for the presence and/or concentration of one or more biomarkers indicative of CNS inflammation or CNS inflammatory dysfunction prior to the initiation of treatment with the 5-HT$_{2A}$ or 5-HT$_{2A}$/D2 receptor ligand (e.g., Compound of Formula I, optionally in deuterated form), and/or subsequent to the initiation of said treatment, and optionally comparing the pre-treatment and one or more post-treatment results thereof to quantify the effectiveness of the treatment in the patient and/or to adjust the treatment regimen;

2.88 Method 2.87, wherein the biomarkers are selected from one or more of TNF-α, IFN-γ, IL-1 (IL-1α and/or IL-1β), IL-6, IL-8, IL-12, IL-15, IL-17, IL-18, CRP, SAA, Csf1, YKL-40, Nlrp3, Flt-1, ICAM-1, VCAM-1, E-selectin, P-selectin, Cldn5, Occludin, and ZO-1, soluble isoforms thereof (e.g., sICAM-1, sVCAM1, sP-selectin, sE-selectin), TNF-β, IFN-α, IL-4, and IL-10;

2.89 Method 2.87 or 2.88, wherein the one or more body fluids or tissues are selected from blood, plasma, serum, peripheral blood mononuclear cells (PBMC) (e.g., isolated from blood), urine, CSF, and/or CNS microglial cells (e.g., isolated from CSF), or brain biopsy tissue samples;

2.90 Any foregoing method, wherein the method further comprises the step of non-invasively testing the central nervous system of the patient for the presence and/or concentration of one or more biomarkers indicative of CNS inflammation or CNS inflammatory dysfunction prior to the initiation of treatment with the 5-HT$_{2A}$ or 5-HT$_{2A}$/D2 receptor ligand (e.g., Compound of Formula I, optionally in deuterated form), and/or subsequent to the initiation of said treatment, and optionally comparing the pre-treatment and one or more post-treatment results thereof to quantify the effectiveness of the treatment in the patient and/or to adjust the treatment regimen;

2.91 Method 2.90, wherein the biomarkers are selected from one or more of TNF-α, IFN-γ, IL-1 (IL-1α and/or IL-1β), IL-6, IL-12, IL-15, IL-17, IL-18, CRP, SAA, Csf1, YKL-40, Nlrp3, Flt-1, ICAM-1, VCAM-1, E-selectin, P-selectin, Cldn5, Occludin, and ZO-1, soluble isoforms thereof (e.g., sICAM-1, sVCAM1, sP-selectin, sE-selectin), TNF-β, IFN-α, IL-4, and IL-10;

2.92 Method 2.90 or 2.91, wherein the step comprises an imaging method, such as magnetic resonance imaging (MRI), positron emission tomography (PET), functional MRI (fMRI), to evaluate the presence and/or concentration of said biomarkers;

2.93 Any of Methods 2.90-2.92, wherein the method comprises the step of initiating, altering, or terminating, the treatment regimen (e.g., the selected 5-HT$_{2A}$ or 5-HT$_{2A}$/D2 receptor ligand, the dose thereof, the route of administration thereof, the frequency of administration thereof, the form of administration thereof, and/or the combination of the selected 5-HT$_{2A}$ or 5-HT$_{2A}$/D2 receptor ligand with any another therapeutic agent), based on the observed changes in the levels of one or more of said biomarkers;

2.94 Any foregoing method, wherein the patient has elevated levels of one or more biomarkers indicative of peripheral inflammation, e.g., selected from type-I interferons, including IFN-α, IFN-β, and/or IFN-δ, in the blood, plasma, serum, peripheral blood mononuclear cells (PBMC) (e.g., isolated from blood), or urine;

2.95 Method 2.94, wherein after treatment with the 5-HT$_{2A}$ or 5-HT$_{2A}$/D2 receptor ligand (e.g., Compound of Formula I, optionally in deuterated form), the patient has a reduced level of the one or more biomarkers indicative of peripheral inflammation, e.g., selected type-I interferons, including IFN-α, IFN-β, and/or IFN-δ, in the blood, plasma, serum, peripheral blood mononuclear cells (PBMC) (e.g., isolated from blood), or urine, compared to a pre-treatment baseline, e.g., within 28 days of the initiation of treatment;

2.96 Method 2.95, wherein the patient has at least a 5%, 10%, 15%, 20%, or 25%, 30%, 35%, 40%, 45%, or 50%, reduction in the level of the one or more biomarkers indicative of peripheral inflammation, e.g., within 28 days of the initiation of treatment;

2.97 Any foregoing method, wherein the patient has peripheral serotonin deficiency, e.g., reduced concentration in the plasma and/or platelets, for example, a plasma serotonin concentration less than 3000 nM, less than 2500 nM, less than 2000 nM, less than 1800 nM, less than 1600 nM, less than 1400 nM, less than 1200 nM, less than 1000 nM, less than 800 nM, less than 600 nM, less than 500 nM, less than 400 nM, less than 300 nM, or less than 250 nM;

2.98 Method 2.97, wherein after treatment with the 5-HT$_{2A}$ or 5-HT$_{2A}$/D2 receptor ligand (e.g., Compound of Formula I, optionally in deuterated form), the patient has recovered from peripheral serotonin deficiency, e.g., a normal concentration in the plasma and/or platelets, for example, a plasma serotonin concentration of greater than 500 nM, or 500 to 3000 nM, or 1000 to 3000 nM, or 1500 to 3000 nM, or 2000 to 3000 nM, or greater than 3000 nM nM, less than 800 nM, less than 600 nM, less than 500 nM, less than 400 nM, less than 300 nM, or less than 250 nM;

2.99 Method 2.97 or 2.98, wherein the psychiatric disorder or psychiatric symptoms are caused by, or thought to be caused by, peripheral serotonin deficiency, e.g., due to reduced plasma serotonin concentration and/or reduced vagal nerve afferent sensory activity (e.g., due to reduced serotonin-mediated 5-HT$_3$ signaling)

2.100 Any foregoing method, wherein the patient is suffering from a post-viral syndrome, e.g., Long COVID;

2.101 Any foregoing method, wherein the patient has thrombocytopenia or platelet hypercoagulability (e.g., as shown by reduced prothrombin time and/or partial thromboplastin time), 2.102 Any foregoing method, wherein the method further comprises the step of obtaining a tissue sample from the patient and testing the tissue sample for the level of any one or more of: (a) serum antibody or antigen for one or more of: Herpes simplex Virus 1, Herpes Simplex Virus 2, West Nile Virus, Nipah Virus, human immunodeficiency virus, rabies virus, Epstein-Barr Virus, cytomegalovirus, coronavirus (e.g., MERS-CoV, SARS-CoV, SARS-Cov2, or influenza virus (e.g., influenza A, such as H1N1, H2N2, H3N2, H5N1, H7N7); (b) serum autoantibodies against the NMDA receptor, the AMPA receptor, the voltage-gated potassium, channel (VGKC), the LGL1 protein, the GABA receptor, the glycine receptor, the glutamate receptor, or the CASPR2 receptor; (c) biomarkers selected from TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1; (d) biomarkers selected from ICAM-1, VCAM-1, E-selectin, P-selectin, or soluble isoforms thereof (e.g., sICAM-1, sVCAM1, sP-selectin, sE-selectin), Cldn5, Occludin, and/or ZO-1; (e) biomarkers selected from TNF-β, IFN-α, IL-4, and IL-10; (f) type-I interferons, including IFN-α, IFN-β, and/or IFN-δ; (f) serotonin; and (g) platelet count, prothrombin time, and/or partial thromboplastin time;

2.103 Method 2.102, wherein the tissue sample is selected from blood, plasma, serum, peripheral blood mononuclear cells (PBMC) (e.g., isolated from blood), urine, CSF, and/or CNS microglial cells (e.g., isolated from CSF);

2.104 Method 2.102 or 2.103, wherein the method further comprises adjusting the course of treatment based on the results of one more of said tissue sample measurements, optionally wherein said tissue sample measurements are taken at one or more times during the course of therapy, e.g., for comparison to earlier measurements or measurements taken before initiating therapy.

In another aspect, the disclosure provides a 5-HT$_{2A}$ or 5-HT$_{2A}$/D2 receptor ligand, e.g., a compound of Formula I, as hereinbefore described, for example lumateperone, in free base or salt form, optionally in deuterated form, for use in protecting or reinforcing the blood-brain barrier, e.g., for use in any of Methods 2, et seq.

In another aspect, the disclosure provides the use of a 5-HT$_{2A}$ or 5-HT$_{2A}$/D2 receptor ligand, e.g., a compound of Formula I, as hereinbefore described, for example lumateperone, in free base or salt form, optionally in deuterated form, in in the manufacture of a medicament for protecting or reinforcing the blood-brain barrier, e.g., for any of Methods 2, et seq.

In a particular embodiment, the present disclosure provides a method (Method 3) for the treatment of psychiatric disorders in a patient in need thereof, wherein the patient has elevated levels of pro-inflammatory cytokines in the CNS (e.g., in the cerebrospinal fluid), such as TNF-α, IFN-γ, IL-1 (IL-1α and/or IL-1β), IL-6, IL-8, IL-12, IL-15, IL-17, IL-18, or elevated levels of C-reactive protein (CRP), or Csf1, and/or depressed levels of anti-inflammatory cytokines in the CNS (e.g., in the cerebrospinal fluid), such as TNF-β, IFN-α, IL-4, and IL-10, the method comprising administering a therapeutically effective amount of a 5-HT$_{2A}$ or 5-HT$_{2A}$/D2 receptor ligand to the patient, for example, a compound of Formula I:

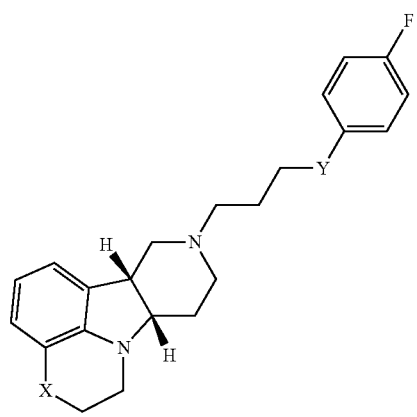

Formula I wherein:
X is —N(H)—, —N(CH$_3$)— or —O—;
Y is —C(=O)—, —C(H)(OH)— or —C(H)(OR$_1$)—;
R$_1$ is —C(O)—C$_{1-21}$alkyl (e.g., —C(O)—C$_{1-5}$alkyl, —C(O)—C$_{6-15}$alkyl or —C(O)—C$_{16-21}$alkyl), preferably said alkyl is a straight chain, optionally saturated or unsaturated and optionally substituted with one or more hydroxy or C$_{1-22}$alkoxy (e.g., ethoxy) groups, for example R$_1$ is —C(O)—C$_6$alkyl, —C(O)—C$_7$alkyl, —C(O)—C$_9$alkyl, —C(O)—C$_{11}$alkyl, —C(O)—C$_{13}$alkyl or —C(O)—C$_{15}$alkyl, wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand, optionally in deuterated form,
in free base, pharmaceutically acceptable salt, or prodrug form. For example, Method 3 may be as follows:

3.1. Method 3, wherein X in the compound of Formula I is —N(H)—, —N(CH$_3$)— or —O—;

3.2. Method 3 or 3.1, wherein X in the compound of Formula I is —N(H);

3.3. Method 3 or 3.1, wherein X in the compound of Formula I is —N(CH$_3$)—;

3.4. Method 3 or 3.1, wherein X in the compound of Formula I is —O—;

3.5. Method 3 or any of formulae 3.1-3.4, wherein Y in the compound of Formula I is —C(=O)—, —C(H)(OH)— or —C(H)(OR₁)—;

3.6. Method 3 or any of formulae 3.1-3.4, wherein Y in the compound of Formula I is —C(=O)—;

3.7. Method 3 or any of formulae 3.1-3.4, wherein Y in the compound of Formula I is —C(H)(OH)—;

3.8. Method 3 or any of formulae 3.1-3.4, wherein Y in the compound of Formula I is —C(H)(OR₁)—;

3.9. Method 3, or any of 3.1-3.5 or 3.8, wherein R₁ in the compound of Formula I is —C(O)—C₁₋₂₁alkyl (e.g., —C(O)—C₁₋₅alkyl, —C(O)—C₆₋₁₅alkyl or —C(O)—C₁₆₋₂₁alkyl), preferably said alkyl is a straight chain, optionally saturated or unsaturated and optionally substituted with one or more hydroxy or C₁₋₂₂alkoxy (e.g., ethoxy) groups, for example R₁ is —C(O)—C₆alkyl, —C(O)—C₇alkyl, —C(O)—C₉alkyl, —C(O)—C₁₁alkyl, —C(O)—C₁₃alkyl or —C(O)—C₁₅alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand; e.g., wherein R₁ in the compound of Formula I is —C(O)—C₆₋₁₅alkyl, e.g., —C(O)—C₉alkyl; or wherein R₁ in the compound of Formula I is —C(O)—C₁₋₅alkyl, e.g., —C(O)—C₃alkyl;

3.10. Method 3 or any of 3.1-3.5, or 3.71.7, wherein the Compound of Formula I is:

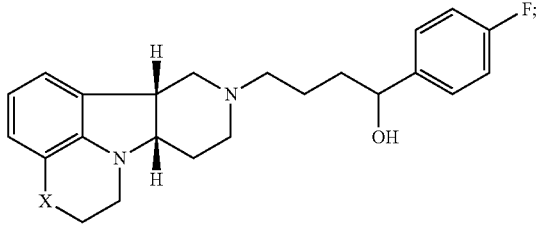

3.11. Method 3 or any of 3.1-3.5 or 3.7, wherein the Compound of Formula I is:

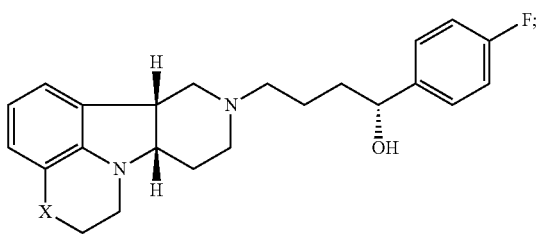

3.12. Method 3, or any of 3.1, 3.3, 3.5, or 3.6, wherein the Compound of Formula I is lumateperone:

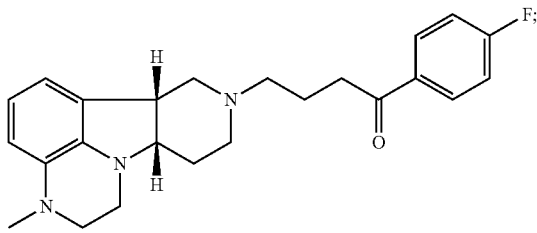 [SMILES: CN1CCN2c3c(cccc31)[C@@H]1CN(CCCC(=O)c3ccc(F)cc3)CC[C@@H]12]

3.13. Method 3, or any of 3.1-1.12, e.g., Method 1.12, wherein the Compound of Formula I is in the form of a pharmaceutically acceptable salt, e.g., a tosylate salt;

3.14. Method 3, or any of 3.1-1.12, e.g., Method 1.12, wherein the Compound of Formula I is in the form of the free base;

3.15. Method 3 or any of 3.1-1.14 wherein the Compound of Formula I is in deuterated form, e.g., wherein the deuterium:protium ratio for a specified carbon-bound hydrogen atom is significantly higher, e.g., at least 2×, for example at least 10× higher, than the natural isotope ratios;

3.16. Method 3.15, wherein the Compound of Formula I is a deuterated form of lumateperone, for example, selected from:

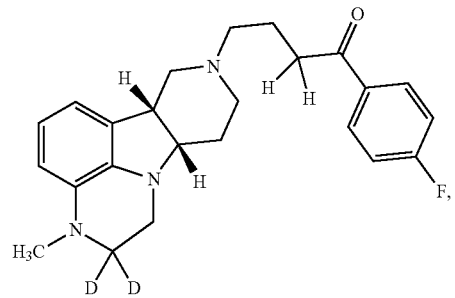

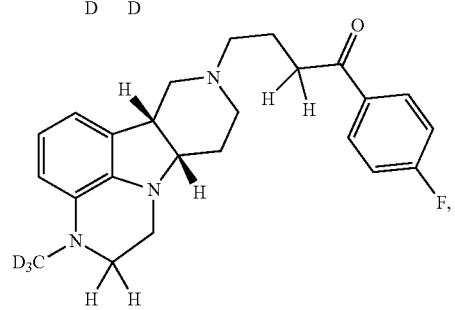

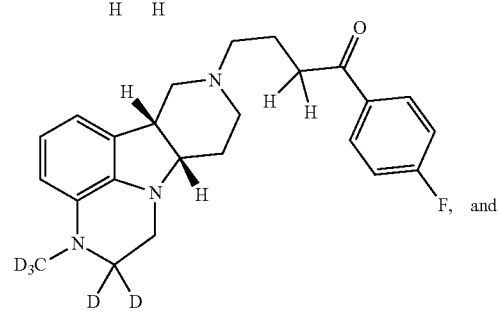

-continued

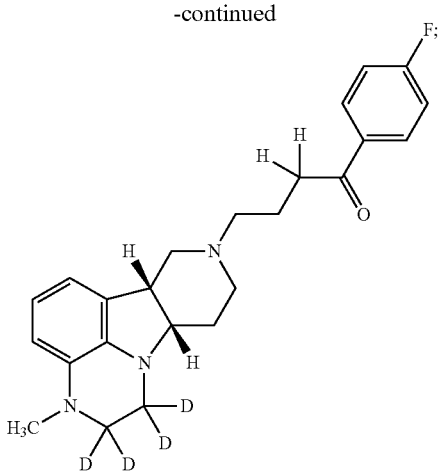

wherein D represents a hydrogen position with substantially greater than natural deuterium incorporation (i.e., substantially greater than 0.0156%), e.g., greater than 60%, or greater than 70%, or greater than 80%, or greater than 90% or greater than 95%, or greater than 96%, or greater than 97%, or greater than 98%, or greater than 99%, in free base or pharmaceutically acceptable salt form, e.g., tosylate salt form;

3.17. Any foregoing method, wherein the 5-HT$_{2A}$ or 5-HT$_{2A}$/D2 receptor ligand is a compound of Formula I in free base or pharmaceutically acceptable salt form, e.g., tosylate salt form, administered in a daily dose equivalent to 1 to 100 mg of free base, e.g., in an amount equivalent to 1 to 75 mg, or 1 to 60 mg, or 1 to 40 mg, or 1 to 20 mg, or 1 to 10 mg, of free base;

3.18. Method 3.17, wherein the method comprises once daily administration of a unit dosage for oral administration, for example a tablet or capsule, comprising the compound of Formula I in free base or pharmaceutically acceptable salt form, e.g., in tosylate salt form, in an amount equivalent 1 to 100 mg of free base, e.g., in an amount equivalent to 1 to 75 mg, or 1 to 60 mg, or 1 to 40 mg, or 1 to 30 mg, or 1 to 20 mg, or 1 to 10 mg, or 1 to 5 mg, or 40 to 60 mg, or 20 to 40 mg, or 10 to 20 mg, or about 60 mg, or about 40 mg, or about 30 mg, or about 20 mg, or about 10 mg, or about 5 mg, of free base, and a pharmaceutically acceptable diluent or carrier;

3.19. Method 3.17, wherein the method comprises once daily administration of a unit dosage for oral transmucosal administration, e.g., a sublingual or buccal orally disintegrating tablet, wafer, or film, comprising the compound of Formula I in free base or pharmaceutically acceptable salt form, e.g., in tosylate salt form, in an amount equivalent to 0.5 to 30 mg of free base, e.g., in an amount equivalent to 1 to 30 mg, or 1 to 20 mg, or 1 to 15 mg, or 1 to 10 mg, or 20 to 30 mg, or 10 to 20 mg, or about 5 mg, or about 10 mg, or about 15 mg, or about 20 mg, of free base, and a pharmaceutically acceptable diluent or carrier;

3.20. Any foregoing method wherein the condition to be treated is alleviated within one week, e.g., within three days, e.g., within one day;

3.21. Any foregoing method, wherein the patient has or is diagnosed with a viral, bacterial, or autoimmune encephalitis;

3.22. Method 3.21, wherein the patient's psychiatric disorder is caused by, or is suspected to be caused by, the viral, bacterial, or autoimmune encephalitis;

3.23. Method 3.21 or 3.22, wherein the encephalitis is viral encephalitis;

3.24. Method 3.23, wherein the viral encephalitis is caused by, or suspected to be caused by, Herpes simplex Virus 1, Herpes Simplex Virus 2, West Nile Virus, Nipah Virus, human immunodeficiency virus, rabies virus, Epstein-Barr Virus, cytomegalovirus, coronavirus (e.g., MERS-CoV, SARS-CoV, SARS-Cov2), or influenza virus (e.g., influenza A, such as H1N1, H2N2, H3N2, H5N1, H7N7);

3.25. Method 3.21, 3.22 or 3.23, wherein the viral encephalitis is acute viral encephalitis;

3.26. Method 3.21, wherein the encephalitis is bacterial encephalitis;

3.27. Method 3.26, wherein the encephalitis is caused by, or believed to be caused by, toxoplasmosis, *rickettsia, mycoplasma, Borrelia* (e.g., Lyme disease), or malaria;

3.28. Method 3.21, wherein the encephalitis is autoimmune encephalitis;

3.29. Method 3.28, wherein the encephalitis is caused by, or believed to be caused by, autoantibodies against the NMDA receptor, the AMPA receptor, the voltage-gated potassium, channel (VGKC), the LGL1 protein, the GABA receptor, the glycine receptor, the glutamate receptor, or the CASPR2 receptor;

3.30. Any of Methods 3.21-3.29, wherein the patient has no prior history of psychiatric disorders or psychiatric symptoms before the diagnosis of encephalitis;

3.31. Any of Methods 3.21-3.29, wherein the patient has no prior history of one or more of depression, anxiety, psychosis, post-traumatic stress-disorder, anhedonia, dementia, memory loss, impairment of executive function, difficulty concentrating, seizures, difficulty sleeping, hallucination, or change in personality, before the diagnosis of encephalitis;

3.32. Any foregoing method, wherein the psychiatric disorder is depression (e.g., acute depression, depression of MDD, depression of bipolar disorder), anxiety, (e.g., acute anxiety), psychosis (e.g., schizophrenia), post-traumatic stress-disorder, anhedonia, memory loss, impairment of executive functioning, difficulty concentrating, seizures, difficulty sleeping, hallucination, change in personality, or any combination thereof;

3.33. Any foregoing method wherein the psychiatric disorder is depression (e.g., acute depression, depression of MDD, depression of bipolar disorder);

3.34. Any foregoing method wherein the psychiatric disorder is anxiety (e.g., acute anxiety);

3.35. Any foregoing method wherein the psychiatric disorder is anhedonia;

3.36. Any foregoing method wherein the patient is diagnosed as having suicidal ideation and/or suicidal tendencies;

3.37. Any foregoing method wherein the 5-HT$_{2A}$ or 5-HT$_{2A}$/D2 receptor ligand is administered in combination (e.g., a fixed combination in a unit dosage form, or a free combination administered sequentially or simultaneously or within a 24-hour period) with a therapeutically effective amount of an anxiolytic or antidepressant agent;

3.38. Method 3.37, wherein the anxiolytic or antidepressant agent is selected from one or more compounds in free base or pharmaceutically acceptable salt form, selected from selective serotonin reuptake inhibitors (SSRIs), serotonin-norepinephrine reuptake inhibitors (SNRIs), tricyclic antidepressants (TCAs), and atypical antipsychotics, e.g., one or more compounds in free base or pharmaceutically acceptable salt form, selected from:
- (a) Selective serotonin reuptake inhibitors (SSRIs), e.g., Citalopram (Celexa), Escitalopram (Lexapro, Cipralex), Paroxetine (Paxil, Seroxat), Fluoxetine (Prozac), Fluvoxamine (Luvox) Sertraline (Zoloft, Lustral);
- (b) Serotonin-norepinephrine reuptake inhibitors (SNRIs), e.g., Desvenlafaxine (Pristiq), Duloxetine (Cymbalta), Levomilnacipran (Fetzima), Milnacipran (Ixel, Savella), Tofenacin (Elamol, Tofacine), Venlafaxine (Effexor);
- (c) Tricyclic antidepressants (TCAs), e.g., Amitriptyline (Elavil, Endep), Amitriptylinoxide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Nitroxazepine (Sintamil), Nortriptyline (Pamelor, Aventyl), Noxiptiline (Agedal, Elronon, Nogedal), Pipofezine (Azafen/Azaphen), Protriptyline (Vivactil), Trimipramine (Surmontil);
- (d) Benzodiazepines, e.g., selected from 2-keto compounds (e.g., clorazepate, diazepam, flurazepam, halazepam, prazepam); 3-hydroxy compounds (lorazepam, lormetazepam, oxazepam, temazepam); 7-nitro compounds (e.g., clonazepam, flunitrazepam, nimetazepam, nitrazepam); triazolo compounds (e.g., adinazolam, alprazolam, estazolam, triazolam); and imidazo compounds (climazolam, loprazolam, midazolam);

3.39. Any foregoing method, wherein the 5-HT$_{2A}$ or 5-HT$_{2A}$/D2 receptor ligand, e.g., the compound of Formula I is administered intra-nasally, subcutaneously, intramuscularly, intravenously, orally, sub-lingually, intra-peritoneally, or buccally, such as an oral rapidly dissolving tablet, wafer, or film, which dissolves in the oral cavity for transmucosal absorption;

3.40. Any foregoing method, wherein the method further comprises the concurrent administration of an antidepressant agent (e.g., selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), a serotonin receptor antagonist, or any combination thereof), e.g., administered simultaneously, separately or sequentially;

3.41. Any foregoing method, wherein the method further comprises the concurrent administration of an NMDA receptor antagonist, for example, selected from ketamine (e.g., S-ketamine and/or R-ketamine), hydroxynorketamine, memantine, dextromethorphan, dextroallorphan, dextrorphan, amantadine, and agmatine, or any combination thereof, e.g., administered simultaneously, separately or sequentially;

3.42. Any foregoing method, wherein the method further comprises the concurrent administration of a NMDA receptor allosteric modulator, e.g., a NMDA receptor glycine-site modulator, such as rapastinel, nebostinel, apimostinel, D-cycloserine, or any combination thereof, e.g., administered simultaneously, separately or sequentially;

3.43. Any foregoing method, wherein the method provides the patient with an acute response to treatment with the therapeutic agent or agents (e.g., the 5-HT$_{2A}$ or 5-HT$_{2A}$/D2 receptor ligand, the Compound of Formula I, or the combination of the Compound or Formula I and the Compound of Formula II, and/or any additional antidepressant agents);

3.44. Method 3.43, wherein the patient shows an acute response to treatment within less than 3 weeks, for example, less than 2 weeks, or less than 1 week, or from 1 to 7 days, or 1 to 5 days, or 1 to 3 days, or 1 to 2 days, or about 1 day, or less than 2 days, or less than 1 day (e.g., 12-24 hours, 6-12 hours, or 3-6 hours);

3.45. Any foregoing method, wherein the patient has not responded to, or has not responded adequately to, or who suffers undesirable side effects from, treatment with another antidepressant agent, for example, any one or more of a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor, or a serotonin receptor antagonist;

3.46. Any foregoing method, wherein the psychiatric disorder is not associated with schizophrenia or dementia;

3.47. Any foregoing method, wherein the patient does not suffer from (or has not previously been diagnosed with) schizophrenia or dementia;

3.48. Any foregoing method, wherein the method protects or reinforces the blood-brain barrier;

3.49. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the 5-HT$_{2A}$ receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

3.50. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the D2 receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

3.51. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the D1 receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

3.52. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the serotonin transporter (SERT), e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said transporter (agonism or antagonism);

3.53. Any foregoing method, wherein the 5-$HT_{2A}$ or 5-$HT_{2A}$/D2 receptor ligand is lumateperone, in free base or pharmaceutically acceptable salt form, optionally in a deuterated form;

3.54. Any foregoing method, wherein the 5-$HT_{2A}$ or 5-$HT_{2A}$/D2 receptor ligand is lumateperone, in a tosylate salt form (e.g., monotosylate salt), optionally in a deuterated form, and optionally in crystalline or amorphous tosylate salt form;

3.55. Any foregoing method, wherein the 5-$HT_{2A}$ or 5-$HT_{2A}$/D2 receptor ligand is lumateperone, in free base form, optionally in a deuterated form;

3.56. Any foregoing method, wherein the 5-$HT_{2A}$ or 5-$HT_{2A}$/D2 receptor ligand is administered in the form of a long-acting injectable (LAI) composition, e.g., for intramuscular or subcutaneous injection;

3.57. Method 3.56, wherein the dose of the LAI composition is sufficient to provide the equivalent of a daily dose of 1 to 100 mg of free base, e.g., 1 to 75 mg, or 1 to 60 mg, or 1 to 40 mg, or 1 to 20 mg, or 1 to 10 mg, of free base, released over a period of time ranging from about 1 week to about 3 months, e.g., about 1 week to about 8 weeks, or about 1 week to about 6 weeks, or about 1 week to about 4 weeks, or about 1 week to about 3 weeks, or about 1 week to about 2 weeks;

3.58. Method 3.56 or 3.57, wherein the LAI composition comprises the compound of Formula I dissolved, dispersed, suspended, or encapsulated in a polymeric matrix;

3.59. Method 3.58, wherein the polymeric matrix comprises one or more biocompatible and biodegradable polymers as defined herein, e.g., poly(hydroxycarboxylic acids), poly(amino acids), cellulose polymers, modified cellulose polymers, polyamides, and polyesters;

3.60. Method 3.59, wherein the one or more polymers comprises polylactic acid, polyglycolic acid, polycitric acid, polymalic acid, poly-beta-hydroxybutyric acid, poly(lactic acid-glycolic acid) copolymer, 2-hydroxybutyric acid-glycolic acid copolymer, polylactic acid-polyethylene glycol copolymer, polyglycolic acid-polyethylene glycol copolymer, PEG-PLGA copolymer or block copolymer, poly(alkyl alpha-cyanoacrylate) such as poly(butyl cyanoacrylate) or poly(2-octyl cyanoacrylate), poly(ortho ester), polycarbonate, polyortho-carbonate, a polyamino acid, (for example poly-gamma.-L-alanine, poly-.gamma.-benzyl-L-glutamic acid or poly-y-methyl-L-glutamic acid), and/or hyaluronic acid ester;

3.61. Method 3.60, wherein the one or more polymers comprises polyortho esters (POE), polylactic acid, polyglycolic acid, polycitric acid, polymalic acid, or a poly(lactic acid-glycolic acid) copolymer;

3.62. Method 3.60, wherein the one or more polymers comprises a poly(lactic acid-glycolic acid) copolymer, e.g., poly-d,l-lactide-co-glycolide (PLGA), for example, a PLGA copolymer with a lactide-to-glycolide molar ratio of about 50:50 to 90:10, or 50:50 to 85:15, or 50:50 to 75:25, and/or a molecular weight of 5,000 to 500,000 Daltons, or 5,000 to 150,000 Daltons, or 20,000 to 200,000 Daltons, or 24,000 to 38,000 Daltons;

3.63. Any foregoing method, wherein the 5-$HT_{2A}$ or 5-$HT_{2A}$/D2 receptor ligand is administered as monotherapy, e.g., it is not administered concurrently or in conjunction with an anti-depressant, anti-psychotic, or anti-anxiety agent;

3.64. Any foregoing method, wherein the 5-$HT_{2A}$ or 5-$HT_{2A}$/D2 receptor ligand is administered without the direct supervision of a health care professional (e.g., the compound is self-administered by the patient);

3.65. Any foregoing method, wherein the method does not comprise supervision or observation of the patient by a health care professional during or after (e.g., within 2 hours after) administration of a dose of the 5-$HT_{2A}$ or 5-$HT_{2A}$/D2 receptor ligand;

3.66. Any foregoing method, wherein the method does not put the patient at risk for sedation, dissociation, abuse, misuse, or suicidal ideation;

3.67. Any foregoing method, wherein the method does not result in hypertension (e.g., systolic and/or diastolic hypertension) within four hours after administration of a dose of the 5-$HT_{2A}$ or 5-$HT_{2A}$/D2 receptor ligand, e.g., an increase of more than 10 mm Hg, or more than 20 mm Hg, or more than 30 mm Hg, or more than 40 mm Hg, in systolic and/or diastolic blood pressure within 30 minutes to 4 hours after said dose;

3.68. Any foregoing method, wherein the method does not result in cognitive decline;

3.69. Any foregoing method, wherein the patient has (e.g., has been diagnosed with), or is at risk of, aneurysmal vascular disease (e.g., thoracic aorta, abdominal aorta, intracranial, or peripheral arterial aneurysms), arteriovenous malformation or intracerebral hemorrhage;

3.70. Any foregoing method, wherein the patient is under concurrent treatment with an oral antidepressant selected from duloxetine, escitalopram, sertraline, or venlafaxine;

3.71. Any foregoing method, wherein the patient is not under concurrent treatment with an oral antidepressant selected from duloxetine, escitalopram, sertraline, or venlafaxine;

3.72. Any foregoing method, wherein the patient is unresponsive to, or cannot be treated with ketamine (e.g., S-ketamine), e.g., because it is contraindicated in said patient;

3.73. Any foregoing method, wherein the 5-$HT_{2A}$ or 5-$HT_{2A}$/D2 receptor ligand is administered to the patient concurrently with a PDE1 (cyclic nucleoside phosphodiesterase 1) inhibitor (e.g., administered simultaneously, separately, or sequentially), in free base or pharmaceutically acceptable salt form;

3.74. Method 3.73, wherein the PDE1 inhibitor is a compound according to Formula II:

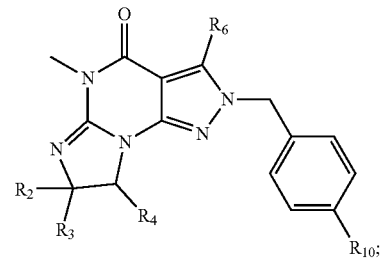

wherein R₂ is H and R₃ and R₄ together form a tri- or tetra-methylene bridge [pref. with the carbons carrying R₃ and R₄ having the R and S configuration respectively]; or R₂ and R₃ are each methyl and R₄ is H; or R₂ and R₄ are H and R₃ is isopropyl [pref. the carbon carrying R₃ having the R configuration];

R₆ is (optionally halo-substituted) phenylamino or (optionally halo-substituted) benzylamino;

R₁₀ is (optionally halo-substituted) phenyl, (optionally halo-substituted) pyridyl (for example 3-fluoropyrid-2-yl), thiadiazolyl (e.g., 1,2,3-thiadiazol-4-yl), or C₁₋₆alkylcarbonyl (e.g., methylcarbonyl);

in free base or pharmaceutically acceptable salt form;

3.75. Method 3.74, wherein, in the Compound of Formula II, R₆ is phenylamino or 4-fluorophenylamino;

3.76. Method 3.74, wherein, in the Compound of Formula II, R₁₀ is 3-fluoropyrid-2-yl or methylcarbonyl;

3.77. Method 3.74, wherein, in the Compound of Formula II, R₆ is phenylamino or 4-fluorophenylamino and R₁₀ is 3-fluoropyrid-2-yl or methylcarbonyl;

3.78. Any Methods 3.74-3.77, wherein the Compound of Formula II is

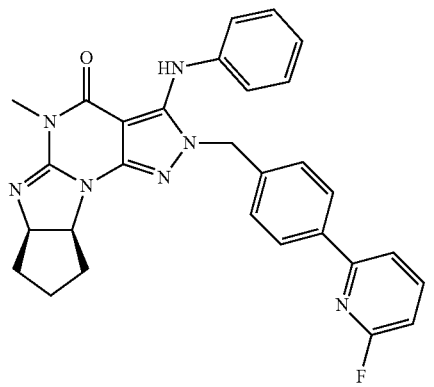

or

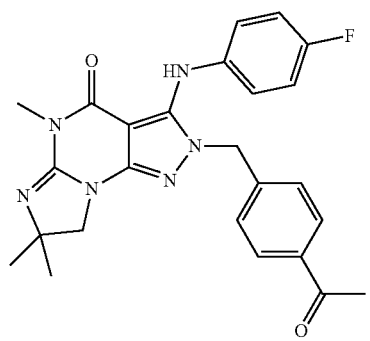

in free base or pharmaceutically acceptable salt form;

3.79. Method 3.77, wherein the Compound of Formula II is in the form of the monophosphate salt;

3.80. Any of Methods 3.74-3.79, wherein the Compound of Formula I is:

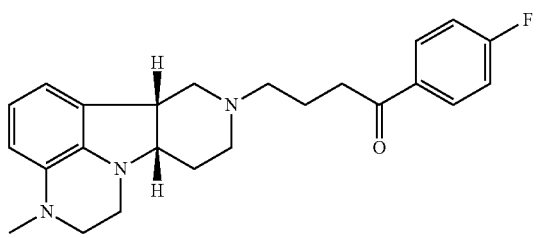 [SMILES: CN1CCN2c3c(cccc31)[C@@H]1CN(CCCC(=O)c3ccc(F)cc3)CC[C@@H]12]

in free base or pharmaceutically acceptable salt form, e.g., tosylate salt form, optionally in a deuterated form; and the Compound of Formula II is:

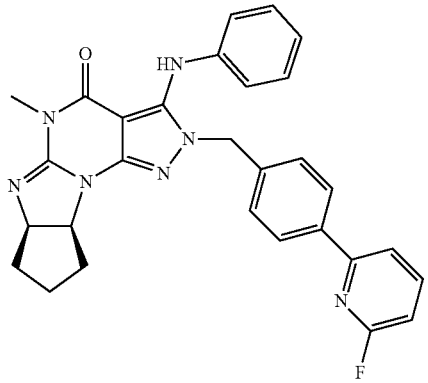 [SMILES: CN1C(=O)c2c(nn(Cc3ccc(-c4cccc(F)n4)cc3)c2Nc2ccccc2)N2C1=N[C@@H]1CCC[C@@H]12]

in free base or pharmaceutically acceptable salt form, e.g., monophosphate salt form;

3.81 Any of Methods 3.74-3.80, comprising administration of a pharmaceutical composition comprising therapeutically effective amounts of both a Compound of Formula I and a Compound of Formula II;

3.82 Any preceding method, wherein the 5-HT₂ₐ or 5-HT₂ₐ/D2 receptor ligand is a compound of Formula I, in free base or pharmaceutically acceptable salt from, optionally in deuterated form, and wherein the compound is administered in the form of a long-acting injectable (LAI) composition comprising the compound of Formula I dissolved or dispersed or in a pharmaceutically acceptable carrier and a polymeric matrix comprising polymers selected from polyortho esters (POE), polylactic acid, polyglycolic acid, polycitric acid, polymalic acid, or a poly(lactic acid-glycolic acid) copolymer;

3.83 Method 3.82, wherein the pharmaceutically acceptable carrier comprises water (e.g., an aqueous buffer) and/or an organic solvent (e.g., a water-miscible organic solvent);

3.84 Method 3.82 or 3.83, wherein the polymers comprise a polylactic acid and/or a polyglycolic acid polymer;

3.85 Method 3.82 or 3.83, wherein the polymers comprise a poly(lactic acid-glycolic acid) copolymer, e.g., poly-d,l-lactide-co-glycolide (PLGA), for example, a PLGA copolymer with a lactide-to-glycolide molar ratio of about 50:50 to 90:10, or 50:50 to 85:15, or 50:50 to 75:25, and/or a molecular weight of 5,000 to 500,000 Daltons, or 5,000 to 150,000 Daltons, or 20,000 to 200,000 Daltons, or 24,000 to 38,000 Daltons;

3.86 Any of Methods 3.82-3.85, wherein the LAI composition is administered by, or formulated for administration by, intramuscular or subcutaneous injection;

3.87 Method 3, or any of 3.1-3.86, wherein the patient has no prior history of depression;

3.88 Method 3, or any of 3.1-3.87, wherein the patient shows evidence of cerebral damage or cerebral disease on magnetic resonance imaging (MRI) prior to administration of the 5-$HT_{2A}$ or 5-$HT_{2A}$/D2 receptor ligand;

3.89 Method 3, or any of 3.1-3.88, wherein the patient has a positive serum antibody or antigen test for one or more of Herpes simplex Virus 1, Herpes Simplex Virus 2, West Nile Virus, Nipah Virus, human immunodeficiency virus, rabies virus, Epstein-Barr Virus, cytomegalovirus, coronavirus (e.g., MERS-CoV, SARS-CoV, SARS-Cov2, or influenza virus (e.g., influenza A, such as H1N1, H2N2, H3N2, H5N1, H7N7), prior to administration of the 5-$HT_{2A}$ or 5-$HT_{2A}$/D2 receptor ligand;

3.90 Method 3, or any of 3.1-3.89, wherein the patient has a positive serum antibody test for autoantibodies against the NMDA receptor, the AMPA receptor, the voltage-gated potassium, channel (VGKC), the LGL1 protein, the GABA receptor, the glycine receptor, the glutamate receptor, or the CASPR2 receptor;

3.91 Any foregoing method, wherein the patient has elevated levels of one or more biomarkers indicative of CNS inflammation, e.g., selected from TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1, in the blood, plasma, serum, peripheral blood mononuclear cells (PBMC) (e.g., isolated from blood), urine, CSF, and/or CNS microglial cells (e.g., isolated from CSF);

3.92 Any foregoing method, wherein the patient has changes in levels of one or more biomarkers indicative of CNS inflammation and/or loss of BBB integrity, e.g., increased levels of ICAM-1, VCAM-1, E-selectin, P-selectin, or soluble isoforms thereof (e.g., sICAM-1, sVCAM1, sP-selectin, sE-selectin), or reduced levels of Cldn5, Occludin, and/or ZO-1, in the serum or CSF;

3.93 Any foregoing method, wherein the patient has depressed levels of one or more anti-inflammatory biomarkers indicative of CNS inflammatory dysfunction, e.g., TNF-β, IFN-α, IL-4, and IL-10, in the blood, plasma, serum, peripheral blood mononuclear cells (PBMC) (e.g., isolated from blood), urine, CSF, and/or CNS microglial cells (e.g., isolated from CSF);

3.94 Any foregoing method, wherein after treatment with the 5-$HT_{2A}$ or 5-$HT_{2A}$/D2 receptor ligand (e.g., Compound of Formula I, optionally in deuterated form), the patient has a reduced level of one or more biomarkers indicative of CNS inflammation, e.g., TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1, in the blood, plasma, serum, peripheral blood mononuclear cells (PBMC) (e.g., isolated from blood), urine, CSF, and/or CNS microglial cells (e.g., isolated from CSF), compared to a pre-treatment baseline, e.g., within 28 days of the initiation of treatment;

3.95 Method 3.94, wherein the patient has at least a 5%, 10%, 15%, 20%, or 25%, 30%, 35%, 40%, 45%, or 50%, reduction in the level of the one or more biomarkers indicative of CNS inflammation, e.g., within 28 days of the initiation of treatment;

3.96 Any foregoing method, wherein after treatment with the 5-$HT_{2A}$ or 5-$HT_{2A}$/D2 receptor ligand (e.g., Compound of Formula I, optionally in deuterated form), the patient has favorable changes in levels of one or more biomarkers indicative of CNS inflammation and/or loss of BBB integrity, e.g., increased levels of ICAM-1, VCAM-1, E-selectin, P-selectin, or soluble isoforms thereof (e.g., sICAM-1, sVCAM1, sP-selectin, sE-selectin), or reduced levels of Cldn5, Occludin, and/or ZO-1, in the serum or CSF, compared to a pre-treatment baseline, e.g., within 28 days of the initiation of treatment;

3.97 Method 3.96, wherein the patient has at least a 5%, 10%, 15%, 20%, 25%, 30%, 35%, 40%, 45%, or 50%, reduction or increase in the level of the one or more biomarkers indicative of CNS inflammation, e.g., within 28 days of the initiation of treatment;

3.98 Any foregoing method, wherein after treatment with the 5-$HT_{2A}$ or 5-$HT_{2A}$/D2 receptor ligand (e.g., Compound of Formula I, optionally in deuterated form), the patient has an increased level of one or more anti-inflammatory biomarkers indicative of CNS inflammatory dysfunction, e.g., TNF-β, IFN-α, IL-4, and IL-10, in the blood, plasma, serum, peripheral blood mononuclear cells (PBMC) (e.g., isolated from blood), urine, CSF, and/or CNS microglial cells (e.g., isolated from CSF), compared to a pre-treatment baseline, e.g., within 28 days of the initiation of treatment;

3.99 Method 3.98, wherein the patient has an increase of at least a 5%, 10%, 15%, 20%, 25%, 30%, 35%, 40%, 45%, or 50%, in the levels of the one or more anti-inflammatory biomarkers indicative CNS inflammatory dysfunction, e.g., within 28 days of the initiation of treatment, e.g., within 28 days of the initiation of treatment;

3.100 Any foregoing method, wherein the method further comprises the step of testing one or more body fluids or tissues from the patient for the presence and/or concentration of one or more biomarkers indicative of CNS inflammation or CNS inflammatory dysfunction prior to the initiation of treatment with the 5-$HT_{2A}$ or 5-$HT_{2A}$/D2 receptor ligand (e.g., Compound of Formula, optionally in deuterated form), and/or subsequent to the initiation of said treatment, and optionally comparing the pre-treatment and one or more post-treatment results thereof to quantify the effectiveness of the treatment in the patient and/or to adjust the treatment regimen;

3.101 Method 3.100, wherein the biomarkers are selected from one or more of TNF-α, IFN-γ, IL-1 (IL-1α and/or IL-1β), IL-6, IL-8, IL-12, IL-15, IL-17, IL-18, CRP, SAA, Csf1, YKL-40, Nlrp3, Flt-1, ICAM-1, VCAM-1, E-selectin, P-selectin, Cldn5, Occludin, and ZO-1, soluble isoforms thereof (e.g., sICAM-1, sVCAM1, sP-selectin, sE-selectin), TNF-β, IFN-α, IL-4, and IL-10;

3.102 Method 3.100 or 3.101, wherein the one or more body fluids or tissues are selected from blood, plasma, serum, peripheral blood mononuclear cells (PBMC) (e.g., isolated from blood), urine, CSF, and/or CNS microglial cells (e.g., isolated from CSF), or brain biopsy tissue samples;

3.103 Any foregoing method, wherein the method further comprises the step of non-invasively testing the central nervous system of the patient for the presence and/or concentration of one or more biomarkers indicative of CNS inflammation or CNS inflammatory dysfunction prior to the initiation of treatment with the 5-HT$_{2A}$ or 5-HT$_{2A}$/D2 receptor ligand (e.g., Compound of Formula I, optionally in deuterated form), and/or subsequent to the initiation of said treatment, and optionally comparing the pre-treatment and one or more post-treatment results thereof to quantify the effectiveness of the treatment in the patient and/or to adjust the treatment regimen;

3.104 Method 3.103, wherein the biomarkers are selected from one or more of TNF-α, IFN-γ, IL-1 (IL-1α and/or IL-1β), IL-6, IL-12, IL-15, IL-17, IL-18, CRP, SAA, Csf1, YKL-40, Nlrp3, Flt-1, ICAM-1, VCAM-1, E-selectin, P-selectin, Cldn5, Occludin, and ZO-1, soluble isoforms thereof (e.g., sICAM-1, sVCAM1, sP-selectin, sE-selectin), TNF-β, IFN-α, IL-4, and IL-10;

3.105 Method 3.103 or 3.104, wherein the step comprises an imaging method, such as magnetic resonance imaging (MRI), positron emission tomography (PET), functional MRI (fMRI), to evaluate the presence and/or concentration of said biomarkers;

3.106 Any of Methods 3.100-3.105, wherein the method comprises the step of initiating, altering, or terminating, the treatment regimen (e.g., the selected 5-HT$_{2A}$ or 5-HT$_{2A}$/D2 receptor ligand, the dose thereof, the route of administration thereof, the frequency of administration thereof, the form of administration thereof, and/or the combination of the selected 5-HT$_{2A}$ or 5-HT$_{2A}$/D2 receptor ligand with any another therapeutic agent), based on the observed changes in the levels of one or more of said biomarkers;

3.107 Any foregoing method, wherein the patient has elevated levels of one or more biomarkers indicative of peripheral inflammation, e.g., selected from type-I interferons, including IFN-α, IFN-β, and/or IFN-δ, in the blood, plasma, serum, peripheral blood mononuclear cells (PBMC) (e.g., isolated from blood), or urine;

3.108 Method 3.107, wherein after treatment with the 5-HT$_{2A}$ or 5-HT$_{2A}$/D2 receptor ligand (e.g., Compound of Formula I, optionally in deuterated form), the patient has a reduced level of the one or more biomarkers indicative of peripheral inflammation, e.g., selected type-I interferons, including IFN-α, IFN-β, and/or IFN-δ, in the blood, plasma, serum, peripheral blood mononuclear cells (PBMC) (e.g., isolated from blood), or urine, compared to a pre-treatment baseline, e.g., within 28 days of the initiation of treatment;

3.109 Method 3.108, wherein the patient has at least a 5%, 10%, 15%, 20%, or 25%, 30%, 35%, 40%, 45%, or 50%, reduction in the level of the one or more biomarkers indicative of peripheral inflammation, e.g., within 28 days of the initiation of treatment;

3.110 Any foregoing method, wherein the patient has peripheral serotonin deficiency, e.g., reduced concentration in the plasma and/or platelets, for example, a plasma serotonin concentration less than 3000 nM, less than 2500 nM, less than 2000 nM, less than 1800 nM, less than 1600 nM, less than 1400 nM, less than 1200 nM, less than 1000 nM, less than 800 nM, less than 600 nM, less than 500 nM, less than 400 nM, less than 300 nM, or less than 250 nM;

3.111 Method 3.110, wherein after treatment with the 5-HT$_{2A}$ or 5-HT$_{2A}$/D2 receptor ligand (e.g., Compound of Formula I, optionally in deuterated form), the patient has recovered from peripheral serotonin deficiency, e.g., a normal concentration in the plasma and/or platelets, for example, a plasma serotonin concentration of greater than 500 nM, or 500 to 3000 nM, or 1000 to 3000 nM, or 1500 to 3000 nM, or 2000 to 3000 nM, or greater than 3000 nM nM, less than 800 nM, less than 600 nM, less than 500 nM, less than 400 nM, less than 300 nM, or less than 250 nM;

3.112 Method 3.110 or 3.111, wherein the psychiatric disorder or psychiatric symptoms are caused by, or thought to be caused by, peripheral serotonin deficiency, e.g., due to reduced plasma serotonin concentration and/or reduced vagal nerve afferent sensory activity (e.g., due to reduced serotonin-mediated 5-HT$_3$ signaling)

3.113 Any foregoing method, wherein the patient is suffering from a post-viral syndrome, e.g., Long COVID;

3.114 Any foregoing method, wherein the patient has thrombocytopenia or platelet hypercoagulability (e.g., as shown by reduced prothrombin time and/or partial thromboplastin time), 3.115 Any foregoing method, wherein the method further comprises the step of obtaining a tissue sample from the patient and testing the tissue sample for the level of any one or more of: (a) serum antibody or antigen for one or more of Herpes simplex Virus 1, Herpes Simplex Virus 2, West Nile Virus, Nipah Virus, human immunodeficiency virus, rabies virus, Epstein-Barr Virus, cytomegalovirus, coronavirus (e.g., MERS-CoV, SARS-CoV, SARS-Cov2, or influenza virus (e.g., influenza A, such as H1N1, H2N2, H3N2, H5N1, H7N7); (b) serum autoantibodies against the NMDA receptor, the AMPA receptor, the voltage-gated potassium, channel (VGKC), the LGL1 protein, the GABA receptor, the glycine receptor, the glutamate receptor, or the CASPR2 receptor; (c) biomarkers selected from TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1; (d) biomarkers selected from ICAM-1, VCAM-1, E-selectin, P-selectin, or soluble isoforms thereof (e.g., sICAM-1, sVCAM1, sP-selectin, sE-selectin), Cldn5, Occludin, and/or ZO-1; (e) biomarkers selected from TNF-β, IFN-α, IL-4, and IL-10; (f) type-I interferons, including IFN-α, IFN-β, and/or IFN-δ; (f) serotonin; and (g) platelet count, prothrombin time, and/or partial thromboplastin time;

3.116 Method 3.115, wherein the tissue sample is selected from blood, plasma, serum, peripheral blood mononuclear cells (PBMC) (e.g., isolated from blood), urine, CSF, and/or CNS microglial cells (e.g., isolated from CSF);

3.117 Method 3.115 or 3.116, wherein the method further comprises adjusting the course of treatment based on the results of one more of said tissue sample measurements, optionally wherein said tissue sample measurements are taken at one or more times during the course of therapy, e.g., for comparison to earlier measurements or measurements taken before initiating therapy.

In another aspect, the disclosure provides a 5-HT$_{2A}$ or 5-HT$_{2A}$/D2 receptor ligand, e.g., a compound of Formula I, as hereinbefore described, for example lumateperone, in free base or salt form, optionally in deuterated form, for use in the treatment of psychiatric disorders in a patient in need thereof, wherein the patient has elevated levels of pro-inflammatory cytokines in the CNS (e.g., in the cerebrospinal fluid), such as TNF-α, IFN-γ, IL-1 (IL-1α and/or IL-1β), IL-6, IL-8, IL-12, IL-15, IL-17, IL-18, or elevated levels of C-reactive protein (CRP), or Csf1, and/or depressed levels of anti-inflammatory cytokines in the CNS (e.g., in the cerebrospinal fluid), such as TNF-β, IFN-α, IL-4, and IL-10, e.g., for use in any of Methods 3, et seq.

In another aspect, the disclosure provides the use of a 5-HT$_{2A}$ or 5-HT$_{2A}$/D2 receptor ligand, e.g. a compound of Formula I, as hereinbefore described, for example lumateperone, in free base or salt form, optionally in deuterated form, in in the manufacture of a medicament for treatment of psychiatric disorders in a patient in need thereof, wherein the patient has elevated levels of pro-inflammatory cytokines in the CNS (e.g., in the cerebrospinal fluid), such as TNF-α, IFN-γ, IL-1 (IL-1α and/or IL-1β), IL-6, IL-8, IL-12, IL-15, IL-17, IL-18, or elevated levels of C-reactive protein (CRP), or Csf1, and/or depressed levels of anti-inflammatory cytokines in the CNS (e.g., in the cerebrospinal fluid), such as TNF-β, IFN-α, IL-4, and IL-10, e.g., for any of Methods 3, et seq.

In another aspect, the present disclosure provides a method (Method 4) for the treatment or normalization of pathologic inflammation, comprising administering to a patient in need thereof, a therapeutically effective amount of a 5-HT$_{2A}$ or 5-HT$_{2A}$/D2 receptor ligand, for example, a compound of Formula I:

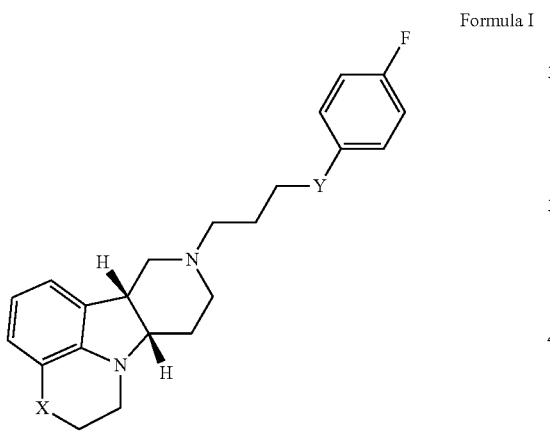

Formula I wherein:
X is —N(H)—, —N(CH$_3$)— or —O—;
Y is —C(=O)—, —C(H)(OH)— or —C(H)(OR$_1$)—;
R$_1$ is —C(O)—C$_{1-21}$alkyl (e.g., —C(O)—C$_{1-5}$alkyl, —C(O)—C$_{6-15}$alkyl or —C(O)—C$_{16-21}$alkyl), preferably said alkyl is a straight chain, optionally saturated or unsaturated and optionally substituted with one or more hydroxy or C$_{1-22}$alkoxy (e.g., ethoxy) groups, for example R$_1$ is —C(O)—C$_6$alkyl, —C(O)—C$_7$alkyl, —C(O)—C$_9$alkyl, —C(O)—C$_{11}$alkyl, —C(O)—C$_{13}$alkyl or —C(O)—C$_{15}$alkyl, wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand,
optionally in deuterated form,
in free base, pharmaceutically acceptable salt, or prodrug form. For example, Method 4 may be as follows:

4.1. Method 4, wherein X in the compound of Formula I is —N(H)—, —N(CH$_3$)— or —O—;

4.2. Method 4 or 1.1, wherein X in the compound of Formula I is —N(H);

4.3. Method 4 or 1.1, wherein X in the compound of Formula I is —N(CH$_3$)—;

4.4. Method 4 or 1.1, wherein X in the compound of Formula I is —O—;

4.5. Method 4 or any of formulae 1.1-1.4, wherein Y in the compound of Formula I is —C(=O)—, —C(H)(OH)— or —C(H)(OR$_1$)—;

4.6. Method 4 or any of formulae 1.1-1.4, wherein Y in the compound of Formula I is —C(=O)—;

4.7. Method 4 or any of formulae 1.1-1.4, wherein Y in the compound of Formula I is —C(H)(OH)—;

4.8. Method 4 or any of formulae 1.1-1.4, wherein Y in the compound of Formula I is —C(H)(OR$_1$)—;

4.9. Method 4, or any of 4.1-4.5 or 1.8, wherein R$_1$ in the compound of Formula I is —C(O)—C$_{1-21}$alkyl (e.g., —C(O)—C$_{1-5}$alkyl, —C(O)—C$_{6-15}$alkyl or —C(O)—C$_{16-21}$alkyl), preferably said alkyl is a straight chain, optionally saturated or unsaturated and optionally substituted with one or more hydroxy or C$_{1-22}$alkoxy (e.g., ethoxy) groups, for example R$_1$ is —C(O)—C$_6$alkyl, —C(O)—C$_7$alkyl, —C(O)—C$_9$alkyl, —C(O)—C$_{11}$alkyl, —C(O)—C$_{13}$alkyl or —C(O)—C$_{15}$alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand; e.g., wherein R$_1$ in the compound of Formula I is —C(O)—C$_{6-15}$alkyl, e.g., —C(O)—C$_9$alkyl; or wherein R$_1$ in the compound of Formula I is —C(O)—C$_{1-5}$alkyl, e.g., —C(O)—C$_3$alkyl;

4.10. Method 4 or any of 1.1-1.5 or 1.7, wherein the Compound of Formula I is:

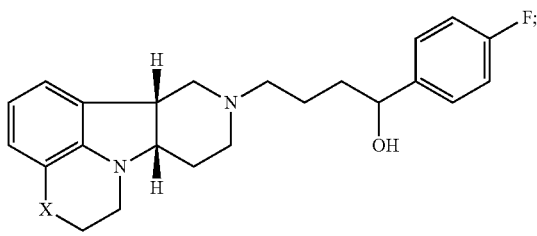

4.11. Method 4 or any of 1.1-1.5 or 1.7, wherein the Compound of Formula I is:

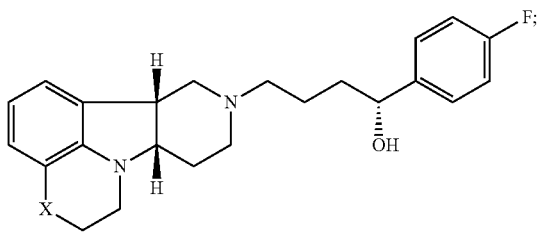

4.12. Method 4, or any of 4.1, 4.3, 4.5, or 4.6, wherein the Compound of Formula I is lumateperone:

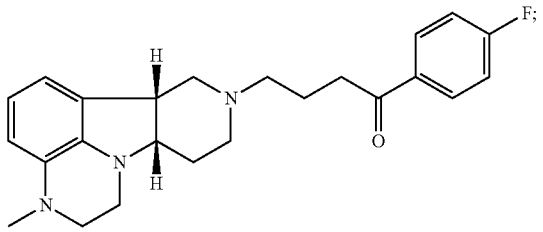 [SMILES: CN1CCN2c3c(cccc31)[C@@H]1CN(CCCC(=O)c3ccc(F)cc3)CC[C@@H]12]

4.13. Method 4, or any of 4.1-4.12, e.g., Method 4.12, wherein the Compound of Formula I is in the form of a pharmaceutically acceptable salt, e.g., a tosylate salt;

4.14. Method 4, or any of 4.1-4.12, e.g., Method 4.12, wherein the Compound of Formula I is in the form of the free base;

4.15. Method 4 or any of 4.1-4.14 wherein the Compound of Formula I is in deuterated form, e.g., wherein the deuterium:protium ratio for a specified carbon-bound hydrogen atom is significantly higher, e.g., at least 2×, for example at least 10× higher, than the natural isotope ratios;

4.16. Method 4.15 wherein the Compound of Formula I is a deuterated form of lumateperone, for example, selected from:

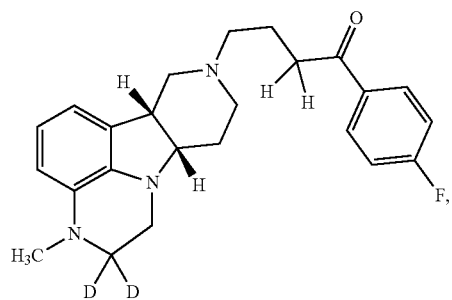

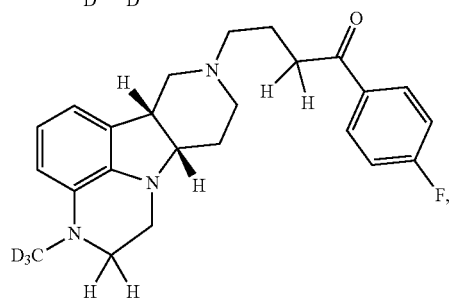

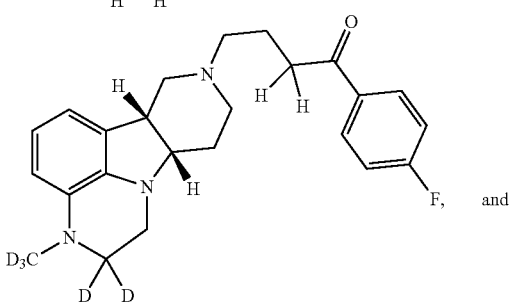

and

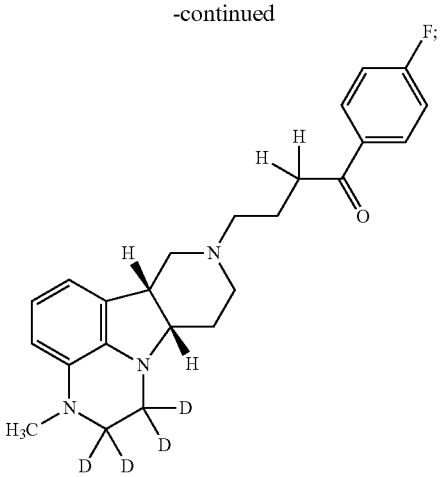

wherein D represents a hydrogen position with substantially greater than natural deuterium incorporation (i.e., substantially greater than 0.0156%), e.g., greater than 60%, or greater than 70%, or greater than 80%, or greater than 90% or greater than 95%, or greater than 96%, or greater than 97%, or greater than 98%, or greater than 99%, in free base or pharmaceutically acceptable salt form, e.g., tosylate salt form;

4.17. Any foregoing method, wherein the 5-HT$_{2A}$ or 5-HT$_{2A}$/D2 receptor ligand is a compound of Formula I in free base or pharmaceutically acceptable salt form, e.g., tosylate salt form, administered in a daily dose equivalent to 1 to 100 mg of free base, e.g., in an amount equivalent to 1 to 75 mg, or 1 to 60 mg, or 1 to 40 mg, or 1 to 20 mg, or 1 to 10 mg, of free base;

4.18. Method 4.17 wherein the method comprises once daily administration of a unit dosage for oral administration, for example a tablet or capsule, comprising the compound of Formula I in free base or pharmaceutically acceptable salt form, e.g., in tosylate salt form, in an amount equivalent 1 to 100 mg of free base, e.g., in an amount equivalent to 1 to 75 mg, or 1 to 60 mg, or 1 to 40 mg, or 1 to 30 mg, or 1 to 20 mg, or 1 to 10 mg, or 1 to 5 mg, or 40 to 60 mg, or 20 to 40 mg, or 10 to 20 mg, or about 60 mg, or about 40 mg, or about 30 mg, or about 20 mg, or about 10 mg, or about 5 mg, of free base, and a pharmaceutically acceptable diluent or carrier;

4.19. Method 4.17 wherein the method comprises once daily administration of a unit dosage for oral transmucosal administration, e.g., a sublingual or buccal orally disintegrating tablet, wafer, or film, comprising the compound of Formula I in free base or pharmaceutically acceptable salt form, e.g., in tosylate salt form, in an amount equivalent to 0.5 to 30 mg of free base, e.g., in an amount equivalent to 1 to 30 mg, or 1 to 20 mg, or 1 to 15 mg, or 1 to 10 mg, or 20 to 30 mg, or 10 to 20 mg, or about 5 mg, or about 10 mg, or about 15 mg, or about 20 mg, of free base, and a pharmaceutically acceptable diluent or carrier;

4.20. Any foregoing method wherein the pathologic inflammation is treated or normalized within one week, e.g., within three days, e.g., within one day;

4.21. Any foregoing method, wherein the pathologic inflammation is caused by viral, bacterial, or autoimmune encephalitis;

4.22. Any foregoing method, wherein the pathologic inflammation is a symptom of viral, bacterial, and autoimmune encephalitis;

4.23. Method 4.21 or 4.22, wherein the encephalitis is viral encephalitis;

4.24. Method 4.23, wherein the encephalitis is caused by, or suspected to be caused by, Herpes simplex Virus 1, Herpes Simplex Virus 2, West Nile Virus, Nipah Virus, human immunodeficiency virus, rabies virus, Epstein-Barr Virus, cytomegalovirus, coronavirus (e.g., MERS-CoV, SARS-CoV, SARS-Cov2), or influenza virus (e.g., influenza A, such as H1N1, H2N2, H3N2, H5N1, H7N7);

4.25. Method 4.23 or 4.24, wherein the patient has acute viral encephalitis;

4.26. Method 4.21 or 4.22, wherein the encephalitis is bacterial encephalitis;

4.27. Method 4.26, wherein the encephalitis is caused by, or believed to be caused by, toxoplasmosis, *rickettsia, mycoplasma, Borrelia* (e.g., Lyme disease), or malaria;

4.28. Method 4.21 or 4.22, wherein the encephalitis is autoimmune encephalitis;

4.29. Method 4.28, wherein the encephalitis is caused by, or believed to be caused by, autoantibodies against the NMDA receptor, the AMPA receptor, the voltage-gated potassium, channel (VGKC), the LGL1 protein, the GABA receptor, the glycine receptor, the glutamate receptor, or the CASPR2 receptor;

4.30. Any foregoing method, wherein the patient suffers from depression (e.g., acute depression, depression of MDD, depression of bipolar disorder), anxiety, (e.g., acute anxiety), psychosis (e.g., schizophrenia), post-traumatic stress-disorder, anhedonia, memory loss, impairment of executive functioning, difficulty concentrating, seizures, difficulty sleeping, hallucination, change in personality, or any combination thereof;

4.31. Any foregoing method wherein the patient suffers from depression (e.g., acute depression, depression of MDD, depression of bipolar disorder);

4.32. Any foregoing method wherein the patient suffers from anxiety (e.g., acute anxiety);

4.33. Any foregoing method wherein the patient suffers from anhedonia;

4.34. Any foregoing method wherein the patient is diagnosed as having suicidal ideation and/or suicidal tendencies;

4.35. Any foregoing method, wherein the patient has no prior history of psychiatric disorders or psychiatric symptoms;

4.36. Any foregoing method wherein the 5-HT$_{2A}$ or 5-HT$_{2A}$/D2 receptor ligand is administered in combination (e.g., a fixed combination in a unit dosage form, or a free combination administered sequentially or simultaneously or within a 24-hour period) with a therapeutically effective amount of an anxiolytic or antidepressant agent;

4.37. Method 4.36, wherein the anxiolytic or antidepressant agent is selected from one or more compounds in free base or pharmaceutically acceptable salt form, selected from selective serotonin reuptake inhibitors (SSRIs), serotonin-norepinephrine reuptake inhibitors (SNRIs), tricyclic antidepressants (TCAs), and atypical antipsychotics, e.g., one or more compounds in free base or pharmaceutically acceptable salt form, selected from:
(a) Selective serotonin reuptake inhibitors (SSRIs), e.g., Citalopram (Celexa), Escitalopram (Lexapro, Cipralex), Paroxetine (Paxil, Seroxat), Fluoxetine (Prozac), Fluvoxamine (Luvox) Sertraline (Zoloft, Lustral);
(b) Serotonin-norepinephrine reuptake inhibitors (SNRIs), e.g., Desvenlafaxine (Pristiq), Duloxetine (Cymbalta), Levomilnacipran (Fetzima), Milnacipran (Ixel, Savella), Tofenacin (Elamol, Tofacine), Venlafaxine (Effexor);
(c) Tricyclic antidepressants (TCAs), e.g., Amitriptyline (Elavil, Endep), Amitriptylinoxide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Nitroxazepine (Sintamil), Nortriptyline (Pamelor, Aventyl), Noxiptiline (Agedal, Elronon, Nogedal), Pipofezine (Azafen/Azaphen), Protriptyline (Vivactil), Trimipramine (Surmontil);
(d) Benzodiazepines, e.g., selected from 2-keto compounds (e.g., clorazepate, diazepam, flurazepam, halazepam, prazepam); 3-hydroxy compounds (lorazepam, lormetazepam, oxazepam, temazepam); 7-nitro compounds (e.g., clonazepam, flunitrazepam, nimetazepam, nitrazepam); triazolo compounds (e.g., adinazolam, alprazolam, estazolam, triazolam); and imidazo compounds (climazolam, loprazolam, midazolam);

4.38. Any foregoing method, wherein the 5-HT$_{2A}$ or 5-HT$_{2A}$/D2 receptor ligand, e.g., the compound of Formula I is administered intra-nasally, subcutaneously, intramuscularly, intravenously, orally, sub-lingually, intra-peritoneally, or buccally, such as an oral rapidly dissolving tablet, wafer, or film, which dissolves in the oral cavity for transmucosal absorption;

4.39. Any foregoing method, wherein the method further comprises the concurrent administration of an antidepressant agent (e.g., selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), a serotonin receptor antagonist, or any combination thereof), e.g., administered simultaneously, separately or sequentially;

4.40. Any foregoing method, wherein the method further comprises the concurrent administration of an NMDA receptor antagonist, for example, selected from ketamine (e.g., S-ketamine and/or R-ketamine), hydroxynorketamine, memantine, dextromethorphan, dextroallorphan, dextrorphan, amantadine, and agmatine, or any combination thereof, e.g., administered simultaneously, separately or sequentially;

4.41. Any foregoing method, wherein the method further comprises the concurrent administration of a NMDA receptor allosteric modulator, e.g., a NMDA receptor glycine-site modulator, such as rapastinel, nebostinel, apimostinel, D-cycloserine, or any combination thereof, e.g., administered simultaneously, separately or sequentially;

4.42. Any foregoing method, wherein the method provides the patient with an acute response to treatment with the therapeutic agent or agents (e.g., the 5-HT$_{2A}$ or 5-HT$_{2A}$/D2 receptor ligand, the Compound of Formula I, or the combination of the Compound or Formula I and the Compound of Formula II, and/or any additional antidepressant agents);

4.43. Method 4.42, wherein the patient shows an acute response to treatment within less than 3 weeks, for example, less than 2 weeks, or less than 1 week, or from 1 to 7 days, or 1 to 5 days, or 1 to 3 days, or 1 to 2 days, or about 1 day, or less than 2 days, or less than 1 day (e.g., 12-24 hours, 6-12 hours, or 3-6 hours);

4.44. Any foregoing method, wherein the patient has not responded to, or has not responded adequately to, or who suffers undesirable side effects from, treatment with another antidepressant agent, for example, any one or more of a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor, or a serotonin receptor antagonist;

4.45. Any foregoing method, wherein the patient does not suffer from schizophrenia or dementia;

4.46. Any foregoing method, wherein the patient has not previously been diagnosed with schizophrenia or dementia;

4.47. Any foregoing method, wherein the method protects or reinforces the blood-brain barrier;

4.48. Any foregoing method, wherein the patient has elevated levels of pro-inflammatory cytokines in the CNS (e.g., in the cerebrospinal fluid), such as TNF-α, IFN-γ, IL-1 (IL-1α and/or IL-1β), IL-6, IL-8, IL-12, IL-15, IL-17, IL-18, or elevated levels of C-reactive protein (CRP) of Csf1, and/or depressed levels of anti-inflammatory cytokines in the CNS (e.g., in the cerebrospinal fluid), such as TNF-β, IFN-α, IL-4, and IL-10;

4.49. Any foregoing method, wherein the 5-$HT_{2A}$ or 5-$HT_{2A}$/D2 receptor ligand has an $IC_{50}$ of less than 250 nM or an $EC_{50}$ of less than 250 nM for activity (agonism and/or antagonism) at the 5-$HT_{2A}$ receptor, e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

4.50. Any foregoing method, wherein the 5-$HT_{2A}$ or 5-$HT_{2A}$/D2 receptor ligand has an $IC_{50}$ of less than 250 nM or an $EC_{50}$ of less than 250 nM for activity (agonism and/or antagonism) at the D2 receptor, e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

4.51. Any foregoing method, wherein the 5-$HT_{2A}$ or 5-$HT_{2A}$/D2 receptor ligand has an $IC_{50}$ of less than 250 nM or an $EC_{50}$ of less than 250 nM for activity (agonism and/or antagonism) at the D1 receptor, e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

4.52. Any foregoing method, wherein the 5-$HT_{2A}$ or 5-$HT_{2A}$/D2 receptor ligand has an $IC_{50}$ of less than 250 nM or an $EC_{50}$ of less than 250 nM for activity (agonism and/or antagonism) at the serotonin transporter (SERT), e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said transporter (agonism or antagonism);

4.53. Any foregoing method, wherein the 5-$HT_{2A}$ or 5-$HT_{2A}$/D2 receptor ligand is lumateperone, in free base or pharmaceutically acceptable salt form, optionally in a deuterated form;

4.54. Any foregoing method, wherein the 5-$HT_{2A}$ or 5-$HT_{2A}$/D2 receptor ligand is lumateperone, in a tosylate salt form (e.g., monotosylate salt), optionally in a deuterated form, and optionally in crystalline or amorphous tosylate salt form;

4.55. Any foregoing method, wherein the 5-$HT_{2A}$ or 5-$HT_{2A}$/D2 receptor ligand is lumateperone, in free base form, optionally in a deuterated form;

4.56. Any foregoing method, wherein the 5-$HT_{2A}$ or 5-$HT_{2A}$/D2 receptor ligand is administered in the form of a long-acting injectable (LAI) composition, e.g., for intramuscular or subcutaneous injection;

4.57. Method 4.56, wherein the dose of the LAI composition is sufficient to provide the equivalent of a daily dose of 1 to 100 mg of free base, e.g., 1 to 75 mg, or 1 to 60 mg, or 1 to 40 mg, or 1 to 20 mg, or 1 to 10 mg, of free base, released over a period of time ranging from about 1 week to about 3 months, e.g., about 1 week to about 8 weeks, or about 1 week to about 6 weeks, or about 1 week to about 4 weeks, or about 1 week to about 3 weeks, or about 1 week to about 2 weeks;

4.58. Method 4.56 or 4.57, wherein the LAI composition comprises the compound of Formula I dissolved, dispersed, suspended, or encapsulated in a polymeric matrix;

4.59. Method 4.58, wherein the polymeric matrix comprises one or more biocompatible and biodegradable polymers as defined herein, e.g., poly(hydroxycarboxylic acids), poly(amino acids), cellulose polymers, modified cellulose polymers, polyamides, and polyesters;

4.60. Method 4.59, wherein the one or more polymers comprises polylactic acid, polyglycolic acid, polycitric acid, polymalic acid, poly-beta-hydroxybutyric acid, poly(lactic acid-glycolic acid) copolymer, 2-hydroxybutyric acid-glycolic acid copolymer, polylactic acid-polyethylene glycol copolymer, polyglycolic acid-polyethylene glycol copolymer, PEG-PLGA copolymer or block copolymer, PEG-PLGA copolymer or block copolymer, poly(alkyl alpha-cyanoacrylate) such as poly(butyl cyanoacrylate) or poly(2-octyl cyanoacrylate), poly(ortho ester), polycarbonate, poly-ortho-carbonate, a polyamino acid, (for example poly-gamma.-L-alanine, poly-.gamma.-benzyl-L-glutamic acid or poly-γ-methyl-L-glutamic acid), and/or hyaluronic acid ester;

4.61. Method 4.60, wherein the one or more polymers comprises polyortho esters (POE), polylactic acid, polyglycolic acid, polycitric acid, polymalic acid, or a poly(lactic acid-glycolic acid) copolymer;

4.62. Method 4.60, wherein the one or more polymers comprises a poly(lactic acid-glycolic acid) copolymer, e.g., poly-d,l-lactide-co-glycolide (PLGA), for example, a PLGA copolymer with a lactide-to-glycolide molar ratio of about 50:50 to 90:10, or 50:50 to 85:15, or 50:50 to 75:25, and/or a molecular weight of 5,000 to 500,000 Daltons, or 5,000 to 150,000 Daltons, or 20,000 to 200,000 Daltons, or 24,000 to 38,000 Daltons;

4.63. Any foregoing method, wherein the 5-$HT_{2A}$ or 5-$HT_{2A}$/D2 receptor ligand is administered as monotherapy, e.g., it is not administered concurrently or in conjunction with an anti-depressant, anti-psychotic, or anti-anxiety agent;

4.64. Any foregoing method, wherein the 5-$HT_{2A}$ or 5-$HT_{2A}$/D2 receptor ligand is administered without the direct supervision of a health care professional (e.g., the compound is self-administered by the patient);

4.65. Any foregoing method, wherein the method does not comprise supervision or observation of the patient by a health care professional during or after (e.g., within 2 hours after) administration of a dose of the 5-$HT_{2A}$ or 5-$HT_{2A}$/D2 receptor ligand;

4.66. Any foregoing method, wherein the method does not put the patient at risk for sedation, dissociation, abuse, misuse, or suicidal ideation;

4.67. Any foregoing method, wherein the method does not result in hypertension (e.g., systolic and/or diastolic hypertension) within four hours after administration of a dose of the 5-$HT_{2A}$ or 5-$HT_{2A}$/D2 receptor ligand, e.g., an increase of more than 10 mm Hg, or more than 20 mm Hg, or more than 30 mm Hg, or more than 40 mm Hg, in systolic and/or diastolic blood pressure within 30 minutes to 4 hours after said dose;

4.68. Any foregoing method, wherein the method does not result in cognitive decline;

4.69. Any foregoing method, wherein the patient has (e.g., has been diagnosed with), or is at risk of, aneurysmal vascular disease (e.g., thoracic aorta, abdominal aorta, intracranial, or peripheral arterial aneurysms), arteriovenous malformation or intracerebral hemorrhage;

4.70. Any foregoing method, wherein the patient is under concurrent treatment with an oral antidepressant selected from duloxetine, escitalopram, sertraline, or venlafaxine;

4.71. Any foregoing method, wherein the patient is not under concurrent treatment with an oral antidepressant selected from duloxetine, escitalopram, sertraline, or venlafaxine;

4.72. Any foregoing method, wherein the patient is unresponsive to, or cannot be treated with ketamine (e.g., S-ketamine), e.g., because it is contraindicated in said patient;

4.73. Any foregoing method, wherein the 5-$HT_{2A}$ or 5-$HT_{2A}$/D2 receptor ligand is administered to the patient concurrently with a PDE1 (cyclic nucleoside phosphodiesterase 1) inhibitor (e.g., administered simultaneously, separately, or sequentially), in free base or pharmaceutically acceptable salt form;

4.74. Method 4.73, wherein the PDE1 inhibitor is a compound according to Formula II:

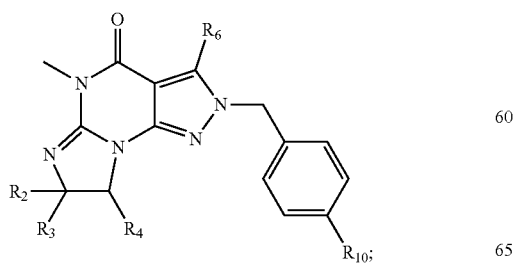

wherein $R_2$ is H and $R_3$ and $R_4$ together form a tri- or tetra-methylene bridge [pref. with the carbons carrying $R_3$ and $R_4$ having the R and S configuration respectively]; or $R_2$ and $R_3$ are each methyl and $R_4$ is H; or $R_2$ and $R_4$ are H and $R_3$ is isopropyl [pref. the carbon carrying $R_3$ having the R configuration];

$R_6$ is (optionally halo-substituted) phenylamino or (optionally halo-substituted) benzylamino;

$R_{10}$ is (optionally halo-substituted) phenyl, (optionally halo-substituted) pyridyl (for example 3-fluoropyrid-2-yl), thiadiazolyl (e.g., 1,2,3-thiadiazol-4-yl), or $C_{1-6}$alkylcarbonyl (e.g., methylcarbonyl);

in free base or pharmaceutically acceptable salt form;

4.75. Method 4.74, wherein, in the Compound of Formula II, $R_6$ is phenylamino or 4-fluorophenylamino;

4.76. Method 4.74, wherein, in the Compound of Formula II, $R_{10}$ is 3-fluoropyrid-2-yl or methylcarbonyl;

4.77. Method 4.74, wherein, in the Compound of Formula II, $R_6$ is phenylamino or 4-fluorophenylamino and $R_{10}$ is 3-fluoropyrid-2-yl or methylcarbonyl;

4.78. Any Methods 4.74-4.77, wherein the Compound of Formula II is

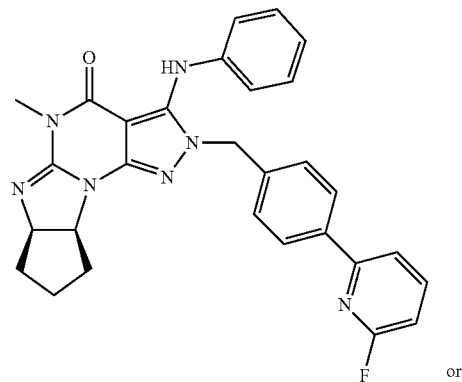

or

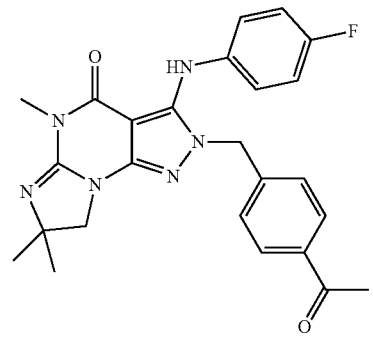

in free base or pharmaceutically acceptable salt form;
4.79. Method 4.78, wherein the Compound of Formula II is in the form of the monophosphate salt;
4.80. Any of Methods 4.74-4.79, wherein the Compound of Formula I is:

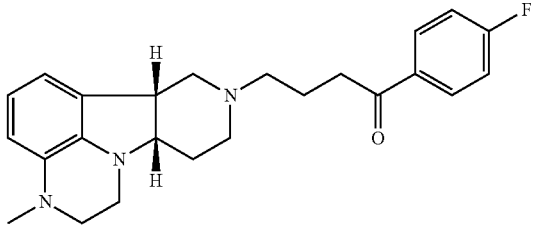 [SMILES: CN1CCN2c3c(cccc31)[C@@H]1CN(CCCC(=O)c3ccc(F)cc3)CC[C@@H]12]

in free base or pharmaceutically acceptable salt form, e.g., tosylate salt form, optionally in a deuterated form; and the Compound of Formula II is:

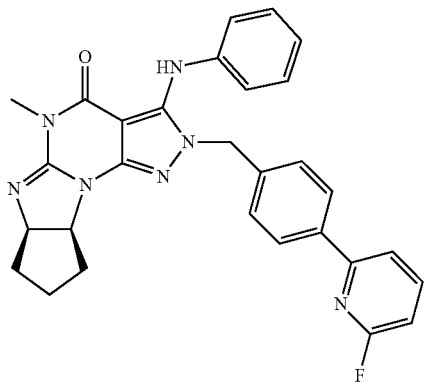 [SMILES: CN1C(=O)c2c(nn(Cc3ccc(-c4cccc(F)n4)cc3)c2Nc2ccccc2)N2C1=N[C@@H]1CCC[C@@H]12]

in free base or pharmaceutically acceptable salt form, e.g., monophosphate salt form;
4.81. Any of Methods 4.74-4.80, comprising administration of a pharmaceutical composition comprising therapeutically effective amounts of both a Compound of Formula I and a Compound of Formula II;
4.82. Any preceding method, wherein the 5-HT$_{2A}$ or 5-HT$_{2A}$/D2 receptor ligand is a compound of Formula I, in free base or pharmaceutically acceptable salt from, optionally in deuterated form, and wherein the compound is administered in the form of a long-acting injectable (LAI) composition comprising the compound of Formula I dissolved or dispersed or in a pharmaceutically acceptable carrier and a polymeric matrix comprising polymers selected from polyortho esters (POE), polylactic acid, polyglycolic acid, polycitric acid, polymalic acid, or a poly(lactic acid-glycolic acid) copolymer;
4.83. Method 4.82, wherein the pharmaceutically acceptable carrier comprises water (e.g., an aqueous buffer) and/or an organic solvent (e.g., a water-miscible organic solvent);
4.84. Method 4.82 or 4.83, wherein the polymers comprise a polylactic acid and/or a polyglycolic acid polymer;
4.85. Method 4.82 or 4.83, wherein the polymers comprise a poly(lactic acid-glycolic acid) copolymer, e.g., poly-d,l-lactide-co-glycolide (PLGA), for example, a PLGA copolymer with a lactide-to-glycolide molar ratio of about 50:50 to 90:10, or 50:50 to 85:15, or 50:50 to 75:25, and/or a molecular weight of 5,000 to 500,000 Daltons, or 5,000 to 150,000 Daltons, or 20,000 to 200,000 Daltons, or 24,000 to 38,000 Daltons;
4.86. Any of Methods 4.82-4.85, wherein the LAI composition is administered by, or formulated for administration by, intramuscular or subcutaneous injection;
4.87. Method 4, or any of 4.1-4.86, wherein the patient has no prior history of depression;
4.88. Method 4, or any of 4.1-4.87, wherein the patient shows evidence of cerebral damage or cerebral disease on magnetic resonance imaging (MRI) prior to administration of the 5-HT$_{2A}$ or 5-HT$_{2A}$/D2 receptor ligand;
4.89. Method 4, or any of 4.1-4.88, wherein the patient has a positive serum antibody or antigen test for one or more of Herpes simplex Virus 1, Herpes Simplex Virus 2, West Nile Virus, Nipah Virus, human immunodeficiency virus, rabies virus, Epstein-Barr Virus, cytomegalovirus, coronavirus (e.g., MERS-CoV, SARS-CoV, SARS-Cov2, or influenza virus (e.g., influenza A, such as H1N1, H2N2, H3N2, H5N1, H7N7), prior to administration of the 5-HT$_{2A}$ or 5-HT$_{2A}$/D2 receptor ligand;
4.90. Method 4, or any of 4.1-4.89, wherein the patient has a positive serum antibody test for autoantibodies against the NMDA receptor, the AMPA receptor, the voltage-gated potassium, channel (VGKC), the LGL1 protein, the GABA receptor, the glycine receptor, the glutamate receptor, or the CASPR2 receptor;
4.91. Any foregoing method, wherein the patient has elevated levels of one or more biomarkers indicative of CNS inflammation, e.g., selected from TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1, in the blood, plasma, serum, peripheral blood mononuclear cells (PBMC) (e.g., isolated from blood), urine, CSF, and/or CNS microglial cells (e.g., isolated from CSF);
4.92. Any foregoing method, wherein the patient has changes in levels of one or more biomarkers indicative of CNS inflammation and/or loss of BBB integrity, e.g., increased levels of ICAM-1, VCAM-1, E-selectin, P-selectin, or soluble isoforms thereof (e.g., sICAM-1, sVCAM1, sP-selectin, sE-selectin), or reduced levels of Cldn5, Occludin, and/or ZO-1, in the serum or CSF;
4.93. Any foregoing method, wherein the patient has depressed levels of one or more anti-inflammatory biomarkers indicative of CNS inflammatory dysfunction, e.g., TNF-β, IFN-α, IL-4, and IL-10, in the blood, plasma, serum, peripheral blood mononuclear cells (PBMC) (e.g., isolated from blood), urine, CSF, and/or CNS microglial cells (e.g., isolated from CSF);
4.94. Any foregoing method, wherein after treatment with the 5-HT$_{2A}$ or 5-HT$_{2A}$/D2 receptor ligand (e.g., Compound of Formula I, optionally in deuterated form), the patient has a reduced level of one or more biomarkers indicative of CNS inflammation, e.g., TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1, in the blood, plasma, serum, peripheral blood mononuclear cells (PBMC) (e.g., isolated from blood), urine, CSF, and/or CNS microglial cells (e.g., isolated from CSF), compared to a pretreatment baseline, e.g., within 28 days of the initiation of treatment;

4.95. Method 4.94, wherein the patient has at least a 5%, 10%, 15%, 20%, or 25%, 30%, 35%, 40%, 45%, or 50%, reduction in the level of the one or more biomarkers indicative of CNS inflammation, e.g., within 28 days of the initiation of treatment;

4.96. Any foregoing method, wherein after treatment with the 5-$HT_{2A}$ or 5-$HT_{2A}$/D2 receptor ligand (e.g., Compound of Formula I, optionally in deuterated form), the patient has favorable changes in levels of one or more biomarkers indicative of CNS inflammation and/or loss of BBB integrity, e.g., decreased levels of ICAM-1, VCAM-1, E-selectin, P-selectin, or soluble isoforms thereof (e.g., sICAM-1, sVCAM1, sP-selectin, sE-selectin), or increased levels of Cldn5, Occludin, and/or ZO-1, in the serum or CSF, compared to a pre-treatment baseline, e.g., within 28 days of the initiation of treatment;

4.97. Method 4.96, wherein the patient has at least a 5%, 10%, 15%, 20%, 25%, 30%, 35%, 40%, 45%, or 50%, reduction or increase in the level of the one or more biomarkers indicative of CNS inflammation, e.g., within 28 days of the initiation of treatment;

4.98. Any foregoing method, wherein after treatment with the 5-$HT_{2A}$ or 5-$HT_{2A}$/D2 receptor ligand (e.g., Compound of Formula I, optionally in deuterated form), the patient has an increased level of one or more anti-inflammatory biomarkers indicative of CNS inflammatory dysfunction, e.g., TNF-β, IFN-α, IL-4, and IL-10, in the blood, plasma, serum, peripheral blood mononuclear cells (PBMC) (e.g., isolated from blood), urine, CSF, and/or CNS microglial cells (e.g., isolated from CSF), compared to a pre-treatment baseline, e.g., within 28 days of the initiation of treatment;

4.99. Method 4.98, wherein the patient has an increase of at least 5%, 10%, 15%, 20%, 25%, 30%, 35%, 40%, 45%, or 50%, in the levels of the one or more anti-inflammatory biomarkers indicative CNS inflammatory dysfunction, e.g., within 28 days of the initiation of treatment, e.g., within 28 days of the initiation of treatment;

4.100. Any foregoing method, wherein the method further comprises the step of testing one or more body fluids or tissues from the patient for the presence and/or concentration of one or more biomarkers indicative of CNS inflammation or CNS inflammatory dysfunction or loss of BBB integrity prior to the initiation of treatment with the 5-$HT_{2A}$ or 5-$HT_{2A}$/D2 receptor ligand (e.g., Compound of Formula, optionally in deuterated form), and/or subsequent to the initiation of said treatment, and optionally comparing the pre-treatment and one or more post-treatment results thereof to quantify the effectiveness of the treatment in the patient and/or to adjust the treatment regimen;

4.101. Method 4.100, wherein the biomarkers are selected from one or more of TNF-α, IFN-γ, IL-1 (IL-1α and/or IL-1β), IL-6, IL-8, IL-12, IL-15, IL-17, IL-18, CRP, SAA, Csf1, YKL-40, Nlrp3, Flt-1, ICAM-1, VCAM-1, E-selectin, P-selectin, Cldn5, Occludin, and ZO-1, soluble isoforms thereof (e.g., sICAM-1, sVCAM1, sP-selectin, sE-selectin), TNF-β, IFN-α, IL-4, and IL-10;

4.102. Method 4.100 or 4.101, wherein the one or more body fluids or tissues are selected from blood, plasma, serum, peripheral blood mononuclear cells (PBMC) (e.g., isolated from blood), urine, CSF, and/or CNS microglial cells (e.g., isolated from CSF), or brain biopsy tissue samples;

4.103. Any foregoing method, wherein the method further comprises the step of non-invasively testing the central nervous system of the patient for the presence and/or concentration of one or more biomarkers indicative of CNS inflammation or CNS inflammatory dysfunction prior to the initiation of treatment with the 5-$HT_{2A}$ or 5-$HT_{2A}$/D2 receptor ligand (e.g., Compound of Formula I, optionally in deuterated form), and/or subsequent to the initiation of said treatment, and optionally comparing the pre-treatment and one or more post-treatment results thereof to quantify the effectiveness of the treatment in the patient and/or to adjust the treatment regimen;

4.104. Method 4.103, wherein the biomarkers are selected from one or more of TNF-α, IFN-γ, IL-1 (IL-1α and/or IL-1β), IL-6, IL-12, IL-15, IL-17, IL-18, CRP, SAA, Csf1, YKL-40, Nlrp3, Flt-1, ICAM-1, VCAM-1, E-selectin, P-selectin, Cldn5, Occludin, and ZO-1, soluble isoforms thereof (e.g., sICAM-1, sVCAM1, sP-selectin, sE-selectin), TNF-β, IFN-α, IL-4, and IL-10;

4.105. Method 4.103 or 4.104, wherein the step comprises an imaging method, such as magnetic resonance imaging (MRI), positron emission tomography (PET), functional MRI (fMRI), to evaluate the presence and/or concentration of said biomarkers;

4.106. Any of Methods 4.100-4.105, wherein the method comprises the step of initiating, altering, or terminating, the treatment regimen (e.g., the selected 5-$HT_{2A}$ or 5-$HT_{2A}$/D2 receptor ligand, the dose thereof, the route of administration thereof, the frequency of administration thereof, the form of administration thereof, and/or the combination of the selected 5-$HT_{2A}$ or 5-$HT_{2A}$/D2 receptor ligand with any another therapeutic agent), based on the observed changes in the levels of one or more of said biomarkers;

4.107. Any foregoing method, wherein the patient has elevated levels of one or more biomarkers indicative of peripheral inflammation, e.g., selected from type-I interferons, including IFN-α, IFN-β, and/or IFN-δ, in the blood, plasma, serum, peripheral blood mononuclear cells (PBMC) (e.g., isolated from blood), or urine;

4.108. Method 4.107, wherein after treatment with the 5-$HT_{2A}$ or 5-$HT_{2A}$/D2 receptor ligand (e.g., Compound of Formula I, optionally in deuterated form), the patient has a reduced level of the one or more biomarkers indicative of peripheral inflammation, e.g., selected type-I interferons, including IFN-α, IFN-β, and/or IFN-δ, in the blood, plasma, serum, peripheral blood mononuclear cells (PBMC) (e.g., isolated from blood), or urine, compared to a pre-treatment baseline, e.g., within 28 days of the initiation of treatment;

4.109. Method 4.108, wherein the patient has at least a 5%, 10%, 15%, 20%, or 25%, 30%, 35%, 40%, 45%, or 50%, reduction in the level of the one or more biomarkers indicative of peripheral inflammation, e.g., within 28 days of the initiation of treatment;

4.110. Any foregoing method, wherein the patient has peripheral serotonin deficiency, e.g., reduced concentration in the plasma and/or platelets, for example, a plasma serotonin concentration less than 3000 nM, less than 2500 nM, less than 2000 nM, less than 1800 nM, less than 1600 nM, less than 1400 nM, less than 1200 nM, less than 1000 nM, less than 800 nM, less than 600 nM, less than 500 nM, less than 400 nM, less than 300 nM, or less than 250 nM;

4.111. Method 4.110, wherein after treatment with the 5-$HT_{2A}$ or 5-$HT_{2A}$/D2 receptor ligand (e.g., Compound of Formula I, optionally in deuterated form), the patient has recovered from peripheral serotonin deficiency, e.g., a normal concentration in the plasma and/or platelets, for example, a plasma serotonin concentration of greater than 500 nM, or 500 to 3000 nM, or 1000 to 3000 nM, or 1500 to 3000 nM, or 2000 to 3000 nM, or greater than 3000 nM nM, less than 800 nM, less than 600 nM, less than 500 nM, less than 400 nM, less than 300 nM, or less than 250 nM;

4.112. Method 4.110 or 4.111, wherein the psychiatric disorder or psychiatric symptoms are caused by, or thought to be caused by, peripheral serotonin deficiency, e.g., due to reduced plasma serotonin concentration and/or reduced vagal nerve afferent sensory activity (e.g., due to reduced serotonin-mediated 5-$HT_3$ signaling)

4.113. Any foregoing method, wherein the patient is suffering from a post-viral syndrome, e.g., Long COVID;

4.114. Any foregoing method, wherein the patient has thrombocytopenia or platelet hypercoagulability (e.g., as shown by reduced prothrombin time and/or partial thromboplastin time), 4.115. Any foregoing method, wherein the method further comprises the step of obtaining a tissue sample from the patient and testing the tissue sample for the level of any one or more of: (a) serum antibody or antigen for one or more of Herpes simplex Virus 1, Herpes Simplex Virus 2, West Nile Virus, Nipah Virus, human immunodeficiency virus, rabies virus, Epstein-Barr Virus, cytomegalovirus, coronavirus (e.g., MERS-CoV, SARS-CoV, SARS-Cov2, or influenza virus (e.g., influenza A, such as H1N1, H2N2, H3N2, H5N1, H7N7); (b) serum autoantibodies against the NMDA receptor, the AMPA receptor, the voltage-gated potassium, channel (VGKC), the LGL1 protein, the GABA receptor, the glycine receptor, the glutamate receptor, or the CASPR2 receptor; (c) biomarkers selected from TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1; (d) biomarkers selected from ICAM-1, VCAM-1, E-selectin, P-selectin, or soluble isoforms thereof (e.g., sICAM-1, sVCAM1, sP-selectin, sE-selectin), Cldn5, Occludin, and/or ZO-1; (e) biomarkers selected from TNF-β, IFN-α, IL-4, and IL-10; (f) type-I interferons, including IFN-α, IFN-β, and/or IFN-δ; (f) serotonin; and (g) platelet count, prothrombin time, and/or partial thromboplastin time;

4.116. Method 4.115, wherein the tissue sample is selected from blood, plasma, serum, peripheral blood mononuclear cells (PBMC) (e.g., isolated from blood), urine, CSF, and/or CNS microglial cells (e.g., isolated from CSF);

4.117. Method 4.115 or 4.116, wherein the method further comprises adjusting the course of treatment based on the results of one more of said tissue sample measurements, optionally wherein said tissue sample measurements are taken at one or more times during the course of therapy, e.g., for comparison to earlier measurements or measurements taken before initiating therapy.

In another aspect, the disclosure provides a 5-$HT_{2A}$ or 5-$HT_{2A}$/D2 receptor ligand, e.g., a compound of Formula I, as hereinbefore described, for example lumateperone, in free base or salt form, optionally in deuterated form, for use in the treatment or normalization of pathologic inflammation, e.g., for use in any of Methods 4, et seq.

In another aspect, the disclosure provides the use of a 5-$HT_{2A}$ or 5-$HT_{2A}$/D2 receptor ligand, e.g., a compound of Formula I, as hereinbefore described, for example lumateperone, in free base or salt form, optionally in deuterated form, in in the manufacture of a medicament for the treatment or normalization of pathologic inflammation, e.g., for any of Methods 4, et seq.

In another aspect, the present disclosure provides a method (Method 5) for the treatment or prevention of post-viral syndrome (e.g., Long COVID), comprising administering to a patient in need thereof, a therapeutically effective amount of a 5-$HT_{2A}$ or 5-$HT_{2A}$/D2 receptor ligand, for example, a compound of Formula I:

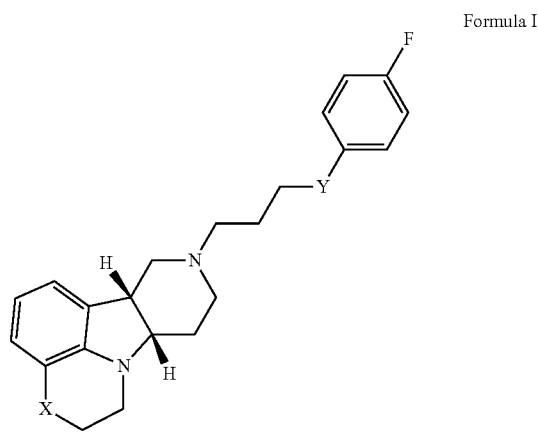

Formula I wherein:
X is —N(H)—, —N($CH_3$)— or —O—;
Y is —C(=O)—, —C(H)(OH)— or —C(H)(O$R_1$)—;
$R_1$ is —C(O)—$C_{1-21}$alkyl (e.g., —C(O)—$C_{1-5}$alkyl, —C(O)—$C_{6-15}$alkyl or —C(O)—$C_{16-21}$alkyl), preferably said alkyl is a straight chain, optionally saturated or unsaturated and optionally substituted with one or more hydroxy or $C_{1-22}$alkoxy (e.g., ethoxy) groups, for example $R_1$ is —C(O)—$C_6$alkyl, —C(O)—$C_7$alkyl, —C(O)—$C_9$alkyl, —C(O)—$C_{11}$alkyl, —C(O)—$C_{13}$alkyl or —C(O)—$C_{15}$alkyl, wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand,
optionally in deuterated form,
in free base, pharmaceutically acceptable salt, or prodrug form. For example, Method 5 may be as follows:

5.1. Method 5, wherein X in the compound of Formula I is —N(H)—, —N($CH_3$)— or —O—;

5.2. Method 5 or 1.1, wherein X in the compound of Formula I is —N(H);

5.3. Method 5 or 1.1, wherein X in the compound of Formula I is —N($CH_3$)—;

5.4. Method 5 or 1.1, wherein X in the compound of Formula I is —O—;

5.5. Method 5 or any of formulae 1.1-1.4, wherein Y in the compound of Formula I is —C(=O)—, —C(H)(OH)— or —C(H)(O$R_1$)—;

5.6. Method 4 or any of formulae 1.1-1.4, wherein Y in the compound of Formula I is —C(=O)—;

5.7. Method 5 or any of formulae 1.1-1.4, wherein Y in the compound of Formula I is —C(H)(OH)—;

5.8. Method 5 or any of formulae 1.1-1.4, wherein Y in the compound of Formula I is —C(H)(OR$_1$)—;

5.9. Method 5, or any of 5.1-5.5 or 1.8, wherein R$_1$ in the compound of Formula I is —C(O)—C$_{1-21}$alkyl (e.g., —C(O)—C$_{1-5}$alkyl, —C(O)—C$_{6-15}$alkyl or —C(O)—C$_{16-21}$alkyl), preferably said alkyl is a straight chain, optionally saturated or unsaturated and optionally substituted with one or more hydroxy or C$_{1-22}$alkoxy (e.g., ethoxy) groups, for example R$_1$ is —C(O)—C$_6$alkyl, —C(O)—C$_7$alkyl, —C(O)—C$_9$alkyl, —C(O)—C$_{11}$alkyl, —C(O)—C$_{13}$alkyl or —C(O)—C$_{15}$alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand; e.g., wherein R$_1$ in the compound of Formula I is —C(O)—C$_{6-15}$alkyl, e.g., —C(O)—C$_9$alkyl; or wherein R$_1$ in the compound of Formula I is —C(O)—C$_{1-5}$alkyl, e.g., —C(O)—C$_3$alkyl;

5.10. Method 5 or any of 1.1-1.5 or 1.7, wherein the Compound of Formula I is:

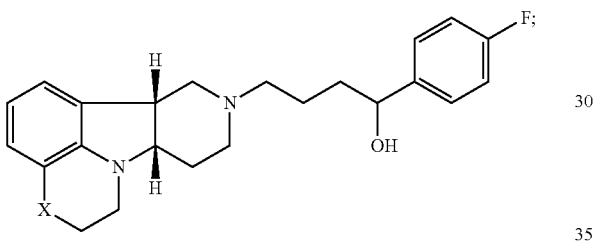

5.11. Method 5 or any of 1.1-1.5 or 1.7, wherein the Compound of Formula I is:

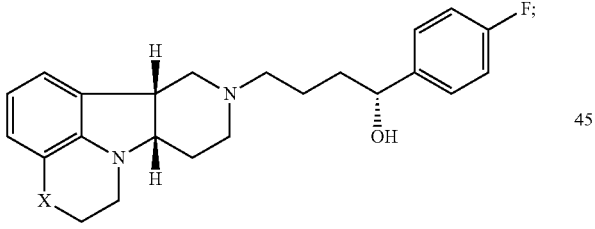

5.12. Method 5, or any of 5.1, 5.3, 5.5, or 5.6, wherein the Compound of Formula I is lumateperone:

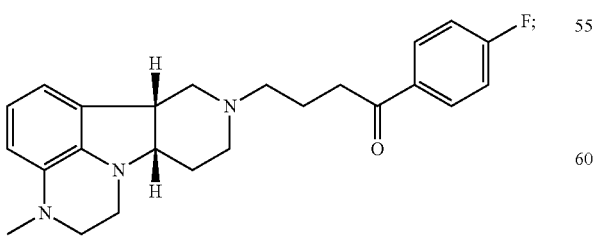

5.13. Method 5, or any of 5.1-5.12, e.g., Method 5.12, wherein the Compound of Formula I is in the form of a pharmaceutically acceptable salt, e.g., a tosylate salt;

5.14. Method 5, or any of 5.1-5.12, e.g., Method 5.12, wherein the Compound of Formula I is in the form of the free base;

5.15. Method 5 or any of 5.1-5.14 wherein the Compound of Formula I is in deuterated form, e.g., wherein the deuterium:protium ratio for a specified carbon-bound hydrogen atom is significantly higher, e.g., at least 2×, for example at least 10× higher, than the natural isotope ratios;

5.16. Method 5.15 wherein the Compound of Formula I is a deuterated form of lumateperone, for example, selected from:

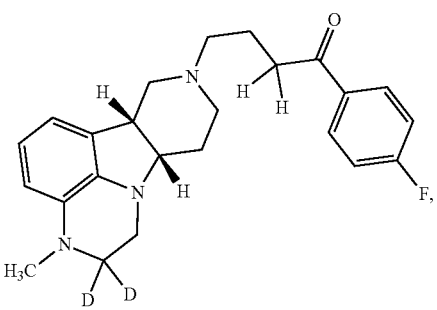

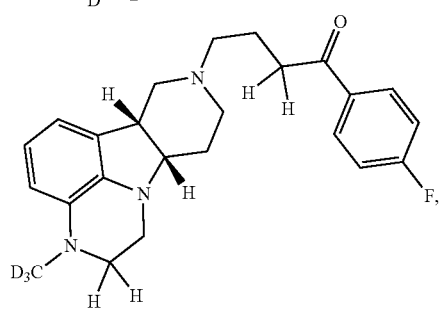

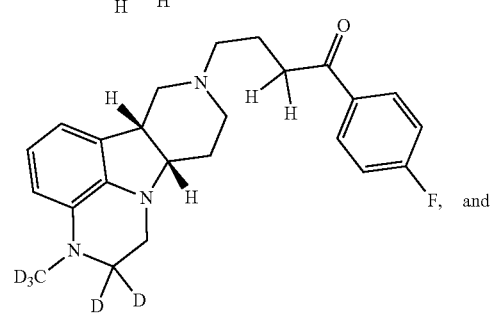

and

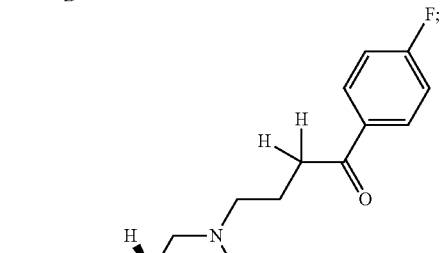

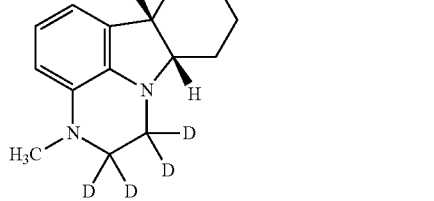

wherein D represents a hydrogen position with substantially greater than natural deuterium incorporation (i.e., substantially greater than 0.0156%), e.g., greater than 60%, or greater than 70%, or greater than 80%, or greater than 90% or greater than 95%, or greater than 96%, or greater than 97%, or greater than 98%, or greater than 99%, in free base or pharmaceutically acceptable salt form, e.g., tosylate salt form;

5.17. Any foregoing method, wherein the 5-HT$_{2A}$ or 5-HT$_{2A}$/D2 receptor ligand is a compound of Formula I in free base or pharmaceutically acceptable salt form, e.g., tosylate salt form, administered in a daily dose equivalent to 1 to 100 mg of free base, e.g., in an amount equivalent to 1 to 75 mg, or 1 to 60 mg, or 1 to 40 mg, or 1 to 20 mg, or 1 to 10 mg, of free base;

5.18. Method 5.17 wherein the method comprises once daily administration of a unit dosage for oral administration, for example a tablet or capsule, comprising the compound of Formula I in free base or pharmaceutically acceptable salt form, e.g., in tosylate salt form, in an amount equivalent 1 to 100 mg of free base, e.g., in an amount equivalent to 1 to 75 mg, or 1 to 60 mg, or 1 to 40 mg, or 1 to 30 mg, or 1 to 20 mg, or 1 to 10 mg, or 1 to 5 mg, or 40 to 60 mg, or 20 to 40 mg, or 10 to 20 mg, or about 60 mg, or about 40 mg, or about 30 mg, or about 20 mg, or about 10 mg, or about 5 mg, of free base, and a pharmaceutically acceptable diluent or carrier;

5.19. Method 5.17 wherein the method comprises once daily administration of a unit dosage for oral transmucosal administration, e.g., a sublingual or buccal orally disintegrating tablet, wafer, or film, comprising the compound of Formula I in free base or pharmaceutically acceptable salt form, e.g., in tosylate salt form, in an amount equivalent to 0.5 to 30 mg of free base, e.g., in an amount equivalent to 1 to 30 mg, or 1 to 20 mg, or 1 to 15 mg, or 1 to 10 mg, or 20 to 30 mg, or 10 to 20 mg, or about 5 mg, or about 10 mg, or about 15 mg, or about 20 mg, of free base, and a pharmaceutically acceptable diluent or carrier;

5.20. Any foregoing method wherein the post-viral syndrome is treated within one week, e.g., within three days, e.g., within one day;

5.21. Any foregoing method, wherein the post-viral syndrome is associated with a viral encephalitis;

5.22. Any foregoing method, wherein the post-viral syndrome is subsequent to a confirmed acute viral infection;

5.23. Method 5.22, wherein the acute viral infection was a viral encephalitis;

5.24. Any foregoing method, wherein the post-viral syndrome is caused by, or suspected to be caused by, Herpes simplex Virus 1, Herpes Simplex Virus 2, West Nile Virus, Nipah Virus, human immunodeficiency virus, rabies virus, Epstein-Barr Virus, cytomegalovirus, coronavirus (e.g., MERS-CoV, SARS-CoV, SARS-Cov2), or influenza virus (e.g., influenza A, such as H1N1, H2N2, H3N2, H5N1, H7N7);

5.25. Method 5.24, wherein the post-viral syndrome is caused by, or suspected to be caused by, a coronavirus (e.g., MERS-CoV, SARS-CoV, SARS-Cov2);

5.26. Method 5.25, wherein the post-viral syndrome is caused by, or suspected to be caused by, SARS-Cov2;

5.27. Any foregoing method, wherein the post-viral syndrome is caused by, or suspected to be caused by vesicular stomatitis virus and lymphocytic choriomeningitis virus;

5.28. Any foregoing method, wherein the patient is more than 2 weeks post-acute infection, e.g., more than 4 weeks, or more than 6 weeks, or more than 8 weeks, post-acute infection;

5.29. Any foregoing method, wherein the patient has not responded to antiviral medication during the post-acute infection (e.g., the post-viral syndrome), e.g., amantadine, rimantadine, pleconaril, raltegravir, elvitegravir, dolutegravir, rifampicin, acyclovir, ensitrelvir, famciclovir, ganciclovir, nirmatrelvir, ritonavir, olsatemivir, remdesivir;

5.30. Any foregoing method, wherein the patient suffers from depression (e.g., acute depression, depression of MDD, depression of bipolar disorder), anxiety, (e.g., acute anxiety), psychosis (e.g., schizophrenia), post-traumatic stress-disorder, anhedonia, memory loss, impairment of executive functioning, difficulty concentrating, seizures, difficulty sleeping, hallucination, change in personality, or any combination thereof;

5.31. Any foregoing method wherein the patient suffers from depression (e.g., acute depression, depression of MDD, depression of bipolar disorder);

5.32. Any foregoing method wherein the patient suffers from anxiety (e.g., acute anxiety);

5.33. Any foregoing method wherein the patient suffers from anhedonia;

5.34. Any foregoing method wherein the patient is diagnosed as having suicidal ideation and/or suicidal tendencies;

5.35. Any foregoing method, wherein the patient has no prior history of psychiatric disorders or psychiatric symptoms;

5.36. Any foregoing method wherein the 5-HT$_{2A}$ or 5-HT$_{2A}$/D2 receptor ligand is administered in combination (e.g., a fixed combination in a unit dosage form, or a free combination administered sequentially or simultaneously or within a 24-hour period) with a therapeutically effective amount of an anxiolytic or antidepressant agent;

5.37. Method 5.36, wherein the anxiolytic or antidepressant agent is selected from one or more compounds in free base or pharmaceutically acceptable salt form, selected from selective serotonin reuptake inhibitors (SSRIs), serotonin-norepinephrine reuptake inhibitors (SNRIs), tricyclic antidepressants (TCAs), and atypical antipsychotics, e.g., one or more compounds in free base or pharmaceutically acceptable salt form, selected from:

(a) Selective serotonin reuptake inhibitors (SSRIs), e.g., Citalopram (Celexa), Escitalopram (Lexapro, Cipralex), Paroxetine (Paxil, Seroxat), Fluoxetine (Prozac), Fluvoxamine (Luvox) Sertraline (Zoloft, Lustral);

(b) Serotonin-norepinephrine reuptake inhibitors (SNRIs), e.g., Desvenlafaxine (Pristiq), Duloxetine (Cymbalta), Levomilnacipran (Fetzima), Milnacipran (Ixel, Savella), Tofenacin (Elamol, Tofacine), Venlafaxine (Effexor);

(c) Tricyclic antidepressants (TCAs), e.g., Amitriptyline (Elavil, Endep), Amitriptylinoxide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Nitroxazepine (Sintamil), Nortriptyline (Pamelor, Aventyl), Noxiptiline (Agedal, Elronon, Nogedal), Pipofezine (Azafen/Azaphen), Protriptyline (Vivactil), Trimipramine (Surmontil);

(d) Benzodiazepines, e.g., selected from 2-keto compounds (e.g., clorazepate, diazepam, flurazepam, halazepam, prazepam); 3-hydroxy compounds (lorazepam, lormetazepam, oxazepam, temazepam); 7-nitro compounds (e.g., clonazepam, flunitrazepam, nimetazepam, nitrazepam); triazolo compounds (e.g., adinazolam, alprazolam, estazolam, triazolam); and imidazo compounds (climazolam, loprazolam, midazolam);

5.38. Any foregoing method, wherein the 5-HT$_{2A}$ or 5-HT$_{2A}$/D2 receptor ligand, e.g., the compound of Formula I is administered intra-nasally, subcutaneously, intramuscularly, intravenously, orally, sub-lingually, intra-peritoneally, or buccally, such as an oral rapidly dissolving tablet, wafer, or film, which dissolves in the oral cavity for transmucosal absorption;

5.39. Any foregoing method, wherein the method further comprises the concurrent administration of an anti-depressant agent (e.g., selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), a serotonin receptor antagonist, or any combination thereof), e.g., administered simultaneously, separately or sequentially;

5.40. Any foregoing method, wherein the method further comprises the concurrent administration of an NMDA receptor antagonist, for example, selected from ketamine (e.g., S-ketamine and/or R-ketamine), hydroxynorketamine, memantine, dextromethorphan, dextroallorphan, dextrorphan, amantadine, and agmatine, or any combination thereof, e.g., administered simultaneously, separately or sequentially;

5.41. Any foregoing method, wherein the method further comprises the concurrent administration of a NMDA receptor allosteric modulator, e.g., a NMDA receptor glycine-site modulator, such as rapastinel, nebostinel, apimostinel, D-cycloserine, or any combination thereof, e.g., administered simultaneously, separately or sequentially;

5.42. Any foregoing method, wherein the method provides the patient with an acute response to treatment with the therapeutic agent or agents (e.g., the 5-HT$_{2A}$ or 5-HT$_{2A}$/D2 receptor ligand, the Compound of Formula I, or the combination of the Compound or Formula I and the Compound of Formula II, and/or any additional antidepressant agents);

5.43. Method 5.42, wherein the patient shows an acute response to treatment within less than 3 weeks, for example, less than 2 weeks, or less than 1 week, or from 1 to 7 days, or 1 to 5 days, or 1 to 3 days, or 1 to 2 days, or about 1 day, or less than 2 days, or less than 1 day (e.g., 12-24 hours, 6-12 hours, or 3-6 hours);

5.44. Any foregoing method, wherein the patient has not responded to, or has not responded adequately to, or who suffers undesirable side effects from, treatment with another antidepressant agent, for example, any one or more of a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor, or a serotonin receptor antagonist;

5.45. Any foregoing method, wherein the patient does not suffer from schizophrenia or dementia;

5.46. Any foregoing method, wherein the patient has not previously been diagnosed with schizophrenia or dementia;

5.47. Any foregoing method, wherein the method protects or reinforces the blood-brain barrier;

5.48. Any foregoing method, wherein the patient has elevated levels of pro-inflammatory cytokines in the CNS (e.g., in the cerebrospinal fluid), such as TNF-α, IFN-γ, IL-1 (IL-1α and/or IL-1β), IL-6, IL-8, IL-12, IL-15, IL-17, IL-18, or elevated levels of C-reactive protein (CRP) of Csf1, and/or depressed levels of anti-inflammatory cytokines in the CNS (e.g., in the cerebrospinal fluid), such as TNF-β, IFN-α, IL-4, and IL-10;

5.49. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the 5-HT$_{2A}$ receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

5.50. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the D2 receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

5.51. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the D1 receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

5.52. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the serotonin transporter (SERT), e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said transporter (agonism or antagonism);

5.53. Any foregoing method, wherein the 5-HT$_{2A}$ or 5-HT$_{2A}$/D2 receptor ligand is lumateperone, in free base or pharmaceutically acceptable salt form, optionally in a deuterated form;

5.54. Any foregoing method, wherein the 5-HT$_{2A}$ or 5-HT$_{2A}$/D2 receptor ligand is lumateperone, in a tosylate salt form (e.g., monotosylate salt), optionally in a deuterated form, and optionally in crystalline or amorphous tosylate salt form;

5.55. Any foregoing method, wherein the 5-HT$_{2A}$ or 5-HT$_{2A}$/D2 receptor ligand is lumateperone, in free base form, optionally in a deuterated form;

5.56. Any foregoing method, wherein the 5-HT$_{2A}$ or 5-HT$_{2A}$/D2 receptor ligand is administered in the form of a long-acting injectable (LAI) composition, e.g., for intramuscular or subcutaneous injection;

5.57. Method 5.56, wherein the dose of the LAI composition is sufficient to provide the equivalent of a daily dose of 1 to 100 mg of free base, e.g., 1 to 75 mg, or 1 to 60 mg, or 1 to 40 mg, or 1 to 20 mg, or 1 to 10 mg, of free base, released over a period of time ranging from about 1 week to about 3 months, e.g., about 1 week to about 8 weeks, or about 1 week to about 6 weeks, or about 1 week to about 4 weeks, or about 1 week to about 3 weeks, or about 1 week to about 2 weeks;

5.58. Method 5.56 or 5.57, wherein the LAI composition comprises the compound of Formula I dissolved, dispersed, suspended, or encapsulated in a polymeric matrix;

5.59. Method 5.58, wherein the polymeric matrix comprises one or more biocompatible and biodegradable polymers as defined herein, e.g., poly(hydroxycarboxylic acids), poly(amino acids), cellulose polymers, modified cellulose polymers, polyamides, and polyesters;

5.60. Method 5.59, wherein the one or more polymers comprises polylactic acid, polyglycolic acid, polycitric acid, polymalic acid, poly-beta-hydroxybutyric acid, poly(lactic acid-glycolic acid) copolymer, 2-hydroxybutyric acid-glycolic acid copolymer, polylactic acid-polyethylene glycol copolymer, polyglycolic acid-polyethylene glycol copolymer, PEG-PLGA copolymer or block copolymer, PEG-PLGA copolymer or block copolymer, poly(alkyl alpha-cyanoacrylate) such as poly(butyl cyanoacrylate) or poly(2-octyl cyanoacrylate), poly(ortho ester), polycarbonate, poly-ortho-carbonate, a polyamino acid, (for example poly-gamma.-L-alanine, poly-.gamma.-benzyl-L-glutamic acid or poly-y-methyl-L-glutamic acid), and/or hyaluronic acid ester;

5.61. Method 5.60, wherein the one or more polymers comprises polyortho esters (POE), polylactic acid, polyglycolic acid, polycitric acid, polymalic acid, or a poly(lactic acid-glycolic acid) copolymer;

5.62. Method 5.60, wherein the one or more polymers comprises a poly(lactic acid-glycolic acid) copolymer, e.g., poly-d,l-lactide-co-glycolide (PLGA), for example, a PLGA copolymer with a lactide-to-glycolide molar ratio of about 50:50 to 90:10, or 50:50 to 85:15, or 50:50 to 75:25, and/or a molecular weight of 5,000 to 500,000 Daltons, or 5,000 to 150,000 Daltons, or 20,000 to 200,000 Daltons, or 24,000 to 38,000 Daltons;

5.63. Any foregoing method, wherein the 5-HT$_{2A}$ or 5-HT$_{2A}$/D2 receptor ligand is administered as monotherapy, e.g., it is not administered concurrently or in conjunction with an anti-depressant, anti-psychotic, or anti-anxiety agent;

5.64. Any foregoing method, wherein the 5-HT$_{2A}$ or 5-HT$_{2A}$/D2 receptor ligand is administered without the direct supervision of a health care professional (e.g., the compound is self-administered by the patient);

5.65. Any foregoing method, wherein the method does not comprise supervision or observation of the patient by a health care professional during or after (e.g., within 2 hours after) administration of a dose of the 5-HT$_{2A}$ or 5-HT$_{2A}$/D2 receptor ligand;

5.66. Any foregoing method, wherein the method does not put the patient at risk for sedation, dissociation, abuse, misuse, or suicidal ideation;

5.67. Any foregoing method, wherein the method does not result in hypertension (e.g., systolic and/or diastolic hypertension) within four hours after administration of a dose of the 5-HT$_{2A}$ or 5-HT$_{2A}$/D2 receptor ligand, e.g., an increase of more than 10 mm Hg, or more than 20 mm Hg, or more than 30 mm Hg, or more than 40 mm Hg, in systolic and/or diastolic blood pressure within 30 minutes to 4 hours after said dose;

5.68. Any foregoing method, wherein the method does not result in cognitive decline;

5.69. Any foregoing method, wherein the patient has (e.g., has been diagnosed with), or is at risk of, aneurysmal vascular disease (e.g., thoracic aorta, abdominal aorta, intracranial, or peripheral arterial aneurysms), arteriovenous malformation or intracerebral hemorrhage;

5.70. Any foregoing method, wherein the patient is under concurrent treatment with an oral antidepressant selected from duloxetine, escitalopram, sertraline, or venlafaxine;

5.71. Any foregoing method, wherein the patient is not under concurrent treatment with an oral antidepressant selected from duloxetine, escitalopram, sertraline, or venlafaxine;

5.72. Any foregoing method, wherein the patient is unresponsive to, or cannot be treated with ketamine (e.g., S-ketamine), e.g., because it is contraindicated in said patient;

5.73. Any foregoing method, wherein the 5-HT$_{2A}$ or 5-HT$_{2A}$/D2 receptor ligand is administered to the patient concurrently with a PDE1 (cyclic nucleoside phosphodiesterase 1) inhibitor (e.g., administered simultaneously, separately, or sequentially), in free base or pharmaceutically acceptable salt form;

5.74. Method 5.73, wherein the PDE1 inhibitor is a compound according to Formula II:

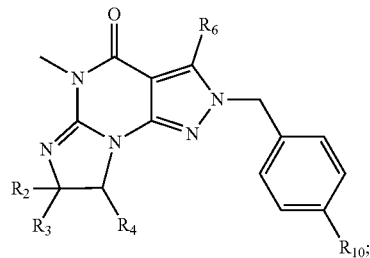

wherein $R_2$ is H and $R_3$ and $R_4$ together form a tri- or tetra-methylene bridge [pref. with the carbons carrying $R_3$ and $R_4$ having the R and S configuration respectively]; or $R_2$ and $R_3$ are each methyl and $R_4$ is H; or $R_2$ and $R_4$ are H and $R_3$ is isopropyl [pref. the carbon carrying $R_3$ having the R configuration];

$R_6$ is (optionally halo-substituted) phenylamino or (optionally halo-substituted) benzylamino;

$R_{10}$ is (optionally halo-substituted) phenyl, (optionally halo-substituted) pyridyl (for example 3-fluoro-pyrid-2-yl), thiadiazolyl (e.g., 1,2,3-thiadiazol-4-yl), or $C_{1-6}$alkylcarbonyl (e.g., methylcarbonyl);

in free base or pharmaceutically acceptable salt form;

5.75. Method 5.74, wherein, in the Compound of Formula II, $R_6$ is phenylamino or 4-fluorophenylamino;

5.76. Method 5.74, wherein, in the Compound of Formula II, $R_{10}$ is 3-fluoropyrid-2-yl or methylcarbonyl;

5.77. Method 5.74, wherein, in the Compound of Formula II, $R_6$ is phenylamino or 4-fluorophenylamino and $R_{10}$ is 3-fluoropyrid-2-yl or methylcarbonyl;

5.78. Any Methods 5.74-5.77, wherein the Compound of Formula II is

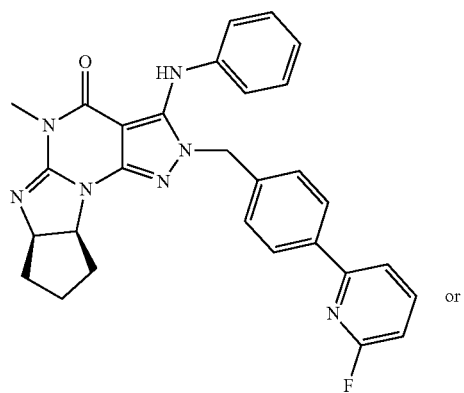

or

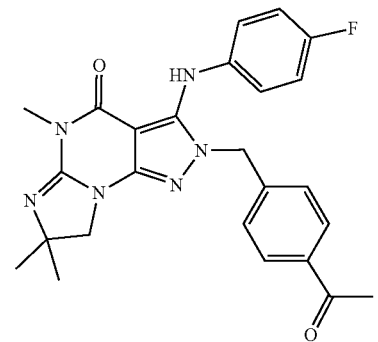

in free base or pharmaceutically acceptable salt form;

5.79. Method 5.78, wherein the Compound of Formula II is in the form of the monophosphate salt;

5.80. Any of Methods 5.74-5.79, wherein the Compound of Formula I is:

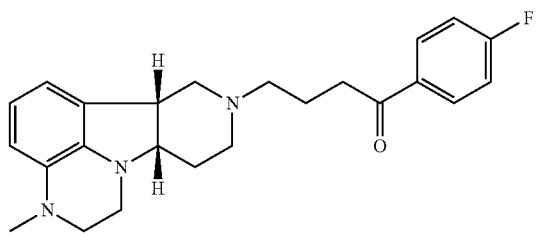 [SMILES: CN1CCN2c3c(cccc31)[C@@H]1CN(CCCC(=O)c3ccc(F)cc3)CC[C@@H]12]

in free base or pharmaceutically acceptable salt form, e.g., tosylate salt form, optionally in a deuterated form; and the Compound of Formula II is:

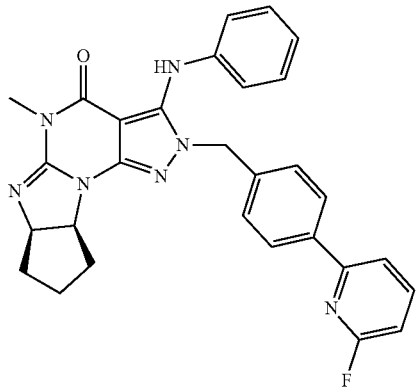 [SMILES: CN1C(=O)c2c(nn(Cc3ccc(-c4cccc(F)n4)cc3)c2Nc2ccccc2)N2C1=N[C@@H]1CCC[C@@H]12]

in free base or pharmaceutically acceptable salt form, e.g., monophosphate salt form;

5.81. Any of Methods 5.74-5.80, comprising administration of a pharmaceutical composition comprising therapeutically effective amounts of both a Compound of Formula I and a Compound of Formula II;

5.82. Any preceding method, wherein the 5-HT$_{2A}$ or 5-HT$_{2A}$/D2 receptor ligand is a compound of Formula I, in free base or pharmaceutically acceptable salt from, optionally in deuterated form, and wherein the compound is administered in the form of a long-acting injectable (LAI) composition comprising the compound of Formula I dissolved or dispersed or in a pharmaceutically acceptable carrier and a polymeric matrix comprising polymers selected from polyortho esters (POE), polylactic acid, polyglycolic acid, polycitric acid, polymalic acid, or a poly(lactic acid-glycolic acid) copolymer;

5.83. Method 5.82, wherein the pharmaceutically acceptable carrier comprises water (e.g., an aqueous buffer) and/or an organic solvent (e.g., a water-miscible organic solvent);

5.84. Method 5.82 or 5.83, wherein the polymers comprise a polylactic acid and/or a polyglycolic acid polymer;

5.85. Method 5.82 or 5.83, wherein the polymers comprise a poly(lactic acid-glycolic acid) copolymer, e.g., poly-d,l-lactide-co-glycolide (PLGA), for example, a PLGA copolymer with a lactide-to-glycolide molar ratio of about 50:50 to 90:10, or 50:50 to 85:15, or 50:50 to 75:25, and/or a molecular weight of 5,000 to 500,000 Daltons, or 5,000 to 150,000 Daltons, or 20,000 to 200,000 Daltons, or 24,000 to 38,000 Daltons;

5.86. Any of Methods 5.82-5.85, wherein the LAI composition is administered by, or formulated for administration by, intramuscular or subcutaneous injection;

5.87. Method 5, or any of 5.1-5.86, wherein the patient has no prior history of depression;

5.88. Method 5, or any of 5.1-5.87, wherein the patient shows evidence of cerebral damage or cerebral disease on magnetic resonance imaging (MRI) prior to administration of the 5-HT$_{2A}$ or 5-HT$_{2A}$/D2 receptor ligand;

5.89. Method 5, or any of 5.1-5.88, wherein the patient has a positive serum antibody or antigen test for one or more of Herpes simplex Virus 1, Herpes Simplex Virus 2, West Nile Virus, Nipah Virus, human immunodeficiency virus, rabies virus, Epstein-Barr Virus, cytomegalovirus, coronavirus (e.g., MERS-CoV, SARS- CoV, SARS-Cov2, or influenza virus (e.g., influenza A, such as H1N1, H2N2, H3N2, H5N1, H7N7), prior to administration of the 5-HT$_{2A}$ or 5-HT$_{2A}$/D2 receptor ligand;

5.90. Method 5, or any of 5.1-5.89, wherein the patient has a positive serum antibody test for autoantibodies against the NMDA receptor, the AMPA receptor, the voltage-gated potassium, channel (VGKC), the LGL1 protein, the GABA receptor, the glycine receptor, the glutamate receptor, or the CASPR2 receptor;

5.91. Any foregoing method, wherein the patient has elevated levels of one or more biomarkers indicative of CNS inflammation, e.g., selected from TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1, in the blood, plasma, serum, peripheral blood mononuclear cells (PBMC) (e.g., isolated from blood), urine, CSF, and/or CNS microglial cells (e.g., isolated from CSF);

5.92. Any foregoing method, wherein the patient has changes in levels of one or more biomarkers indicative of CNS inflammation and/or loss of BBB integrity, e.g., increased levels of ICAM-1, VCAM-1, E-selectin, P-selectin, or soluble isoforms thereof (e.g., sICAM-1, sVCAM1, sP-selectin, sE-selectin), or reduced levels of Cldn5, Occludin, and/or ZO-1, in the serum or CSF;

5.93. Any foregoing method, wherein the patient has depressed levels of one or more anti-inflammatory biomarkers indicative of CNS inflammatory dysfunction, e.g., TNF-β, IFN-α, IL-4, and IL-10, in the blood, plasma, serum, peripheral blood mononuclear cells (PBMC) (e.g., isolated from blood), urine, CSF, and/or CNS microglial cells (e.g., isolated from CSF);

5.94. Any foregoing method, wherein after treatment with the 5-HT$_{2A}$ or 5-HT$_{2A}$/D2 receptor ligand (e.g., Compound of Formula I, optionally in deuterated form), the patient has a reduced level of one or more biomarkers indicative of CNS inflammation, e.g., TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1, in the blood, plasma, serum, peripheral blood mononuclear cells (PBMC) (e.g., isolated from blood), urine, CSF, and/or CNS microglial cells (e.g., isolated from CSF), compared to a pre-treatment baseline, e.g., within 28 days of the initiation of treatment;

5.95. Method 5.94, wherein the patient has at least a 5%, 10%, 15%, 20%, or 25%, 30%, 35%, 40%, 45%, or 50%, reduction in the level of the one or more biomarkers indicative of CNS inflammation, e.g., within 28 days of the initiation of treatment;

5.96. Any foregoing method, wherein after treatment with the 5-HT$_{2A}$ or 5-HT$_{2A}$/D2 receptor ligand (e.g., Compound of Formula I, optionally in deuterated form), the patient has favorable changes in levels of one or more biomarkers indicative of CNS inflammation and/or loss of BBB integrity, e.g., decreased levels of ICAM-1, VCAM-1, E-selectin, P-selectin, or soluble isoforms thereof (e.g., sICAM-1, sVCAM1, sP-selectin, sE-selectin), or increased levels of Cldn5, Occludin, and/or ZO-1, in the serum or CSF, compared to a pre-treatment baseline, e.g., within 28 days of the initiation of treatment;

5.97. Method 5.96, wherein the patient has at least a 5%, 10%, 15%, 20%, 25%, 30%, 35%, 40%, 45%, or 50%, reduction or increase in the level of the one or more biomarkers indicative of CNS inflammation, e.g., within 28 days of the initiation of treatment;

5.98. Any foregoing method, wherein after treatment with the 5-HT$_{2A}$ or 5-HT$_{2A}$/D2 receptor ligand (e.g., Compound of Formula I, optionally in deuterated form), the patient has an increased level of one or more anti-inflammatory biomarkers indicative of CNS inflammatory dysfunction, e.g., TNF-β, IFN-α, IL-4, and IL-10, in the blood, plasma, serum, peripheral blood mononuclear cells (PBMC) (e.g., isolated from blood), urine, CSF, and/or CNS microglial cells (e.g., isolated from CSF), compared to a pre-treatment baseline, e.g., within 28 days of the initiation of treatment;

5.99. Method 5.98, wherein the patient has an increase of at least 5%, 10%, 15%, 20%, 25%, 30%, 35%, 40%, 45%, or 50%, in the levels of the one or more anti-inflammatory biomarkers indicative CNS inflammatory dysfunction, e.g., within 28 days of the initiation of treatment, e.g., within 28 days of the initiation of treatment;

5.100. Any foregoing method, wherein the method further comprises the step of testing one or more body fluids or tissues from the patient for the presence and/or concentration of one or more biomarkers indicative of CNS inflammation or CNS inflammatory dysfunction or loss of BBB integrity prior to the initiation of treatment with the 5-HT$_{2A}$ or 5-HT$_{2A}$/D2 receptor ligand (e.g., Compound of Formula, optionally in deuterated form), and/or subsequent to the initiation of said treatment, and optionally comparing the pre-treatment and one or more post-treatment results thereof to quantify the effectiveness of the treatment in the patient and/or to adjust the treatment regimen;

5.101. Method 5.100, wherein the biomarkers are selected from one or more of TNF-α, IFN-γ, IL-1 (IL-1α and/or IL-1β), IL-6, IL-8, IL-12, IL-15, IL-17, IL-18, CRP, SAA, Csf1, YKL-40, Nlrp3, Flt-1, ICAM-1, VCAM-1, E-selectin, P-selectin, Cldn5, Occludin, and ZO-1, soluble isoforms thereof (e.g., sICAM-1, sVCAM1, sP-selectin, sE-selectin), TNF-β, IFN-α, IL-4, and IL-10;

5.102. Method 5.100 or 5.101, wherein the one or more body fluids or tissues are selected from blood, plasma, serum, peripheral blood mononuclear cells (PBMC) (e.g., isolated from blood), urine, CSF, and/or CNS microglial cells (e.g., isolated from CSF), or brain biopsy tissue samples;

5.103. Any foregoing method, wherein the method further comprises the step of non-invasively testing the central nervous system of the patient for the presence and/or concentration of one or more biomarkers indicative of CNS inflammation or CNS inflammatory dysfunction prior to the initiation of treatment with the 5-HT$_{2A}$ or 5-HT$_{2A}$/D2 receptor ligand (e.g., Compound of Formula I, optionally in deuterated form), and/or subsequent to the initiation of said treatment, and optionally comparing the pre-treatment and one or more post-treatment results thereof to quantify the effectiveness of the treatment in the patient and/or to adjust the treatment regimen;

5.104. Method 5.103, wherein the biomarkers are selected from one or more of TNF-α, IFN-γ, IL-1 (IL-1α and/or IL-1β), IL-6, IL-12, IL-15, IL-17, IL-18, CRP, SAA, Csf1, YKL-40, Nlrp3, Flt-1, ICAM-1, VCAM-1, E-selectin, P-selectin, Cldn5, Occludin, and ZO-1, soluble isoforms thereof (e.g., sICAM-1, sVCAM1, sP-selectin, sE-selectin), TNF-β, IFN-α, IL-4, and IL-10;

5.105. Method 5.103 or 5.104, wherein the step comprises an imaging method, such as magnetic resonance imaging (MRI), positron emission tomography (PET), functional MRI (fMRI), to evaluate the presence and/or concentration of said biomarkers;

5.106. Any of Methods 5.100-5.105, wherein the method comprises the step of initiating, altering, or terminating, the treatment regimen (e.g., the selected 5-HT$_{2A}$ or 5-HT$_{2A}$/D2 receptor ligand, the dose thereof, the route of administration thereof, the frequency of administration thereof, the form of administration thereof, and/or the combination of the selected 5-HT$_{2A}$ or 5-HT$_{2A}$/D2 receptor ligand with any another therapeutic agent), based on the observed changes in the levels of one or more of said biomarkers;

5.107. Any foregoing method, wherein the patient has elevated levels of one or more biomarkers indicative of peripheral inflammation, e.g., selected from type-I interferons, including IFN-α, IFN-β, and/or IFN-δ, in the blood, plasma, serum, peripheral blood mononuclear cells (PBMC) (e.g., isolated from blood), or urine;

5.108. Method 5.107, wherein after treatment with the 5-HT$_{2A}$ or 5-HT$_{2A}$/D2 receptor ligand (e.g., Compound of Formula I, optionally in deuterated form), the patient has a reduced level of the one or more biomarkers indicative of peripheral inflammation, e.g., selected type-I interferons, including IFN-α, IFN-β, and/or IFN-δ, in the blood, plasma, serum, peripheral blood mononuclear cells (PBMC) (e.g., isolated from blood), or urine, compared to a pre-treatment baseline, e.g., within 28 days of the initiation of treatment;

5.109. Method 5.108, wherein the patient has at least a 5%, 10%, 15%, 20%, or 25%, 30%, 35%, 40%, 45%, or 50%, reduction in the level of the one or more biomarkers indicative of peripheral inflammation, e.g., within 28 days of the initiation of treatment;

5.110. Any foregoing method, wherein the patient has peripheral serotonin deficiency, e.g., reduced concentration in the plasma and/or platelets, for example, a plasma serotonin concentration less than 3000 nM, less than 2500 nM, less than 2000 nM, less than 1800 nM, less than 1600 nM, less than 1400 nM, less than 1200 nM, less than 1000 nM, less than 800 nM, less than 600 nM, less than 500 nM, less than 400 nM, less than 300 nM, or less than 250 nM;

5.111. Method 5.110, wherein after treatment with the 5-HT$_{2A}$ or 5-HT$_{2A}$/D2 receptor ligand (e.g., Compound of Formula I, optionally in deuterated form), the patient has recovered from peripheral serotonin deficiency, e.g., a normal concentration in the plasma and/or platelets, for example, a plasma serotonin concentration of greater than 500 nM, or 500 to 3000 nM, or 1000 to 3000 nM, or 1500 to 3000 nM, or 2000 to 3000 nM, or greater than 3000 nM nM, less than 800 nM, less than 600 nM, less than 500 nM, less than 400 nM, less than 300 nM, or less than 250 nM;

5.112. Method 5.110 or 5.111, wherein the post-viral syndrome is caused by, or thought to be caused by, peripheral serotonin deficiency, e.g., due to reduced plasma serotonin concentration and/or reduced vagal nerve afferent sensory activity (e.g., due to reduced serotonin-mediated 5-HT$_3$ signaling)

5.113. Any foregoing method, wherein the patient is suffering from Long COVID;

5.114. Any foregoing method, wherein the patient has thrombocytopenia or platelet hypercoagulability (e.g., as shown by reduced prothrombin time and/or partial thromboplastin time), 5.115. Any foregoing method, wherein the method further comprises the step of obtaining a tissue sample from the patient and testing the tissue sample for the level of any one or more of: (a) serum antibody or antigen for one or more of Herpes simplex Virus 1, Herpes Simplex Virus 2, West Nile Virus, Nipah Virus, human immunodeficiency virus, rabies virus, Epstein-Barr Virus, cytomegalovirus, coronavirus (e.g., MERS-CoV, SARS-CoV, SARS-Cov2, or influenza virus (e.g., influenza A, such as H1N1, H2N2, H3N2, H5N1, H7N7); (b) serum autoantibodies against the NMDA receptor, the AMPA receptor, the voltage-gated potassium, channel (VGKC), the LGL1 protein, the GABA receptor, the glycine receptor, the glutamate receptor, or the CASPR2 receptor; (c) biomarkers selected from TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1; (d) biomarkers selected from ICAM-1, VCAM-1, E-selectin, P-selectin, or soluble isoforms thereof (e.g., sICAM-1, sVCAM1, sP-selectin, sE-selectin), Cldn5, Occludin, and/or ZO-1; (e) biomarkers selected from TNF-β, IFN-α, IL-4, and IL-10; (f) type-I interferons, including IFN-α, IFN-β, and/or IFN-δ; (f) serotonin; and (g) platelet count, prothrombin time, and/or partial thromboplastin time;

5.116. Method 5.115, wherein the tissue sample is selected from blood, plasma, serum, peripheral blood mononuclear cells (PBMC) (e.g., isolated from blood), urine, CSF, and/or CNS microglial cells (e.g., isolated from CSF);

5.117. Method 5.115 or 5.116, wherein the method further comprises adjusting the course of treatment based on the results of one more of said tissue sample measurements, optionally wherein said tissue sample measurements are taken at one or more times during the course of therapy, e.g., for comparison to earlier measurements or measurements taken before initiating therapy.

In another aspect, the disclosure provides a 5-HT$_{2A}$ or 5-HT$_{2A}$/D2 receptor ligand, e.g., a compound of Formula I, as hereinbefore described, for example lumateperone, in free base or salt form, optionally in deuterated form, for use in the treatment or prevention of post-viral syndrome (e.g., Long COVID), e.g., for use in any of Methods 5, et seq.

In another aspect, the disclosure provides the use of a 5-HT$_{2A}$ or 5-HT$_{2A}$/D2 receptor ligand, e.g., a compound of Formula I, as hereinbefore described, for example lumateperone, in free base or salt form, optionally in deuterated form, in in the manufacture of a medicament for the treatment or prevention of post-viral syndrome (e.g., Long COVID), e.g., for any of Methods 5, et seq.

In a particular embodiment, the present disclosure provides a method (Method 6) for the treating or preventing peripheral serotonin deficiency, comprising administering to a patient in need thereof, a therapeutically effective amount of a 5-HT$_{2A}$ or 5-HT$_{2A}$/D2 receptor ligand, for example, a compound of Formula I:

Formula I

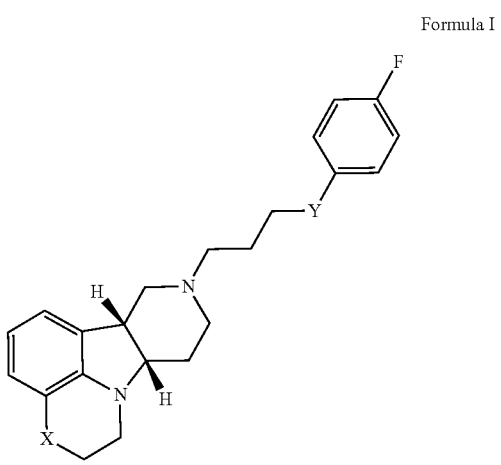

wherein:
X is —N(H)—, —N(CH$_3$)— or —O—;
Y is —C(=O)—, —C(H)(OH)— or —C(H)(OR$_1$)—;
R$_1$ is —C(O)—C$_{1-21}$alkyl (e.g., —C(O)—C$_{1-5}$alkyl, —C(O)—C$_{6-15}$alkyl or —C(O)—C$_{16-21}$alkyl), preferably said alkyl is a straight chain, optionally saturated or unsaturated and optionally substituted with one or more hydroxy or C$_{1-22}$alkoxy (e.g., ethoxy) groups, for example R$_1$ is —C(O)—C$_6$alkyl, —C(O)—C$_7$alkyl, —C(O)—C$_9$alkyl, —C(O)—C$_{11}$alkyl, —C(O)—C$_{13}$alkyl or —C(O)—C$_{15}$alkyl, wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand,
optionally in deuterated form,
in free base, pharmaceutically acceptable salt, or prodrug form. For example, Method 5 may be as follows:

6.1. Method 6, wherein X in the compound of Formula I is —N(H)—, —N(CH$_3$)— or —O—;
6.2. Method 6 or 1.1, wherein X in the compound of Formula I is —N(H);
6.3. Method 6 or 1.1, wherein X in the compound of Formula I is —N(CH$_3$)—;
6.4. Method 6 or 1.1, wherein X in the compound of Formula I is —O—;
6.5. Method 6 or any of formulae 1.1-1.4, wherein Y in the compound of Formula I is —C(=O)—, —C(H)(OH)— or —C(H)(OR$_1$)—;
6.6. Method 4 or any of formulae 1.1-1.4, wherein Y in the compound of Formula I is —C(=O)—;
6.7. Method 6 or any of formulae 1.1-1.4, wherein Y in the compound of Formula I is —C(H)(OH)—;
6.8. Method 6 or any of formulae 1.1-1.4, wherein Y in the compound of Formula I is —C(H)(OR$_1$)—;
6.9. Method 6, or any of 6.1-6.5 or 1.8, wherein R$_1$ in the compound of Formula I is —C(O)—C$_{1-21}$alkyl (e.g., —C(O)—C$_{1-5}$alkyl, —C(O)—C$_{6-15}$alkyl or —C(O)—C$_{16-21}$alkyl), preferably said alkyl is a straight chain, optionally saturated or unsaturated and optionally substituted with one or more hydroxy or C$_{1-22}$alkoxy (e.g., ethoxy) groups, for example R$_1$ is —C(O)—C$_6$alkyl, —C(O)—C$_7$alkyl, —C(O)—C$_9$alkyl, —C(O)—C$_{11}$alkyl, —C(O)—C$_{13}$alkyl or —C(O)—C$_{15}$alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand; e.g., wherein R$_1$ in the compound of Formula I is —C(O)—C$_{6-15}$alkyl, e.g., —C(O)—C$_9$alkyl; or wherein R$_1$ in the compound of Formula I is —C(O)—C$_{1-5}$alkyl, e.g., —C(O)—C$_3$alkyl;

6.10. Method 6 or any of 1.1-1.5 or 1.7, wherein the Compound of Formula I is:

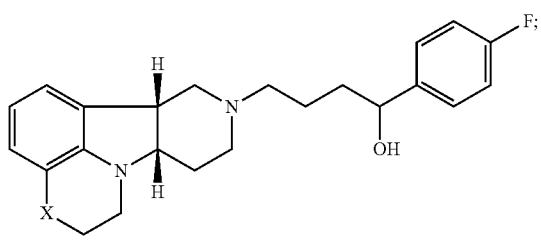

6.11. Method 6 or any of 1.1-1.5 or 1.7, wherein the Compound of Formula I is:

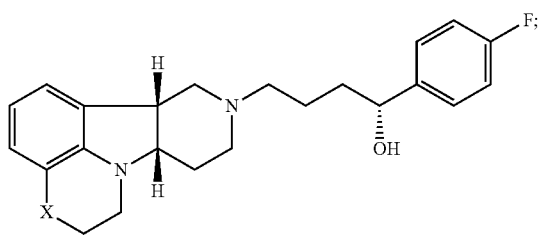

6.12. Method 6, or any of 6.1, 6.3, 6.5, or 6.6, wherein the Compound of Formula I is lumateperone:

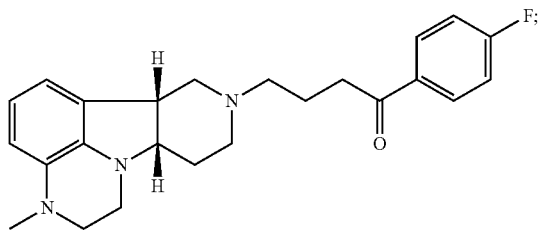 [SMILES: CN1CCN2c3c(cccc31)[C@@H]1CN(CCCC(=O)c3ccc(F)cc3)CC[C@@H]12]

6.13. Method 6, or any of 6.1-6.12, e.g., Method 6.12, wherein the Compound of Formula I is in the form of a pharmaceutically acceptable salt, e.g., a tosylate salt;
6.14. Method 6, or any of 6.1-6.12, e.g., Method 6.12, wherein the Compound of Formula I is in the form of the free base;
6.15. Method 6 or any of 6.1-6.14 wherein the Compound of Formula I is in deuterated form, e.g., wherein the deuterium:protium ratio for a specified carbon-bound hydrogen atom is significantly higher, e.g., at least 2×, for example at least 10× higher, than the natural isotope ratios;
6.16. Method 6.15 wherein the Compound of Formula I is a deuterated form of lumateperone, for example, selected from:

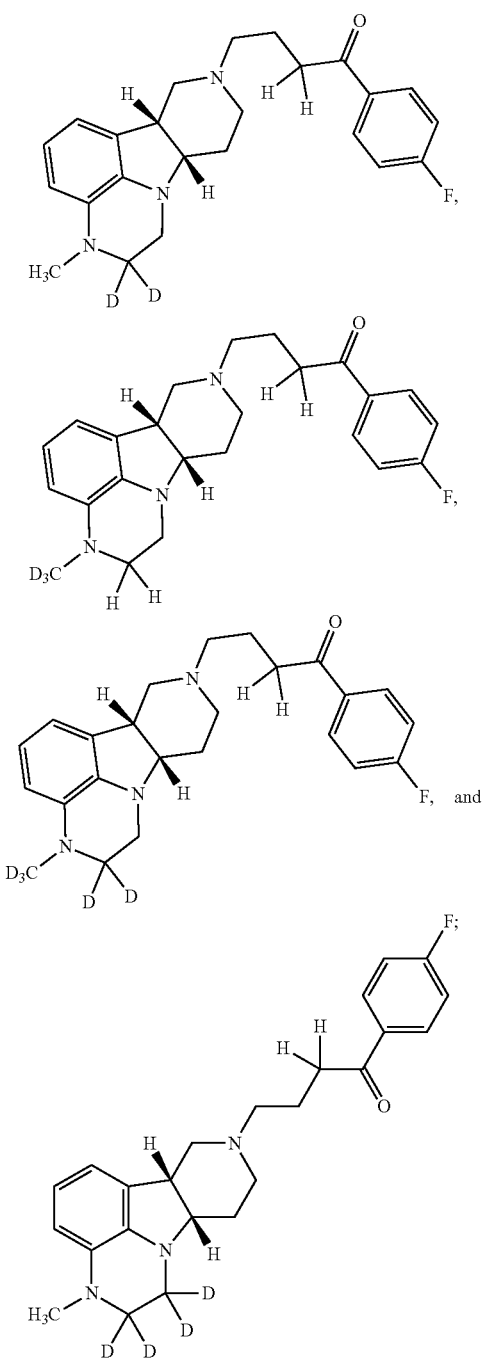

wherein D represents a hydrogen position with substantially greater than natural deuterium incorporation (i.e., substantially greater than 0.0156%), e.g., greater than 60%, or greater than 70%, or greater than 80%, or greater than 90% or greater than 95%, or greater than 96%, or greater than 97%, or greater than 98%, or greater than 99%, in free base or pharmaceutically acceptable salt form, e.g., tosylate salt form;

6.17. Any foregoing method, wherein the 5-HT$_{2A}$ or 5-HT$_{2A}$/D2 receptor ligand is a compound of Formula I in free base or pharmaceutically acceptable salt form, e.g., tosylate salt form, administered in a daily dose equivalent to 1 to 100 mg of free base, e.g., in an amount equivalent to 1 to 75 mg, or 1 to 60 mg, or 1 to 40 mg, or 1 to 20 mg, or 1 to 10 mg, of free base;

6.18. Method 6.17 wherein the method comprises once daily administration of a unit dosage for oral administration, for example a tablet or capsule, comprising the compound of Formula I in free base or pharmaceutically acceptable salt form, e.g., in tosylate salt form, in an amount equivalent 1 to 100 mg of free base, e.g., in an amount equivalent to 1 to 75 mg, or 1 to 60 mg, or 1 to 40 mg, or 1 to 30 mg, or 1 to 20 mg, or 1 to 10 mg, or 1 to 5 mg, or 40 to 60 mg, or 20 to 40 mg, or 10 to 20 mg, or about 60 mg, or about 40 mg, or about 30 mg, or about 20 mg, or about 10 mg, or about 5 mg, of free base, and a pharmaceutically acceptable diluent or carrier;

6.19. Method 6.17 wherein the method comprises once daily administration of a unit dosage for oral transmucosal administration, e.g., a sublingual or buccal orally disintegrating tablet, wafer, or film, comprising the compound of Formula I in free base or pharmaceutically acceptable salt form, e.g., in tosylate salt form, in an amount equivalent to 0.5 to 30 mg of free base, e.g., in an amount equivalent to 1 to 30 mg, or 1 to 20 mg, or 1 to 15 mg, or 1 to 10 mg, or 20 to 30 mg, or 10 to 20 mg, or about 5 mg, or about 10 mg, or about 15 mg, or about 20 mg, of free base, and a pharmaceutically acceptable diluent or carrier;

6.20. Any foregoing method wherein the peripheral serotonin deficiency is treated within one week, e.g., within three days, e.g., within one day;

6.21. Any foregoing method, wherein the peripheral serotonin deficiency is associated with a viral infection;

6.22. Method 6.21, wherein the peripheral serotonin deficiency is associated with a post-viral syndrome;

6.23. Method 6.21, wherein the viral infection is an acute viral infection;

6.24. Any of Methods 6.21-6.23, wherein the viral infection or syndrome is caused by, or suspected to be caused by, Herpes simplex Virus 1, Herpes Simplex Virus 2, West Nile Virus, Nipah Virus, human immunodeficiency virus, rabies virus, Epstein-Barr Virus, cytomegalovirus, coronavirus (e.g., MERS-CoV, SARS-CoV, SARS-Cov2), or influenza virus (e.g., influenza A, such as H1N1, H2N2, H3N2, H5N1, H7N7);

6.25. Method 6.24, wherein the viral infection or syndrome is caused by, or suspected to be caused by, a coronavirus (e.g., MERS-CoV, SARS-CoV, SARS-Cov2);

6.26. Method 6.25, wherein the viral infection or syndrome is caused by, or suspected to be caused by, SARS-Cov2;

6.27. Any of Methods 6.21-6.23, wherein the viral infection or syndrome is caused by, or suspected to be caused by vesicular stomatitis virus and lymphocytic choriomeningitis virus;

6.28. Any of Methods 6.21-6.27, wherein the patient is more than 2 weeks post-acute infection, e.g., more than 4 weeks, or more than 6 weeks, or more than 8 weeks, post-acute infection;

6.29. Any of Methods 6.21-6.28, wherein the patient has not responded to antiviral medication during the post-acute infection (e.g., the post-viral syndrome), e.g., amantadine, rimantadine, pleconaril, raltegravir, elvitegravir, dolutegravir, rifampicin, acyclovir, ensitrelvir, famciclovir, ganciclovir, nirmatrelvir, ritonavir, olsatemivir, remdesivir;

6.30. Any foregoing method, wherein the patient suffers from depression (e.g., acute depression, depression of MDD, depression of bipolar disorder), anxiety, (e.g., acute anxiety), psychosis (e.g., schizophrenia), post-traumatic stress-disorder, anhedonia, memory loss, impairment of executive functioning, difficulty concentrating, seizures, difficulty sleeping, hallucination, change in personality, or any combination thereof;

6.31. Any foregoing method wherein the patient suffers from depression (e.g., acute depression, depression of MDD, depression of bipolar disorder);

6.32. Any foregoing method wherein the patient suffers from anxiety (e.g., acute anxiety);

6.33. Any foregoing method wherein the patient suffers from anhedonia;

6.34. Any foregoing method wherein the patient is diagnosed as having suicidal ideation and/or suicidal tendencies;

6.35. Any foregoing method, wherein the patient has no prior history of psychiatric disorders or psychiatric symptoms;

6.36. Any foregoing method wherein the $5\text{-}HT_{2A}$ or $5\text{-}HT_{2A}/D2$ receptor ligand is administered in combination (e.g., a fixed combination in a unit dosage form, or a free combination administered sequentially or simultaneously or within a 24-hour period) with a therapeutically effective amount of an anxiolytic or antidepressant agent;

6.37. Method 6.36, wherein the anxiolytic or antidepressant agent is selected from one or more compounds in free base or pharmaceutically acceptable salt form, selected from selective serotonin reuptake inhibitors (SSRIs), serotonin-norepinephrine reuptake inhibitors (SNRIs), tricyclic antidepressants (TCAs), and atypical antipsychotics, e.g., one or more compounds in free base or pharmaceutically acceptable salt form, selected from:

(a) Selective serotonin reuptake inhibitors (SSRIs), e.g., Citalopram (Celexa), Escitalopram (Lexapro, Cipralex), Paroxetine (Paxil, Seroxat), Fluoxetine (Prozac), Fluvoxamine (Luvox) Sertraline (Zoloft, Lustral);

(b) Serotonin-norepinephrine reuptake inhibitors (SNRIs), e.g., Desvenlafaxine (Pristiq), Duloxetine (Cymbalta), Levomilnacipran (Fetzima), Milnacipran (Ixel, Savella), Tofenacin (Elamol, Tofacine), Venlafaxine (Effexor);

(c) Tricyclic antidepressants (TCAs), e.g., Amitriptyline (Elavil, Endep), Amitriptylinoxide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Nitroxazepine (Sintamil), Nortriptyline (Pamelor, Aventyl), Noxiptiline (Agedal, Elronon, Nogedal), Pipofezine (Azafen/Azaphen), Protriptyline (Vivactil), Trimipramine (Surmontil);

(d) Benzodiazepines, e.g., selected from 2-keto compounds (e.g., clorazepate, diazepam, flurazepam, halazepam, prazepam); 3-hydroxy compounds (lorazepam, lormetazepam, oxazepam, temazepam); 7-nitro compounds (e.g., clonazepam, flunitrazepam, nimetazepam, nitrazepam); triazolo compounds (e.g., adinazolam, alprazolam, estazolam, triazolam); and imidazo compounds (climazolam, loprazolam, midazolam);

6.38. Any foregoing method, wherein the $5\text{-}HT_{2A}$ or $5\text{-}HT_{2A}/D2$ receptor ligand, e.g., the compound of Formula I is administered intra-nasally, subcutaneously, intramuscularly, intravenously, orally, sub-lingually, intra-peritoneally, or buccally, such as an oral rapidly dissolving tablet, wafer, or film, which dissolves in the oral cavity for transmucosal absorption;

6.39. Any foregoing method, wherein the method further comprises the concurrent administration of an antidepressant agent (e.g., selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), a serotonin receptor antagonist, or any combination thereof), e.g., administered simultaneously, separately or sequentially;

6.40. Any foregoing method, wherein the method further comprises the concurrent administration of an NMDA receptor antagonist, for example, selected from ketamine (e.g., S-ketamine and/or R-ketamine), hydroxynorketamine, memantine, dextromethorphan, dextroallorphan, dextrorphan, amantadine, and agmatine, or any combination thereof, e.g., administered simultaneously, separately or sequentially;

6.41. Any foregoing method, wherein the method further comprises the concurrent administration of a NMDA receptor allosteric modulator, e.g., a NMDA receptor glycine-site modulator, such as rapastinel, nebostinel, apimostinel, D-cycloserine, or any combination thereof, e.g., administered simultaneously, separately or sequentially;

6.42. Any foregoing method, wherein the method provides the patient with an acute response to treatment with the therapeutic agent or agents (e.g., the $5\text{-}HT_{2A}$ or $5\text{-}HT_{2A}/D2$ receptor ligand, the Compound of Formula I, or the combination of the Compound or Formula I and the Compound of Formula II, and/or any additional antidepressant agents);

6.43. Method 6.42, wherein the patient shows an acute response to treatment within less than 3 weeks, for example, less than 2 weeks, or less than 1 week, or from 1 to 7 days, or 1 to 5 days, or 1 to 3 days, or 1 to 2 days, or about 1 day, or less than 2 days, or less than 1 day (e.g., 12-24 hours, 6-12 hours, or 3-6 hours);

6.44. Any foregoing method, wherein the patient has not responded to, or has not responded adequately to, or who suffers undesirable side effects from, treatment with another antidepressant agent, for example, any one or more of a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor, or a serotonin receptor antagonist;

6.45. Any foregoing method, wherein the patient does not suffer from schizophrenia or dementia;

6.46. Any foregoing method, wherein the patient has not previously been diagnosed with schizophrenia or dementia;

6.47. Any foregoing method, wherein the method protects or reinforces the blood-brain barrier;

6.48. Any foregoing method, wherein the patient has elevated levels of pro-inflammatory cytokines in the CNS (e.g., in the cerebrospinal fluid), such as TNF-α, IFN-γ, IL-1 (IL-1α and/or IL-1β), IL-6, IL-8, IL-12, IL-15, IL-17, IL-18, or elevated levels of C-reactive protein (CRP) of Csf1, and/or depressed levels of anti-inflammatory cytokines in the CNS (e.g., in the cerebrospinal fluid), such as TNF-β, IFN-α, IL-4, and IL-10; 6.49. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the 5-HT$_{2A}$ receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

6.50. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the D2 receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

6.51. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the D1 receptor, e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

6.52. Any foregoing method, wherein the 5-HT$_{2A}$ or 5-HT$_{2A}$/D2 receptor ligand has an IC$_{50}$ of less than 250 nM or an EC$_{50}$ of less than 250 nM for activity (agonism and/or antagonism) at the serotonin transporter (SERT), e.g., an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said transporter (agonism or antagonism);

6.53. Any foregoing method, wherein the 5-HT$_{2A}$ or 5-HT$_{2A}$/D2 receptor ligand is lumateperone, in free base or pharmaceutically acceptable salt form, optionally in a deuterated form;

6.54. Any foregoing method, wherein the 5-HT$_{2A}$ or 5-HT$_{2A}$/D2 receptor ligand is lumateperone, in a tosylate salt form (e.g., monotosylate salt), optionally in a deuterated form, and optionally in crystalline or amorphous tosylate salt form;

6.55. Any foregoing method, wherein the 5-HT$_{2A}$ or 5-HT$_{2A}$/D2 receptor ligand is lumateperone, in free base form, optionally in a deuterated form;

6.56. Any foregoing method, wherein the 5-HT$_{2A}$ or 5-HT$_{2A}$/D2 receptor ligand is administered in the form of a long-acting injectable (LAI) composition, e.g., for intramuscular or subcutaneous injection;

6.57. Method 6.56, wherein the dose of the LAI composition is sufficient to provide the equivalent of a daily dose of 1 to 100 mg of free base, e.g., 1 to 75 mg, or 1 to 60 mg, or 1 to 40 mg, or 1 to 20 mg, or 1 to 10 mg, of free base, released over a period of time ranging from about 1 week to about 3 months, e.g., about 1 week to about 8 weeks, or about 1 week to about 6 weeks, or about 1 week to about 4 weeks, or about 1 week to about 3 weeks, or about 1 week to about 2 weeks;

6.58. Method 6.56 or 6.57, wherein the LAI composition comprises the compound of Formula I dissolved, dispersed, suspended, or encapsulated in a polymeric matrix;

6.59. Method 6.58, wherein the polymeric matrix comprises one or more biocompatible and biodegradable polymers as defined herein, e.g., poly(hydroxycarboxylic acids), poly(amino acids), cellulose polymers, modified cellulose polymers, polyamides, and polyesters;

6.60. Method 6.59, wherein the one or more polymers comprises polylactic acid, polyglycolic acid, polycitric acid, polymalic acid, poly-beta-hydroxybutyric acid, poly(lactic acid-glycolic acid) copolymer, 2-hydroxybutyric acid-glycolic acid copolymer, polylactic acid-polyethylene glycol copolymer, polyglycolic acid-polyethylene glycol copolymer, PEG-PLGA copolymer or block copolymer, PEG-PLGA copolymer or block copolymer, poly(alkyl alpha-cyanoacrylate) such as poly(butyl cyanoacrylate) or poly(2-octyl cyanoacrylate), poly(ortho ester), polycarbonate, poly-ortho-carbonate, a polyamino acid, (for example poly-gamma.-L-alanine, poly-.gamma.-benzyl-L-glutamic acid or poly-y-methyl-L-glutamic acid), and/or hyaluronic acid ester;

6.61. Method 6.60, wherein the one or more polymers comprises polyortho esters (POE), polylactic acid, polyglycolic acid, polycitric acid, polymalic acid, or a poly(lactic acid-glycolic acid) copolymer;

6.62. Method 6.60, wherein the one or more polymers comprises a poly(lactic acid-glycolic acid) copolymer, e.g., poly-d,l-lactide-co-glycolide (PLGA), for example, a PLGA copolymer with a lactide-to-glycolide molar ratio of about 50:50 to 90:10, or 50:50 to 85:15, or 50:50 to 75:25, and/or a molecular weight of 5,000 to 500,000 Daltons, or 5,000 to 150,000 Daltons, or 20,000 to 200,000 Daltons, or 24,000 to 38,000 Daltons;

6.63. Any foregoing method, wherein the 5-HT$_{2A}$ or 5-HT$_{2A}$/D2 receptor ligand is administered as monotherapy, e.g., it is not administered concurrently or in conjunction with an anti-depressant, anti-psychotic, or anti-anxiety agent;

6.64. Any foregoing method, wherein the 5-HT$_{2A}$ or 5-HT$_{2A}$/D2 receptor ligand is administered without the direct supervision of a health care professional (e.g., the compound is self-administered by the patient);

6.65. Any foregoing method, wherein the method does not comprise supervision or observation of the patient by a health care professional during or after (e.g., within 2 hours after) administration of a dose of the 5-HT$_{2A}$ or 5-HT$_{2A}$/D2 receptor ligand;

6.66. Any foregoing method, wherein the method does not put the patient at risk for sedation, dissociation, abuse, misuse, or suicidal ideation;

6.67. Any foregoing method, wherein the method does not result in hypertension (e.g., systolic and/or diastolic hypertension) within four hours after administration of a dose of the 5-HT$_{2A}$ or 5-HT$_{2A}$/D2 receptor ligand, e.g., an increase of more than 10 mm Hg, or more than 20 mm Hg, or more than 30 mm Hg, or more than 40 mm Hg, in systolic and/or diastolic blood pressure within 30 minutes to 4 hours after said dose;

6.68. Any foregoing method, wherein the method does not result in cognitive decline;

6.69. Any foregoing method, wherein the patient has (e.g., has been diagnosed with), or is at risk of, aneurysmal vascular disease (e.g., thoracic aorta, abdominal aorta, intracranial, or peripheral arterial aneurysms), arteriovenous malformation or intracerebral hemorrhage;

6.70. Any foregoing method, wherein the patient is under concurrent treatment with an oral antidepressant selected from duloxetine, escitalopram, sertraline, or venlafaxine;

6.71. Any foregoing method, wherein the patient is not under concurrent treatment with an oral antidepressant selected from duloxetine, escitalopram, sertraline, or venlafaxine;

6.72. Any foregoing method, wherein the patient is unresponsive to, or cannot be treated with ketamine (e.g., S-ketamine), e.g., because it is contraindicated in said patient;

6.73. Any foregoing method, wherein the 5-HT$_{2A}$ or 5-HT$_{2A}$/D2 receptor ligand is administered to the patient concurrently with a PDE1 (cyclic nucleoside phosphodiesterase 1) inhibitor (e.g., administered simultaneously, separately, or sequentially), in free base or pharmaceutically acceptable salt form;

6.74. Method 6.73, wherein the PDE1 inhibitor is a compound according to Formula II:

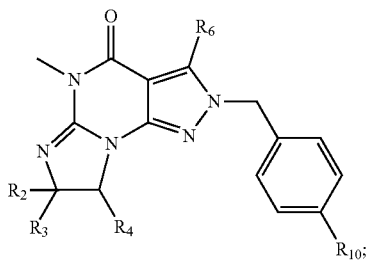

wherein $R_2$ is H and $R_3$ and $R_4$ together form a tri- or tetra-methylene bridge [pref. with the carbons carrying $R_3$ and $R_4$ having the R and S configuration respectively]; or $R_2$ and $R_3$ are each methyl and $R_4$ is H; or $R_2$ and $R_4$ are H and $R_3$ is isopropyl [pref. the carbon carrying $R_3$ having the R configuration];

$R_6$ is (optionally halo-substituted) phenylamino or (optionally halo-substituted) benzylamino;

$R_{10}$ is (optionally halo-substituted) phenyl, (optionally halo-substituted) pyridyl (for example 3-fluoropyrid-2-yl), thiadiazolyl (e.g., 1,2,3-thiadiazol-4-yl), or $C_{1-6}$alkylcarbonyl (e.g., methylcarbonyl);

in free base or pharmaceutically acceptable salt form;

6.75. Method 6.74, wherein, in the Compound of Formula II, $R_6$ is phenylamino or 4-fluorophenylamino;

6.76. Method 6.74, wherein, in the Compound of Formula II, $R_{10}$ is 3-fluoropyrid-2-yl or methylcarbonyl;

6.77. Method 6.74, wherein, in the Compound of Formula II, $R_6$ is phenylamino or 4-fluorophenylamino and $R_{10}$ is 3-fluoropyrid-2-yl or methylcarbonyl;

6.78. Any Methods 6.74-6.77, wherein the Compound of Formula II is

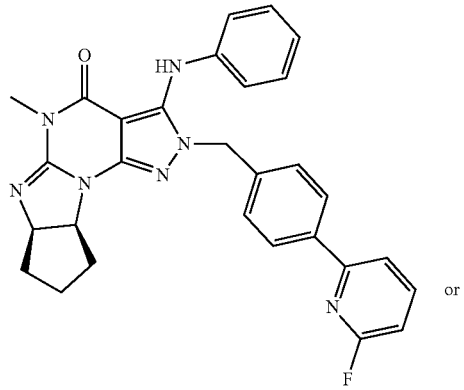

or

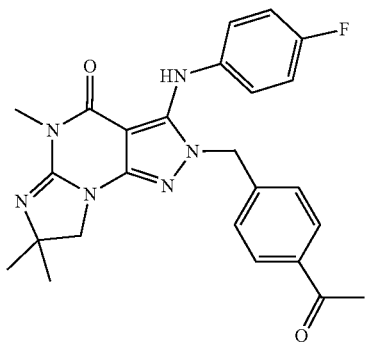

in free base or pharmaceutically acceptable salt form;

6.79. Method 6.78, wherein the Compound of Formula II is in the form of the monophosphate salt;

6.80. Any of Methods 6.74-6.79, wherein the Compound of Formula I is:

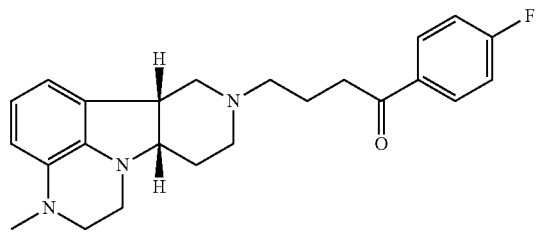 [SMILES: CN1CCN2c3c(cccc31)[C@@H]1CN(CCCC(=O)c3ccc(F)cc3)CC[C@@H]12]

in free base or pharmaceutically acceptable salt form, e.g., tosylate salt form, optionally in a deuterated form; and the Compound of Formula II is:

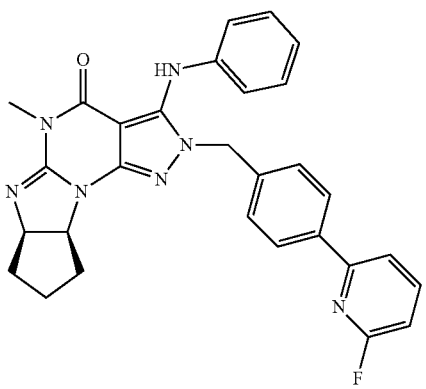 [SMILES: CN1C(=O)c2c(nn(Cc3ccc(-c4cccc(F)n4)cc3)c2Nc2ccccc2)N2C1=N[C@@H]1CCC[C@@H]12]

in free base or pharmaceutically acceptable salt form, e.g., monophosphate salt form;
6.81. Any of Methods 6.74-6.80, comprising administration of a pharmaceutical composition comprising therapeutically effective amounts of both a Compound of Formula I and a Compound of Formula II;
6.82. Any preceding method, wherein the 5-HT$_{2A}$ or 5-HT$_{2A}$/D2 receptor ligand is a compound of Formula I, in free base or pharmaceutically acceptable salt from, optionally in deuterated form, and wherein the compound is administered in the form of a long-acting injectable (LAI) composition comprising the compound of Formula I dissolved or dispersed or in a pharmaceutically acceptable carrier and a polymeric matrix comprising polymers selected from polyortho esters (POE), polylactic acid, polyglycolic acid, polycitric acid, polymalic acid, or a poly(lactic acid-glycolic acid) copolymer;
6.83. Method 6.82, wherein the pharmaceutically acceptable carrier comprises water (e.g., an aqueous buffer) and/or an organic solvent (e.g., a water-miscible organic solvent);
6.84. Method 6.82 or 6.83, wherein the polymers comprise a polylactic acid and/or a polyglycolic acid polymer;
6.85. Method 6.82 or 6.83, wherein the polymers comprise a poly(lactic acid-glycolic acid) copolymer, e.g., poly-d,l-lactide-co-glycolide (PLGA), for example, a PLGA copolymer with a lactide-to-glycolide molar ratio of about 50:50 to 90:10, or 50:50 to 85:15, or 50:50 to 75:25, and/or a molecular weight of 5,000 to 500,000 Daltons, or 5,000 to 150,000 Daltons, or 20,000 to 200,000 Daltons, or 24,000 to 38,000 Daltons;
6.86. Any of Methods 6.82-6.85, wherein the LAI composition is administered by, or formulated for administration by, intramuscular or subcutaneous injection;
6.87. Method 6, or any of 6.1-6.86, wherein the patient has no prior history of depression;
6.88. Method 6, or any of 6.1-6.87, wherein the patient shows evidence of cerebral damage or cerebral disease on magnetic resonance imaging (MRI) prior to administration of the 5-HT$_{2A}$ or 5-HT$_{2A}$/D2 receptor ligand;
6.89. Method 6, or any of 6.1-6.88, wherein the patient has a positive serum antibody or antigen test for one or more of Herpes simplex Virus 1, Herpes Simplex Virus 2, West Nile Virus, Nipah Virus, human immunodeficiency virus, rabies virus, Epstein-Barr Virus, cytomegalovirus, coronavirus (e.g., MERS-CoV, SARS-CoV, SARS-Cov2, or influenza virus (e.g., influenza A, such as H1N1, H2N2, H3N2, H5N1, H7N7), prior to administration of the 5-HT$_{2A}$ or 5-HT$_{2A}$/D2 receptor ligand;
6.90. Method 6, or any of 6.1-6.89, wherein the patient has a positive serum antibody test for autoantibodies against the NMDA receptor, the AMPA receptor, the voltage-gated potassium, channel (VGKC), the LGL1 protein, the GABA receptor, the glycine receptor, the glutamate receptor, or the CASPR2 receptor;
6.91. Any foregoing method, wherein the patient has elevated levels of one or more biomarkers indicative of CNS inflammation, e.g., selected from TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1, in the blood, plasma, serum, peripheral blood mononuclear cells (PBMC) (e.g., isolated from blood), urine, CSF, and/or CNS microglial cells (e.g., isolated from CSF);
6.92. Any foregoing method, wherein the patient has changes in levels of one or more biomarkers indicative of CNS inflammation and/or loss of BBB integrity, e.g., increased levels of ICAM-1, VCAM-1, E-selectin, P-selectin, or soluble isoforms thereof (e.g., sICAM-1, sVCAM1, sP-selectin, sE-selectin), or reduced levels of Cldn5, Occludin, and/or ZO-1, in the serum or CSF;
6.93. Any foregoing method, wherein the patient has depressed levels of one or more anti-inflammatory biomarkers indicative of CNS inflammatory dysfunction, e.g., TNF-β, IFN-α, IL-4, and IL-10, in the blood, plasma, serum, peripheral blood mononuclear cells (PBMC) (e.g., isolated from blood), urine, CSF, and/or CNS microglial cells (e.g., isolated from CSF);
6.94. Any foregoing method, wherein after treatment with the 5-HT$_{2A}$ or 5-HT$_{2A}$/D2 receptor ligand (e.g., Compound of Formula I, optionally in deuterated form), the patient has a reduced level of one or more biomarkers indicative of CNS inflammation, e.g., TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1, in the blood, plasma, serum, peripheral blood mononuclear cells (PBMC) (e.g., isolated from blood), urine, CSF, and/or CNS microglial cells (e.g., isolated from CSF), compared to a pre-treatment baseline, e.g., within 28 days of the initiation of treatment;
6.95. Method 6.94, wherein the patient has at least a 5%, 10%, 15%, 20%, or 25%, 30%, 35%, 40%, 45%, or 50%, reduction in the level of the one or more biomarkers indicative of CNS inflammation, e.g., within 28 days of the initiation of treatment;
6.96. Any foregoing method, wherein after treatment with the 5-HT$_{2A}$ or 5-HT$_{2A}$/D2 receptor ligand (e.g., Compound of Formula I, optionally in deuterated form), the patient has favorable changes in levels of one or more biomarkers indicative of CNS inflammation and/or loss of BBB integrity, e.g., decreased levels of ICAM-1, VCAM-1, E-selectin, P-selectin, or soluble isoforms thereof (e.g., sICAM-1, sVCAM1, sP-selectin, sE-selectin), or increased levels of Cldn5, Occludin, and/or ZO-1, in the serum or CSF, compared to a pre-treatment baseline, e.g., within 28 days of the initiation of treatment;
6.97. Method 6.96, wherein the patient has at least a 5%, 10%, 15%, 20%, 25%, 30%, 35%, 40%, 45%, or 50%, reduction or increase in the level of the one or more biomarkers indicative of CNS inflammation, e.g., within 28 days of the initiation of treatment;

6.98. Any foregoing method, wherein after treatment with the 5-HT$_{2A}$ or 5-HT$_{2A}$/D2 receptor ligand (e.g., Compound of Formula I, optionally in deuterated form), the patient has an increased level of one or more anti-inflammatory biomarkers indicative of CNS inflammatory dysfunction, e.g., TNF-β, IFN-α, IL-4, and IL-10, in the blood, plasma, serum, peripheral blood mononuclear cells (PBMC) (e.g., isolated from blood), urine, CSF, and/or CNS microglial cells (e.g., isolated from CSF), compared to a pre-treatment baseline, e.g., within 28 days of the initiation of treatment;

6.99. Method 6.98, wherein the patient has an increase of at least 5%, 10%, 15%, 20%, 25%, 30%, 35%, 40%, 45%, or 50%, in the levels of the one or more anti-inflammatory biomarkers indicative CNS inflammatory dysfunction, e.g., within 28 days of the initiation of treatment, e.g., within 28 days of the initiation of treatment;

6.100. Any foregoing method, wherein the method further comprises the step of testing one or more body fluids or tissues from the patient for the presence and/or concentration of one or more biomarkers indicative of CNS inflammation or CNS inflammatory dysfunction or loss of BBB integrity prior to the initiation of treatment with the 5-HT$_{2A}$ or 5-HT$_{2A}$/D2 receptor ligand (e.g., Compound of Formula, optionally in deuterated form), and/or subsequent to the initiation of said treatment, and optionally comparing the pre-treatment and one or more post-treatment results thereof to quantify the effectiveness of the treatment in the patient and/or to adjust the treatment regimen;

6.101. Method 6.100, wherein the biomarkers are selected from one or more of TNF-α, IFN-γ, IL-1 (IL-1α and/or IL-1β), IL-6, IL-8, IL-12, IL-15, IL-17, IL-18, CRP, SAA, Csf1, YKL-40, Nlrp3, Flt-1, ICAM-1, VCAM-1, E-selectin, P-selectin, Cldn5, Occludin, and ZO-1, soluble isoforms thereof (e.g., sICAM-1, sVCAM1, sP-selectin, sE-selectin), TNF-β, IFN-α, IL-4, and IL-10;

6.102. Method 6.100 or 6.101, wherein the one or more body fluids or tissues are selected from blood, plasma, serum, peripheral blood mononuclear cells (PBMC) (e.g., isolated from blood), urine, CSF, and/or CNS microglial cells (e.g., isolated from CSF), or brain biopsy tissue samples;

6.103. Any foregoing method, wherein the method further comprises the step of non-invasively testing the central nervous system of the patient for the presence and/or concentration of one or more biomarkers indicative of CNS inflammation or CNS inflammatory dysfunction prior to the initiation of treatment with the 5-HT$_{2A}$ or 5-HT$_{2A}$/D2 receptor ligand (e.g., Compound of Formula I, optionally in deuterated form), and/or subsequent to the initiation of said treatment, and optionally comparing the pre-treatment and one or more post-treatment results thereof to quantify the effectiveness of the treatment in the patient and/or to adjust the treatment regimen;

6.104. Method 6.103, wherein the biomarkers are selected from one or more of TNF-α, IFN-γ, IL-1 (IL-1α and/or IL-1β), IL-6, IL-12, IL-15, IL-17, IL-18, CRP, SAA, Csf1, YKL-40, Nlrp3, Flt-1, ICAM-1, VCAM-1, E-selectin, P-selectin, Cldn5, Occludin, and ZO-1, soluble isoforms thereof (e.g., sICAM-1, sVCAM1, sP-selectin, sE-selectin), TNF-β, IFN-α, IL-4, and IL-10;

6.105. Method 6.103 or 6.104, wherein the step comprises an imaging method, such as magnetic resonance imaging (MRI), positron emission tomography (PET), functional MRI (fMRI), to evaluate the presence and/or concentration of said biomarkers;

6.106. Any of Methods 6.100-6.105, wherein the method comprises the step of initiating, altering, or terminating, the treatment regimen (e.g., the selected 5-HT$_{2A}$ or 5-HT$_{2A}$/D2 receptor ligand, the dose thereof, the route of administration thereof, the frequency of administration thereof, the form of administration thereof, and/or the combination of the selected 5-HT$_{2A}$ or 5-HT$_{2A}$/D2 receptor ligand with any another therapeutic agent), based on the observed changes in the levels of one or more of said biomarkers;

6.107. Any foregoing method, wherein the patient has elevated levels of one or more biomarkers indicative of peripheral inflammation, e.g., selected from type-I interferons, including IFN-ca, IFN-β, and/or IFN-δ, in the blood, plasma, serum, peripheral blood mononuclear cells (PBMC) (e.g., isolated from blood), or urine;

6.108. Method 6.107, wherein after treatment with the 5-HT$_{2A}$ or 5-HT$_{2A}$/D2 receptor ligand (e.g., Compound of Formula I, optionally in deuterated form), the patient has a reduced level of the one or more biomarkers indicative of peripheral inflammation, e.g., selected type-I interferons, including IFN-α, IFN-β, and/or IFN-δ, in the blood, plasma, serum, peripheral blood mononuclear cells (PBMC) (e.g., isolated from blood), or urine, compared to a pre-treatment baseline, e.g., within 28 days of the initiation of treatment;

6.109. Method 6.108, wherein the patient has at least a 5%, 10%, 15%, 20%, or 25%, 30%, 35%, 40%, 45%, or 50%, reduction in the level of the one or more biomarkers indicative of peripheral inflammation, e.g., within 28 days of the initiation of treatment;

6.110. Any foregoing method, wherein the patient has peripheral serotonin deficiency characterized by a reduced concentration in the plasma and/or platelets, for example, a plasma serotonin concentration less than 3000 nM, less than 2500 nM, less than 2000 nM, less than 1800 nM, less than 1600 nM, less than 1400 nM, less than 1200 nM, less than 1000 nM, less than 800 nM, less than 600 nM, less than 500 nM, less than 400 nM, less than 300 nM, or less than 250 nM;

6.111. Method 6.110, wherein after treatment with the 5-HT$_{2A}$ or 5-HT$_{2A}$/D2 receptor ligand (e.g., Compound of Formula I, optionally in deuterated form), the patient has recovered from peripheral serotonin deficiency, e.g., a normal concentration in the plasma and/or platelets, for example, a plasma serotonin concentration of greater than 500 nM, or 500 to 3000 nM, or 1000 to 3000 nM, or 1500 to 3000 nM, or 2000 to 3000 nM, or greater than 3000 nM nM, less than 800 nM, less than 600 nM, less than 500 nM, less than 400 nM, less than 300 nM, or less than 250 nM;

6.112. Method 6.110 or 6.111, wherein the patient has psychiatric symptoms caused by, or thought to be caused by, the peripheral serotonin deficiency, e.g., due to reduced plasma serotonin concentration and/or reduced vagal nerve afferent sensory activity (e.g., due to reduced serotonin-mediated 5-HT$_3$ signaling)

6.113. Any foregoing method, wherein the patient is suffering from Long COVID;

6.114. Any foregoing method, wherein the patient has thrombocytopenia or platelet hypercoagulability (e.g., as shown by reduced prothrombin time and/or partial thromboplastin time), 6.115. Any foregoing method, wherein the method further comprises the step of obtaining a tissue sample from the patient and testing the tissue sample for the level of any one or more of: (a) serum antibody or antigen for one or more of Herpes simplex Virus 1, Herpes Simplex Virus 2, West Nile Virus, Nipah Virus, human immunodeficiency virus, rabies virus, Epstein-Barr Virus, cytomegalovirus, coronavirus (e.g., MERS-CoV, SARS-CoV, SARS-Cov2, or influenza virus (e.g., influenza A, such as H1N1, H2N2, H3N2, H5N1, H7N7); (b) serum autoantibodies against the NMDA receptor, the AMPA receptor, the voltage-gated potassium, channel (VGKC), the LGL1 protein, the GABA receptor, the glycine receptor, the glutamate receptor, or the CASPR2 receptor; (c) biomarkers selected from TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1; (d) biomarkers selected from ICAM-1, VCAM-1, E-selectin, P-selectin, or soluble isoforms thereof (e.g., sICAM-1, sVCAM1, sP-selectin, sE-selectin), Cldn5, Occludin, and/or ZO-1; (e) biomarkers selected from TNF-β, IFN-α, IL-4, and IL-10; (f) type-I interferons, including IFN-α, IFN-β, and/or IFN-δ; (f) serotonin; and (g) platelet count, prothrombin time, and/or partial thromboplastin time;

6.116. Method 6.115, wherein the tissue sample is selected from blood, plasma, serum, peripheral blood mononuclear cells (PBMC) (e.g., isolated from blood), urine, CSF, and/or CNS microglial cells (e.g., isolated from CSF);

6.117. Method 6.115 or 6.116, wherein the method further comprises adjusting the course of treatment based on the results of one more of said tissue sample measurements, optionally wherein said tissue sample measurements are taken at one or more times during the course of therapy, e.g., for comparison to earlier measurements or measurements taken before initiating therapy.

In another aspect, the disclosure provides a 5-HT$_{2A}$ or 5-HT$_{2A}$/D2 receptor ligand, e.g., a compound of Formula I, as hereinbefore described, for example lumateperone, in free base or salt form, optionally in deuterated form, for use in the treatment or prevention of peripheral serotonin deficiency, e.g., for use in any of Methods 6, et seq.

In another aspect, the disclosure provides the use of a 5-HT$_{2A}$ or 5-HT$_{2A}$/D2 receptor ligand, e.g., a compound of Formula I, as hereinbefore described, for example lumateperone, in free base or salt form, optionally in deuterated form, in in the manufacture of a medicament for the treatment or prevention of peripheral serotonin deficiency, e.g., for any of Methods 6, et seq.

In some embodiments described herein, particularly suitable patients for carrying out the disclosed methods may be identified by measuring the levels of certain biomarkers in body fluids or tissues from said patients. These biomarkers may indicate the presence of CNS inflammation, or the presence of CNS inflammatory dysfunction, either due to infection, autoimmunity, or other causes. Thus, psychological symptoms in said patients may be particularly attributed to such inflammatory changes, and may particularly benefit from the unique properties and activities of the compounds described herein. Biomarkers indicative of CNS inflammation include TNF-α, IFN-γ, IL-1 (IL-1α and/or IL-1β), IL-6, IL-8, IL-12, IL-15, IL-17, IL-18, CRP, SAA, Csf1, ICAM-1, VCAM-1, YKL-40, Nlrp3, and Flt-1, which may be identified or quantified in samples taken from blood, plasma, serum, peripheral blood mononuclear cells (PBMC) (e.g., isolated from blood), urine, cerebrospinal fluid (CSF), and/or microglial cells isolated from CSF). In particular, changes in certain biomarkers are indicative of a breakdown of the integrity of the blood-brain barrier, such as ICAM-1, VCAM-1, E-selectin, P-selectin, Cldn5, Occludin, and/or ZO-1, or soluble isoforms thereof (e.g., sICAM-1, sVCAM1, sP-selectin, sE-selectin), which may be identified or quantified in the serum or CSF. Disruption of the BBB can lead to cellular damage and cell lysis, leading to the presence of tight junction proteins that are normally membrane-bound in the CSF and plasma. Alternatively, CNS inflammation induced by inflammatory cytokines can upregulate proteins that loosen the BBB or downregulate proteins that tighten the BBB, in order to allow infiltration of immune cells into the CSF. Changes in levels of any or all of these biomarkers may be indicative of CNS inflammation and/or BBB damage or loss of BBB integrity. Similarly, another class of biomarkers are those associated with anti-inflammatory properties, such as the anti-inflammatory cytokines. Decreases in the levels of such biomarkers may be indicative of CNS inflammatory dysfunction, i.e., dysfunction of the normal bodily controls on cellular inflammation. Examples of such biomarkers include TNF-β, IFN-α, IL-4, and IL-10, which likewise may be identified or quantified in samples taken from blood, plasma, serum, peripheral blood mononuclear cells (PBMC) (e.g., isolated from blood), urine, cerebrospinal fluid (CSF), and/or microglial cells isolated from CSF. In addition to detecting these biomarkers in body fluids and tissues, much works has been accomplished on non-invasive imaging technologies (e.g., MRI, PET) to obtain the same information, especially in hard-to-access body compartments such as the CNS. Additional information on methods of measuring such biomarkers and for interpreting changes in these biomarker's levels may be found in: Zhu et al., "Circulating tight junction proteins mirror blood-brain barrier integrity in leukaemia central nervous system metastasis," *Hematol Oncol*, 35(3):365-373 (2017); Abe, et al. "Soluble cell adhesion molecules in hypertriglyceridemia and potential significance on monocyte adhesion,". *Arterioscler. Thromb. Vasc. Biol.*, 18(5): 723-31 (1998); Janelidze et al., "CSF Biomarkers of neuroinflammation and cerebrovascular dysfunction in early Alzheimer disease," *Neurology*, 91(9):e867-e877 (2018); Beanio et al., "Towards PET imaging of the dynamic phenotypes of microglia." *Clinical and Experimental Immunology*, 206(3): 282-300 (2021).

The term "5-HT$_{2A}$ receptor ligand" refers to a compound which displays, at least, pharmacological activity at the serotonin 5-HT$_{2A}$ receptor, for example, compounds having an IC$_{50}$ of less than 250 nM or an EC$_{50}$ of less than 250 nM for activity (agonism and/or antagonism) at said receptor. In some embodiments, this term refers to a compound having an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism).

The term "5-HT$_{2A}$/D2 receptor ligand" refers to a compound which displays, at least, pharmacological activity at both the serotonin 5-HT$_{2A}$ receptor and at the D2 receptor, for example, compounds having an IC$_{50}$ of less than 250 nM or an EC$_{50}$ of less than 250 nM for activity (agonism and/or antagonism) at each of said receptors. In some embodiments, this term refers to a compound having an IC$_{50}$ or EC$_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at one or both of these receptors (agonism or antagonism).

The words "treatment" and "treating" are to be understood accordingly as embracing prophylaxis and treatment or amelioration of symptoms of disease and/or treatment of the cause of the disease. In particular embodiments, the words "treatment" and "treating" refer to prophylaxis or amelioration of symptoms of the disease.

The term "patient" may include a human or non-human patient.

If not otherwise specified or clear from context, the following terms herein have the following meanings:

"Alkyl" as used herein is a saturated or unsaturated hydrocarbon moiety, e.g., one to twenty-one carbon atoms in length, which may be linear or branched (e.g., n-butyl or tert-butyl), preferably linear, unless otherwise specified. For example, "$C_{1-21}$ alkyl" denotes an alkyl group having 1 to 21 carbon atoms. In one embodiment, alkyl is optionally substituted with one or more hydroxy or $C_{1-22}$alkoxy (e.g., ethoxy) groups. In another embodiment, alkyl contains 1 to 21 carbon atoms, preferably straight chain and optionally saturated or unsaturated, for example $R_1$ may be an alkyl chain containing 1 to 21 carbon atoms, preferably 6-15 carbon atoms, 16-21 carbon atoms, e.g., so that together with the —C(O)— to which it attaches, e.g., when cleaved from the compound of Formula I, forms the residue of a natural or unnatural, saturated or unsaturated fatty acid.

The 5-$HT_{2A}$ or 5-$HT_{2A}$/D2 receptor ligand, for example a substituted heterocycle fused gamma-carboline as described herein, may be in free base, pharmaceutically acceptable salt, or prodrug form. Pharmaceutically acceptable salts include, for example, the tosylate salts in the case of Compounds of Formula I. Where dosages or amounts of a salt are given by weight, e.g., milligrams per day or milligrams per unit dose, the dosage amount of the salt is given as the weight of the corresponding free base, unless otherwise indicated.

In any and all embodiments described herein, the 5-$HT_{2A}$ or 5-$HT_{2A}$/D2 receptor ligand may also be a SERT ligand, i.e., said compounds may be a 5-$HT_{2A}$/SERT or a 5-$HT_{2A}$/D2/SERT receptor ligand.

In any and all embodiments described herein, the 5-$HT_{2A}$ or 5-$HT_{2A}$/D2 receptor ligand may be free or substantially free of any opioid receptor activity (e.g., free or substantially free of mu-opioid receptor activity, e.g., having an $IC_{50}$ greater than 50 nM or greater than 100 nM or greater than 150 nM).

The 5-$HT_{2A}$ or 5-$HT_{2A}$/D2 receptor ligand may in some cases also exist in prodrug form. A prodrug form is compound which converts in the body to the active compound. For example, compounds which contain hydroxy or carboxy substituents may form physiologically hydrolysable and acceptable esters. As used herein, "physiologically hydrolysable and acceptable ester" means esters which are hydrolysable under physiological conditions to yield acids (in the case of compounds which have hydroxy substituents) or alcohols (in the case of compounds which have carboxy substituents) which are themselves physiologically tolerable at doses to be administered. For example, wherein Y of the compound of Formula I is —C(H)(OR$_1$), and R$_1$ is —C(O)—$C_{1-21}$alkyl, e.g., —C(O)—$C_3$alkyl or —C(O)—$C_9$alkyl, these compounds may hydrolyze under physiological condition to yield a compound of Formula I wherein Y is —C(H)(OH) on the one hand and $C_{1-21}$alkyl-C(O)OH, e.g., $C_3$alkyl-C(O)OH or $C_9$alkyl-C(O)OH on the other hand. As will be appreciated the term thus embraces conventional pharmaceutical prodrug forms. When a prodrug (e.g., the compound of formula (I) wherein $R_1$ is —C(O)—$C_{1-21}$alkyl) is used, the dosage amount is calculated based on the amount of the compound of formula (I) wherein Y is —C(=O)— or —CH(OH)—, in free base form.

The term "concurrently" when referring to a therapeutic use means administration of two or more active ingredients to a patient as part of a regimen for the treatment of a disease or disorder, whether the two or more active agents are given at the same or different times or whether given by the same or different routes of administrations. Concurrent administration of the two or more active ingredients may be at different times on the same day, or on different dates or at different frequencies.

The term "simultaneously" when referring to a therapeutic use means administration of two or more active ingredients at or about the same time by the same route of administration.

The term "separately" when referring to a therapeutic use means administration of two or more active ingredients at or about the same time by different route of administration.

With respect to concurrent treatment using a 5-$HT_{2A}$ or 5-$HT_{2A}$/D2 receptor ligand (e.g., a compound of Formula I) and an NMDA receptor antagonist (e.g., ketamine), without being bound by theory, it is believed that the combination of these agents would permit lower doses of both agents to be used to treat depression, or other neuropsychiatric disorders described herein, such that the dissociative effects produced by the NMDA receptor antagonist would be minimized while the synergistic antidepressants effects would be maximized.

Dosages employed in practicing the present disclosure will of course vary depending, e.g., on the particular disease or condition to be treated, the particular active compounds used, the mode of administration, and the therapy desired. Unless otherwise indicated, an amount of an active compound for administration (whether administered as a free base or as a salt form) refers to or is based on the amount of the compound in free base form (i.e., the calculation of the amount is based on the amount of active moiety in free base form, not taking into account the weight of the counter ion in the case of a salt).

The 5-$HT_{2A}$ or 5-$HT_{2A}$/D2 receptor ligand may be administered by any suitable route, including orally, intra-muscularly, subcutaneously, parenterally, transmucosally, or transdermally, but are preferably administered orally or transmucosally. The 5-$HT_{2A}$ or 5-$HT_{2A}$/D2 receptor ligand may be administered, for example, in the form of a tablet, a capsule, a wafer, an injection (e.g., intravenous, intramuscular, or subcutaneous injection), or an oral, rapidly disintegrating tablet, wafer, or film for sublingual or buccal administration.

For the avoidance of doubt, any disclosure of a numerical range, e.g., "up to X" amount is intended to include the upper numerical limit X. Therefore, a disclosure of "up to 60 mg" is intended to include 60 mg.

Pharmaceutical compositions comprising compounds of the Disclosure may be prepared using conventional diluents or excipients and techniques known in the galenic art. Thus, oral dosage forms may include tablets, capsules, solutions, suspensions and the like.

Compounds of the present disclosure may be included as a long-acting injectable formulation (i.e., depot formulation), e.g., by dispersing, dissolving, suspending, or encapsulating the Compounds of the Invention in a polymeric matrix as described in herein, such that the Compound is continually released as the polymer degrades over time. The release of the Compounds of the Invention from the polymeric matrix provides for the controlled- and/or delayed- and/or sustained-release of the Compounds, e.g., from the pharmaceutical depot composition, into a subject, for example a warm-blooded animal such as man, to which the pharmaceutical depot is administered. Thus, the pharmaceutical depot delivers the Compounds of the Invention to the subject at concentrations effective for treatment of the particular disease or medical condition over a sustained period of time, e.g., 1 week to 3 months.

Polymers useful for the polymeric matrix in the Composition of the Invention (e.g., Depot composition of the Invention) may include a polyester of a hydroxyfatty acid and derivatives thereof or other agents such as polylactic acid, polyglycolic acid, polycitric acid, polymalic acid, poly-beta.-hydroxybutyric acid, epsilon.-capro-lactone ring opening polymer, lactic acid-glycolic acid copolymer, 2-hydroxybutyric acid-glycolic acid copolymer, polylactic acid-polyethylene glycol copolymer or polyglycolic acid-polyethylene glycol copolymer), PEG-PLGA copolymer or block copolymer, a polymer of an alkyl alpha-cyanoacrylate (for example poly(butyl 2-cyanoacrylate)), a polyalkylene oxalate (for example polytrimethylene oxalate or polytetramethylene oxalate), a polyortho ester, a polycarbonate (for example polyethylene carbonate or polyethylenepropylene carbonate), a polyortho-carbonate, a polyamino acid (for example poly-gamma.-L-alanine, poly-.gamma.-benzyl-L-glutamic acid or poly-y-methyl-L-glutamic acid), a hyaluronic acid ester, and the like, and one or more of these polymers can be used.

If the polymers are copolymers, they may be any of random, block and/or graft copolymers. When the above alpha-hydroxycarboxylic acids, hydroxydicarboxylic acids and hydroxytricarboxylic acids have optical activity in their molecules, any one of D-isomers, L-isomers and/or DL-isomers may be used. Among others, alpha-hydroxycarboxylic acid polymer (preferably lactic acid-glycolic acid polymer), its ester, poly-alpha-cyanoacrylic acid esters, etc. may be used, and lactic acid-glycolic acid copolymer (also referred to as poly(lactide-alpha-glycolide) or poly(lactic-co-glycolic acid), and hereinafter referred to as PLGA) are preferred. Thus, in one aspect the polymer useful for the polymeric matrix is PLGA. As used herein, the term PLGA includes polymers of lactic acid (also referred to as poly-lactide, poly(lactic acid), or PLA). Most preferably, the polymer is the biodegradable poly(d,l-lactide-co-glycolide) polymer, such as PLGA 50:50, PLGA 85:15 and PLGA 90:10.

In a preferred embodiment, the polymeric matrix of the invention is a biocompatible and biodegradable polymeric material. The term "biocompatible" is defined as a polymeric material that is not toxic, is not carcinogenic, and does not significantly induce inflammation in body tissues. The matrix material should be biodegradable wherein the polymeric material should degrade by bodily processes to products readily disposable by the body and should not accumulate in the body. The products of the biodegradation should also be biocompatible with the body in that the polymeric matrix is biocompatible with the body. Particular useful examples of polymeric matrix materials include poly (glycolic acid), poly-D,L-lactic acid, poly-L-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. The preferred polymers for use in the practice of this aspect of the disclosure are polylactide, polyglycolide, and poly(d,l-lactide-co-glycolide). It is preferred that the molar ratio of lactide to glycolide in such a copolymer be in the range of from about 75:25 to 50:50.

In the case of polyester polymers, including polylactide, polyglycolide, and poly(d,l-lactide-co-glycolide), it is understood that the polymers can have either carboxylic acid end groups or carboxylic ester end groups. Particularly useful are poly(d,l-lactide-co-glycolide) copolymers (PLGA copolymers) with a lactide-to-glycolide molar ratio of about 50:50 to 90:10, or 50:50 to 85:15, or 50:50 to 75:25, and/or a molecular weight of 5,000 to 500,000 Daltons, or 5,000 to 150,000 Daltons, or 20,000 to 200,000 Daltons, or 24,000 to 38,000 Daltons.

Useful PLGA polymers may have a weight-average molecular weight of from about 5,000 to 500,000 Daltons, preferably about 150,000 Daltons. Dependent on the rate of degradation to be achieved, different molecular weight of polymers may be used. For a diffusional mechanism of drug release, the polymer should remain intact until all of the drug is released from the polymeric matrix and then degrade. The drug can also be released from the polymeric matrix as the polymeric excipient bioerodes.

The PLGA may be prepared by any conventional method, or may be commercially available. For example, PLGA can be produced by ring-opening polymerization with a suitable catalyst from cyclic lactide, glycolide, etc. (see EP-0058481B2; Effects of polymerization variables on PLGA properties: molecular weight, composition and chain structure).

It is believed that PLGA is biodegradable by means of the degradation of the entire solid polymer composition, due to the break-down of hydrolysable and enzymatically cleavable ester linkages under biological conditions (for example in the presence of water and biological enzymes found in tissues of warm-blooded animals such as humans) to form lactic acid and glycolic acid. Both lactic acid and glycolic acid are water-soluble, non-toxic products of normal metabolism, which may further biodegrade to form carbon dioxide and water. In other words, PLGA is believed to degrade by means of hydrolysis of its ester groups in the presence of water, for example in the body of a warm-blooded animal such as man, to produce lactic acid and glycolic acid and create the acidic microclimate. Lactic and glycolic acid are by-products of various metabolic pathways in the body of a warm-blooded animal such as man under normal physiological conditions and therefore are well tolerated and produce minimal systemic toxicity.

For long-acting injectable compositions, the $5-HT_{2A}$ or $5-HT_{2A}/D2$ receptor ligand may be dissolved, dispersed, or suspended in the polymeric matrix, and/or further admixed with a pharmaceutically acceptable diluent or carrier. Such carrier may be aqueous, such as water suitable for injection (e.g., an aqueous buffer), or non-aqueous, such as an organic solvent, or a mixture of a water and an organic solvent (e.g., a water-miscible organic solvent). In some embodiments, the $5-HT_{2A}$ or $5-HT_{2A}/D2$ receptor ligand is encapsulated in microspheres or microparticles which are suspended or dispersed in the pharmaceutically acceptable diluent or carrier, as described in U.S. Pat. Nos. 9,708,322, and 9,956,227, the contents of each of which are hereby incorporated by reference in their entireties. Further information for the preparation of microparticles can be found in U.S. 2008/0069885, the contents of which are incorporated herein by reference in its entirety.

EXAMPLES

Drugs and Experimental Design. Lumateperone, also known as ITI-007 or IC200056 tosylate salt, is the Compound of Formula I, wherein X is N(CH$_3$), and Y is C═O:

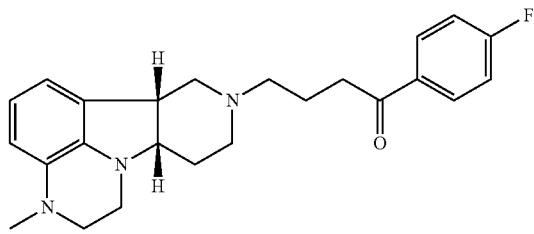 [SMILES: CN1CCN2c3c(cccc31)[C@@H]1CN(CCCC(=O)c3ccc(F)cc3)CC[C@@H]12]

in the form of its tosylate salt. It is approved by the U.S. Food & Drug Administration (FDA) for the treatment for schizophrenia, and bipolar depression in adults. Lumateperone provides selective and simultaneous modulation of serotonin, dopamine and glutamate neurotransmission and is particularly of interest in the context of psychiatric disorders.

All other reagents are obtained in the highest purity available from Sigma-Aldrich (St. Louis, MO) unless otherwise noted. For most experiments, mice or rats at least 8 weeks of age are given an intraperitoneal (IP) injection of lumateperone (0.3, 1, 3, or 8 mg/kg) or its vehicle (v/v: 5% DMSO, 5% Tween 20, 15% polyethylene glycol [PEG] 400, and 75% pure HPLC water). Some rodents are given a cotreatment with a subcutaneous (SC) injection of lipopolysaccharide (LPS, 500 µg/kg; Sigma-Aldrich, ref #0127: B8) diluted in 0.9% injectable saline while control group animals receive injections of all vehicles matching the experimental conditions. In experiments in which delayed administration of lumateperone is studied, mice (n=4-9 per group) first receive a subcutaneous injection of LPS or saline followed by an IP injection of lumateperone (3 mg/kg) or its vehicle 30 minutes later. In experiments using restraint stress, mice assigned to the restraint stress group receive a single injection of lumateperone (3 mg/kg) or its vehicle and are immediately placed in a rodent restraint bag. In behavioral experiments, rats receive a pretreatment of lumateperone (1 mg/kg) or its vehicle on day 1. On day 2, either no injection for naïve rats, or saline or LPS is injected (1 mg/kg, SC). On day 3, rats receive another injection of either lumateperone or saline and are tested the following day (day 4).

Animals. Adult, male C$_{57}$BL/6 mice weighing 28-30 grams at the time of the experiment are housed in groups of 4 or 5 in small cages. Adult, male Sprague-Dawley rats weighing 175-200 grams at the time of arrival after shipping are housed in pairs. All animals are housed under standard laboratory housing conditions with a 12-hour light/dark cycle and ad libitum access to food and water.

Tissue Collection. Mice are euthanized 2 hours after lumateperone injection (for cotreatment studies with LPS) or application of restraint stress for sample collection. Rats are euthanized 18 hours after LPS injection for sample collection. Hippocampi from mice and rats are rapidly dissected under RNAse-free conditions and placed in 1.5 mL Eppendorf tubes. When appropriate, samples are snap frozen in liquid nitrogen prior to storage at −80° C. until further analysis. Trunk blood is collected from mice into serum collection tubes, allowed to clot at room temperature for 1 hour, then centrifuged at 1,500 g for 10 minutes at 4° C.

Multiplex Assays. In mouse serum, protein levels of IL-1b, IL-6, IL-10 and TNF-alpha are measured using a V-Plex Meso Scale Discovery (MSD) Multiplex spot assay Mouse Neuroinflammation 1 panel (Meso Scale Diagnostics, Rockville, MD). All samples are run in duplicates or triplicates according to manufacturer instructions and analyzed with MSD Discovery Workbench software (Meso Scale Diagnostics).

Quantitative Real-Time PCR. Mouse hippocampal tissue is homogenized with glass beads in 1 mL of TRIzol reagent using a BeadBeater (Biospec Products, Bartlesville, OK). Heavy phase-lock gel tubes enabled separation of phases following the addition of 400 µL chloroform to the sample and centrifugation at 12,000 rpm for 10 minutes at room temperature. RNA is extracted using Qiagen Rneasy kit (Qiagen, Hilden, Germany). For cDNA synthesis, 2 µg of total RNA is used (SuperScript IV Reverse Transcriptase; ThermoFisher Scientific, Waltham, MA). The purity and concentration of RNA is measured with a Nanodrop spectrophotometer; the optical density (OD) 260/280 and OD 260/230 are within 1.8-2.3. In the hippocampus, 4 key markers of pro- and anti-inflammatory cytokines and chemokines (Il1b: ID Mm00434228_m1, Tnfa: ID Mm00443258_m1, 116: ID Mm00446190_m1, and I110: ID Mm01288386_m1; ThermoFisher Scientific) are initially chosen for analysis (n=5-12 per group). In subsequent experiments, the transcripts for other markers of inflammation are chosen for analysis including Icam1 (ID Mm00516023_m1; a cell adhesion molecule involved in immune cell migration), Cldn5 (ID Mm00727012_s1; a tight junctions protein), colony stimulating factor 1 (Csf1: ID Mm00432686_m1; a factor that regulates microglia function) and its receptor Csf1r (ID Mm01266652_m1), and the nucleotide binding and oligomerization domain-like receptor family pyrin domain-containing 3 inflammasome complex (Nlrp3: Mm00840904_m1). Gapdh (ID Mm99999915_g1) is chosen as a housekeeping gene. QuantStudio 7 (ThermoFisher Scientific) is used for analyzing the plates (MicroAmp Optical 384-well plates; Applied Biosystems, Waltham, MA, and ThermoFisher Scientific) that are loaded with TaqMan Universal Master Mix II without uracil-DNA glycosylate in a 20 µl reaction volume using 100 ng cDNA per well. All mRNAs are measured by qRT-PCR on ABI Prism 7900HT system using TaqMan Gene Expression Assays. Ct values of genes of interest are normalized to that of the reference gene (Gapdh).

NanoString. The mouse neuropathology panel includes 770 genes associated with themes of neurotransmission, neuron-glia interaction, neuroplasticity, cell structure integrity, neuroinflammation and metabolism. A total of 13 housekeeping genes are used for expression normalization (Aars: NM_146217.4, Asb10: NM_080444.4, Ccdc127: NM_024201.3, Cnot10: NM_153585.5, Csnk2a2: NM_009974.3, Fam104a: NM_138598.5, Gusb: NM_010368.1, Lars: NM_134137.2, Mto1: NM_026658.2, Supt7l: NM_028150.1, Tada2b: NM_001170454.1:3224, Tbp: NM_013684.3:70, and Xpnpep1: NM_133216.3:1826, see FIG. 1-1). Hippocampal RNA is extracted using the Qiagen microkit (Qiagen) and is evaluated by the Agilent 2100 Bioanalyzer (Agilent Technologies, Santa Clara, CA) to assess RNA concentration, quality, and integrity. Sample preparation, hybridization, and detection (100 ng per sample, n=5-6 per group) are carried out according to NanoString manufacturer's instructions (NanoString Technologies, Seattle, WA). The normalized data are transformed to log 2 score to express the fold change. NanoString results (raw and normalized counts) are derived from RCC files using the nSolver software (version 2.6; NanoString Technologies). A complementary gene software analysis tool, ROSALIND® Advanced Analysis Software (NanoString Technologies), is also used, which provides comprehensive free cloud-based data analysis for nCounter data by directly analyzing raw RCC files generated from NanoString. Data are imported into ROSALIND® Advanced Analysis Software for normalization, calculation of fold-changes, P values, identification of enriched pathways, and heatmaps.

Microglia Enrichment. In male adult rats (8-9 weeks old, n=8-12 per group) that are previously treated with either LPS and lumateperone or vehicle 1 day prior (18 hours), hippocampi are dissected and placed in 1 mL of medium A solution containing 0.6% glucose and 15 mM HEPES. Brain tissue is then processed through a dounce homogenizer followed by passages through 16- and 20-gauge needles. One mL of medium A is added to wash cell suspension, which is passed through a 70 mm cell strainer and kept on ice. Next, 6 mL of 100% Percoll solution (9 parts of Percoll [GE Healthcare, Chicago, IL] and 1 part of HBSS) is added to obtain a 75% Percoll solution. The 75% Percoll cell suspension is then underlaid a layer of 25% Percoll solution containing Phenol red, which has a layer of PBS on top. The discontinuous Percoll density gradient is layered as followed: 75%, 25%, and 0% isotonic Percoll (PBS) to isolate hippocampal microglia. The gradients are then centrifuged at 4° C. for 25 minutes at 3,000 rpm in swinging buckets with minimal acceleration and deceleration and no brake. After centrifugation, the top layer containing myelin and debris (interface PBS/25% Percoll) is removed and the cellular layer at the 25%/75% interphase is collected and washed. Pilot experiments compare the gene expression of the different fractions and validated the presence of microglia in the interphase layer. The final pellet is resuspended in 350 µL of Buffer RLT from Qiagen microkit (Qiagen) to perform RNA extraction according to the manufacturer's instructions.

Restraint Stress Protocol. Acute restraint stress is performed using special rodent "decapicone" restraint bags in the traditional triangle shape (Braintree Scientific, Braintree, MA; ref #MDC-200). Mice (n=11-13 per group) are maintained in their restraint bag while placed on a secure surface at room temperature for 2 hours. Mice are euthanized at the end of the 2 hour stress session and whole hippocampal samples are collected. Control, non-stressed mice remain in their home cages in an adjoining room and are euthanized for sample collection at the same time point as stressed mice.

BBB Permeability Assay. Sodium fluorescein (NaFl) permeability assay is performed as previously described (Olsen et al., "Correlation between breakdown of the blood-brain barrier and disease outcome of viral encephalitis in mice," *Antiviral Res.* 75:104-112 (2007)) with minor adjustments. Mice (n=4-8 per group) are administered lumateperone and either dosed with LPS or restrained as described above. At 45 minutes prior to tissue collection, mice receive 200 µl of 10% NaFl (Cat #F6377, MilliporeSigma), IP. Mice are then euthanized via isoflurane overdose, and blood is collected via cardiac stick and allowed to clot while protected from light. Mice are perfused with 15 ml 1×PBS solution. Brains are then excised and flash frozen, protected from light. Serum is collected from blood samples via centrifugation at 1,500 g at 4° C. for 10 minutes. Brains are homogenized in 1×PBS and centrifuged at 10,000 g at 4° C. for 10 minutes, and the supernatant is collected for both protein concentration via Peirce BCA Protein Assay and further analysis. Proteins from both serum and tissue homogenate are extracted via trichloroacetic acid precipitation (Cat #T6399, MilliporeSigma) on ice, and centrifuged at 10,000 g at 4° C. for 10 minutes. Samples are run in duplicate on a FITC Filter spectrophotometer (EnVision 2105, PerkinElmer, Waltham, MA; excitation: 485 nm, emission: 535 nm). The average fluorescence of sham mice is subtracted from each value prior to calculation. Tissue homogenate fluorescent readings are first normalized to total protein concentration, and the cerebrum/serum ratio of arbitrary fluorescence units is calculated.

Behavioral Evaluation. All behavioral tests are performed in the morning with adult male Sprague-Dawley rats (n=9-11 per group for the experiments with LPS, and n=13-14 per group for the naïve rats).

Novelty Suppressed Feeding Test (NSFT). This test measures consumption of a familiar food in a novel environment, relying on rodents' aversion to eating in a novel environment after a period of food deprivation (Ramaker and Dulawa, "Identifying fast-onset antidepressants using rodent models," *Mol. Psychiatry* 22:656-665 (2017)). Rats are food-deprived overnight and placed in an open field (76.5×76.5×40 cm$^3$) with a small amount of food pellets (6 pellets total). At the time of the test, rats are exposed to the open field for the first time (novelty) and allowed to explore it for a maximum of 15 minutes under red light. The latency for the animal to approach the food pellets and take its first bite is manually scored. A home cage feeding test (HCFT) is performed afterwards to ensure latency measured in NSFT is not a matter of difference in hunger. A home cage food intake analysis evaluated the amount of food eaten (in grams) over a period of 10 minutes following the end of the entire test session.

Novelty Induced Hypophagia (NIH). This conflict-based behavioral task assesses the impact of environmental stressors on conditioned approach response for a palatable food reward (Ramaker and Dulawa, 2017). Rats are habituated with diluted (1:3 milk/water) sweetened condensed milk which is accessible in their home cage for 1 hour each day for 3 consecutive days. Initially, animals are tested in their home cage under normal lighting. For testing after drug treatment, the latency to drink is recorded after rats are placed in a novel clean cage of the same dimensions with no bedding and under dim lighting (~50 lux) with white paper under the cages to enhance aversion.

Open Field Test (OFT). Rats are placed in an open field box (76.5×76.5×40 cm$^3$) under dim lighting and locomotor activity over a 10 minute period is measured using ANY-Maze Software (Stoelting Co., Wood Dale, IL).

Reward Sniffing Test (also known also as female urine sniffing test (FUST)): In this anhedonia-based assay, rats are brought to a well-ventilated testing room under dim lighting. A sterile cotton-tipped applicator is attached to one wall in the home cage for 1 hour to habituate rats to this new object. For the 2 phases of the 5 minute test, rats are first exposed to a new cotton tip dipped in sterile water as a control that is removed at the end of the 5 minutes; 45 minutes later, another cotton tip previously dipped into fresh rat urine collected from females of the same strain is attached to the cage wall. Male behavior is video recorded and latency to first sniff of the cotton tip and total time spent sniffing the cotton-tipped applicator are determined.

Statistical Analysis. Data are expressed as mean±SEM. All statistical analyses are performed using GraphPad version 9 or earlier (GraphPad Software, San Diego, CA). Sample sizes for the experiments are calculated using expected effect size and variance based on previous data. The Kolmogorov-Smirnov test is used as a test of normality. Unpaired t-tests 2-sided are used for comparison between 2 groups. When the normal distribution is not confirmed, the Mann-Whitney U test is used to compare the mean ranks of 2 groups. Multiple group comparisons are made using 1-way ANOVA followed by a Bonferroni post hoc test or Tukey's multiple comparison test. NanoString nCounter analysis is based on multivariate linear regression with Benjamani-Yekutieli adjustment. Probability value is noted in each FIGURE and details on specific tests used are stated in the FIGURE legends. Outliers are removed using the median absolute deviation (MAD) equation (median plus or minus 2.5 times the MAD method for outlier detection).

Example 1: Lumateperone Dose-Dependently Normalizes the Pro-Inflammatory State

Specific cytokines are elevated in serum or plasma of patients with MDD and other psychiatric disorders. Here, the gene and protein expression of a subset of pro- and anti-inflammatory cytokines is measured in mouse brain in response to an inflammatory challenge using a single dose of LPS (500 µg/kg) to induce acute brain inflammation. Samples are collected 2 hours after coinjections of LPS and lumateperone or vehicle. mRNA is isolated and analyzed by qRT-PCR or NanoString Neuropath panel. The ability of lumateperone to ameliorate LPS-induced changes in hippocampal mRNA levels of these cytokines is studied using 3 doses of lumateperone (0.3, 3, and 8 mg/kg, IP). These doses span lumateperone's effective dose range for modulation of antipsychotic-like and antidepressant-like activity in rodents (see Snyder et al., "Functional profile of a novel modulator of serotonin, dopamine, and glutamate neurotransmission," *Psychopharmacology* 232:605-621 (2015)). The results are shown in Table 1A as relative change in mRNA levels for each cytokine gene (Il1b, Il6, Tnfa, Il10) normalized to the control group using the Dct method (n=5-12 per group):

TABLE 1A

Hippocampal cytokine mRNA expression

|  | IL-1b | IL-6 | TNF-alpha | IL-10 |
|---|---|---|---|---|
| Control | 0 | 0 | 0 | 0 |
| LPS | 2.88 | 1.03 | 1.75 | 0.43 |
| Luma, 0.3 mg/kg | 2.26 | 0.52 | 0.43 | −0.28 |
| Luma, 3 mg/kg | 0.85 | 0.15 | −0.09 | 2.53 |
| Luma, 8 mg/kg | 0.43 | 0.16 | −0.24 | 3.73 |

As expected, LPS treatment significantly increases gene expression for pro-inflammatory cytokines in hippocampus but did not significantly alter that of the anti-inflammatory cytokine Il10 relative to control mice, as determined by 1-way ANOVA analyses (effect of LPS treatment on levels of Il1b: $F_{(4,40)}$=16.48, P<0.01; Il6: $F_{(4,43)}$=11.57, P<0.001; Tnfa: $F_{(4,43)}$=24.51, P<0.001; Il10: $F_{(4,41)}$=13.15, P>0.99).

The results show that when administered at the same time as LPS, lumateperone dose-dependently lowers LPS-induced elevations of hippocampal mRNA levels of the pro-inflammatory genes Il1b, Tnfa and Il6 (Il1b: doses of 3 and 8 mg/kg, P<0.001; Il6: dose of 3 mg/kg, P<0.001, 8 mg/kg, P<0.01; Tnfa: all doses, P<0.001). In addition, lumateperone significantly increases hippocampal mRNA levels of the anti-inflammatory cytokine Il10 at doses of 3 and 8 mg/kg when compared with levels seen in animals receiving LPS alone (post hoc comparison of means: P=0.004 and P<0.001 compared with LPS at lumateperone doses of 3 and 8 mg/kg, respectively).

To determine if lumateperone also reduces LPS-induced increases in pro-inflammatory cytokine protein levels in peripheral blood, a dose of 3 mg/kg lumateperone is selected for further analysis based on data from the above dose-response study in hippocampal tissue. An additional experimental group receiving an injection with lumateperone alone is included as an additional control. Protein concentration is measured using the Multiplex MSD assay V-Plex technology. Results are expressed in pg/mL, except for IL-6, which is measured in ng/mL.

TABLE 1B

Serum cytokine concentration

|  | IL-1b | IL-6 | TNF-alpha | IL-10 |
|---|---|---|---|---|
| Saline only | 1.32 | 0.51 | 14.08 | 24.80 |
| LPS | 6.27 | 14.52 | 335.3 | 980.4 |
| Luma | 1.47 | 0.09 | 9.38 | 48.93 |
| Luma + LPS | 2.69 | 1.49 | 56.33 | 1014.3 |

A pattern of results similar to that seen for gene expression changes in hippocampal tissue is obtained when examining protein levels of inflammatory biomarkers in serum. Two-way ANOVA revealed a significant effect of LPS, which elevated the protein levels of all biomarkers studied (Tukey multiple comparison vs control; IL-1b: $F_{(1,17)}$=15.21, P<0.0012; IL-6: $F_{(1, 19)}$=27.77, P<0.0001; TNF-a: $F_{(1, 20)}$=69.12, P<0.0001; IL-10: $F_{(1, 16)}$=38.24, P<0.001).

It is found that lumateperone treatment reduces circulating protein levels in serum of the pro-inflammatory cytokines IL-1b, TNF-α, and IL-6 compared with mice treated with LPS alone (IL-1b: LPS v. LPS+Luma, P=0.0081; IL-6: LPS v. LPS+Luma, P<0.0001; TNF-α: LPS v. LPS+Luma, P<0.0001). Previous work has shown that LPS, which is a cell wall component of gram-negative bacteria, binds to Toll-like receptor 4 (TLR4) and activates nuclear factor kappa B (NFkB) signaling (Hoshino et al., "Cutting edge: Toll-like receptor 4 (TLR4)-deficient mice are hyporesponsive to lipopolysaccharide: evidence for TLR4 as the Lps gene product," *J. Immunol.* 162:3749-3752 (1999)) as well as a mixed gene profile that is not strictly pro-inflammatory, as it is known to also upregulate IL-10 signaling molecules in primary rodent microglia.

In contrast to brain tissue, it is found that LPS challenge increases IL-10 protein levels in serum. Two-way ANOVA did not reveal any drug effect ($F_{(1, 16)}$=0.03489, P=0.8542) for IL-10 protein levels in serum, although lumateperone treatment by itself, without LPS, induces a significant IL-10 increase if compared with control only. These data demonstrate that, compared with vehicle, lumateperone increases the protein levels of the anti-inflammatory cytokine IL-10 while normalizing certain pro-inflammatory cytokines elevated by LPS in serum and brain.

To gain a deeper understanding of the transcriptional pathways and regulatory mechanisms altered by lumateperone in the context of elevated inflammation, NanoString nCounter-based analysis is performed following coinjection of LPS (500 µg/kg) and lumateperone (3 mg/kg) with sample collection 2 hours after injection: The NanoString platform has been effectively used to quantitatively measure in vivo gene expression of target genes in several neuropathological mouse models. When connected with LPS, NanoString software analyses confirmed that lumateperone significantly decreased the expression of genes involved in inflammatory processes, as shown in the following table:

TABLE 1C

Differential expression versus baseline of control group

| Gene set (NanoString) | LPS | LPS + Luma | Luma |
|---|---|---|---|
| Adaptive immune response | 0.571 | 0.938 | 0.344 |
| Angiogenesis | −0.144 | 0.891 | 0.616 |
| Apoptosis | 0.915 | −0.453 | −0.442 |
| Astrocyte function | 1.391 | −0.308 | −0.837 |
| Autophagy | 0.588 | 0.548 | −0.731 |
| Carbohydrate metabolism | 0.507 | 0.668 | −0.837 |
| Cell cycle | −0.148 | 0.385 | −0.75 |
| Cellular stress | 0.499 | 0.813 | −0.432 |
| Cytokine signaling | 0.993 | −0.599 | −0.543 |
| DNA damage | 0.578 | 0.042 | −0.614 |
| Epigenetic regulation | 0.312 | 0.892 | 0.729 |
| Growth factor signaling | 0.76 | 0.698 | 0.226 |
| Inflammatory signaling | 1.086 | −0.93 | −1.032 |
| Innate immune response | 0.939 | −0.655 | −0.611 |
| Insulin signaling | 0.28 | 0.809 | 0.858 |
| Lipid metabolism | −0.192 | 0.89 | −0.818 |
| Matrix remodeling | −0.583 | 0.447 | −0.4 |
| Microglia function | 0.377 | 0.915 | 0.466 |
| Neurons and neurotransmission | −0.422 | 0.979 | 0.435 |
| NF-kB | 1.215 | −0.689 | −0.499 |
| Notch | 0.876 | 1.05 | 0.834 |
| Oligodendrocyte function | 0.181 | 0.48 | −1.176 |
| Wnt | −0.476 | 1.186 | 0.9 |

Generally, directed global significance scores measure the extent to which a given gene is up-regulated or down-regulated relative to a given covariate. It is calculated similarly to a undirected global significance score, but it takes into account the sign of the t-statistic. Scores were calculated by nSolver software, using the control group as a reference.

Thus here, the directed global significance scores measure the extent to which a given gene set is up- or downregulated relative to the control group. The result show that LPS+Lumateperone treatment downregulates gene expression sets involved in cytokine signaling, inflammatory signaling, innate immune response, and the NF-kB pathway. Pathway analysis also documents an increase in genes associated with angiogenesis, epigenetic regulation, and Notch and Wnt pathways in groups injected with lumateperone.

Surprisingly, it is found that lumateperone alone alters gene expression in some of these pathways to a comparable extent (i.e., scored similarly) as did combined treatment with LPS+Lumateperone.

The following table shows the top genes involved in microglial function, neuroprotection, and inflammation which are found to be altered in the LPS+lumateperone group, compared to the LPS group.

TABLE 1D

LPS + Luma vs LPS

| | Gene name | Log2 | P value | Lower | Upper |
|---|---|---|---|---|---|
| Neuroprotect | Fos | 2.27 | $5.6 \times 10^{-7}$ | 1.68 | 2.86 |
| | Egr1 | 0.87 | 0.0031 | 0.37 | 1.37 |
| | Cldn5 | 0.812 | $1.4 \times 10^{-5}$ | 0.541 | 1.08 |
| | Vegfa | 0.227 | 0.0202 | 0.0524 | 0.402 |
| | Ngf | 0.126 | 0.43 | −0.18 | 0.432 |
| Inflammation | Ikbkb | −0.132 | 0.0313 | −0.242 | −0.021 |
| | Tnfrsf1b | −0.31 | 0.313 | −0.896 | 0.275 |
| | Il1r1 | −0.309 | 0.0664 | −0.619 | 0.001 |
| | Myd88 | −0.433 | 0.00442 | −0.695 | −0.172 |
| | Tnfrsf1a | −0.434 | 0.0124 | −0.74 | −0.128 |
| | Nfkb2 | −0.972 | 0.0012 | −1.47 | −0.476 |
| | Ly6a | −0.925 | $6.9 \times 10^{-7}$ | −1.17 | −0.681 |
| | Osmr | −1.21 | $8.6 \times 10^{-8}$ | −1.49 | −0.937 |
| | Il1b | −1.42 | 0.0258 | −2.56 | −0.274 |
| | Lrg1 | −1.67 | 0.00584 | −2.72 | −0.624 |
| | Socs3 | −1.57 | $1.1 \times 10^{-5}$ | −2.08 | −1.06 |
| | Ccr2 | −1.71 | 0.00737 | −2.82 | −0.599 |
| | Casp4 | −2.24 | $7.0 \times 10^{-5}$ | −3.09 | −1.38 |
| Microglia | Maff | 1.21 | 0.00453 | 0.476 | 1.93 |
| | Cd36 | 0.332 | 0.518 | −0.656 | 1.32 |
| | Cx3cr1 | 0.231 | 0.00202 | 0.105 | 0.356 |
| | Tmem144 | 0.227 | 0.0373 | 0.0292 | 0.425 |
| | Tmem100 | 0.186 | 0.0444 | 0.0173 | 0.355 |
| | P2ry12 | 0.14 | 0.0467 | 0.0115 | 0.269 |
| | Ptgs2 | −0.358 | 0.00803 | −0.593 | −0.122 |

As shown in the table above, NanoString software analyses also show that compared with LPS alone, the LPS+Lumateperone combination increased expression of markers of neuroprotection such as Fos, Egr1, Cldn5, Vegfa, and Ngf while robustly decreasing expression of genes involved in inflammation such as Casp4, Ccr2, Socs3, Lrg1, Il1b, Osmr, Ly6a, Myd88, Il1r1, Nfkb2, Tnfrsf1, and Ikbkb.

Microglia markers of homeostasis including Maff, Cx3cr1, Cd36, Trem100, Trem144, and P2ry12 are found to be upregulated by lumateperone, further supporting the potential protective properties of lumateperone in acute inflammatory conditions.

Next, using ROSALIND® Advanced Analysis Software and a filter set to P<0.04999, a heatmap of cytokine-specific gene expression comparing LPS+Luma versus LPS alone is obtained. The data analysis with ROSALIND® confirms that lumateperone significantly downregulates genes that promote inflammation (e.g., Osmr, Tnfrsf1a, Tnfrsf11b, Prl, and Il1r1). Venn diagrams based on this analysis reveal some overlap of significantly altered gene expression changes (P≤0.04999) when group comparisons are performed. The results show that: the receptor for advanced glycation end products (RAGE) pathway is significantly altered when comparing LPS versus control; brain-derived neurotrophic factor (BDNF) signaling pathway is among the most significant pathways altered in the group LPS+Lumateperone versus LPS; and IL-6 regulation is also one of the top pathways altered when comparing Lumateperone versus LPS. In summary, it is discovered that lumateperone reverses acute inflammatory conditions by normalizing key pathways involved in inflammation in parallel with enhancing a gene signature indicative of tissue protection and repair.

Example 2: Lumateperone Reduces Pre-Established LPS-Induced Proinflammatory Cytokine mRNA Levels in the Hippocampus Based on these findings, it was desired to study whether a delayed administration of lumateperone would alter an established state of elevated inflammation and thereby reestablish immune system homeostasis. Adult mice first receive a subcutaneous injection of either LPS injection (500 µg/kg) or vehicle (0.9% saline), and 30 minutes later the mice are injected IP with either lumateperone (3 mg/kg) or vehicle (5% DMSO, 5% Tween-20, 15% PEG-400, 75% water). Samples are collected 1.5 hours later (i.e., 2 hours after LPS injection). The results are shown in Table 2A as relative change in hippocampal mRNA levels for each cytokine gene (Il1b, Il6, Tnfa, Il10) normalized to the control group using the Dct method (n=4-9 per group) as in Example 1:

TABLE 2A

Hippocampal cytokine mRNA expression (delayed injection)

|  | IL-1b | IL-6 | TNF-alpha | IL-10 |
|---|---|---|---|---|
| Saline/Vehicle | 0 | 0 | 0 | 0 |
| Saline/LPS | 2.89 | 1.10 | 2.33 | 1.88 |
| Luma/Vehicle | 0.90 | −0.46 | −0.31 | 2.98 |
| Luma/LPS | 2.07 | −0.10 | 0.34 | 3.87 |

LPS is found to significantly increase hippocampal mRNA levels of Il1b, Il6, and Tnfa (2-way ANOVA, LPS effect: Il1b: $F_{(1, 19)}$=94.51, P<0.0001; Il6: $F_{(1, 20)}$=8.008, P=0.0104; Tnfa: $F_{(1, 20)}$=63.35, P<0.0001), and the delayed injection of lumateperone is found to reduce mRNA levels (Il1b: LPS v. LPS+Luma, P=0.0433; Il6: LPS v. LPS+Luma, P=0.0078; Tnfa: LPS v. LPS+Luma, P<0.0001). These results indicate that lumateperone exhibits similar effects when given as a co-injection with LPS or 30 minutes after the LPS injection. It also shows that the mRNA levels of Il10 are elevated by lumateperone in the presence or absence of LPS. Two-way ANOVA analyses of Il10 show an effect of LPS ($F_{(1, 20)}$=21.31, P=0.0002) and lumateperone ($F_{(1, 20)}$=69.02, P<0.0001) which confirms that lumateperone modulates hippocampal mRNA levels of this anti-inflammatory cytokine.

Supplementary key markers revealed by NanoString analyses are also examined, using the same procedure as described above.

TABLE 2B

Hippocampal cytokine mRNA expression (delayed injection)

|  | Icam1 | Cldn5 | Csf1 |
|---|---|---|---|
| Saline/Vehicle | 0 | 0 | 0 |
| Saline/LPS | 4.33 | −0.63 | 0.41 |
| Luma/Vehicle | 0.28 | 0.33 | 0.05 |
| Luma/LPS | 1.26 | 0.20 | −0.11 |

It is found that there is a significant interaction, treatment (LPS) effect by drug effect (lumateperone) for Cldn5 and Icam1. Lumateperone decreases levels of Icam1 (LPS v. LPS+Luma, P<0.0001) and coadministration of LPS with lumateperone increases Cldn5 (LPS v. LPS+Luma, P<0.0001). Analyses of the levels of Csf1 mRNA show an interaction between drug and treatment and drug effect where lumateperone decreases Csf1 relative to the LPS group (LPS v. LPS+Luma, P=0.0009). Collectively, these results indicate that transcriptional modulation of genes related to inflammation and tissue repair is initiated when lumateperone is administered at a delay following LPS-induced inflammation.

Example 3: Lumateperone Reinforces BBB Integrity in the Hippocampus

Systemic inflammation is associated with increased permeability of the BBB, and this has been discussed as a potential factor underlying depression pathophysiology. In this experiment, mice receive a single injection of lumateperone (3 mg/kg, IP) at the same time (coinjection) or 30 minutes after (delayed) LPS injection. Forty-five minutes before sample collection, mice receive NaFl injections (200 μl of 10% solution, IP) (Table 3).

| Condition (2 h) | Control | Experimental group | Experimental + Luma | Experimental + Luma (delayed) |
|---|---|---|---|---|
| LPS paradigm | *1.000 ± 0.0957 | 1.406 ± 0.0873 | **0.8632 ± 0.1273 | ***0.6515 ± 0.04580 |
| Restraint Stress paradigm | 1.000 ± 0.0311 | 1.132 ± 0.07244 | $0.7278 ± 0.1699 |  |

Mice treated with LPS demonstrate significantly increased NaFl brain penetration, and this is significantly dampened in both the lumateperone coinjection group and in the lumateperone delayed injection group (control=normalized to 1, LPS=1.406, control vs LPS: Tukey's multiple comparison test P<0.05; LPS+Luma=0.863, LPS vs LPS+Luma: P<0.01; LPS+Luma (delayed)=0.652, LPS vs LPS+Luma (delayed): P<0.001—all units in arbitrary units normalized to control. $F_{(3, 21)}=11.49$, P=0.0001. Table 1). These data demonstrate that lumateperone administered in combination with LPS rescued the integrity of the BBB.

Example 4: Lumateperone Attenuates Stress-Induced Inflammation and BBB Permeability To determine if lumateperone could normalize brain pathological inflammation induced by an acute stressor, restraint stress is used, which is a stressor known to evoke increases in inflammation. Mice receive a single injection of lumateperone (3 mg/kg, IP) or vehicle (5% DMSO, 5% Tween-20, 15% PEG-400, 75% water) immediately before being placed in a rodent restraint bag for 2 hours. Control mice receive vehicle treatment and are returned to their home cage before sample collection. Protein concentration is measured using the Multiplex MSD assay V-Plex technology, normalized to the control group. Results are expressed in pg/mL.

TABLE 4A

Serum cytokine concentration

|  | IL-1b | IL-6 | TNF-alpha | IL-10 |
| --- | --- | --- | --- | --- |
| Control | 0.7 | 141.3 | 6.75 | 17.18 |
| Stressed | 1.65 | 627.4 | 10.28 | 86.78 |
| Stressed + Luma | 0.81 | 137.7 | 7.67 | 70.03 |

It is found that acute restraint stress results in significant elevations in serum IL-1b, IL-6, and TNF-α levels while each of these proteins are significantly reduced to control levels in mice receiving lumateperone (IL-1b: Stress v. Stress+Luma, Bonferroni's multiple comparisons test P<0.001; IL-6: Stress v. Stress+Luma, P<0.001; TNF-α: Stress v. Stress+Luma, P=0.007, compared with controls). Corresponding data is collected for hippocampal mRNA expression according to the procedure of Example 1. The results are shown in Table 4B as relative change in mRNA levels for each cytokine gene (Il1b, Il6, Tnfa, Il10) normalized to the control group using the Dct method:

TABLE 4B

Hippocampal cytokine mRNA expression

|  | IL-1b | IL-6 | TNF-alpha | IL-10 |
| --- | --- | --- | --- | --- |
| Control | 0 | 0 | 0 | 0 |
| Stressed | 1.05 | 0.037 | −0.076 | 2.29 |
| Stressed + Luma | 0.39 | −0.051 | −0.407 | 2.87 |

In the hippocampus of the same mice, acute restraint stress leads to an increase in mRNA levels for Il1b (control=normalized to zero, P=0.007) which are not significantly decreased after lumateperone treatment. At this time point, Tnfa and Il6 mRNA levels are not altered by acute restraint stress. Interestingly, IL-10 serum protein and hippocampal mRNA levels are both increased by lumateperone compared with controls (IL-10 protein levels: control v. Stress+Luma, Bonferroni's multiple comparisons test P=0.001; Il10 mRNA levels: control normalized to zero, Stress+Luma, P<0.001).

Using similar procedures as described above, serum corticosterone levels and hippocampal Cldn5 mRNA expression are measured as well (corticosterone is measured using a commercial ELISA kit).

TABLE 4C

Hippocampal mRNA expression

|  | Cldn5 |
| --- | --- |
| Control | 0 |
| Stressed | −0.138 |
| Stressed + Luma | 0.330 |

TABLE 4D

Serum concentration

|  | Corticosterone (ng/mL) |
| --- | --- |
| Control | 22.65 |
| Stressed | 238.5 |
| Stressed + Luma | 167.3 |

The data shows that corticosterone levels are increased in blood serum of stressed mice and the elevated levels are significantly dampened by lumateperone (Stress vs Stress+Luma: P<0.001; $F_{(2, 27)}=124.2$, P<0.001). It is also confirmed that Cldn5 transcripts are significantly elevated by lumateperone in stressed animals (Stress vs Stress+Luma: P<0.001; $F_{(2,36)}=11.44$, P≤0.001).

In a separate cohort, it is found that acute restraint stress does not significantly increase NaFl brain penetration (Control=normalized to 1, Stress=1.132). However, lumateperone alone does significantly decrease NaFl brain penetration in the stress+lumateperone cohort compared with the stress cohort (Stress+Luma=0.7278; Stress vs Stress+Luma: unpaired t-test P<0.05; $t_{(7)}=2.373$; See Table 3, above).

Example 5: Lumateperone Decreases Anxiety and Normalizes LPS-Induced Anhedonia

LPS is administered to induce a transient anhedonic state in rats and behaviors that rely on the reward system are measured by using female urine as a rewarding stimulus to study whether lumateperone could rescue transient LPS-induced deficits.

In a pilot study, a dose response curve is conducted with varying doses of LPS to select an optimal dose for inducing an anhedonic response in rats. Based on these studies, a SC dose of 1 mg/kg LPS is selected. Rats are first injected with pre-treatment lumateperone (1 mg/kg; IP) or vehicle. This is followed 24 hours later by an injection of LPS (1 mg/kg; SC). Then, 24 hours later the rats are injected with post-treatment lumateperone (1 mg/kg; IP) or vehicle. Control rats are administered saline instead of LPS and vehicle instead of lumateperone. Anhedonia is assessed using FUST (female urine sniffing test) and measuring latency to sniff the reward combined with time spent sniffing the reward. Latency sniffing water is used as a control. The results are shown in the table below (time in seconds) with outliers removed using the MAD Method:

TABLE 5A

| | FUST | | |
|---|---|---|---|
| | Latency sniffing reward | Time sniffing reward | Latency sniffing water |
| Control | 28.00 | 16.99 | 190.56 |
| LPS + Vehicle | 164.2 | 11.11 | 274.27 |
| LPS + Luma | 68.13 | 17.38 | 207.60 |

The results show that when exposed to the reward cue (female urine), the LPS-treated male rats who had been administered lumateperone exhibit a decreased latency to sniff the urine-soaked cotton tip, compared with the LPS group. Overall, it is found that lumateperone-treated rats spend as long as control rats sniffing the reward cue during the 5-minute test period. Importantly, rats did not significantly differ with respect to the time spent exploring the water-dipped cotton tip that served as a control test. Locomotion in an open field (track length in meters) is also measured as a control. As shown in the following table, locomotor activity is also affected regardless of the group:

TABLE 5B

| | Locomotion |
|---|---|
| | Latency sniffing water |
| Control | 13.29 |
| LPS + Vehicle | 12.81 |
| LPS + Luma | 12.27 |

Basal levels of anxiety are also tested using 2 commonly used tests, NSFT and novelty induced hypophagia (NIH), in the absence of LPS. It is well documented that rodents experience increased stress levels when placed in a novel environment (Ramaker and Dulawa, 2017). These two tests exploit this feature by measuring latency to feed in food-deprived rats (NSFT), or latency to receive a reward to which they have been habituated prior to the test (NIH).

Similar to the previous study, rats are injected with lumateperone (1 mg/kg; IP) on days 1 and 3. It is found that lumateperone reduces the latency to feed in the NSFT (control: 657.8 s, Luma: 507.9 s, Mann-Whitney U test P=0.0009, Table 6).

| | Control | Luma | Statistical Test | P value |
|---|---|---|---|---|
| NSFT (s) | 657.8 ± 60.4 | 507.9 ± 55.7 | Mann-Whitney U | ***.0009 |
| Control HCFT (g) | 6.0 ± 0.5 | 6.0 ± 0.3 | Unpaired t-test | ns .9897 |
| NIH-novel cage (s) | 65.4 ± 16.4 | 30.5 ± 13.8 | Mann-Whitney U | *.0257 |
| OFT (m) | 17.2 ± 3.4 | 32.8 ± 10.2 | Unpaired t-test | ns .8879 |

In contrast, it is found that there is no effect on feeding itself, as shown in the HCFT (which is a control used for NSFT). Likewise in the NIH test, which measures anxiety in a slightly different setting and does not require food deprivation, lumateperone is found to reduce latency to drink the reward (i.e., diluted condensed milk; control: 65.4 s, Luma: 30.5 s, Mann-Whitney U test P=0.0257, Table 2) when rats are placed in a stress-inducing novel, empty, and brightly lit cage. Here again, locomotion assessed in an open field did not reveal a significant effect for lumateperone between treatment groups (Table 6).

In summary, these results confirm that lumateperone has the potential to reduce anhedonia and to decrease basal levels of anxiety in a stressful situation.

Example 6: Lumateperone Acts on Rat Microglia Isolated from Hippocampus after LPS-Induced Inflammation Based on the associations revealed by gene ontology analyses above, it was desired to study the potential involvement of microglia in the reduction of LPS-induced inflammation mediated by lumateperone administration. Microglia, the resident immune cells of the brain, have emerged as a likely effector for initiating and resolving neuroinflammation in a wide range of conditions and disorders. Therefore, the impact of lumateperone on in vivo inflammatory activity in hippocampal microglia is specifically monitored, interrogating a time window in which inflammation would be detected in enriched preparations of rat brain microglia.

Exploratory experiments reveal that in microglia-enriched fractions from rat hippocampi, inflammation is returned closer to background levels at +26 hours after a dose of LPS. Thus, an earlier time point of +18 h after the LPS injection is selected to assess potential changes indicative of inflammation. Rats are pretreated with the same dose of LPS used for biochemical and RNA-based experiments (500 µg/kg diluted in 0.9% saline) and receive either lumateperone (3 mg/kg in vehicle) or vehicle (5% DMSO, 5% Tween-20, 15% PEG-400, 75% water) injection 16 hours later.

Hippocampi on both sides of the brain are collected 2 hours later (+18 hour from LPS injection) and microglia are rapidly isolated in an enriched fraction by Percoll gradient. RNA is extracted from the resulting, reconstituted cell pellet and RT-qPCR is performed. The results are shown in Table 7 as relative change in mRNA levels for each cytokine gene (Il1b, Il6, Tnfa, Nlrp3, Csf1r) normalized to the control group using the Dct method (n=8-12 per group):

TABLE 7

| Hippocampal microglial cytokine mRNA expression | | | | | |
|---|---|---|---|---|---|
| | IL-1b | IL-6 | TNF-alpha | NLRP3 | Csf1R |
| Control | 0 | 0 | 0 | 0 | 0 |
| LPS | 2.82 | 0.89 | −0.28 | 0.71 | 0.50 |
| LPS + Luma | 0.38 | −0.22 | −1.00 | −0.48 | −0.05 |

The results show that LPS treatment leads to significant increases in Il1b and Il6 gene expression in isolated hippocampal microglia; these increases are significantly suppressed by lumateperone administration (Il1b: 1-way ANOVA $F_{(2,17)}$=15.05, P<0.001; Il6: 1-way ANOVA $F_{(2,20)}$= 6.622, P=0.006). For Nlrp3, lumateperone significantly decreases the gene expression level compared with LPS alone (1-way ANOVA, $F_{(2,26)}$=4.302, P=0.02). At this time point, however, Tnfa gene expression did not differ from controls, most likely reflecting a different response time course in isolated microglia compared with that observed in whole tissue.

Nevertheless, lumateperone administration is found to lead to decreased Tnfa mRNA levels when compared with microglia isolated from either control rats or LPS-treated rats (Tnfa: 1-way ANOVA $F_{(2,20)}$=3.868, P=0.04). LPS shows a trend toward increasing Csf1r mRNA levels in microglia while lumateperone tends to reduce this response (1-way ANOVA $F_{(2, 29)}$=0.9725, P=0.39). This trend parallels the observed effects of lumateperone treatment in whole tissue. In summary, this data suggests that lumateperone suppresses LPS-induction of a subset of proinflammatory genes expressed in hippocampal microglia.

Example 7: Post-Hoc Analysis of Phase 3 Clinical Trial of Lumateperone in Schizophrenic Patients A randomized, double-blind, placebo-controlled, phase 3 clinical trial was conducted with 450 patients with schizophrenia, aged 18 to 60 years, who were experiencing an acute exacerbation of psychosis. Patients were included if they were experiencing an acute exacerbation of psychosis, defined as a total score on the Brief Psychiatric Rating Scale of 15 out of 40 or higher, with a score of 4 or higher on 2 or more positive symptoms, and onset of the acute episode within 4 weeks of screening. Patients were required to have a score of 4 or higher, indicating moderate to severe disease severity, on the Clinical Global Impression-Severity of Illness (CGI-S) at screening and baseline. Severity of illness was confirmed at baseline by a Positive and Negative Syndrome Scale (PANSS) total score of 70 or higher, indicating moderate to extreme symptoms of schizophrenia. A subgroup of these patients experienced co-morbid depression symptoms at baseline (defined as having a Calgary Depression Scale for Schizophrenia (CDSS) score greater than 6 at baseline). Full details of the clinical study were reported in Correll et al., *JAMA Psychiatry*, 77(4): 349-358 (2020).

Patients were randomized 1:1:1 (150 patients in each arm) to receive, once daily for 28 days, either 60 mg lumateperone tosylate (42 mg free base), 40 mg lumateperone tosylate (28 mg free base), or placebo.

The primary efficacy end point was mean change from baseline to day 28 in the Positive and Negative Syndrome Scale (PANSS) total score versus placebo. The key secondary efficacy measure was the Clinical Global Impression-Severity of Illness (CGI-S) score. The PANSS subscale scores, social function, safety, and tolerability were also assessed. Primary and key secondary efficacy measures were assessed weekly. Safety was assessed by treatment-emergent adverse events (TEAEs), modified physical examinations, 12-lead electrocardiograms (ECGs), vital signs, and clinical laboratory tests (blood and urine samples for clinical laboratory analysis were collected from all subjects upon screening and on Days 1, 8, 28, and 33, following overnight fast).

The results from the trial demonstrated that lumateperone is effective for improving the symptoms of schizophrenia and has a favorable safety profile.

Using blood samples stored from the study, a post-hoc analysis of inflammatory biomarkers in PBMCs from the patients with schizophrenia and co-morbid depression is conducted. Analysis is performed on samples from day 0 and day 28 for the patients treated with 60 mg lumateperone. Day 0 samples are available for 20 patients, while day 28 samples are available only for 18 patients. Mean baseline CDSS is 10.0, and mean baseline PANSS total score is 88.7 in the selected patients.

Samples were processed to isolate PBMC according to standard procedures using the Ficoll-Paque method. Statistical analysis was performed using the paired t-test, two-tailed. Samples were tested for C-reactive protein (CRP), serum amyloid A (SAA), soluble CAM-1, soluble VCAM-1, IL-1β, TNF-αL, IL-6, IL-10, IL-2, IL-8, IL-13, and IFN-γ. ICAM-1 and VCAM-1 are expressed by the vascular endothelium, macrophages, and lymphocytes. Upon cytokine stimulation, their concentrations greatly increase. ICAM-1 can be induced by IL-1β and TNF. ICAM and VCAM proteins may also be involved in pathogen transit into CNS.

The results are shown in the table below (biomarker levels expressed in ng/mL; some values of N are less than the patient totals due to samples with levels of biomarker below the minimum for quantification):

| | Biomarker | | | | | | | |
|---|---|---|---|---|---|---|---|---|
| | CRP | | SAA | | sICAM-1 | | sVCAM-1 | |
| Day | Day 0 | Day 28 | Day 0 | Day 28 | Day 0 | Day 28 | Day 0 | Day 28 |
| Average | 78.8 | 50.5 | 286.9 | 157.9 | 184.8 | 119.6 | 78.9 | 49.1 |
| Median | 61.3 | 38.0 | 233.6 | 147.3 | 136.9 | 83.6 | 60.1 | 42.0 |
| STDV | 61.8 | 33.9 | 241.6 | 144.5 | 147.2 | 87.5 | 56.2 | 41.5 |
| 95% CI upper | 105.8 | 58.3 | 392.8 | 221.2 | 249.3 | 116.0 | 103.6 | 67.2 |
| 95% CI lower | 51.7 | 28.6 | 181.0 | 94.6 | 120.3 | 133.4 | 54.3 | 30.9 |
| N= | 20 | 19 | 20 | 20 | 20 | 18 | 20 | 20 |

| | Biomarker | | | | | | | |
|---|---|---|---|---|---|---|---|---|
| | IL-1β | | TNF-α | | IL-6 | | IL-10 | |
| Day | Day 0 | Day 28 | Day 0 | Day 28 | Day 0 | Day 28 | Day 0 | Day 28 |
| Average | 1.76 | 1.01 | 0.27 | 0.83 | 0.20 | 0.55 | 0.09 | 2.14 |
| Median | 1.65 | 0.74 | 0.27 | 0.43 | 0.18 | 0.32 | 0.07 | 0.21 |
| STDV | 0.60 | 0.87 | 0.12 | 0.98 | 0.09 | 0.48 | 0.04 | 4.43 |
| 95% CI upper | 2.03 | 1.53 | 0.34 | 1.34 | 0.24 | 0.78 | 0.09 | 4.30 |
| 95% CI lower | 1.48 | 0.50 | 0.21 | 0.32 | 0.16 | 0.33 | 0.07 | 0.00 |
| N= | 17 | 11 | 15 | 14 | 17 | 17 | 17 | 18 |

-continued

| | Biomarker | | | | | | | |
|---|---|---|---|---|---|---|---|---|
| | IL-2 | | IL-8 | | IL-13 | | IFN-γ | |
| Day | Day 0 | Day 28 | Day 0 | Day 28 | Day 0 | Day 28 | Day 0 | Day 28 |
| Average | 0.18 | 0.37 | 74.5 | 105.3 | 1.31 | 2.38 | 1.11 | 0.86 |
| Median | 0.17 | 0.25 | 36.3 | 44.0 | 1.11 | 1.56 | 1.01 | 0.71 |
| STDV | 0.05 | 0.44 | 34.0 | 131.2 | 0.75 | 2.82 | 0.67 | 0.51 |
| 95% CI upper | 0.20 | 0.57 | 91.2 | 169.6 | 1.67 | 3.68 | 1.43 | 1.30 |
| 95% CI lower | 0.15 | 0.17 | 57.8 | 41.0 | 0.95 | 1.07 | 0.77 | 0.41 |
| N= | 18 | 18 | 16 | 16 | 17 | 18 | 16 | 5 |

These data indicate that patients with schizophrenia and co-morbid depression have elevated levels of inflammatory biomarkers in their blood cells (PBMCs) at baseline, and that after 28 days of treatment with lumateperone treatment, these levels are significantly reduced. These results also demonstrate that patients with a schizophrenia accompanied by depressive symptoms can be identified a priori by measuring inflammatory biomarkers in the blood.

Interestingly, unlike the measurement of depressive symptoms (CDSS), the placebo group did not show significant changes in biomarker levels (data not shown).

We claim:

1. A method for the treatment of psychiatric disorders caused by viral, bacterial, or autoimmune encephalitis, and for treatment of psychiatric symptoms of viral, bacterial, and autoimmune encephalitis comprising administering to a patient in need thereof a Compound of Formula I:

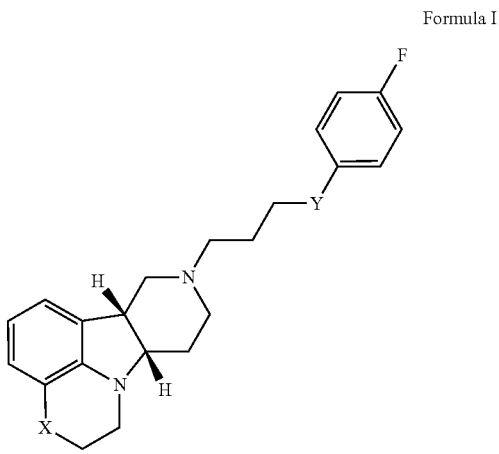

Formula I wherein:
X is —N(CH$_3$)—; and
Y is —C(=O)—;
in free base, or pharmaceutically acceptable salt form;
wherein the patient has elevated levels of one or more biomarkers indicative of peripheral inflammation in the blood, plasma, serum, peripheral blood mononuclear cells (PBMC), or urine; and
wherein the psychiatric disorder and/or the psychiatric symptom is depression, anxiety, psychosis, anhedonia, memory loss, impairment of executive functioning, difficulty concentrating, seizures, difficulty sleeping, hallucination, change in personality, or any combination thereof.

2. The method according to claim 1, wherein the Compound of Formula I is in the form of a tosylate salt.

3. The method according to claim 1, wherein the method comprises once daily administration of a unit dosage for oral administration, comprising the compound of Formula I in free base or in tosylate salt form, in an amount equivalent 1 to 100 mg of free base, and a pharmaceutically acceptable diluent or carrier.

4. The method according to claim 1, wherein the method comprises once daily administration of a unit dosage for oral transmucosal administration selected from a sublingual or buccal orally disintegrating tablet, wafer, or film, comprising the compound of Formula I in free base or in tosylate salt form, in an amount equivalent to 0.5 to 30 mg of free base, and a pharmaceutically acceptable diluent or carrier.

5. The method according to claim 1, wherein the compound of Formula I is administered in the form of a long-acting injectable (LAI) composition.

6. The method according to claim 1, wherein the encephalitis is viral encephalitis.

7. The method according to claim 6, wherein the encephalitis is caused by, or suspected to be caused by, Herpes simplex Virus 1, Herpes Simplex Virus 2, West Nile Virus, Nipah Virus, human immunodeficiency virus, rabies virus, Epstein-Barr Virus, cytomegalovirus, coronavirus, or influenza virus.

8. The method according to claim 1, wherein the encephalitis is bacterial encephalitis.

9. The method according to claim 8, wherein the encephalitis is caused by, or believed to be caused by, toxoplasmosis, *Rickettsia*, *Mycoplasma*, *Borrelia* (e.g., Lyme disease), or malaria.

10. The method according to claim 1, wherein the encephalitis is autoimmune encephalitis.

11. The method according to claim 10, wherein the encephalitis is caused by, or believed to be caused by, autoantibodies against the NMDA receptor, the AMPA receptor, the voltage-gated potassium, channel (VGKC), the LGL1 protein, the GABA receptor, the glycine receptor, the glutamate receptor, or the CASPR2 receptor.

12. The method according to claim 1, wherein the psychiatric disorder and/or the psychiatric symptom is acute depression, depression of MDD, depression of bipolar disorder, acute anxiety, schizophrenia, anhedonia, or any combination thereof.

13. The method according to claim 1, wherein the method protects or reinforces the blood-brain barrier.

14. The method according to claim 1, wherein the patient has elevated levels of pro-inflammatory cytokines in the CNS, or elevated levels of C-reactive protein (CRP) of Csf1, and/or depressed levels of anti-inflammatory cytokines in the CNS.

15. The method according to claim 1, wherein the compound of Formula I is administered intra-nasally subcutaneously, intramuscularly, intravenously, orally, sub-lingually, intra-peritoneally, or buccally.

16. The method according to claim 1, wherein the patient has not responded to, or has not responded adequately to, or who suffers undesirable side effects from, treatment with another antidepressant agent.

17. A method for protecting or reinforcing the blood-brain barrier, comprising administering to a patient in need thereof, a therapeutically effective amount of a Compound of Formula I:

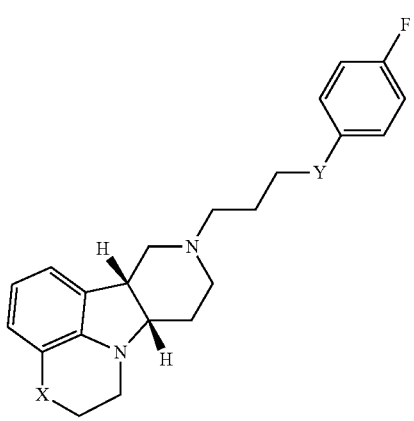

Formula I wherein:
X is —N(CH$_3$)—; and
Y is —C(=O)—;
in free base, or pharmaceutically acceptable salt form;
wherein the patient has elevated levels of one or more biomarkers indicative of peripheral inflammation in the blood, plasma, serum, peripheral blood mononuclear cells (PBMC), or urine.

18. A method for the treatment of psychiatric disorders in a patient in need thereof, wherein the psychiatric disorder and/or the psychiatric symptom is depression, anxiety, psychosis, anhedonia, memory loss, impairment of executive functioning, difficulty concentrating, seizures, difficulty sleeping, hallucination, change in personality, or any combination thereof;
wherein the patient has elevated levels of one or more biomarkers indicative of peripheral inflammation in the blood, plasma, serum, peripheral blood mononuclear cells (PBMC), or urine; and
wherein the patient has elevated levels of pro-inflammatory cytokines in the CNS, or elevated levels of C-reactive protein (CRP), or Csf1, and/or depressed levels of anti-inflammatory cytokines in the CNS, the method comprising administering a therapeutically effective amount of a Compound of Formula I:

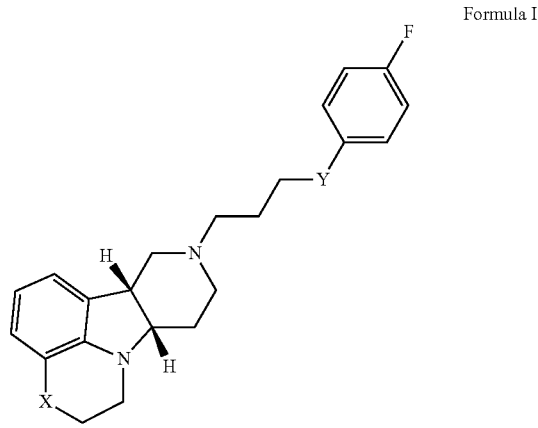

Formula I wherein:
X is —N(CH$_3$)—; and
Y is —C(=O)—;
in free base, or pharmaceutically acceptable salt form, to the patient.

19. The method according to claim 1, wherein the one or more biomarkers indicative of peripheral inflammation are selected from the group consisting of interferon-alpha, interferon-beta, interferon-delta, and combinations thereof.

20. The method according to claim 1, wherein after treatment with the Compound of Formula I, the patient has a reduced level of the one or more biomarkers indicative of peripheral inflammation.

21. The method according to claim 1, wherein the patient has peripheral serotonin deficiency.

22. The method according to claim 17, wherein the one or more biomarkers indicative of peripheral inflammation are selected from the group consisting of interferon-alpha, interferon-beta, interferon-delta, and combinations thereof.

23. The method according to claim 17, wherein after treatment with the Compound of Formula I, the patient has a reduced level of the one or more biomarkers indicative of peripheral inflammation.

24. The method according to claim 17, wherein the patient has peripheral serotonin deficiency.

25. The method according to claim 18, wherein the one or more biomarkers indicative of peripheral inflammation are selected from the group consisting of interferon-alpha, interferon-beta, interferon-delta, and combinations thereof.

26. The method according to claim 18, wherein after treatment with the Compound of Formula I, the patient has a reduced level of the one or more biomarkers indicative of peripheral inflammation.

27. The method according to claim 18, wherein the patient has peripheral serotonin deficiency.

* * * * *

UNITED STATES PATENT AND TRADEMARK OFFICE
CERTIFICATE OF CORRECTION

PATENT NO. : 12,414,948 B2
APPLICATION NO. : 18/518436
DATED : September 16, 2025
INVENTOR(S) : Sophie Dutheil et al.

It is certified that error appears in the above-identified patent and that said Letters Patent is hereby corrected as shown below:

In the Specification

Column 36, Line 65, "Method 1.94" should be changed to "Method 2.81"

Column 41, Line 31, "or 3.71.7" should be changed to "or 3.7"

Column 42, Line 16, "3.1-1.12, e.g., Method 1.12" should be changed to "3.1-3.12, e.g., Method 3.12"

Column 42, Line 19, "3.1-1.12, e.g., Method 1.12" should be changed to "3.1-3.12, e.g., Method 3.12"

Column 42, Line 22, "3.1-1.14" should be changed to "3.1-3.14"

Column 56, Line 1, "or 1.1" should be changed to "or 4.1"

Column 56, Line 3, "or 1.1" should be changed to "or 4.1"

Column 56, Line 5, "or 1.1" should be changed to "or 4.1"

Column 56, Line 7, "1.1-1.4" should be changed to "4.1-4.4"

Column 56, Line 11, "1.1-1.4" should be changed to "4.1-4.4"

Column 56, Line 14, "1.1-1.4" should be changed to "4.1-4.4"

Column 56, Line 16, "1.1-1.4" should be changed to "4.1-4.4"

Column 56, Line 19, "or 1.8" should be changed to "or 4.8"

Signed and Sealed this
Sixteenth Day of December, 2025

John A. Squires
*Director of the United States Patent and Trademark Office*

CERTIFICATE OF CORRECTION (continued)
U.S. Pat. No. 12,414,948 B2

Column 56, Line 39, "1.1-1.5 or 1.7" should be changed to "4.1-4.5 or 4.7"

Column 56, Line 53, "1.1-1.5 or 1.7" should be changed to "4.1-4.5 or 4.7"

Column 70, Line 57, "or 1.1" should be changed to "or 5.1"

Column 70, Line 59, "or 1.1" should be changed to "or 5.1"

Column 70, Line 61, "or 1.1" should be changed to "or 5.1"

Column 70, Line 63, "1.1-1.4" should be changed to "5.1-5.4"

Column 70, Line 66, "Method 4" should be changed to "Method 5"

Column 70, Line 66, "1.1-1.4" should be changed to "5.1-5.4"

Column 71, Line 1, "1.1-1.4" should be changed to "5.1-5.4"

Column 71, Line 3, "1.1-1.4" should be changed to "5.1-5.4"

Column 71, Line 5, "or 1.8" should be changed to "or 5.8"

Column 71, Line 23, "1.1-1.5 or 1.7" should be changed to "5.1-5.5 or 5.7"

Column 71, Line 37, "1.1-1.5 or 1.7" should be changed to "5.1-5.5 or 5.7"

Column 85, Line 40, "Method 5" should be changed to "Method 6"

Column 85, Line 43, "or 1.1" should be changed to "or 6.1"

Column 85, Line 45, "or 1.1" should be changed to "or 6.1"

Column 85, Line 47, "or 1.1" should be changed to "or 6.1"

Column 85, Line 49, "1.1-1.4" should be changed to "6.1-6.4"

Column 85, Line 52, "Method 4" should be changed to "Method 6"

Column 85, Line 52, "1.1-1.4" should be changed to "6.1-6.4"

Column 85, Line 54, "1.1-1.4" should be changed to "6.1-6.4"

CERTIFICATE OF CORRECTION (continued)
U.S. Pat. No. 12,414,948 B2

Column 85, Line 56, "1.1-1.4" should be changed to "6.1-6.4"

Column 85, Line 58, "or 1.8" should be changed to "or 6.8"

Column 86, Line 10, "1.1-1.5 or 1.7" should be changed to "6.1-6.5 or 6.7"

Column 86, Line 24, "1.1-1.5 or 1.7" should be changed to "6.1-6.5 or 6.7"

In the Claims

Column 122, Line 20, Claim 3, "equivalent" should be changed to "equivalent to"

Column 122, Line 53, Claim 11, "potassium, channel" should be changed to "potassium channel"

Column 122, Line 65, Claim 14, "of Csf1" should be changed to "or Csf1"